US005385897A

United States Patent [19]

Teutsch et al.

[11] Patent Number: 5,385,897

[45] Date of Patent: Jan. 31, 1995

[54] 4-THIA-1-AZA-BICYCLO[4,2,0]OCT-2-ENE DERIVATIVES

[75] Inventors: Jean-Georges Teutsch, Pantin; Alain Bonnet, Livry-Gargan; Jozsef Aszodi, Choisy-le-Roi; Solange Gouin d'Ambrieres, Paris, all of France

[73] Assignee: Roussel-UCLAF, France

[21] Appl. No.: 855,324

[22] Filed: Mar. 20, 1992

Related U.S. Application Data

[63] Continuation of Ser. No. 605,982, Oct. 30, 1990, abandoned, which is a continuation-in-part of Ser. No. 151,688, Feb. 2, 1988, Pat. No. 4,832,939, which is a continuation-in-part of Ser. No. 895,175, Aug. 11, 1986, abandoned.

[30] Foreign Application Priority Data

Aug. 9, 1985 [FR] France ................................ 85 12218
Feb. 6, 1987 [FR] France ................................ 87 01456

[51] Int. Cl.$^6$ ..................... C07D 417/12; A61K 31/54
[52] U.S. Cl. .................................... 514/210; 540/221; 540/222; 540/225; 540/214
[58] Field of Search ............... 540/225, 226, 227, 214; 514/210

[56] References Cited

U.S. PATENT DOCUMENTS 4,476,124 10/1984 Heymes et al. ..................... 540/214
4,908,359 3/1990 Costerousse et al. ............... 540/214

*Primary Examiner*—Nicholas S. Rizzo
*Attorney, Agent, or Firm*—Bierman and Muserlian

[57] ABSTRACT

A compound selected from the group consisting of a compound of the formula

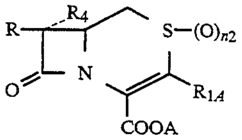

wherein R is selected from the group consisting of

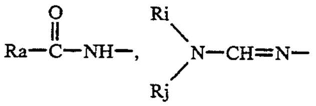

and $R_b$—NH—, Ra is an organic radical, Ri and Rj are individually selected from the group consisting of hydrogen, aliphatic hydrocarbon, aromatic hydrocarbon and heterocycle or taken together with the nitrogen atom to which they are attached form an optionally substituted ring, Rb is selected from the group consisting of carbocyclic aryl and heterocyclic aryl, both optionally substituted, $R_{1A}$ is selected from the group consisting of

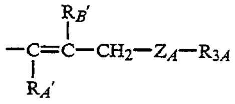

and

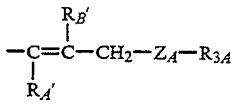

$R_A'$ and $R_B'$ are individually selected from the group consisting of hydrogen and alkyl of 1 to 4 carbon atoms, $Z_A$ is selected from the group consisting of a simple bond, —O— and optionally oxidize sulfur, $R_{3A}$ is selected from the group consisting of optionally substituted carbocyclic aryl and heterocyclic aryl, optionally substitute quaternary ammonium, acetyl, carbamoyl, alkoxycarbonyl, alkyl and haloalkyl of 1 to 4 carbon atoms, —CN and azido, $R_4$ is selected from the group consisting of hydrogen and methoxy, A is selected from the group consisting of hydrogen, alkali metal, alkaline earth metal, magnesium, $—NH_4$, an organic amine and esterified carboxy or —COOA is $—COO^{\ominus}$, $n_2$ is an integer from 0 to 2 and their non-toxic, pharmaceutical acceptable acid addition salts having excellent antibiotic activity.

15 Claims, No Drawings

4-THIA-1-AZA-BICYCLO[4,2,0]OCT-2-ENE DERIVATIVES

This application is a continuation of U.S. patent application Ser. No. 605,982 filed Oct. 30, 1990, now abandoned; which is a continuation of U.S. patent application Ser. No. 07/151,688 filed Feb. 2, 1988, now abandoned; which is a continuation-in-part of Ser. No. 895,175, filed Aug. 11, 1986, now abandoned.

STATE OF THE ART

In European Patent application No. 0153229, there are described new derivatives of 1-dethia 2-thia cephalosporanic acids and their salts, their preparation process and their use as medicaments. The said products have the formula

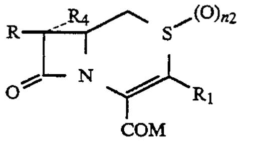

A wherein R is either

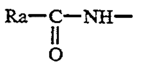

in which Ra is an organic radical, or

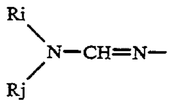

in which Ri and Rj individually are hydrogen or an aliphatic or aromatic hydrocarbon or a heterocyclic or Ri and Rj form with the nitrogen atom to which they are bonded an optionally substituted cyclic or Rb—NH— in which Rb is an optionally substituted carbocyclic or heterocyclic aryl, $R_1$ is a) —Z—$R_2$ in which $R_2$ is an alkyl, alkenyl or alkynyl optionally substituted or interrupted by a heteroatom and Z is an optionally oxidized sulfur, selenium, oxygen or —NH—, b) —$Z_a$—$R_3$ in which $R_3$ is an optionally substituted carbocyclic or heterocyclic aryl or an optionally substituted quaternary ammonium and $Z_a$ is methylene, sulfur, selenium or oxygen or —NH— or $Z_a$ is a simple bond or $Z_a$ is —$CH_2$—S—, c) an alkyl, alkenyl or alkynyl of 2 to 8 carbon atoms optionally substituted or interrupted by a heteroatom, d) halogen, nitrile, optionally esterified or salified carboxy, azido, thiocyanato or isothiocyanato or e) azidomethyl, amino or mono- or di-substituted methyl amino, thiocyanato methyl, isothiocyanato methyl, carbamoyloxymethyl, semicarbazonomethine, optionally substituted arylhydrazonomethine, nitromethyl or di or tri-halomethyl —$CH_2$—$ONO_2$, $CH_2$—$\oplus P$(alk)$_3$ or

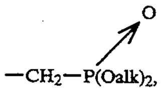

alk is alkyl of 1 to 4 carbon atoms, $R_4$ is hydrogen or methoxy, COM is —$CO_2$—A in which A is hydrogen, an alkali metal, alkaline earth metal, magnesium, ammonium or an organic amine or A is an ester group, or —$CO_2$A is $CO_2^-$, or $R_1$ and $CO_2$A form together with the carbon atoms to which they are bonded.

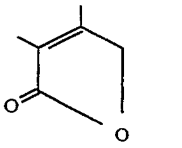

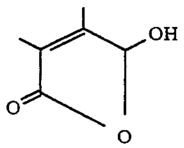

or COM is an optionally substituted carbamoyl and $n_2$ is an integer equal to 0, 1 or 2, as well as the non-toxic, pharmaceutically acceptable addition salts. The products of the above formula can be in racemic or optically-active form.

OBJECTS OF THE INVENTION

It is an object of the invention to provide the novel compounds of formula I and their non-toxic, pharmaceutically acceptable acid addition salts and a novel process for their preparation.

It is another object of the invention to provide novel anti-bacterial compositions and a novel method of combatting bacterial infections in warm-blooded animals.

These and other objects and advantages of the invention will become obvious from the following detailed description.

THE INVENTION

The novel compounds of the invention are selected from the group consisting of a compound of the formula

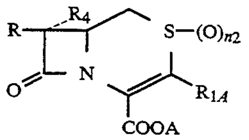

wherein R is selected from the group consisting of

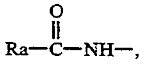

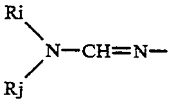

and $R_b$—NH—, Ra is an organic radical, Ri and Rj are individually selected from the group consisting of hydrogen, aliphati hydrocarbon, aromatic hydrocarbon and heterocycle or taken together with the nitrogen atom to which they are attached form an optionally substituted ring, Rb is selected from the group consisting of carbocyclic aryl and heterocyclic aryl, both optionally substituted, $R_{1A}$ is selected from the group consisting of

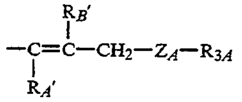

and

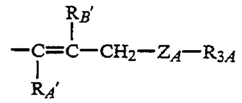

$R_A'$ and $R_B'$ are individually selected from the group consisting of hydrogen and alkyl of 1 to 4 carbon atoms, $Z_A$ is selected from the group consisting of a simple bond, —O— and optionally oxidized sulfur, $R_{3A}$ is selected from the group consisting of optionally substituted carbocyclic aryl and heterocyclic aryl, optionally substituted quaternary ammonium, acetyl, carbamoyl, alkoxycarbonyl, alkyl and haloalkyl of 1 to 4 carbon atoms, —CN and azido, $R_4$ is selected from the group consisting of hydrogen and methoxy, A is selected from the group consisting of hydrogen, alkali metal, alkaline earth metal, magnesium, $—NH_4$, an organic amine and esterified carboxy or —COOA is $—COO^{\ominus}$, $n_2$ is an integer from 0 to 2 and their non-toxic, pharmaceutically acceptable acid addition salts.

Among the products of formula I, wherein $Z_A$ is sulfur or oxygen and R3A is a quaternary ammonium, the products are preferred in which $Z_A$ is not connected directly to the nitrogen atom. The products of formula I can be in the racemic or the optically active form.

Among the preferred values for R, R is acylamino of the formula

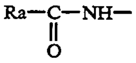

wherein Ra is an organic radical.

Among the values for Ra are

1) $Ar—(CH_2)_n$;

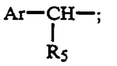

$Ar—CH_2O—$; $Ar—OCH_2—$; $Ar—S—CH_2—$; $Ar—CH_2—S—$;

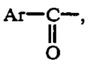

wherein Ar is phenyl optionally mono- or polysubstituted or an aromatic heterocyclic with 5, 6 or 7 ring atoms having 1 to 4 hetero-atoms chosen from sulfur, oxygen and nitrogen, n is an integer from 0 to 4, $R_5$ is selected from the group consisting of amino, hydroxyl, azido, hydrazino, free, esterified or salified carboxyl, free or salified sulfo, sulfoamino, halogen, alkyl hydrazino, phenyl hydrazino and formyloxy.

Among the substituents for phenyl or heterocyclic are halogen and alkyl and alkoxy of 1 to 4 carbon atoms, amino alkyl of 1 to 4 carbon atoms, and preferably aminomethyl, hydroxyl, nitro, amino, trifluoromethyl or cyano. Among the heterocyclic aromatic, there are thiazolyl, furyl, thienyl, pyrrolyl, pyridinyl, pyrazinyl, pyrimidinyl, morpholinyl and tetrazolyl. Furyl, aminothiazolyl, aminohalo thiazolyl, amino thiadiazolyl and amino pyrimidinyl are preferred.

2) Ra may also be alkyl, cycloalkyl, alkoxyl, alkenyl or cycloalkenyl each of which may be mono- or poly-substituted by at least one substituent such as alkylthio or cyanoalkylthio, mercapto, nitro, cyano, or amino.

3) Ra may also be:

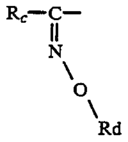

wherein Rc has the same definition as Ar. Among the preferred values for Rc are: 2-amino-4-thiazolyl; 2-amino-5-nitro, 5-chloro, 5-fluoro or 5-bromo thiazolyl; 5-amino-1,2,4-thiadiazolyl, 4-thiazolyl, 2-thienyl or 2-furyl; Rd is hydrogen, acyl, aryl, heteroaryl, arylalkyl, heteroarylalkyl, alkyl, cycloalkyl, alkenyl or cycloalkenyl, alkynyl optionally substituted and optionally interrupted by oxygen or sulfur optionally oxidized or Rd may be optionally substituted carbamoyl.

Among the substituents of Rd are alkyl, halogen, acyl, cyano, carbamoyl, nitro, amino, hydroxy, mercapto, alkylthio, oxo, alkoxy or a free, esterified or salified carboxyl.

Among the values for Rd are hydrogen, alkyl, alkenyl, optionally cyclic, alkynyl, aryl, heteroaryl mono or polycyclic and particularly the values:

$—CH_3$, $—CH_2—CH_3$, $—CHF_2$, $—CH_2—CF_3$, $—CH_2—O—CH_3$, $—CH_2—S—CH_3$, 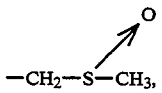

$—CH_2—SO_2—CH_3$, $—CH_2CN$, $—CH_2—CONH_2$,

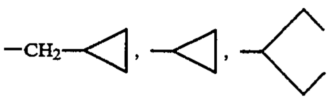 , $—CH_2CO_2H$,

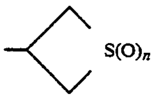 $—CH(CH_3)CO_2H$, $—C(CH_3)_2—CO_2H$,

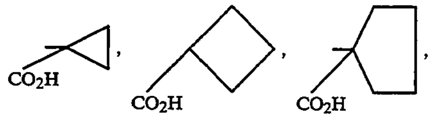

$—CH_2—CH=CH_2$, 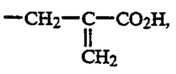

$—CH_2—CH=CH—SO_2H$, 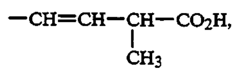

$—CH_2—C≡CH$, phenyl, 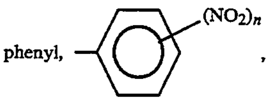 ,

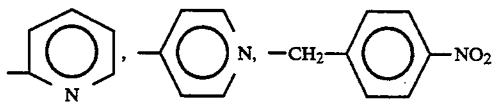

-continued

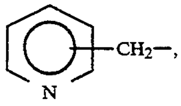 , 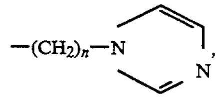 ,

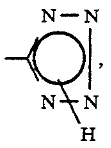 , 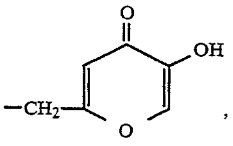 ,

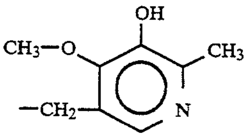 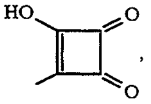 , $CH_2-CO-CH_3$, $-CH_2-CH_2-NH_2$, $-CH_2-CF_2-CO_2H$.

Among the preferred values for Rd are methyl, hydrogen, ethyl, allyl, 1-methyl-1-carboxyethyl, carboxymethyl and difluoromethyl.

4) Ra may also be:

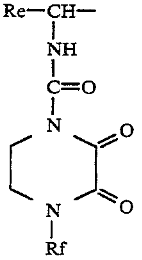

wherein Re has the same values as Ar. The non-substituted phenyl is preferred. Rf is alkyl optionally substituted, or —N═CH—Rg in which Rg is aryl as defined above for Ra. Ethyl, phenyl or furyl are preferred for Rf.

5) Ra may also be:

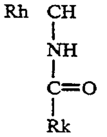

wherein Rh has the values indicated for Ar and Rk is:

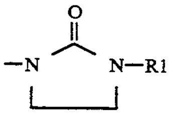

in which Rl is hydrogen, alkylsulfonyl or —N═CH—Rm where Rm has the same value as Ar, in particular furyl; Rk may be an optionally substituted aryl, for example, imidazolyl substituted by a carboxyl. Rk may also be a substituted amino, for example, an acylamido such as N-methyl-benzoylamido or furylcarbonyl or an amino substituted by an optionally substituted heterocycle or Rk may be aryl optionally substituted and condensed; or optionally substituted aralkyl.

In this preferred class of products, Ra may preferably be:

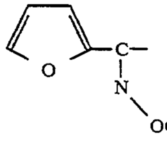 ; 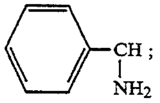 ;

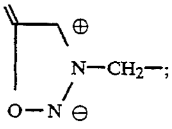 ; 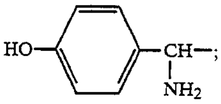 ;

$N\equiv C-CH_2-$; 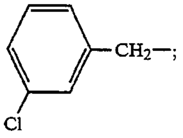 ;

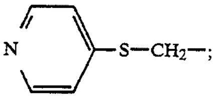 ; 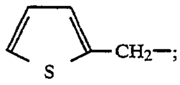 ;

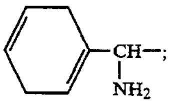 ; 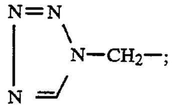 ;

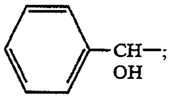 ; 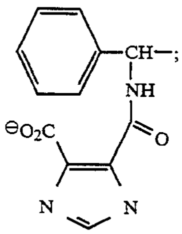 ;

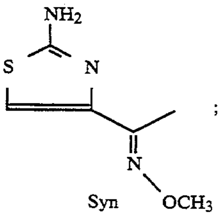 ;

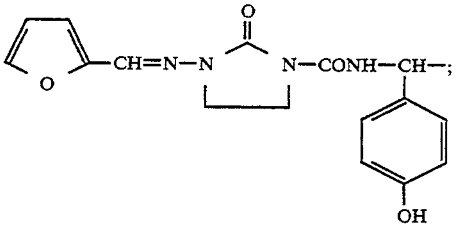 ;

-continued
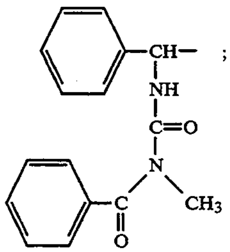
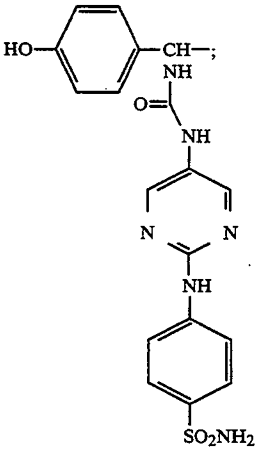
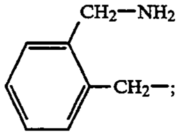
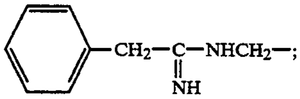
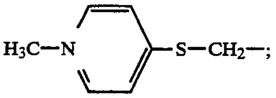
$HOOC—CH_2—S—CH_2—$; $NC—CH=CH—S—CH_2$;
$HO_2C—CH=CH—S—CH_2—$; 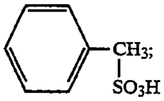
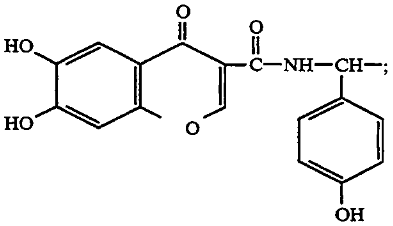
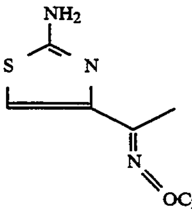
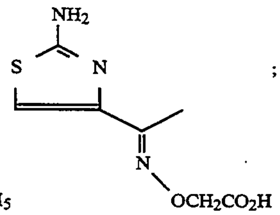
;
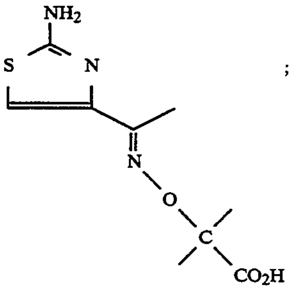
;
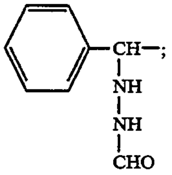
-continued
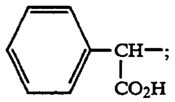
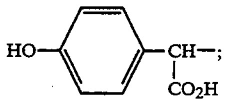
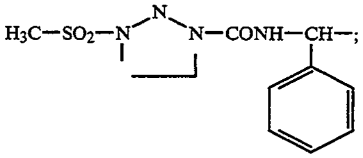
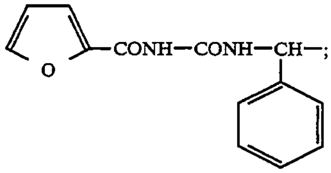
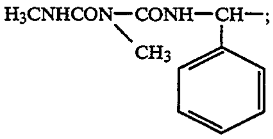
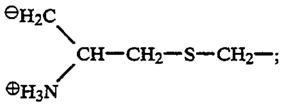
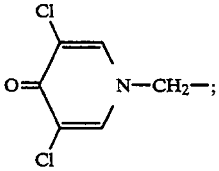
;
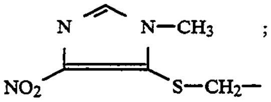
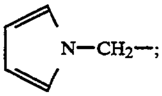
$NC—CH_2—S—CH_2—$;
$F_3C—S—CH_2—$;
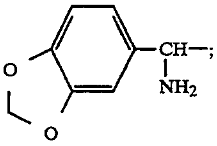
;
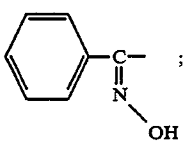
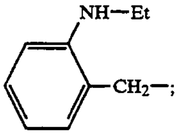
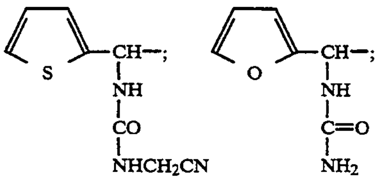

-continued
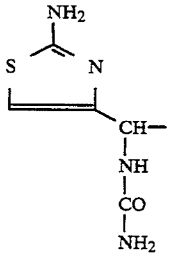
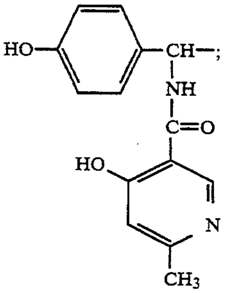
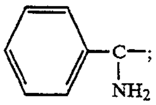
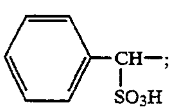
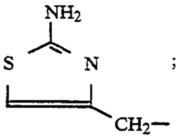
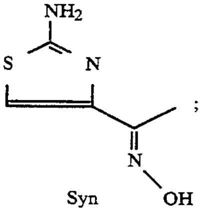
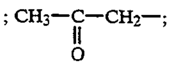
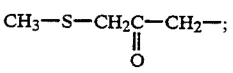
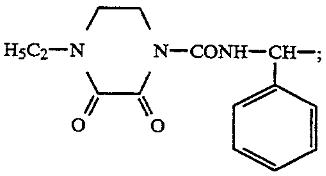
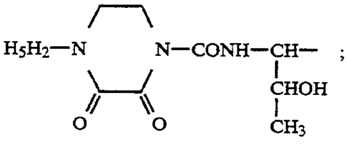
-continued
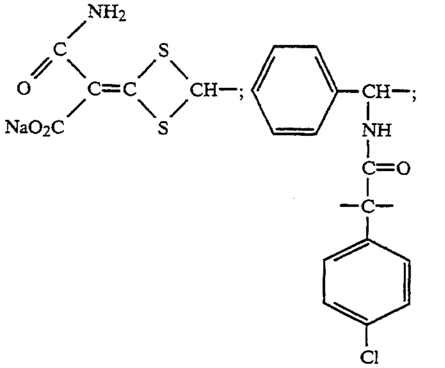
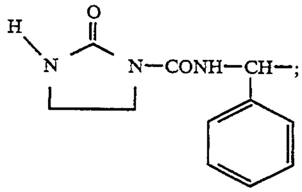
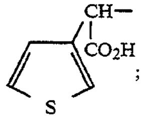
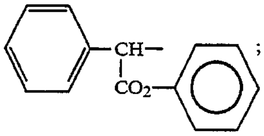
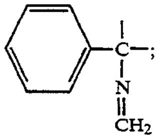
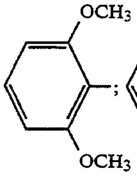
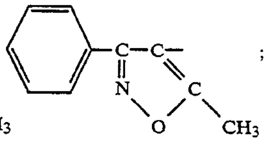
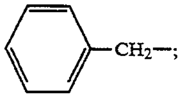
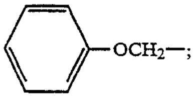
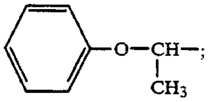
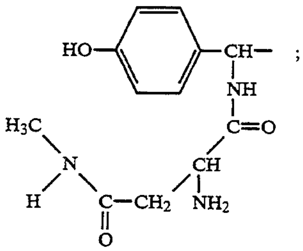
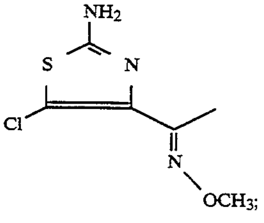

-continued

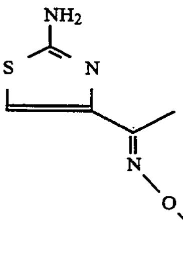

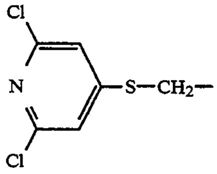

Among other values for R, a second preferred class of products is constituted, preferably, by products in which R is:

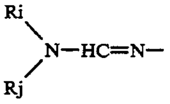

wherein Ri and Rj are individually selected from the group consisting of hydrogen or alkyl of 1 to 8 carbon atoms, or Ri and Rj form with the nitrogen atom to which they are connected a possibly substituted cyclic amine.

Preferably,

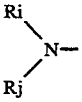 is:

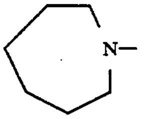 or 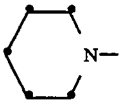 or

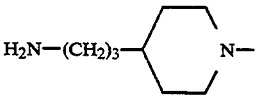

Among other values for R, a third preferred class of products is constituted preferably, by the products in which R is Rb—NH— in which Rb is a carbocyclic or heterocyclic aryl optionally substituted.

Among those preferred values are:

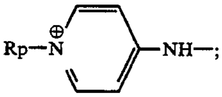; 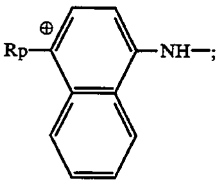;

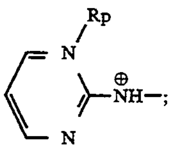; 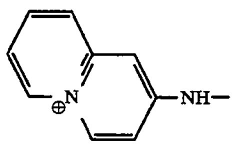

-continued

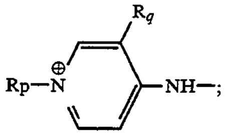; 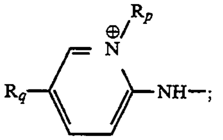;

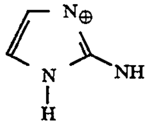 mono or polysubstituted.

in which Rp is alkyl of 1 to 4 carbon atoms, preferably methyl, ethyl, isopropyl optionally interrupted by a hetero-atom such as methoxymethyl, optionally substituted by one or more halogens such as trichlorethoxymethyl or trifluoroethoxymethyl or alkoxy such as ethoxy. Rp may also be arylalkyl such as benzyl or phenethyl optionally substituted by an alkyl such as methyl, alkoxy such as methoxy, cyano or halogen such as fluoro. Rp may also be furfuryl, or optionally substituted phenylmethoxymethyl.

Rq may be hydrogen or alkyl of 1 to 4 carbon atoms such as methyl, an alkoxycarbonyl such as methoxycarbonyl or tert-butyloxycarbonyl.

Among the preferred values for R,

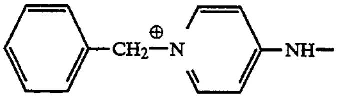

is preferred.

Among the values for $R_{3A}$ there can be cited the following: phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyrimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl, benzoxazole.

Among the different aryls, the following are preferred: thiazol-2-yl, 1,3,4-thiadiazol-5-yl and 1,2,4-thiadiazol-5-yl, imidazol-2-yl, 1,3,4-triazol-5-yl, 1,3,4-thiadiazol-2-yl, 1,2,3-thiadiazol-5-yl, 1H-tetrazol-5-yl, pyridin-2-yl, 1,3,4-triazin-2-yl, 1,3,5-triazin-4-yl, pyridinium, quinolinium, isoquinolinium, cyclopentylpyridinium, trimethylammonium.

$R_{3A}$ can be substituted by at least one radical chosen from alkyls such as methyl, ethyl, propyl, isopropyl, linear or branched butyl which alkyls can themselves be substituted by an aryl such as phenyl or thienyl, aryloxy such as lower phenoxy, alkoxy such as methoxy, alkoxy carbonyl such as ethoxycarbonyl, by a halogen such as chloro or bromo, hydroxy free or protected, free carboxy, esterified or salified, amino, alkylamino or dialkylamino or acylamido.

$R_{3A}$ can also be substituted by at least one alkenyl such as vinyl, allyl, butenyl, alkynyl such as ethynyl or propargyl, aryl such as phenyl, tolyl, halogen such as chloro, bromo, iodo or fluoro, amino or nitro, alkoxy of 1 to 4 carbon atoms such as methoxy, alkylthio such as methylthio, hydroxy, mercapto, amino, free, esterified or salified carboxyl or carbamoyl. $R_{3A}$ can also be substituted by two substituents forming together a cycle such as cyclopentyl or cyclohexyl.

A particularly preferred category is constituted by the substituents $R_{3A}$ including a quaternary ammonium, in particular the substituents:
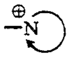
or
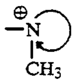
the symbol 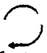 representing the remainder of a ring. $R_3A$ may also preferably be a non-cyclic quaternary ammonium.
Among the values for $R_{1A}$, the following are preferred:
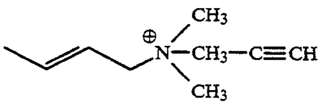
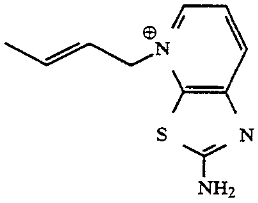
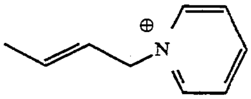
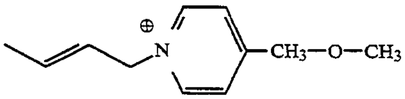
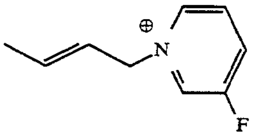
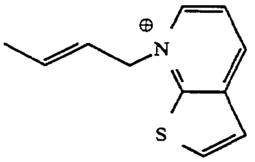
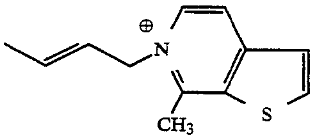
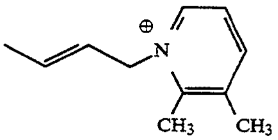
-continued
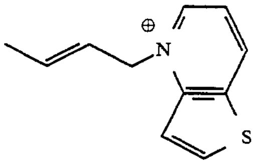
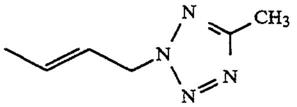
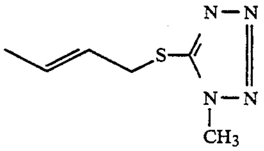
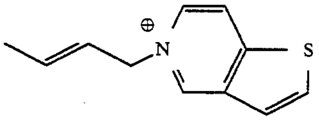
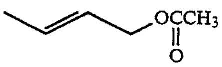
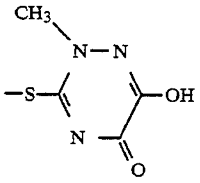
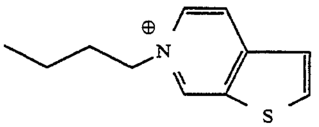
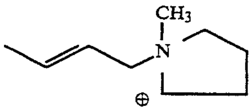
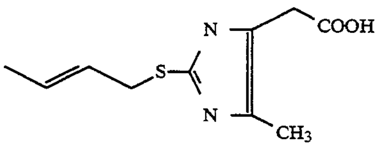
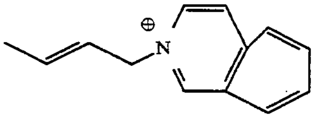
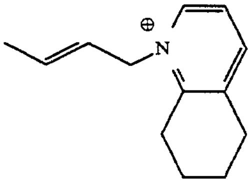

-continued
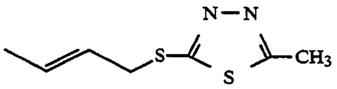
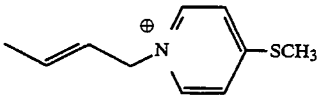
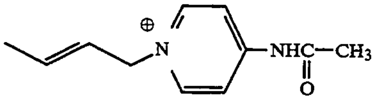
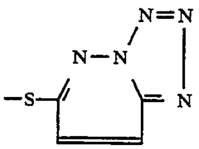
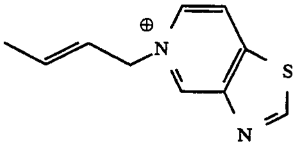
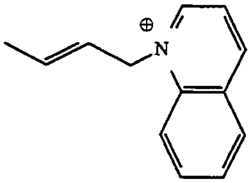
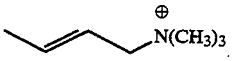
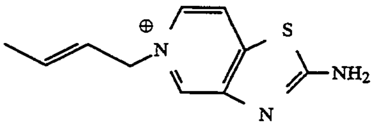
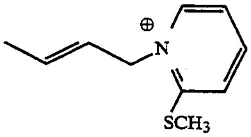
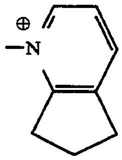
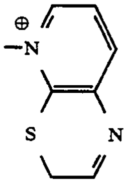
-continued
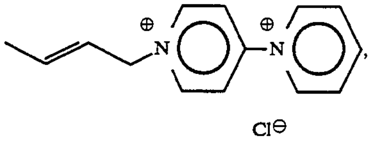
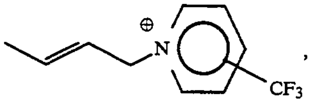
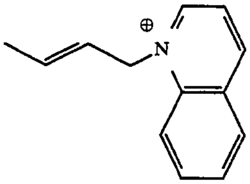
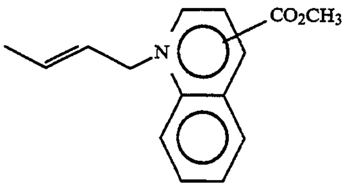
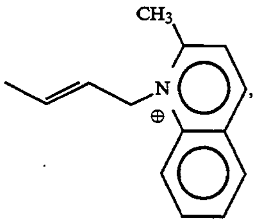
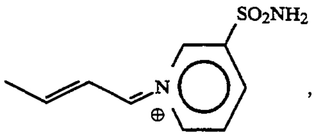
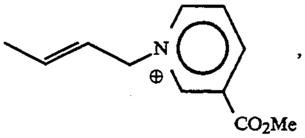
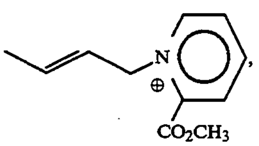
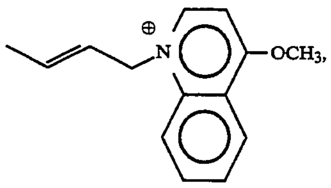

-continued
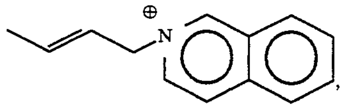
,
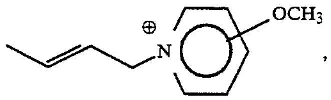
,
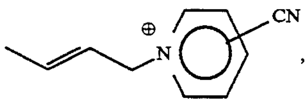
,
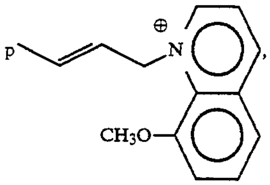
,
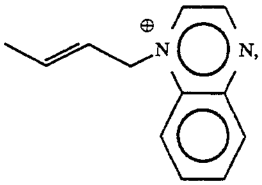
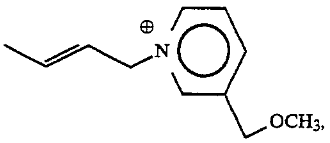
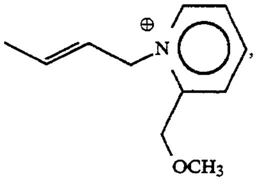
,
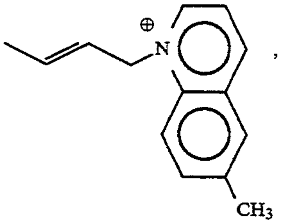
,
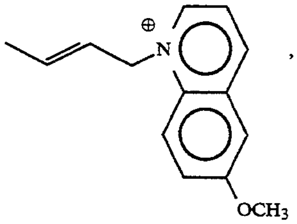
,
-continued
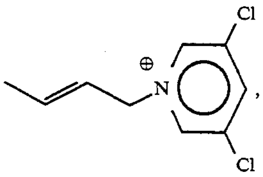
,
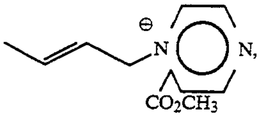
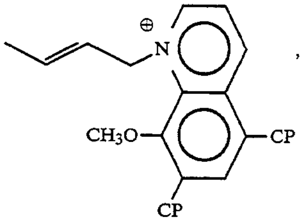
,
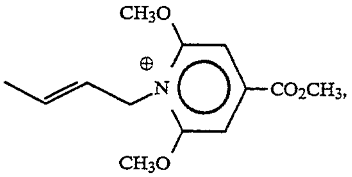
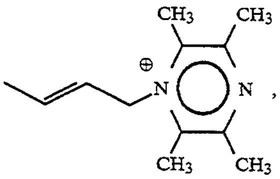
,
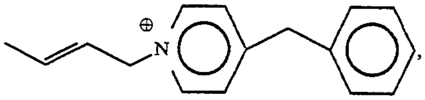
,
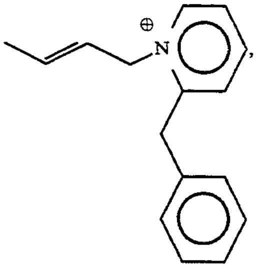
,
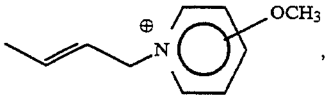
,
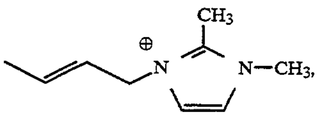

-continued
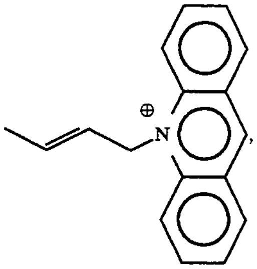
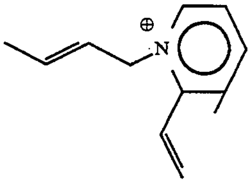
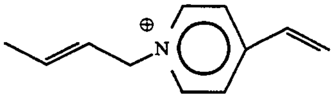
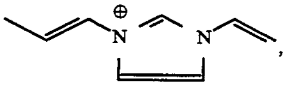
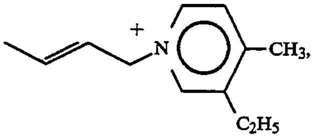
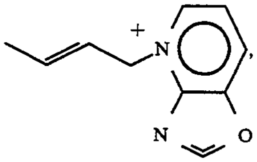
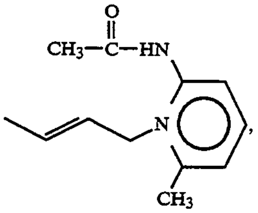
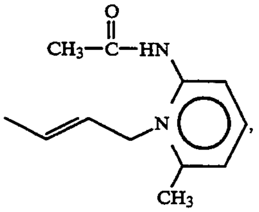
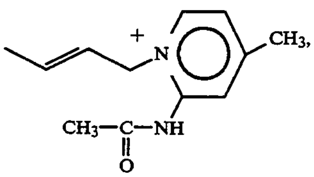
-continued
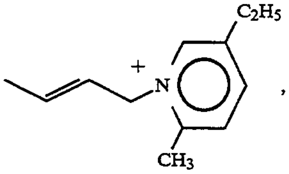
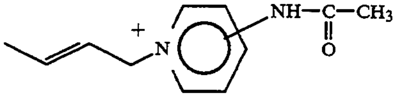
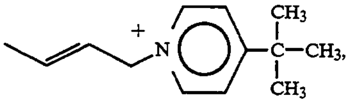
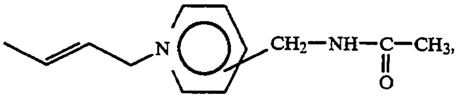
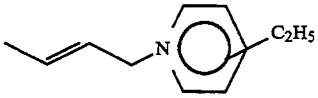
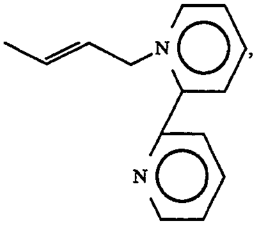
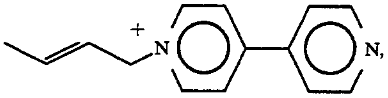
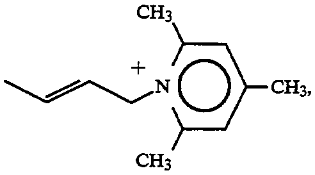
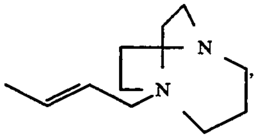
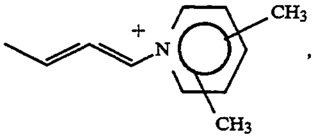

-continued

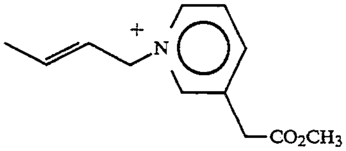

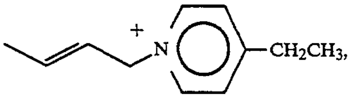

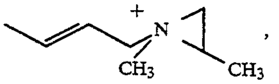

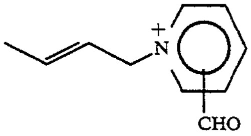

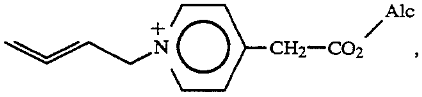

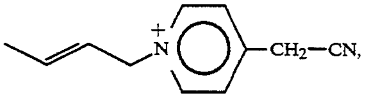

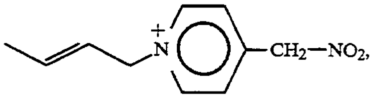

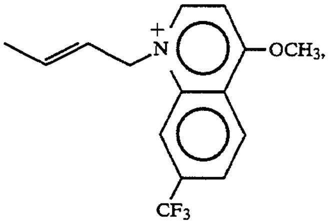

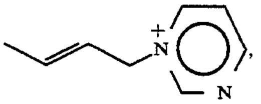

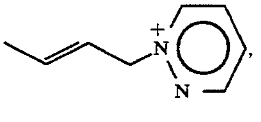

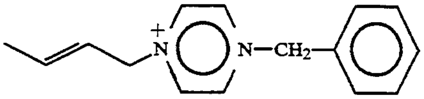

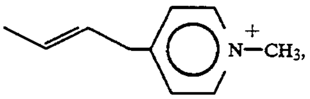

-continued

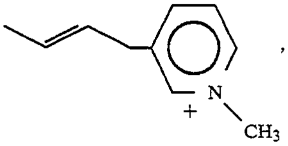

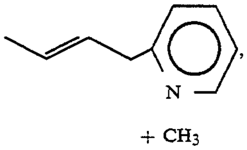

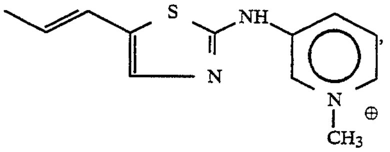

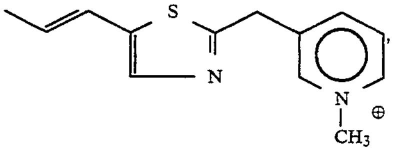

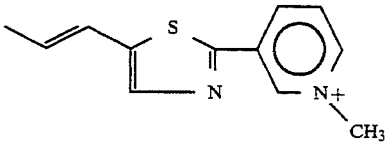

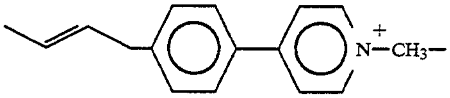

Among the values for A are sodium, potassium, lithium, calcium, magnesium, ammonium or of an organic base such as methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine, and N-methylglucamine. Among residues of easily cleavable esters which A may be are methoxymethyl, ethoxymethyl, isopropyloxymethyl, α-methoxyethyl, α-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxyhexyl, 1-acetyloxyheptyl, phthalidyl, 5,6-dimethoxyphthalidyl, tert-butylcarbonylmethyl, allyl, 2-chloroallyl, methoxycarbonylmethyl, benzyl or tert-butyl.

Other residues of esters which A may be are: methoxyethoxymethyl, dimethylaminoethyl, cyanomethyl, tert-butyloxycarbonymethyl, 2,2-ethylenedioxyethyl, cyanoethyl, 2,2-dimethoxyethyl, 2-chloroethoxymethyl, 2-hydroxyethoxyethyl, 2,3-epoxypropyl, 3-dimethylamino, 2-hydroxypropyl, 2-hydroxyethyl, 2-methylaminoethoxymethyl, 2-aminoethoxymethyl, 3-methoxy-2,4-thiadiazol-5-yl, 2-tetrahydropyranyl, 2-methoxyprop-2-yl, 1-hydroxy-prop-2-yl, isopropyl, carbamoylmethyl, chloromethyl, 2-chloroethyl, acetylmethyl, 2-methylthioethyl or thiocyanatomethyl.

Other residues of ester groups which A may be are: 2-chloro-1-acetyloxyethyl, 2-bromo-1-acetyloxyethyl, 2-fluoro-1-acetyloxyethyl, 2-methoxy-1-acetyloxyethyl, 2-methyl-1-acetyloxypropyl, 2-acetyloxyprop-2-yl, 1-methoxyacetyloxyethyl, 1-acetylcarbonyloxyethyl, 1-hydroxyacetyloxyethyl, 1-formylcarbonyloxyethyl, 1-(2-thienyl)carbonyloxyethyl, 1-(2-furyl)carbonyloxyethyl, 1-(5-nitro-2-furyl)carbonyloxyethyl, 1-(2-pyrrolyl)carbonyloxyethyl, 1-(propionyloxycarbonyloxy)ethyl, 1-(propyloxycarbonyloxy)ethyl, 1-(isopropyloxycarbonyloxy)ethyl, 1-(methoxyethoxycarbonyloxy)ethyl, 1-(allyloxycarbonyloxy)ethyl, 1-(2,3-epoxy)propyloxycarbonyloxyethyl, 1-(2-furyl)methyloxycarbonyloxyethyl, 1-(2-fluoro)ethyloxycarbonyloxyethyl, 1-(methoxycarbonyloxy) propyl, (2-methoxycarbonyloxy)prop-2-yl, (methoxycarbonyloxy)-chloromethyl, 1-(methoxycarbonyloxy)-2-chloroethyl, 1-(methoxycarbonyloxy)-2-methoxyethyl, 1-(methoxycarbonyloxyl)-1-allyl. A may also be:

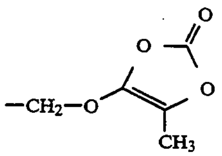

The products of formula I may also be in the form of salts of organic or mineral acids.

Among the acids with which the amino group or groups or the quaternary ammonium group can be salified, there can be mentioned, among others, the following acids: acetic acid, trifluoroacetic acid, maleic acid, tartaric acid, methanesulfonic acid, benzenesulfonic acid, p-toluenesulfonic acid, trifluoromethanesulfonic acid, formic acid, phosphoric acid, sulfuric acid, hydrochloric acid, hydrobromic acid, hydriodic acid. Among the values for A, the preferred esters have the formula

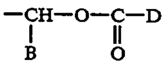

in which B is hydrogen or optionally substituted linear or branched alkyl of 1 to 5 carbon atoms, and D is alkyl or alkoxy optionally substituted of 1 to 15 carbon atoms and particularly 1 to 5 carbon atoms and more particularly the ester in which B is hydrogen or methyl or ethyl and D is methyl, ethyl, methoxy or ethoxy.

Among the values for A, there are

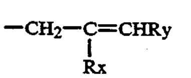

in which Rx is hydrogen, alkyl, particularly methyl and ethyl, halogen, particularly chlorine, and Ry is hydrogen, halogen, aryl, particularly phenyl optionally substituted by methyl, methoxy or halogen, or Ry is alkyl optionally substituted by acyloxy, by alkoxycarbonyl or by halogen.

Among the values for A are

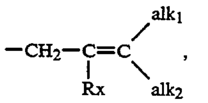

in which Rx is defined as above and $alk_1$ and $alk_2$ are alkyl of 1 to 4 carbon atoms.

Among the compounds of formula I, a preferred group are the syn isomers of the formula $I_A$

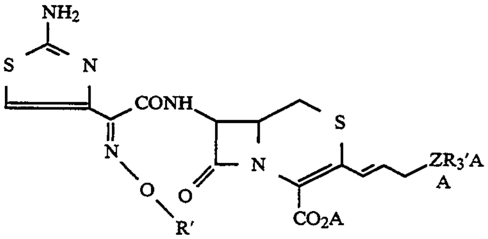

in which R' is hydrogen or optionally substituted alkyl, alkenyl, alkynyl or cycloalkyl up to 6 carbon atoms or aryl, ZA has the value indicated above and $R'_3A$ is phenyl, optionally substituted heterocyclic aryl, or optionally substituted quaternary ammonium, or acetyl or carbamoyl.

VII

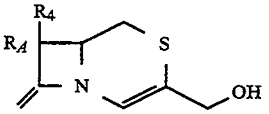

Among the products already mentioned of formula $I_A$, the products are preferred in which R' is hydrogen, or methyl or isopropyl optionally substituted by carboxy, carbamoyl, nitrile, methylthio or methoxy, difluoromethyl or trifluoromethyl, phenyl, cyclobutyl, or cyclopropyl optionally substituted by carboxy, allyl optionally substituted by chlorine or bromine, and the products in which ZA is a simple bond and $R'_3A$ is an optionally substituted pyridinium.

Among the preferred products are those described in the Examples, and particularly the following products:

the internal salt of (6S,7S) 7-[3-[7-[[(2-amino-4-thiazolyl)-2-[Z-(di fluoromethoxy)iminoacetamido]-2-carboxy-8-oxo-4-thia-1-azabicyclo[4,2,0]oct-2-en-3-yl]-2-(E)-propenyl-thieno[2,3-b]pyridinium; the internal salt of the syn isomer of (6S,7S) 5-[3-[7-[[(2-amino-4-thiazolyl)-(methoxyimino)acetamido[2-carboxy-8-oxo-4-thia-1-azabicyclo[4,2,0]oct-2-en-3-yl]-2(E)-propenyl]-2-methyl-thiazolo[4,5,-b]-pyridinium; the internal salt of (6S,7S) 7-[3-[7-[[(2-amino-4-thiazolyl)-2-(Z)-(methoxyimino)-acetamido]-2-carboxy-8-oxo-4-thia-1-azabicyclo[4,2,0]oct-2-en-3-yl]propen-2-(E)-yl]-thieno-[2,3-b]-pyridinium;

The syn isomer of (6S,7S) 7-[[(2-amino-4-thiazolyl)-(methoxyimino)acetamido[3-[[3-(1,3,4-thiadiazol-2-yl)thio]-1-(E)-propenyl]-8-oxo-4-thia-1-azabicyclo-[4,2,0]oct-2-en-2-carboxylic acid; and the internal salt of the Z isomer (6S,7S) 5-[3-[7-[[(2-amino-4-thiazolyl)-(difluoromethoxy)imino-acetamido]-2-carboxy-8-oxo-4-thia-1-azabicyclo-[4,2,0]oct-2-en-3-yl]-2-(E)-propenyl-

[(2-methyl-thiazolo-[4,5,-c]-pyridinium, 6S,7S,ΔZ 5-[3-[7-[(2-aminothiazol-4-yl)-(methoxyimino)acetamido]2-carboxy-8-oxo-4-thia-1-azabicyclo[4,2,0]oct-2-en-3-yl]-2(E)propenyl]thiazolo[4,5-c]pyridinium, 6S,7S syn isomer of 5-[3-[7-[(2-aminothiazol-4-yl)(difluoromethoxyimino)acetamido]2-carboxy-8-oxo-4-thia-1-azabicyclo[4,2,0]oct-2-en-3-yl]-2(E)propenyl]-thiazolo[4,5,c-]pyridinium and 6S,7S syn isomer of 7-[3-[7-(2-aminothiazol-4-yl)(fluoromethoxyimino)acetamido]2-carboxy-8-oxo-4-thia-1-azabicyclo[4,2,0]oct-2-en-3-yl]2-(E)propenyl]thieno[2,3-b]pyridinium.

The process for the preparation of compounds of formula I comprises reacting a compound of the formula

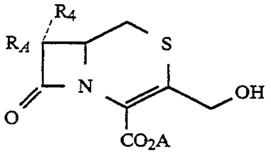

VII in which $R_4$ and A have the significance indicated above and $R_A$ is either a free amino or one protected by a mono or divalent protector group, or $R_A$ is R, R having the significance indicated above, with a halogenation agent, or with a sulfonation agent then with triphenylphosphine, or by a reagent of the formula $P(OAlk)_3$ in which Alk is alkyl of 1 to 4 carbon atoms, to obtain either a product of the formula

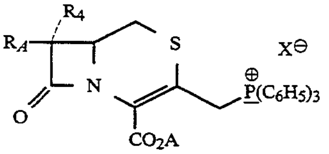

VIIIA in which $R_A$, $R_4$ and A have the previous significance and $X^{\ominus}$ is the residue of an anion, or a product of the formula

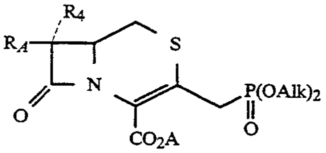

VIII'A in which $R_A$, $R_4$, A and Alk have the previous significance, which products of formulae VIII A or VIII'A, if desired, are treated first with a strong base then with an alkyl halide of the formula Hal—$R''_A$ in which Hal is halogen and $R''_A$ has the values of R'A other than hydrogen to obtain the products of the formulae

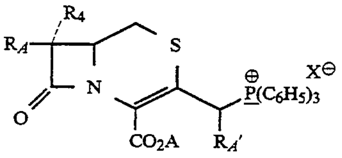

$VIII_B$ or

-continued

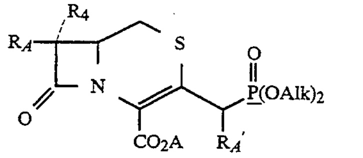

$VIII_{B'}$ wherein $R'_A$ has the significance indicated above, the products with the formulae $VIII_B$ or $VIII'_B$ representing the whole of the starting products $VIII_A$ or $VIII'_A$ and of products obtained after reacting said derivatives with a derivative of formula Hal—$R''_A$, which products of formulae $VIII_B$ or $VIII'_B$ are treated with a product of the formula

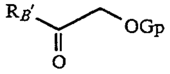

in which $R'_B$ has the value indicated above and Gp is a protector group of the hydroxyl to obtain a product of the formula

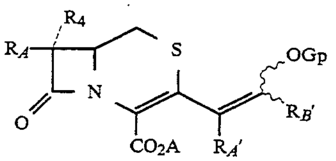

IX in the form of a mixture of E and Z isomers or in the form of isomer E or Z, on which product of formula IX the following reactions are carried out in any order whatsoever:

a) separation of the protector group Gp;

b) when $R_A$ is amino protected by amino- or divalent protector group, elimination of this protector group and treatment of product in which $R_A$ is amino either with an acid of the formula $RaCO_2H$ IVa in which $R_a$ is an organic group or with a functional derivative of the acid, or with a product of the formula

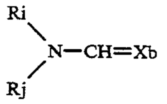

IVb in which Ri and Rj have the significance indicated above and Xb is sulfur or oxygen or with a product of the formula Rb—Xc IVc in which Rb has the significance indicated above and Xc is halogen, c) separation of the isomers E and Z to obtain a product of the formula

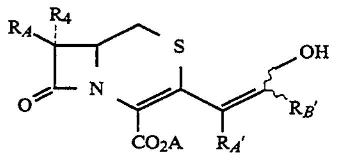

X in which $R'_B$ has the significance indicated above which product is reacted either with a reactive derivative of $R_3A$ to obtain a product of the formula

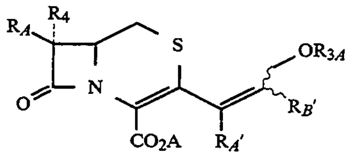

$XI_A$ or with a derivative of an activation group of the hydroxyl then with a derivative or a reactive derivative of $R_{3A}$ to obtain a product of the formula

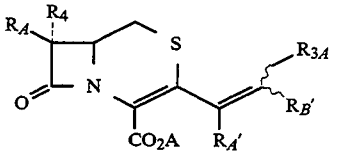

$XI_B$ or with a derivative of an activation group of the hydroxyl then with a product of the formula HS—$R_{3A}$ or a reactive derivative of this product to obtain a product of the formula

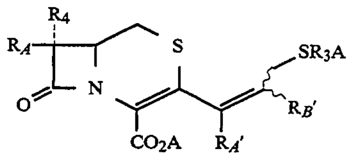

$XI_C$ which products of formulae $XI_A$, $XI_B$ or $XI_C$ are submitted if necessary or if desired, to any one or more of the following reactions in any order whatsoever:

a) separation by hydrolysis, hydrogenolysis or by the action of thiourea of all or part of the protector group or groups.
b) esterification or salification with a base of the carboxy or sulfo group or groups.
c) salification with an acid of the aminos.
d) resolution of the molecule to obtain an optically active product.
e) oxidation of the sulfur atom in position 2 of the isocephem ring.

The halogenation agent which is preferably used is thionyl chloride in a chlorinated solvent such as methylene chloride or in dimethylformamide. Then, intermediately, there is obtained a product of the formula

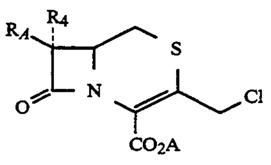

$VII_a$

There can also be used other halogenation reagents such as phosphorus pentachloride, phosphorus oxychloride or tosyl chloride. The sulfonation agent can be, for example, trifluoromethyl-sulfonic anhydride and the operation can then be done in the presence of a base, preferably in 2,6-dimethylpyridine or lutidine. In a general way, the sulfonation products are unstable and are not isolated.

The action of triphenylphosphine or of the reagent of the formula P $(OAlk)_3$ in which Alk is ethyl is carried out under the usual conditions. The action of triphenylphosphine or of the reagent with the formula $P(OAlk)_3$ is preferably carried out in the presence of silica on the halogenated product of formula $VII_a$; generally, the operation is done by heating to reflux a solvent such as toluene or chloroform. If a sulfonation agent is reacted on a product of formula VII, the action of triphenylphosphine or of the product with the formula P $(OAlk)_3$ is preferably carried out at the same time because of the instability of the sulfonation products.

The strong base with which the products of formulae $VIII_A$ and $VIII_A'$ are reacted may be chosen from potassium tert-butylate, lithium tert-butylate, lithium diisopropylamide, or lithium bis-trimethylsilyl amide. The alkyl halide of the formula Hal.R"A is preferably the chloride or the bromide.

The action of the product of the formula

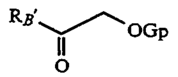

on the products of formulae VIIIB or VIII'B is preferably carried out in a chlorinated solvent such as methylene chloride. The operation can be done in the presence of a relatively weak base such as triethylamine or DBU (1,8-diazabicyclo[5,4,0]undec-7-ene), or DBN (1,5-diazabicyclo[4,3,0]non-5-ene), preferably at ambient temperature or by heating. It is equally possible to operate in the presence of a strong base such as tert-butyl lithium or an alkali metal alcoholate such as lithium tert-butylate, lithium bistrimethylsilyl amide or lithium diisopropylamide. The operation is then done at a low temperature, such as from −70° C. to ambient temperature The protector group which Gp is may be a silyl such as trimethylsilyl or tert-butyl-dimethylsilyl although a group such as tetrahydropyranyl can be used. The separation of the protection group Gp is carried out under standard conditions such as in the presence of an acid or a fluoride ion from hydrofluoric acid or tetrabutylammonium fluoride.

When a product of formula IX is obtained in which $R_A$ is amino, in a preferred way of carrying out the process, the product of formula IX is treated with a functional derivative of a product of formula $IV_a$ which may be a halide, a symmetrical or mixed anhydride, an amide or an activated ester.

An example of a mixed anhydride is that of isobutyl chloroformate and pivaloyl chloride and carboxylic-sulfonic mixed anhydrides formed for example with p-toluenesulfonyl chloride. As an example of an activated ester, the ester formed with 2,4-dinitrophenol and the one formed with hydroxybenzothiazole may be mentioned.

As an example of a halide, the chloride or the bromide can be cited. There can equally be cited the acid azide or the acid amide. The anhydride can be formed in situ by the action of disubstituted NN′ carbodiimide, for example, N,N-dicyclohexylcarbodiimide.

The acylation reaction is preferably carried out in an organic solvent such as methylene chloride but other solvents such as tetrahydrofuran, chloroform or dimethylformamide may be used.

When an acid halide is used, generally when a molecule of a hydrohalide acid is liberated during a reaction, the reaction is preferably carried out in the presence of a base such as sodium hydroxide, potassium hydroxide, the carbonates and bicarbonates of sodium or potassium, sodium acetate, triethylamine, pyridine, morpholine or N-methylmorpholine. The reaction temperature is generally lower than or equal to ambient temperature.

In a preferred way of carrying out the process, the products of formula $IV_b$ are converted into reactive derivatives such as the halides of acids, which can be prepared by reacting the products of formula $IV_b$ with a halogenation agent such as phosgene, oxalyl chloride, thionyl chloride. There can also be prepared complexes with dialkyl sulfates, preferably dimethyl sulfate. The operating condition for such reactions are known to one skilled in the art and such reactions are described, for example, in French Patent No. 2,073,338.

In a preferred way of carrying out the process, the halogens used in the products of formula $IV_c$ are the chloride or the fluoride. It is preferred to use a pyridinium derivative and the counterion is then preferably an iodide, tosylate, bromide, or BF4 ion. The preparation of the products of formula $IV_c$ and the reaction of these products with the products of formula IX are carried out under the conditions described for example in Journal of Medicinal Chemistry (1982) Vol. 25, No. 4, p. 457–469. The subsequent reaction, if required, of separation of the E and Z isomers is carried out according to the usual techniques but it is preferred to use chromatography over silica. The conversion of the products of formula X into products of formula $XI_A$ is also done by standard methods.

The derivative of $R_3A$ which is used can, for example be a halide derived from a carbocylic aryl or heterocyclic aryl optionally substituted. Preferably, the fluoride is then used when $R_3A$ is for example, acetyl or carbamoyl and it is preferred to operate in the presence of a reactive derivative such as an anhydride or a halide.

The conversion of the products of formula X into products of formula XI B is preferably carried out under the following conditions an activated derivative of the hydroxyl is prepared by the action, for example, of a derivative of a sulfonic acid such as the anhydride of trifluoromethylsulfonic acid and is done at low temperatures to ambient temperature. When $R_3A$ is not a quaternary ammonium, it is preferred to operate in the presence of a base.

The conversion of the products of formula X into products of formula $XI_C$ is carried out under similar conditions. First, an activated derivative of the hydroxyl is prepared under the previously stated conditions, particularly starting with the anhydride of trifluoromethylsulfonic acid. The action of the product of formula HS-$R_{3A}$ is preferably carried out in the presence of an organic base such as 2,6-dimethylpyridine and of a soluble iodide source and it is then preferred to operate in the presence of tetra-alkylammonium iodide.

The products of formulae $XI_A$, $XI_B$ and $XI_C$ constitute products of formula $I_A$ when they do not include any protective group and when A is not among the easily cleavable ester groups, one of those which it is desired to eliminate.

In other cases, the action on the products of formula $XI_A$, $XI_B$ or $XI_C$ of one or more hydrolysis or hydrogenolysis agents or of thiourea has the object of eliminating the protective group or groups which the different products may contain. The nature of the reagents to react in all these cases is well known to an expert. Examples of such reactions are given further on in the experimental part. A nonexhaustive list of the means which can be used to eliminate the different groups is now given.

The elimination of the protector group or groups may be done by hydrolysis, with an acid, base, or by using hydrazine. It is preferred to use acid hydrolysis to eliminate optionally substituted alkoxy and cycloalkycarbonyl such as tert-pentyloxycarbonyl or tert-butyloxycarbonyl, optionally substituted aralkoxycarbonyl such as benzyloxycarbonyl, and trityl, benzhydryl, tert-butyl or 4-methoxybenzyl. The acid which is preferably utilized can be selected from the group consisting of hydrochloric acid benzene sulfonic acid or p-toluene-sulfonic acid, formic acid or trifluoroacetic acid. Other mineral or organic acids can however be used.

Basis hydrolysis is preferably used to eliminate acyls such as trifluoroacetyl. The base which is preferably used is an inorganic base such as sodium or potassium hydroxide but also useful are magnesia, baryta, or an alkali metal carbonate or bicarbonate such as the carbonates and bicarbonates of sodium or potassium or other bases. Sodium or potassium acetate can also be used. Hydrolysis using hydrazine is used preferably to eliminate groups such as phthaloyl.

Certain groups can also be eliminated by a zinc-acetic acid system for trichloroethyl. Benzhydryl and benzyloxycarbonyl are preferably eliminated by hydrogen in the presence of a catalyst. The chloroacetyl group is eliminated by the action of thiourea in a neutral or acid medium according to the type of reaction described by MASAKI, J. A. C. S., 90, 4508, (1968). Other methods of deprotection known in the literature can also be used.

Among the preferred groups are formyl, acetyl, ethoxycarbonyl, mesyl, trifluoroacetyl, chloroacetyl, trityl with trityl and chloroacetyl being particularly preferred. The acid preferably used is trifluoro-acetic acid.

Salification of the products can be carried out by the usual methods. Salification can, for example, be obtained by action on a product in the form of an acid or on a solvate, for example the ethanol solvate or a hydrate of this acid of a mineral base such as sodium or potassium hydroxide, the carbonate or bicarbonate of sodium or potassium. There can also be used the salts of mineral acids such as the tri-sodium phosphate. Use can also be made of salts of organic acids.

Salts of organic acids are for example, the sodium salts of aliphatic carboxylic acids, linear or branched, saturated or unsaturated of 1 to 18, and preferably of 2 to 10, carbon atoms. These aliphatic radicals can be interrupted by one or more heteroatoms such as oxygen or sulfur, or can be substituted by aryl, such as, for example: phenyl, thienyl, furyl: or by one or more hydroxyl or by one or more halogens such as fluorine, chlorine or bromine, preferably chlorine; by one or more lower carboxylic or alkoxycarbonyl, preferably methoxycarbonyl, ethoxycarbonyl or propyloxycarbonyl; by one or more aryloxy, preferably phenoxy.

Furthermore, there can be used as organic acids the sufficiently soluble aromatic acids such, for example, as benzoic acids preferably substituted by lower alkyl radicals. Examples of such organic acids are formic acid, acetic acid, acrylic acid, butyric acid, adipic acid isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, the monoethyl ester of adipic acid; the following acids: hexanoic acid, heptanoic acid, decanoic acid, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyic acid, 4-ethylbenzoic, 1-propylbenzoic acid. However, it is preferred to use as salts of sodium, the acetate, the 2-ethylhexanoate or the diethylacetate.

Salification can also be obtained by the action of an organic base such as triethylamine, diethylamine, trimethylamine, propylamine, N,N-dimethylethanolamine, tris(hydroxymethyl)amino methane, methylamine, ethanolamine, pyridine, picoline, dicyclohexylamine, morpholine and benzylamine. It can also be obtained by the action of arginine, of lysine, of procaine, of histidine and of N-methyl glucamine. This salification is preferably carried out in a solvent or a mixture of solvents such as water, ethyl ether, methanol, ethanol or acetone.

The salts are obtained in an amorphous or crystallized form according to the reaction conditions employed. Crystallized salts are preferably prepared by reacting the free acids with one of the salts of aliphatic carboxylic acids mentioned above, preferably with sodium acetate. The salification of the products by mineral or organic acids is carried out in the usual conditions.

The eventual esterification of the products is carried out under standard conditions. In general, the operation is effected by reacting the acid of formula I with a derivative of the formula Z—Rs in which Z is a hydroxyl or halogen such as chlorine, bromine or iodine, and Rs is the ester group to be introduced, of which groups a non-exhaustive list appears above. In certain cases, it is advantageous to carry out an esterification on a product of which the amine is blocked before removing the protector group of the amine.

The possible resolution of the compounds of formulae $XI_A$, $XI_B$ and $XI_C$ can be carried out with an optically active carboxylic or sulfonic acid such as tartaric acid, dibenzoyltartaric acid, camphosulfonic acid or glutamic acid, the decomposition of the salt so obtained being effected with a mineral base such as sodium bicarbonate or an organic base such as a tertiary amine such as triethylamine. In addition, there can also be used an optically active base.

The possible oxidation of the products of formulae $XI_A$, $XI_B$, or $XI_C$ can be carried out with oxygen, peroxides, hydroperoxides, peracids or hydrogen peroxide and the reaction is advantageously sensitized by light. These reagents can be mixed with organic or mineral acids and it is preferred to use m-chloroperbenzoic acid. The reaction conditions are known to an expert such as are set out, for example, in French patent No. 2,387,234.

The novel antibiotic compositions of the invention are comprised of an antibiotically effective amount of at least one compound of formula I and their non-toxic, pharmaceutically acceptable acid addition salts and an inert pharmaceutical carrier or excipient. The compositions may be in the form of tablets, dragees, capsules, granules, suppositories, ointments, creams, gels and injectable solutions or suspensions.

Examples of suitable excipients are talc, gum arabic, lactose, starch, magnesium stearate, cocoa butter, aqueous and non-aqueous vehicles, fatty substances of animal or vegetable origin, paraffin derivatives, glycols, various wetting, dispersing or emulsifying agents and preservatives. Preferably, the compositions are in the form of a powder capable of extemporaneously dissolving in an appropriate vehicle such as apyrogenous sterile water.

The compositions of the invention have an excellent antibacterial activity against gram (+) bacteria such as staphylococci, streptococci and especially penicillin resistant staphylococci. Their effectiveness on the gram (−) bacteria, particularly on coliform, klebsiella, salmonella and proteus bacteria is particularly notable.

These compositions are useful in the treatment of infections by sensitive germs and, notably, of staphylococci such as septicemias by staphylococci, malignant staphylococcal infection of the face or cutaneous, pyrodermitis, septic or suppurating wounds, anthrax, phlegmons, erysipelas, acute primitive or post-influenzal staphyloccocia, bronchopneumonia and pulmonary suppuration. The compositions are useful in the treatment of colibacilloses and associated infections, in infections due to proteus, klebsiella and salmonella and in other affections caused by gram (−) bacteria or for disinfecting surgical instruments.

In a preferred mode, the compositions contain as the active ingredient a compound of formula $I_A$

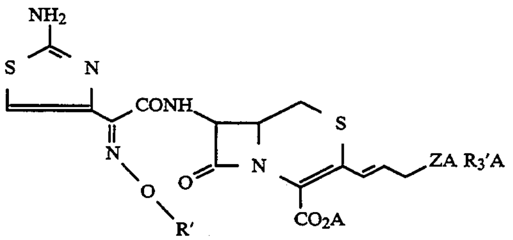

syn isomer, in which R' is hydrogen or alkyl, alkenyl or alkynyl or cycloalkyl with up to 6 carbon atoms, optionally substituted, or aryl, ZA has the values indicated above and $R_3'A$ is phenyl, heterocyclic aryl optionally substituted or quaternary ammonium optionally substituted, or acetyl or carbaloyl.

Particularly preferred compositions are those of formula $I_A$ in which R' is hydrogen, or methyl or isopropyl optionally substituted by carboxy, carbamoyl, nitrile, methylthio or methoxy, difluoromethyl or trifluoromethyl, phenyl, cyclobutyl or cyclopropyl optionally substituted by carboxy, allyl optionally substituted by chlorine or bromine and ZA is a simple bond and $R_3'A$ an optionally substituted pyridinium.

The novel method of the invention of combatting bacterial infections in warm-blooded animals, including humans, comprises administering to warm-blooded animals an antibactericidally effective amount of at least one compound of formula I and their non-toxic, pharmaceutically acceptable acid addition salts. The compounds may be administered orally, rectally, parenterally or topically to the skin or mucous. The usual daily dose is depending on the condition treated, the specific compound and the method of administration. For example, the products of Examples 1, 2, 47 and 51 may be administered intramuscularly at a dose of 6,5 to 13 mg/kg three times a day. When administered orally, it is preferably an easily cleavable ester such as propionyloxymethyl.

The products of formula VII used as starting materials may be prepared by the process of French Patent No. 2,559,486 as illustrated in the examples below.

Examples of products of the formula

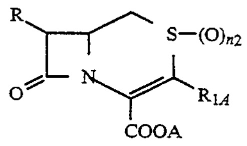

wherein $R_1$, $R_{1A}$, A and $n_2$ have the above definitions are illustrated in the following Tables.

| R | $R_{1A}$ | $n_2$ | $CO_2A$ | R | $R_{1A}$ | $n_2$ | $CO_2A$ |
|---|---|---|---|---|---|---|---|
| 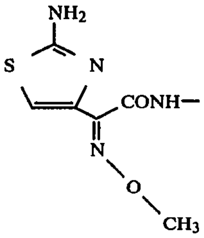 | 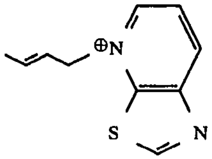 | O | $CO_2^{\ominus}$ | 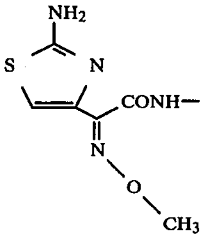 | 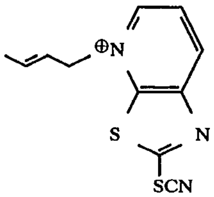 | O | $CO_2^{\ominus}$ |
| " | 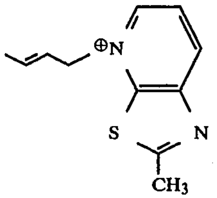 | " | " | " | 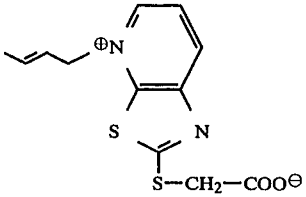 | " | $CO_2H$ |
| " | 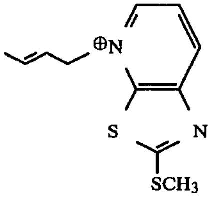 | " | " | " | 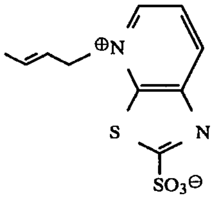 | " | " |
| " | 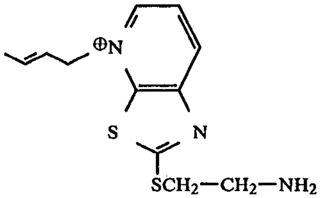 | " | " | " | 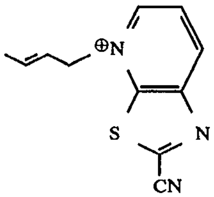 | " | $CO_2^{\ominus}$ |

-continued
| | | | | | | | |
|---|---|---|---|---|---|---|---|
| " | 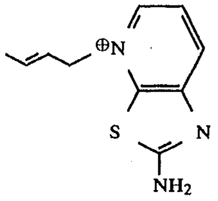 | " | " | " | 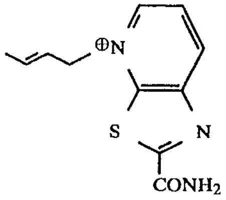 | " | " |
| " | 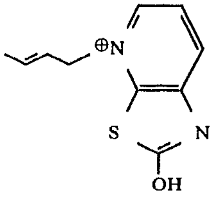 | " | " | " | 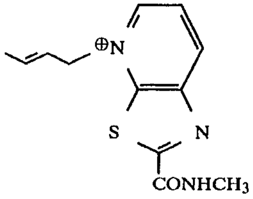 | " | " |
| " | 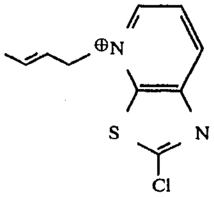 | " | " | " | 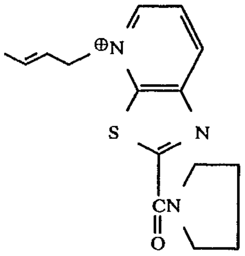 | " | " |
| " | 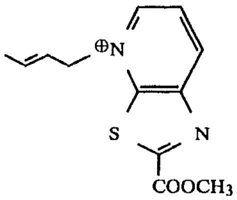 | " | " | " | 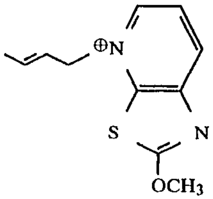 | " | " |

-continued
| | | | | | | | |
|---|---|---|---|---|---|---|---|
| " | 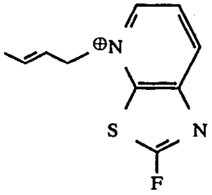 | " | " | " | 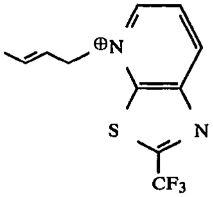 | " | " |
| " | 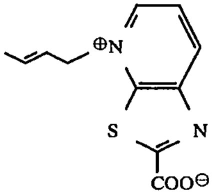 | " | $CO_2H$ | " | 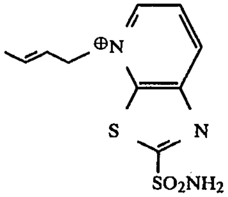 | " | " |
| 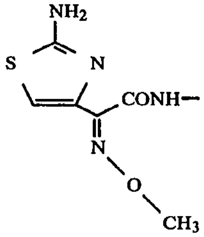 | 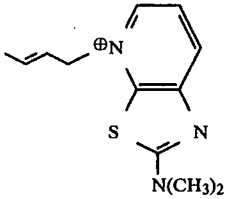 | O | $CO_2^{\ominus}$ | 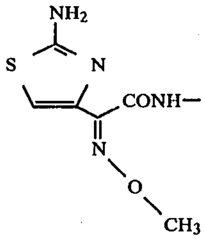 | 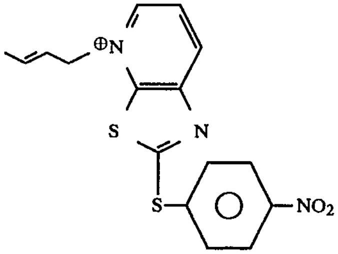 | O | $CO_2^{\ominus}$ |
| " | 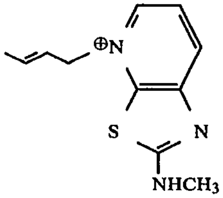 | " | " | " | 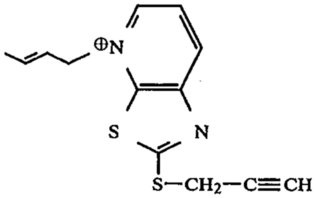 | " | " |

-continued
| | | | | | | |
|---|---|---|---|---|---|---|
| " | 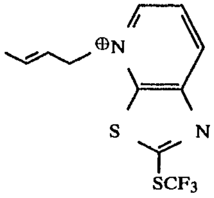 | " | " | " | 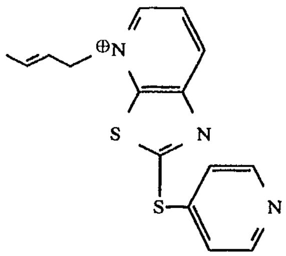 | " | " |
| " | 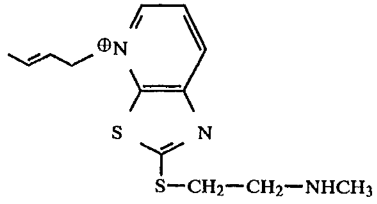 | " | " | " | 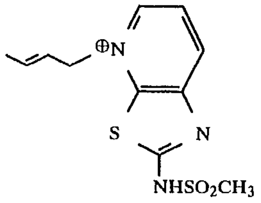 | " | " |
| " | 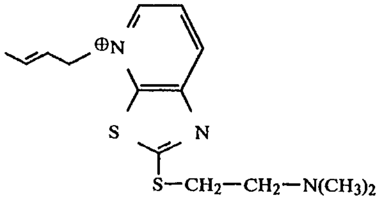 | " | " | " | 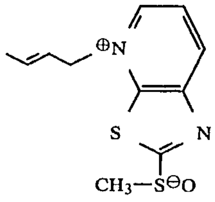 | " | " |
| " | 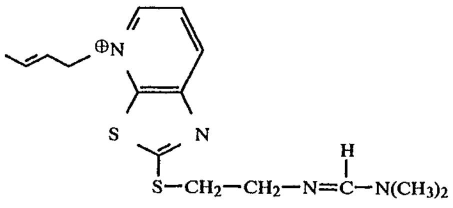 | " | " | " | 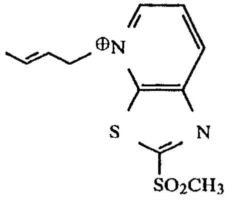 | " | " |

-continued
| | | | | | | | |
|---|---|---|---|---|---|---|---|
| " | 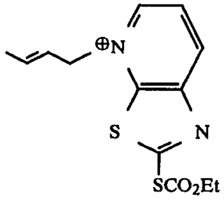 | " | " | " | 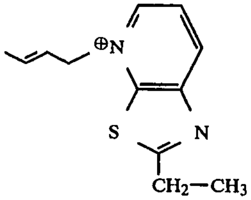 | " | " |
| " | 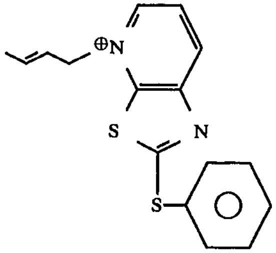 | " | " | " | 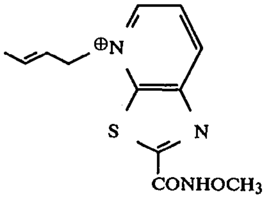 | " | " |
| " | 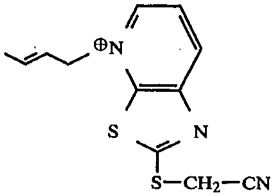 | " | " | " | 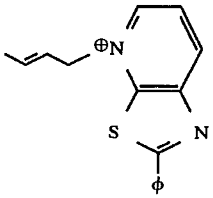 | " | " |
| " | 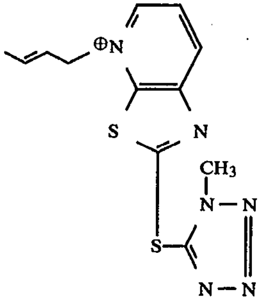 | " | " | " | 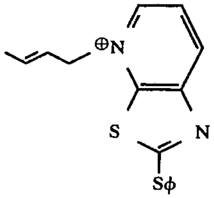 | " | " |

-continued
| | | | |
|---|---|---|---|
| 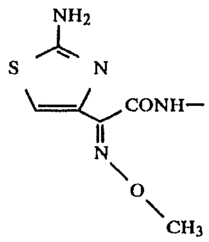 | 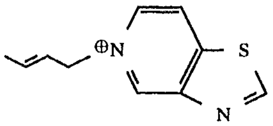 | O | $CO_2^{\ominus}$ |
| " | 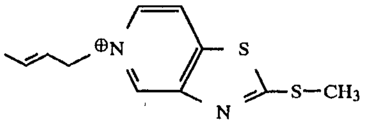 | " | " |
| " | 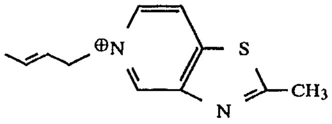 | " | " |
| " | 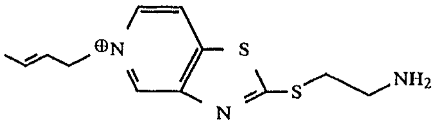 | " | " |
| " | 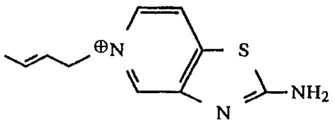 | " | " |
| " | 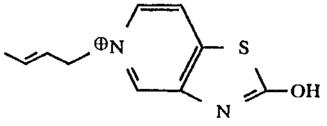 | " | " |
| | | | |
|---|---|---|---|
| 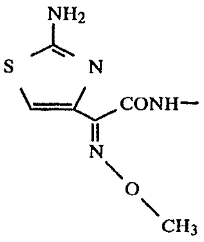 | 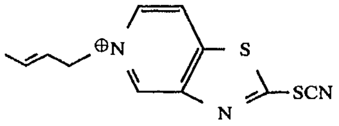 | O | $CO_2^{\ominus}$ |
| " | 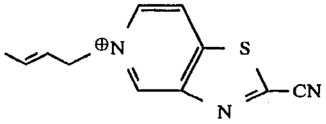 | " | " |
| " | 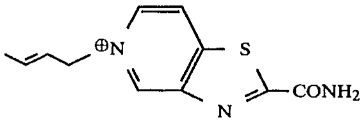 | " | " |
| " | 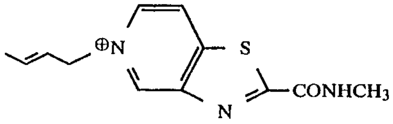 | " | " |
| " | 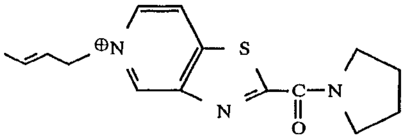 | " | " |
| " | 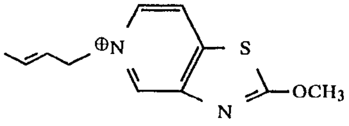 | " | " |

-continued
| | | | | | | | |
|---|---|---|---|---|---|---|---|
| " | 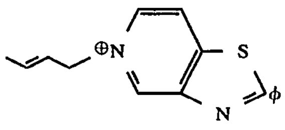 | " | " | " | 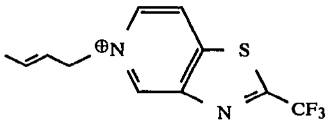 | " | " |
| " | 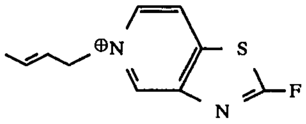 | " | " | " | 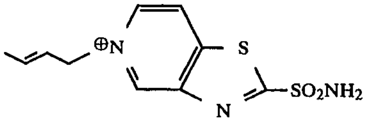 | " | " |
| " | 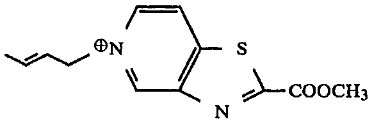 | " | " | " | 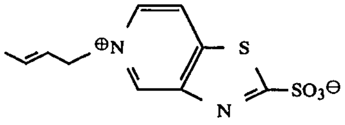 | " | $CO_2H$ |
| " | 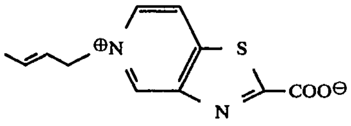 | " | $CO_2H$ | " | 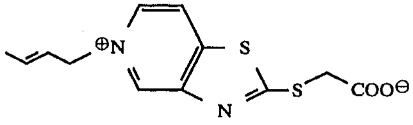 | " | " |

| | | | |
|---|---|---|---|
| 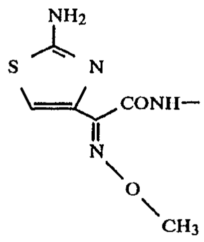 | 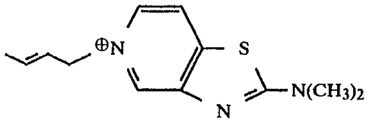 | O | $CO_2^{\ominus}$ |
| " | 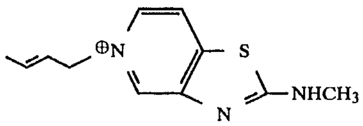 | " | " |
| " | 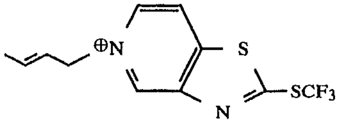 | " | " |
| " | 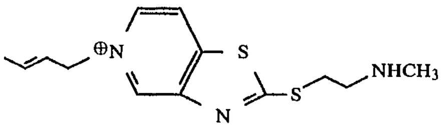 | " | " |
| " | 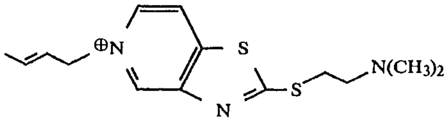 | " | " |
| " | 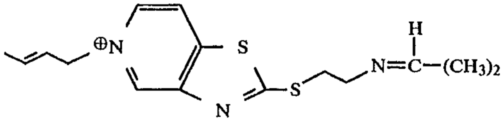 | " | " |
| | | | |
|---|---|---|---|
| 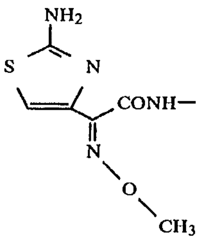 | 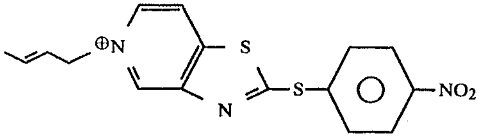 | O | $CO_2^{\ominus}$ |
| " | 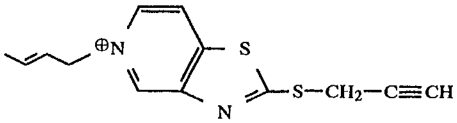 | " | " |
| " | 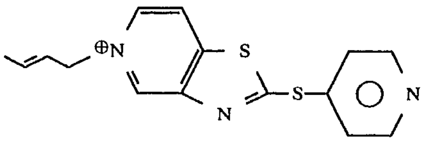 | " | " |
| " | 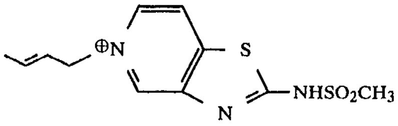 | " | " |
| " | 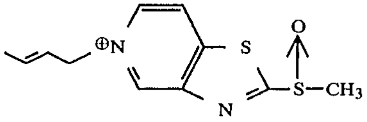 | " | " |
| " | 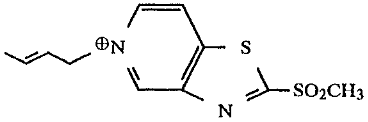 | " | " |

-continued
| | | | | | | | |
|---|---|---|---|---|---|---|---|
| " | 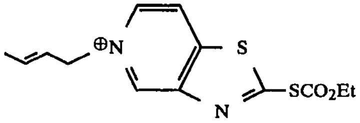 | " | " | " | 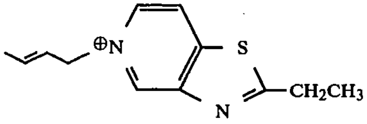 | " | " |
| " | 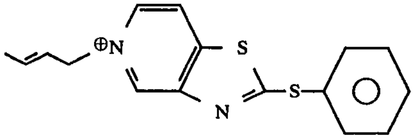 | " | " | " | 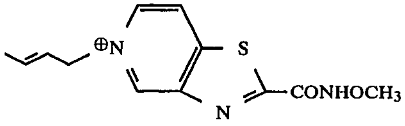 | " | " |
| " | 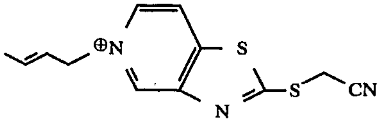 | " | " | " | 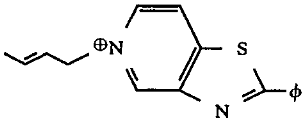 | " | " |
| " | 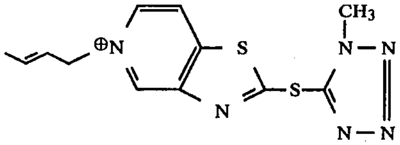 | " | " | " | 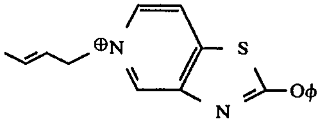 | " | " |
| 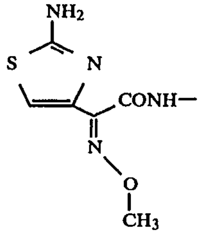 | 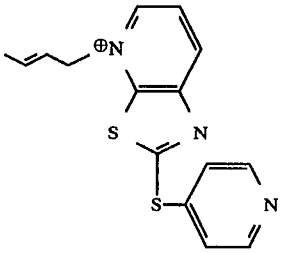 | O | $CO_2^{\ominus}$ | 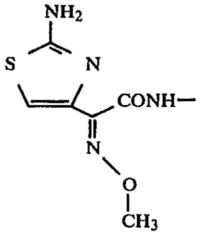 | 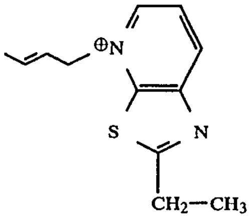 | O | $CO_2^{\ominus}$ |
| " | 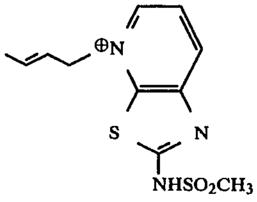 | " | " | " | 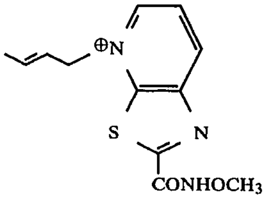 | " | " |

-continued
| | | | | |
|---|---|---|---|---|
| " | 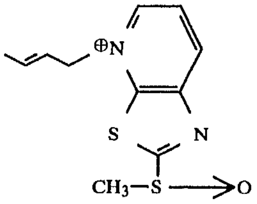 | " | " | " |
| " | 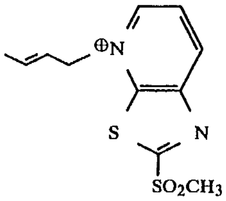 | " | " | " |
| 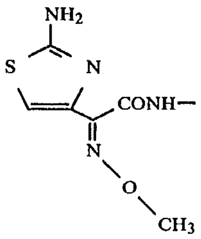 | 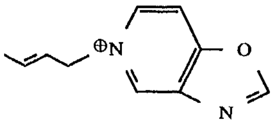 | O | $CO_2^{\ominus}$ | |
| " | 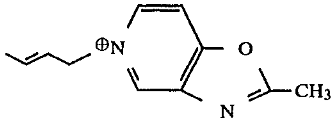 | " | " | " |
| " | 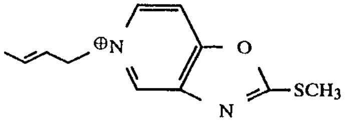 | " | " | " |
| | | | |
|---|---|---|---|
| " | 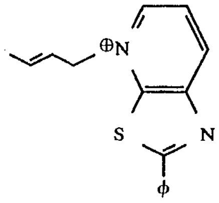 | " | " |
| " | 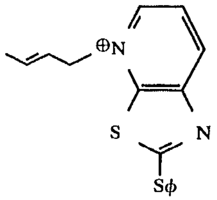 | " | " |
| 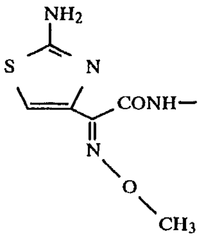 | 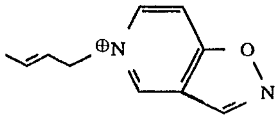 | O | $CO_2^{\ominus}$ |
| " | 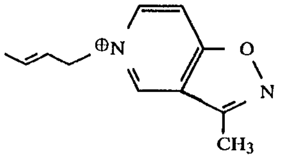 | " | " |
| " | 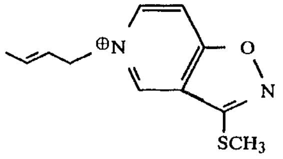 | " | " |

-continued
| | | | | | | | |
|---|---|---|---|---|---|---|---|
| " | 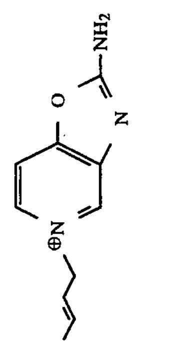 | " | " | " | 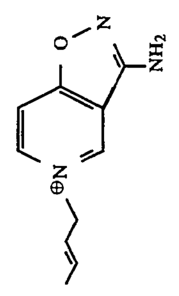 | " | " |
| " | 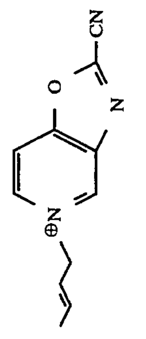 | " | " | " | 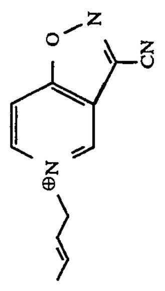 | " | " |
| " | 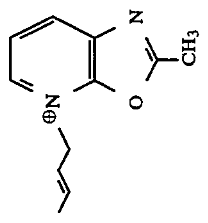 | " | " | " | 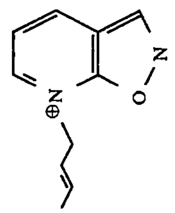 | " | " |
| " | 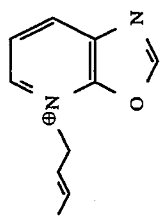 | " | " | " | 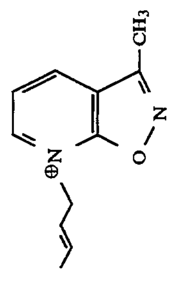 | " | " |
| " | 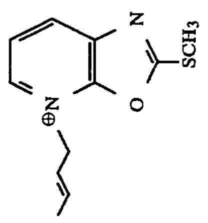 | " | " | " | 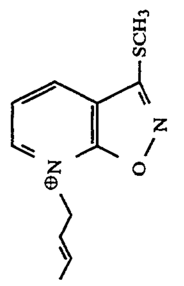 | " | " |

-continued
| | | | | | | | |
|---|---|---|---|---|---|---|---|
| " | 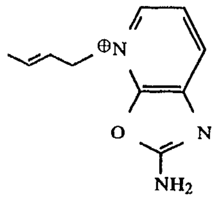 | " | " | " | 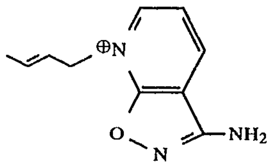 | " | " |
| " | 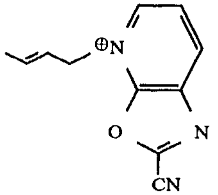 | " | " | " | 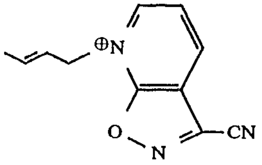 | " | " |
| 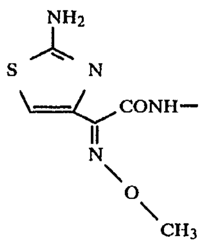 | 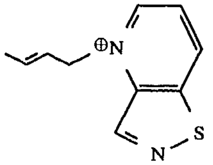 | O | $CO_2^{\ominus}$ | 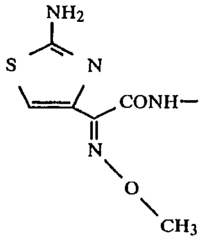 | 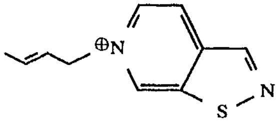 | O | $CO_2^{\ominus}$ |
| " | 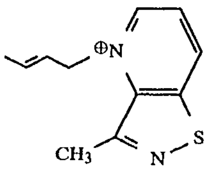 | " | " | " | 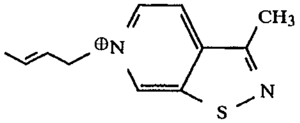 | " | " |
| " | 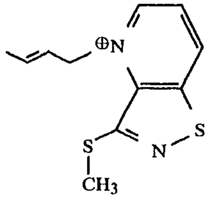 | " | " | " | 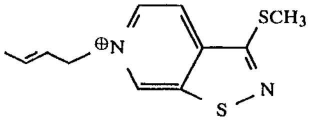 | " | " |

-continued
| | | | | | | | |
|---|---|---|---|---|---|---|---|
| | 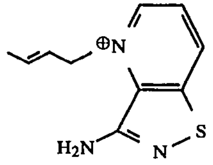 | " | " | " | 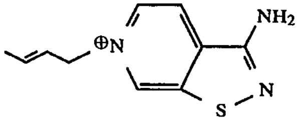 | " | " |
| " | 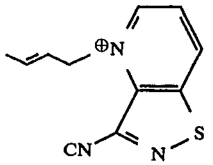 | " | " | " | 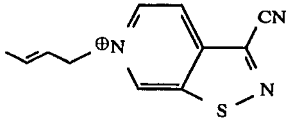 | " | " |
| " | 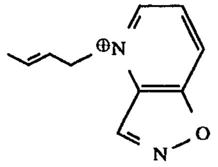 | " | " | " | 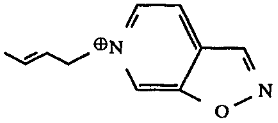 | " | " |
| " | 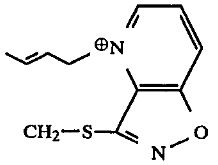 | " | " | " | 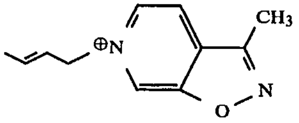 | " | " |
| " | 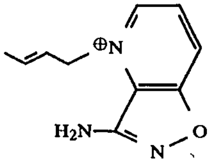 | " | " | " | 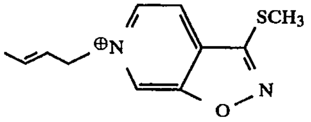 | " | " |
| " | 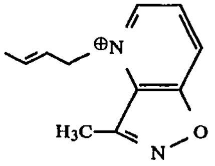 | " | " | " | 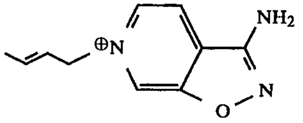 | " | " |

-continued
| | | | | | | | | |
|---|---|---|---|---|---|---|---|---|
| " | 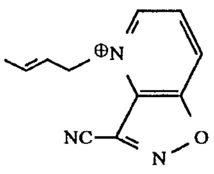 | " | " | " | 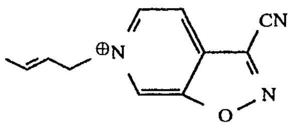 | " | " | |

| | | | |
|---|---|---|---|
| 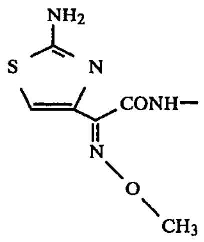 | 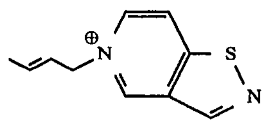 | O | $CO_2^{\ominus}$ |
| " | 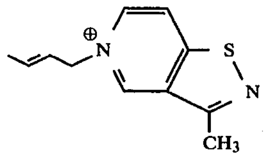 | " | $CO_2H$ |
| " | 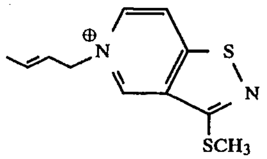 | " | " |
| " | 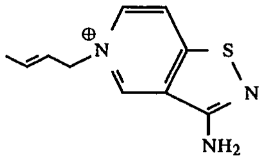 | " | $CO_2^{\ominus}$ |
| " | 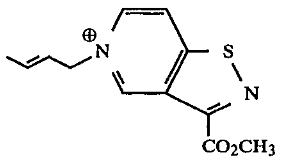 | " | " |
| | | | |
|---|---|---|---|
| 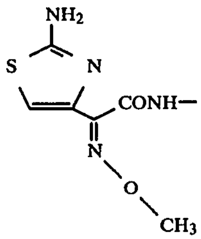 | 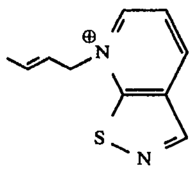 | O | $CO_2^{\ominus}$ |
| " | 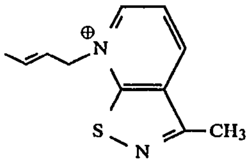 | " | " |
| " | 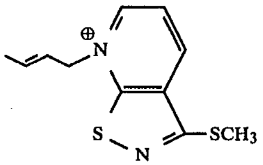 | " | " |
| " | 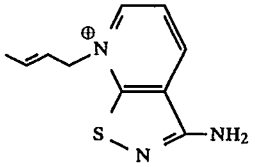 | " | " |
| " | 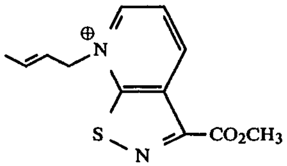 | " | " |

-continued
| | | | | | | | |
|---|---|---|---|---|---|---|---|
| " | 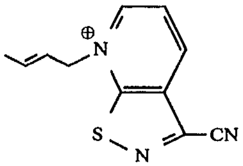 | " | " | " | 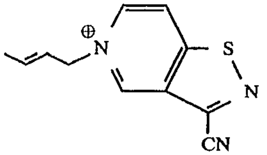 | " | " |
| " | 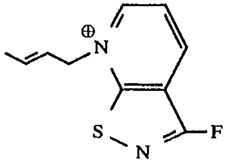 | " | " | " | 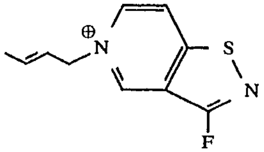 | " | " |
| " | 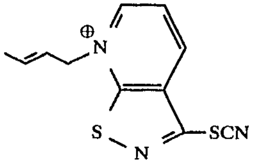 | " | " | " | 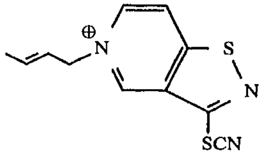 | " | " |
| " | 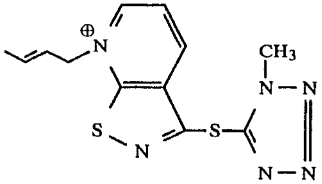 | " | " | " | 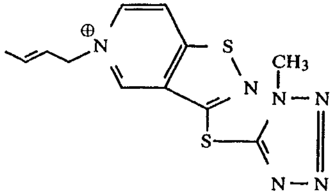 | " | " |
| " | 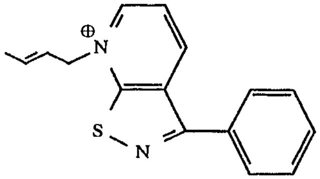 | " | $CO_2H$ | " | 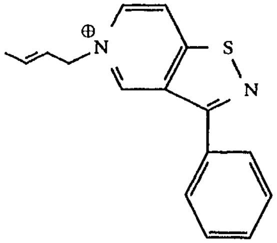 | " | " |

-continued
| | | | | | | | |
|---|---|---|---|---|---|---|---|
| 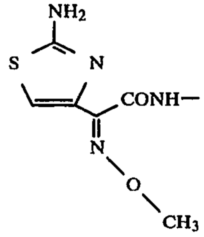 | 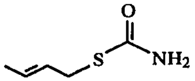 | O | $CO_2H$ | 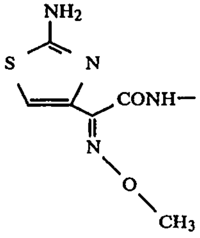 | 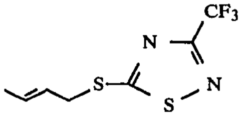 | O | $CO_2H$ |
| " | 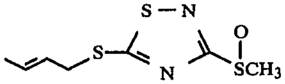 | " | " | " | 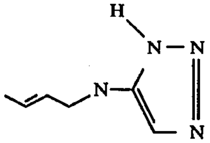 | " | " |
| " | 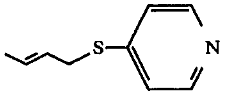 | " | " | " | 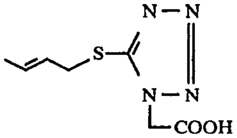 | " | " |
| " | 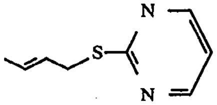 | " | " | " | 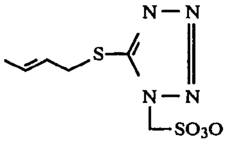 | " | " |
| " | 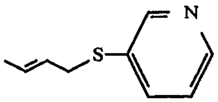 | " | " | " | 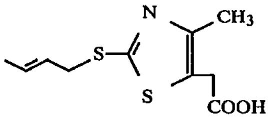 | " | " |
| " | 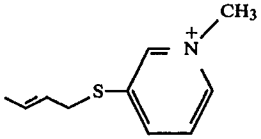 | " | $CO_2^{\ominus}$ | " | 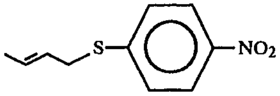 | " | " |

-continued
| | | | | | | | |
|---|---|---|---|---|---|---|---|
| " | 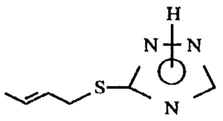 | " | $CO_2H$ | " | 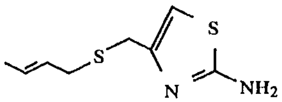 | " | " |
| " | 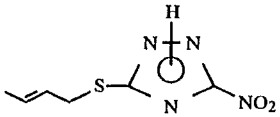 | " | " | " | 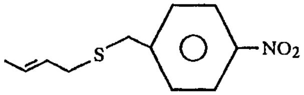 | " | " |
| " | 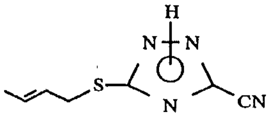 | " | " | " | 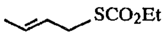 | " | " |
| " | 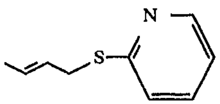 | " | " | " | 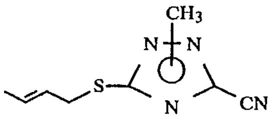 | " | " |
| 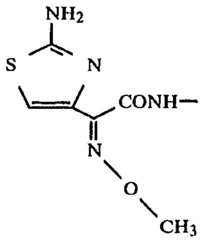 | 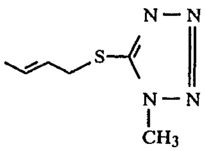 | O | $CO_2H$ | 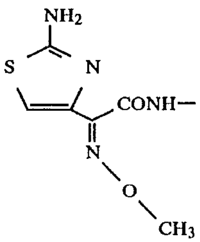 | 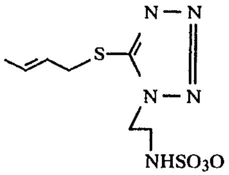 | O | $CO_2H$ |
| " | 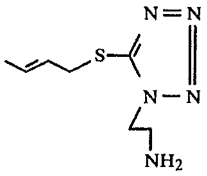 | " | " | " | 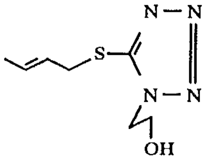 | " | " |

-continued
| | | | | | | | |
|---|---|---|---|---|---|---|---|
| " | 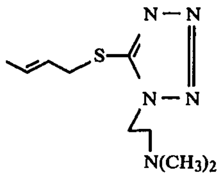 | " | " | " | 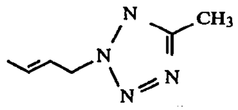 | " | " |
| " | 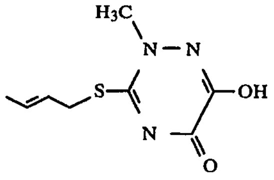 | " | " | " | 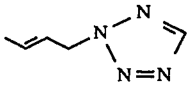 | " | " |
| " | 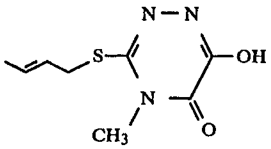 | " | " | " | 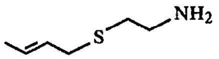 | " | " |
| " | 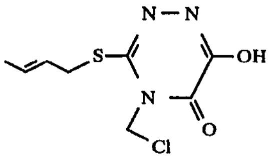 | " | " | " | 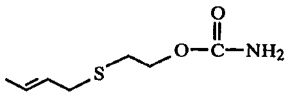 | " | " |
| " | 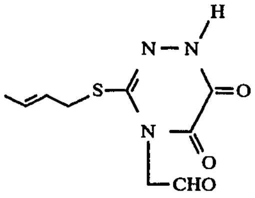 | " | " | " | 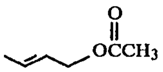 | " | " |
| " | 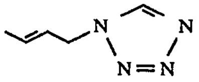 | " | " | " | 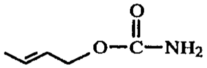 | " | " |

-continued
| | | | | | | | |
|---|---|---|---|---|---|---|---|
| " | 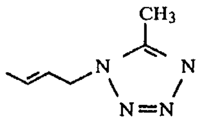 | " | " | " | 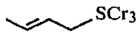 | " | $CO_2H$ |
| " | 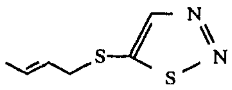 | " | " | " | 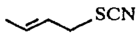 | " | " |

| | | | | | | | |
|---|---|---|---|---|---|---|---|
| 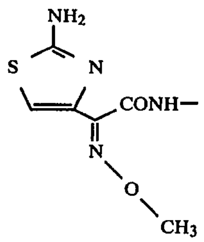 | 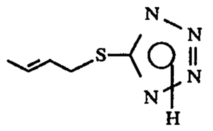 | O | $CO_2H$ | 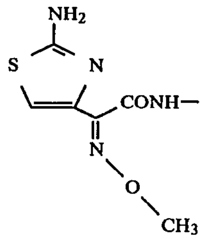 | 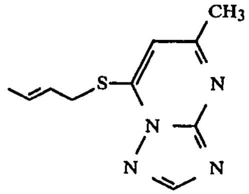 | O | $CO_2H$ |
| " | 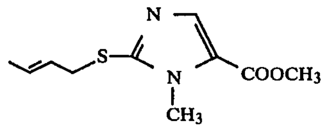 | " | " | " | 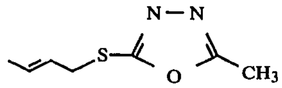 | " | " |
| " | 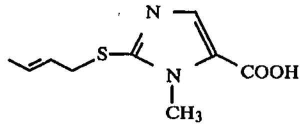 | " | " | " | 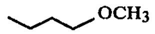 | " | " |
| " | 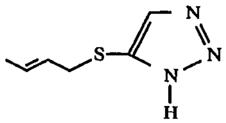 | " | " | " | 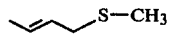 | " | " |
| " | 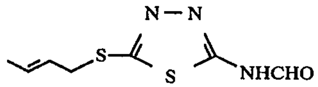 | " | " | " | 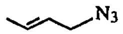 | " | " |
| " | 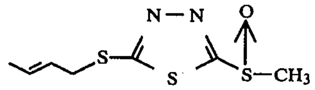 | " | " | " | 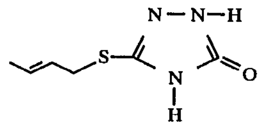 | " | " |
| " | 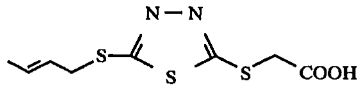 | " | " | " | 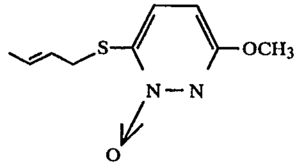 | " | " |

-continued
| | | | | | | | |
|---|---|---|---|---|---|---|---|
| " | 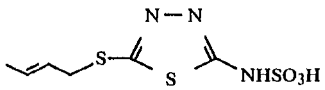 | " | " | " | 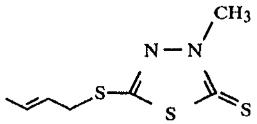 | " | " |
| " | 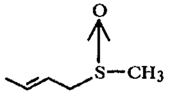 | " | " | " | 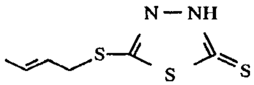 | " | " |
| " | 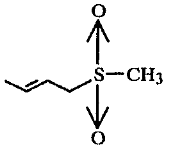 | " | " | " | 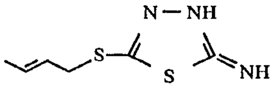 | " | " |
| 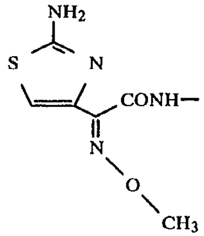 | 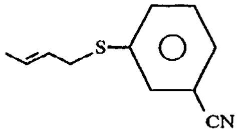 | O | $CO_2H$ | 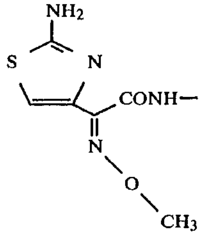 | 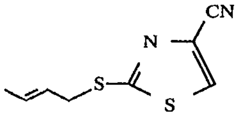 | O | $CO_2H$ |
| " | 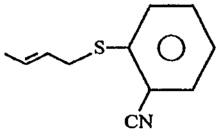 | " | " | " | 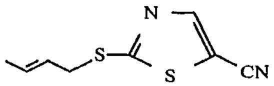 | " | " |
| " | 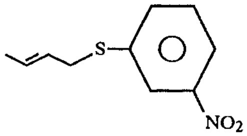 | " | " | " | 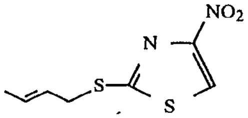 | " | " |

-continued
| | | | | | | | |
|---|---|---|---|---|---|---|---|
| " | 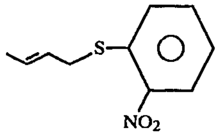 | " | " | " | 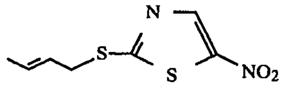 | " | " |
| " | 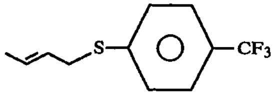 | " | " | " | 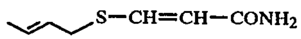 | " | " |
| " | 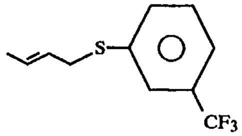 | " | " | " | 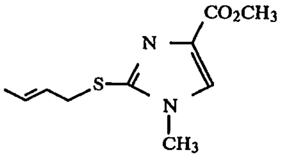 | " | " |
| " | 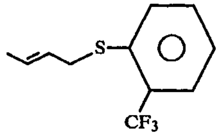 | " | " | " | 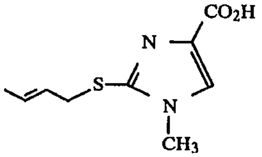 | " | " |
| " | 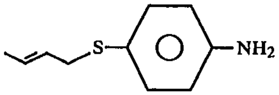 | " | " | " | 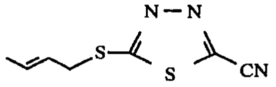 | " | " |
| " | 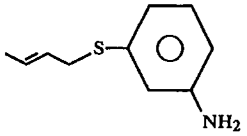 | " | " | " | 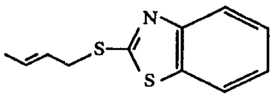 | " | " |
| " | 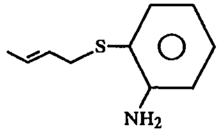 | " | " | " | 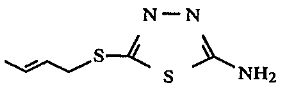 | " | " |

-continued
| | | | | | | | |
|---|---|---|---|---|---|---|---|
| 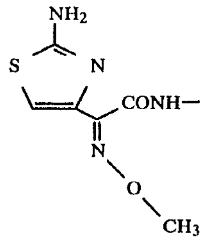 | 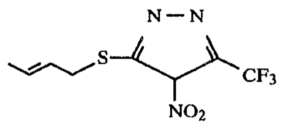 | O | $CO_2H$ | 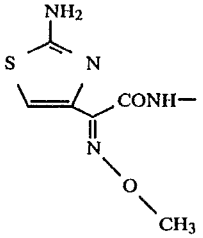 | 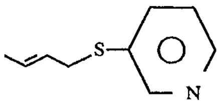 | O | $CO_2H$ |
| " | 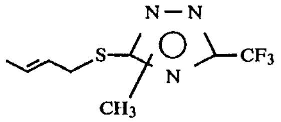 | " | " | " | 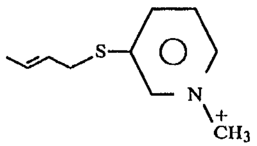 | " | $CO_2^{\ominus}$ |
| " | 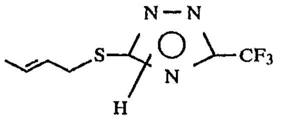 | " | " | " | 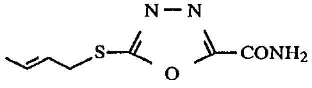 | " | $CO_2H$ |
| " | 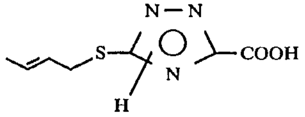 | " | " | " | 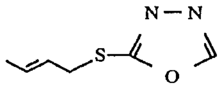 | " | " |
| " | 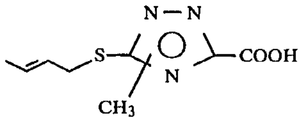 | " | " | " | 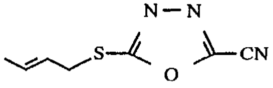 | " | " |
| " | 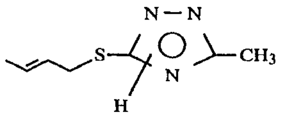 | " | " | " | 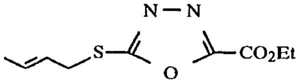 | " | " |
| " | 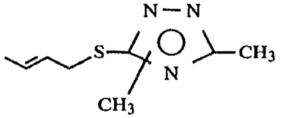 | " | " | " | 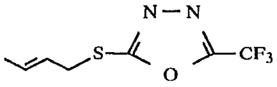 | " | " |

-continued
| | | | | | | | |
|---|---|---|---|---|---|---|---|
| " | 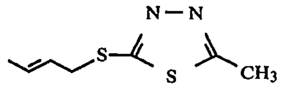 | " | " | " | 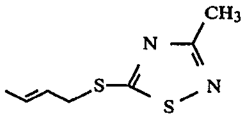 | " | " |
| " | 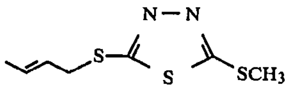 | " | " | " | 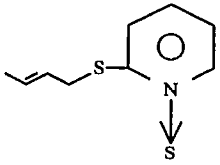 | " | " |
| " | 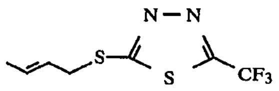 | " | " | " | 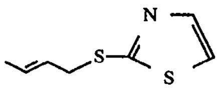 | " | " |

| | | | |
|---|---|---|---|
| 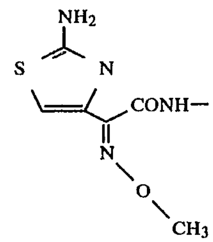 | 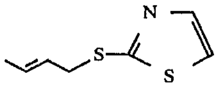 | O | $CO_2H$ |
| " | 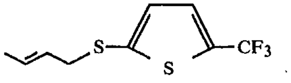 | " | " |
| " | 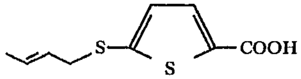 | " | " |
| " | 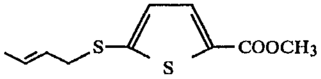 | " | " |
| " | 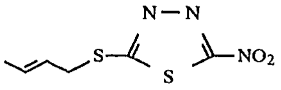 | " | " |
| " | 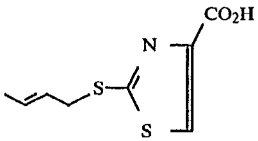 | " | " |
| | | | |
|---|---|---|---|
| 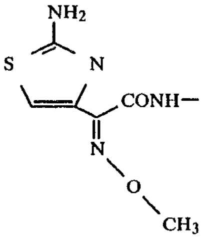 | 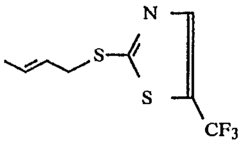 | O | $CO_2H$ |
| " | 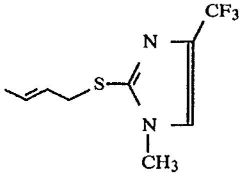 | " | " |
| " | 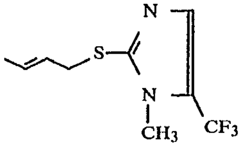 | " | " |
| " | 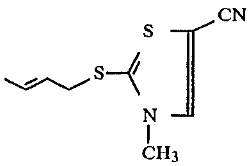 | " | " |
| " | 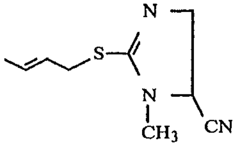 | " | " |
| " | 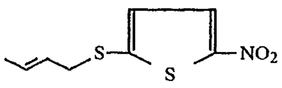 | " | " |

-continued
| | | | | | | | |
|---|---|---|---|---|---|---|---|
| " | 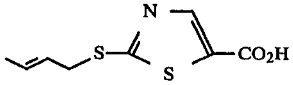 | " | " | " | 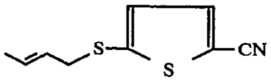 | " | " |
| " | 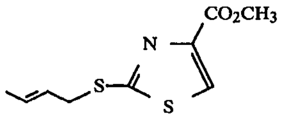 | " | " | " | 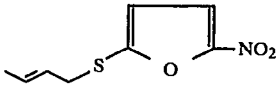 | " | " |
| " | 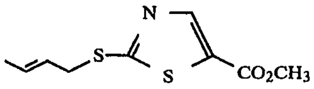 | " | " | " | 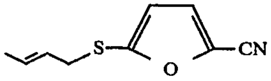 | " | " |
| " | 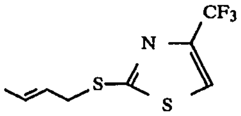 | " | " | " | 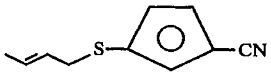 | " | " |
| 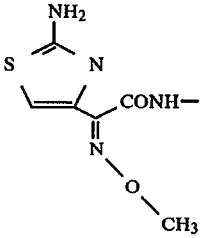 | 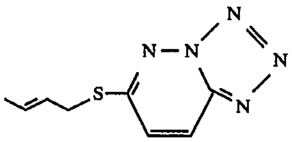 | O | $CO_2H$ | 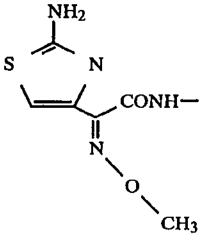 | 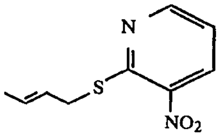 | O | $CO_2H$ |
| " | 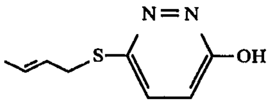 | " | " | " | 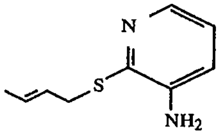 | " | " |
| " | 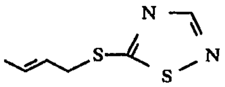 | " | " | " | 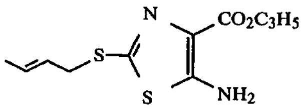 | " | " |

-continued
| | | | | | | | |
|---|---|---|---|---|---|---|---|
| " | 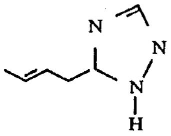 | " | " | " | 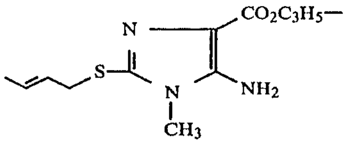 | " | " |
| " | 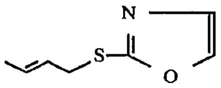 | " | " | " | 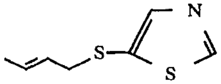 | " | " |
| " | 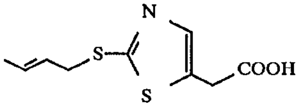 | " | " | " | 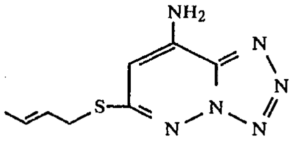 | " | " |
| " | 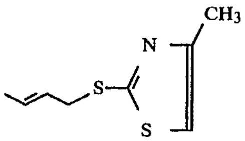 | " | " | " | 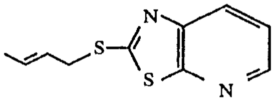 | " | " |
| " | 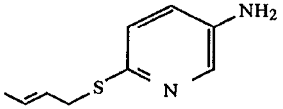 | " | " | " | | " | " |
| " | 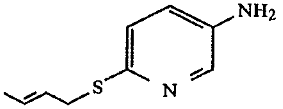 | " | " | " | | " | " |
| " | 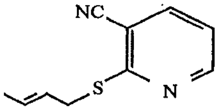 | " | " | " | | " | " |

-continued
| | | | | | | | |
|---|---|---|---|---|---|---|---|
| 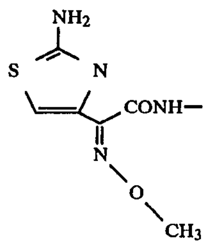 | 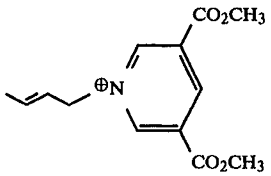 | O | $CO_2^{\ominus}$ | 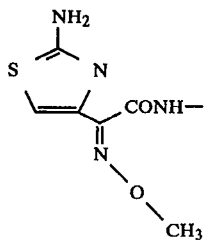 | 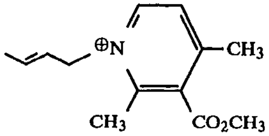 | O | $CO_2^{\ominus}$ |
| " | 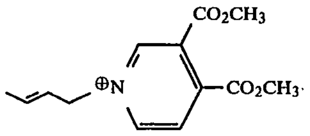 | " | " | " | 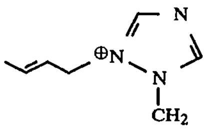 | " | " |
| " | 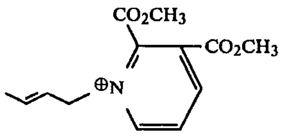 | " | " | " | 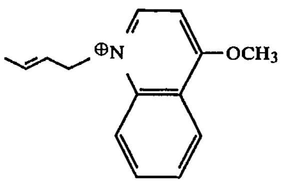 | " | " |
| " | 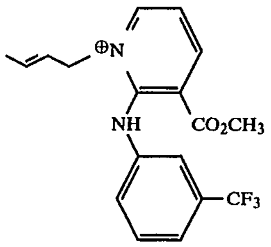 | " | " | " | 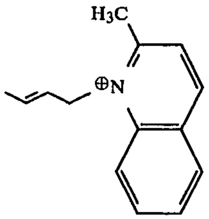 | " | " |
| " | 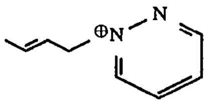 | " | " | " | 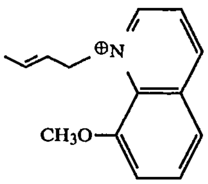 | " | " |

-continued
| | | | | | | | |
|---|---|---|---|---|---|---|---|
| " | 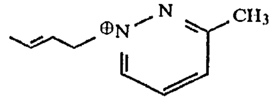 | " | " | " | 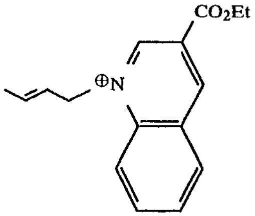 | " | " |
| " | 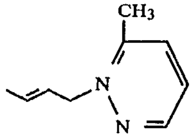 | " | " | " | 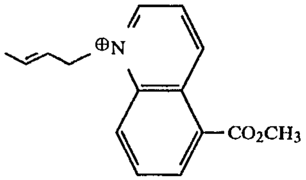 | " | " |
| " | 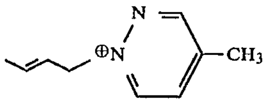 | " | " | " | 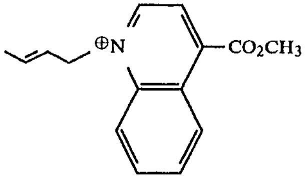 | " | " |
| " | 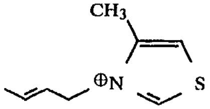 | " | " | " | 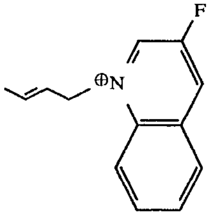 | " | " |
| " | 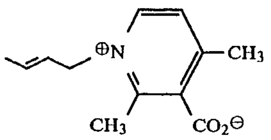 | " | $CO_2H$ | " | 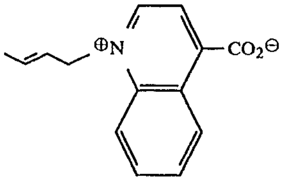 | " | $CO_2H$ |

| | | | | | | | |
|---|---|---|---|---|---|---|---|
| 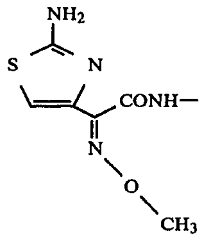 | 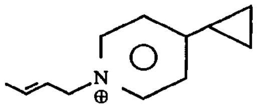 | O | $CO_2^{\ominus}$ | 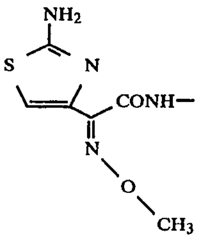 | 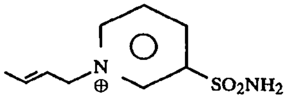 | O | $CO_2^{\ominus}$ |
| " | 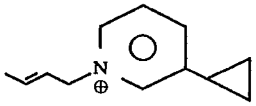 | " | " | " | 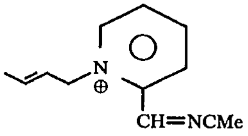 | " | " |
| " | 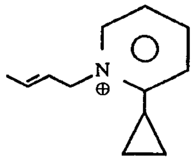 | " | " | " | 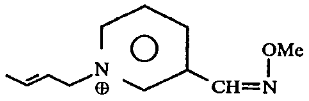 | " | " |
| " | 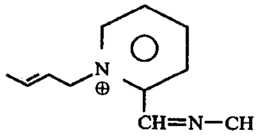 | " | " | " | 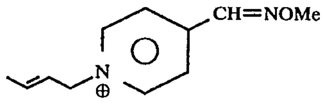 | " | " |
| " | 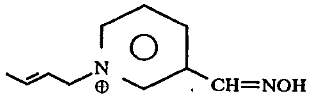 | " | " | " | 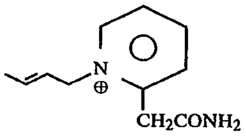 | " | " |
| " | 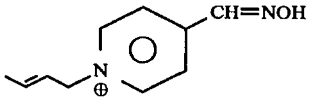 | " | " | " | 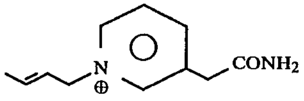 | " | " |

-continued
| | | | | | | | |
|---|---|---|---|---|---|---|---|
| " | 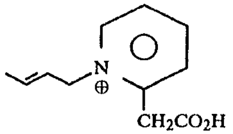 | " | " | " | 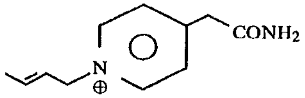 | " | " |
| " | 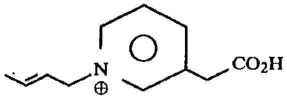 | " | " | " | 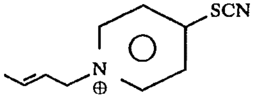 | " | " |
| " | 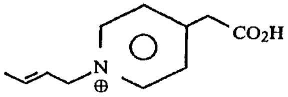 | " | " | " | 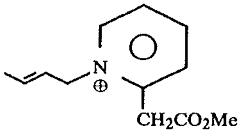 | " | " |
| " | 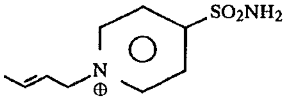 | " | " | " | 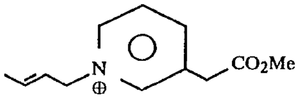 | " | " |
| 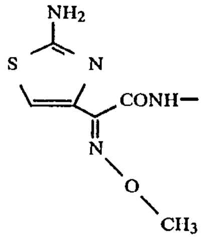 | 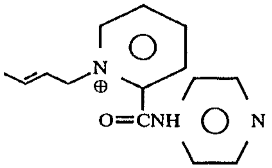 | O | $CO_2^{\ominus}$ | 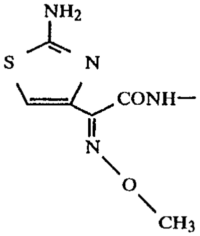 | 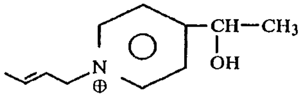 | O | $CO_2^{\ominus}$ |
| " | 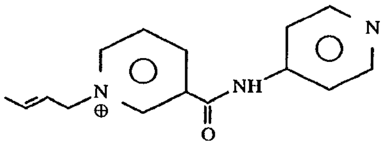 | " | " | " | 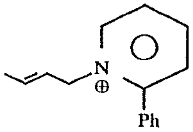 | " | " |
| " | 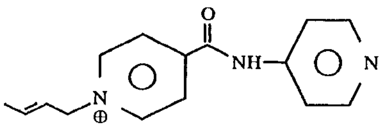 | " | " | " | 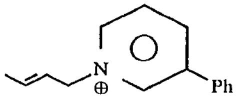 | " | " |

-continued
| | | | | | | | |
|---|---|---|---|---|---|---|---|
| " | 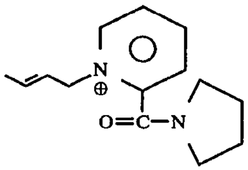 | " | " | " | 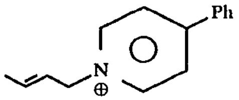 | " | " |
| " | 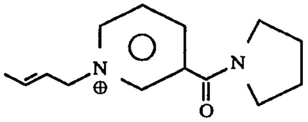 | " | " | " | 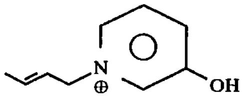 | " | " |
| " | 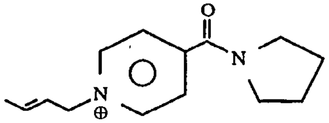 | " | " | " | 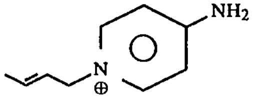 | " | " |
| " | 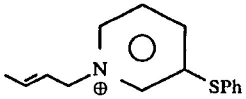 | " | " | " | 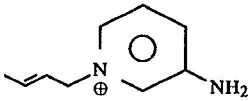 | " | " |
| " | 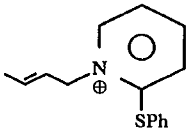 | " | " | " | 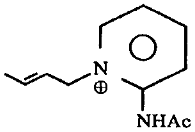 | " | " |
| " | 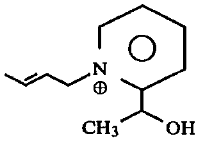 | " | " | " | 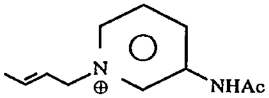 | " | " |
| " | 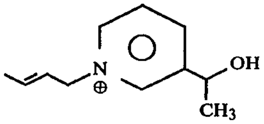 | " | " | " | 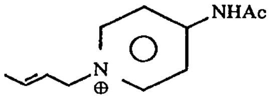 | " | " |

-continued
| | | | | | | | |
|---|---|---|---|---|---|---|---|
| 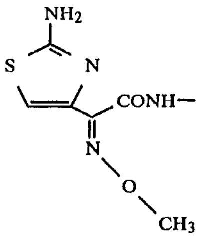 | 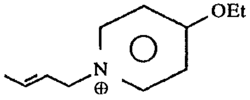 | O | $CO_2^{\ominus}$ | 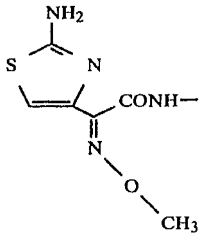 | 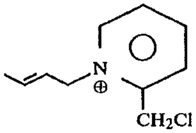 | O | $CO_2^{\ominus}$ |
| " | 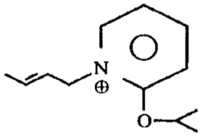 | " | " | " | 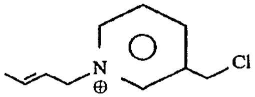 | " | " |
| " | 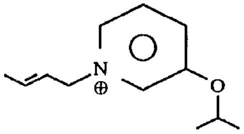 | " | " | " | 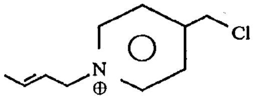 | " | " |
| " | 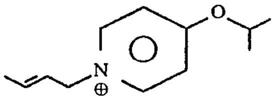 | " | " | " | 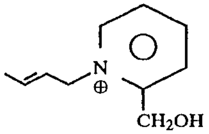 | " | " |
| " | 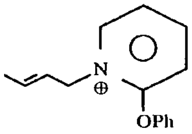 | " | " | " | 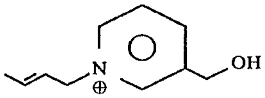 | " | " |
| " | 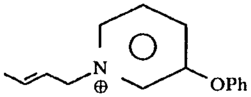 | " | " | " | 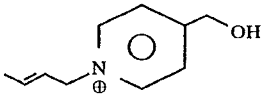 | " | " |

-continued
| | | | | | | | |
|---|---|---|---|---|---|---|---|
| " | 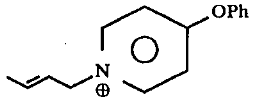 | " | " | " | 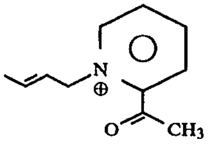 | " | " |
| " | 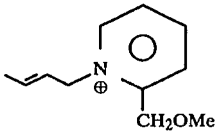 | " | " | " | 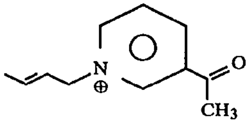 | " | " |
| " | 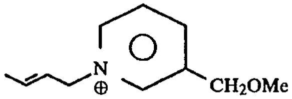 | " | " | " | 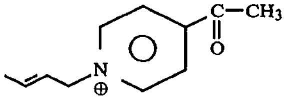 | " | " |
| " | 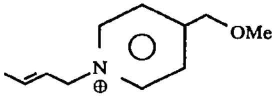 | " | " | " | 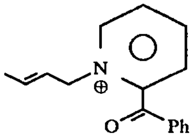 | " | " |

| | | | | | | | |
|---|---|---|---|---|---|---|---|
| 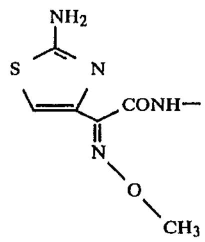 | 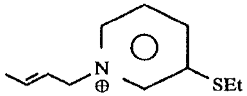 | O | $CO_2^{\ominus}$ | 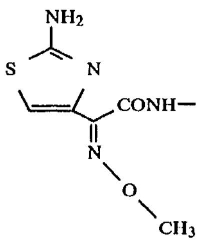 | 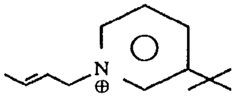 | O | $CO_2^{\ominus}$ |
| ″ | 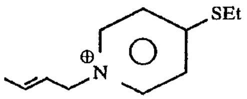 | ″ | ″ | ″ | 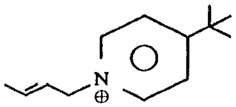 | ″ | ″ |
| ″ | 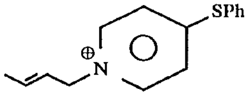 | ″ | ″ | ″ | 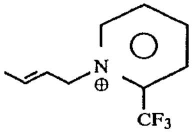 | ″ | ″ |
| ″ | 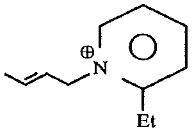 | ″ | ″ | ″ | 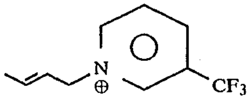 | ″ | $CO_2^{\ominus}$ |
| ″ | 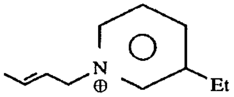 | ″ | ″ | ″ | 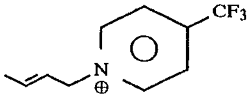 | ″ | ″ |
| ″ | 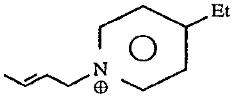 | ″ | ″ | ″ | 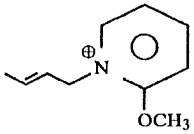 | ″ | ″ |

-continued
| | | | | | | | |
|---|---|---|---|---|---|---|---|
| " | 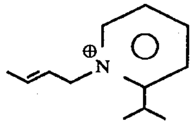 | " | " | " | 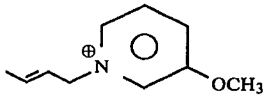 | " | " |
| " | 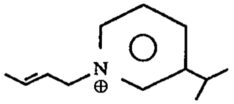 | " | " | " | 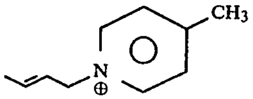 | " | " |
| " | 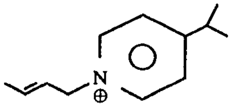 | " | " | " | 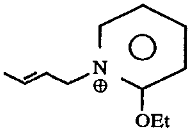 | " | " |
| " | 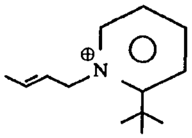 | " | " | " | 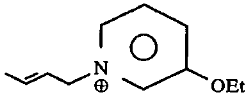 | " | " |
| 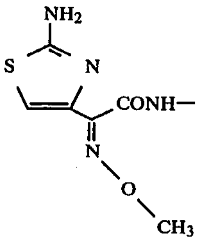 | 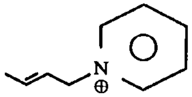 | O | $CO_2^{\ominus}$ | 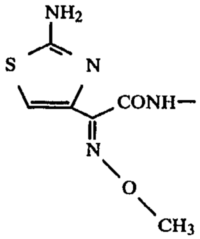 | 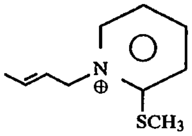 | O | $CO_2^{\ominus}$ |
| " | 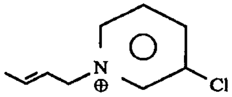 | " | " | " | 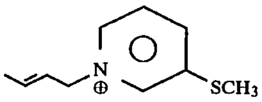 | " | " |
| " | 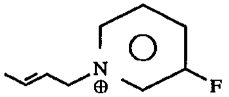 | " | " | " | 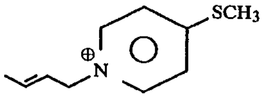 | " | " |

-continued
| | | | | | | | |
|---|---|---|---|---|---|---|---|
| " | 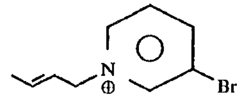 | " | " | " | 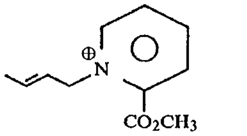 | " | " |
| " | 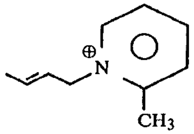 | " | " | " | 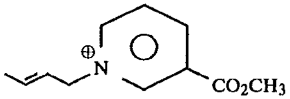 | " | " |
| " | 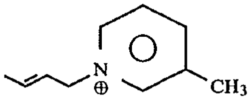 | " | " | " | 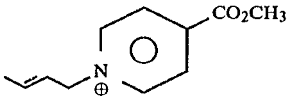 | " | " |
| " | 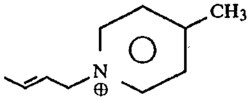 | " | " | " | 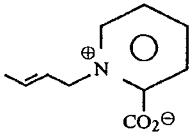 | " | " |
| " | 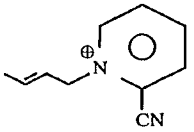 | " | " | " | 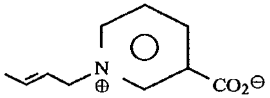 | " | " |
| " | 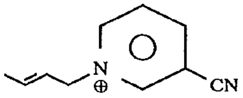 | " | " | " | 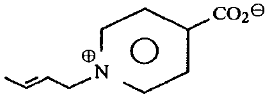 | " | " |
| " | 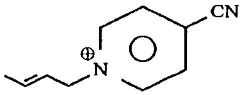 | " | " | " | 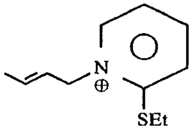 | " | " |

-continued
| | | | | | | | |
|---|---|---|---|---|---|---|---|
| 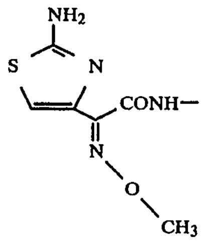 | 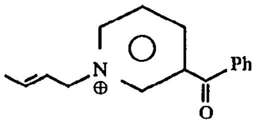 | O | $CO_2^{\ominus}$ | 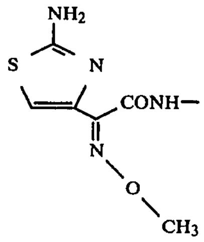 | 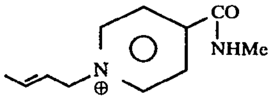 | O | $CO_2^{\ominus}$ |
| " | 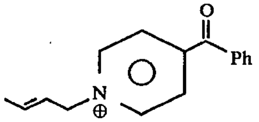 | " | " | " | 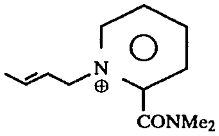 | " | " |
| " | 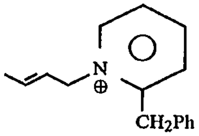 | " | " | " | 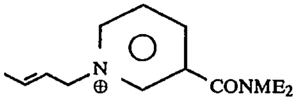 | " | " |
| " | 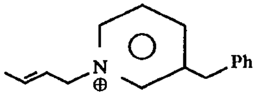 | " | " | " | 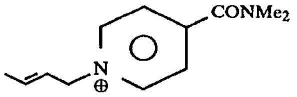 | " | " |
| " | 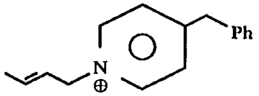 | " | " | " | 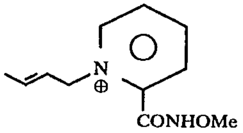 | " | " |
| " | 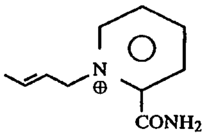 | " | " | " | 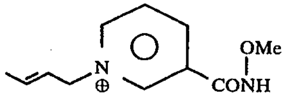 | " | " |

-continued
| | | | | | | | |
|---|---|---|---|---|---|---|---|
| " | 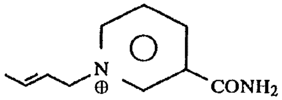 | " | " | " | 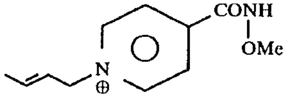 | " | " |
| " | 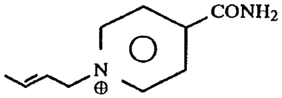 | " | " | " | 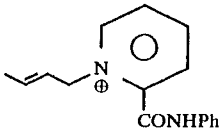 | " | " |
| " | 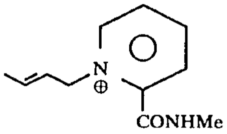 | " | " | " | 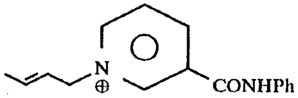 | " | " |
| " | 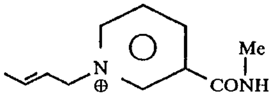 | " | " | " | 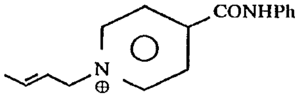 | " | " |

| | | | | | | | |
|---|---|---|---|---|---|---|---|
| 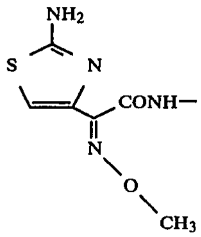 | 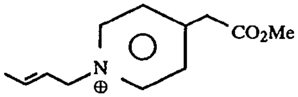 | O | $CO_2^{\ominus}$ | 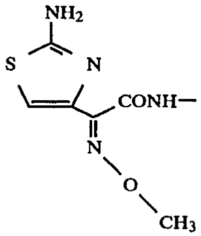 | 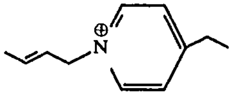 | O | $CO_2^{\sqcup}$ |
| " | 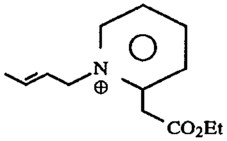 | " | " | " | 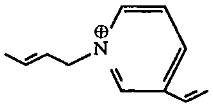 | " | " |
| " | 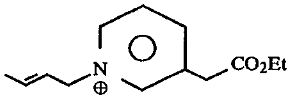 | " | " | " | 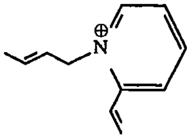 | " | " |
| " | 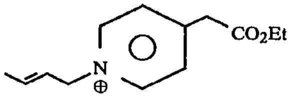 | " | " | " | 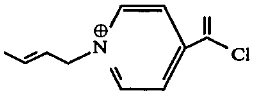 | " | " |
| " | 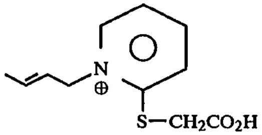 | " | " | " | 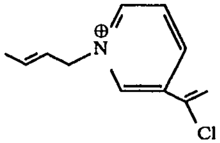 | " | " |
| " | 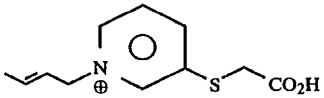 | " | " | " | 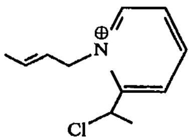 | " | " |

-continued
| | | | | | | | |
|---|---|---|---|---|---|---|---|
| " | 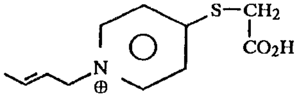 | " | " | " | 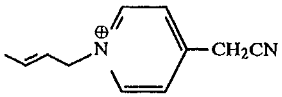 | " | " |
| " | 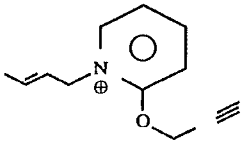 | " | " | " | 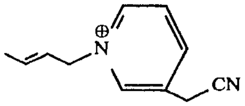 | " | " |
| " | 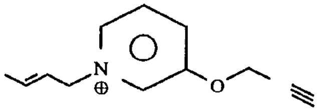 | " | " | " | 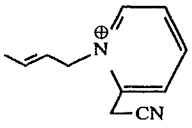 | " | " |
| " | 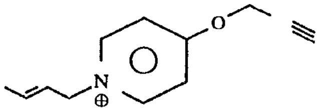 | " | " | " | 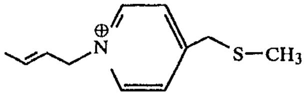 | " | " |
| 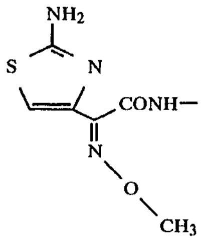 | 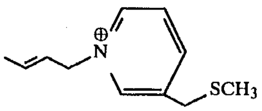 | O | $CO_2^{\ominus}$ | 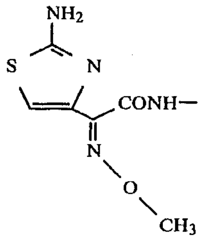 | 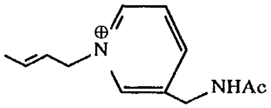 | O | $CO_2^{\ominus}$ |
| " | 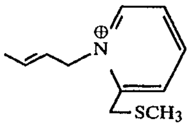 | " | " | " | 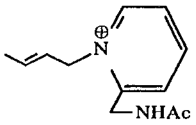 | " | " |

-continued
| | | | | | | | |
|---|---|---|---|---|---|---|---|
| " | 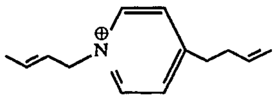 | " | " | " | 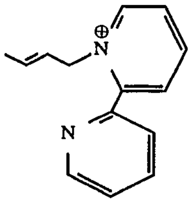 | " | " |
| " | 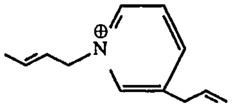 | " | " | " | 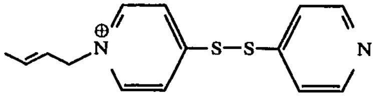 | " | " |
| " | 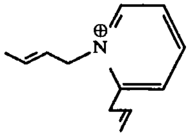 | " | " | " | 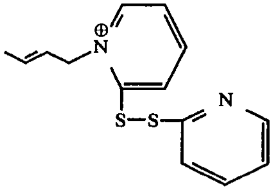 | " | " |
| " | 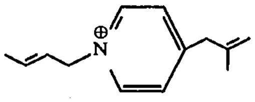 | " | " | " | 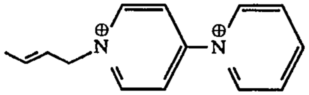 | " | " |
| " | 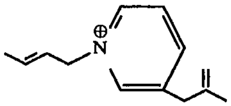 | " | " | " | 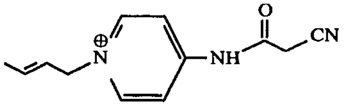 | " | " |
| " | 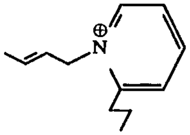 | " | " | " | 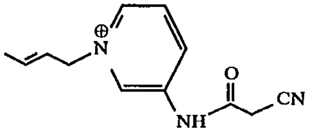 | " | " |

-continued
| | | | | | | | |
|---|---|---|---|---|---|---|---|
| " | 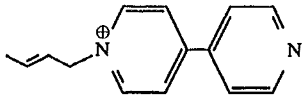 | " | " | " | 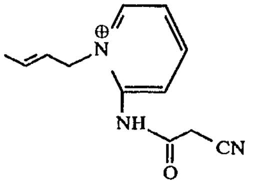 | " | " |
| " | 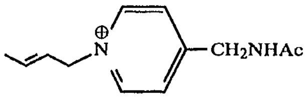 | " | " | " | 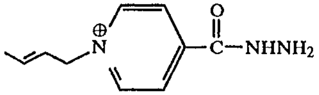 | " | " |
| 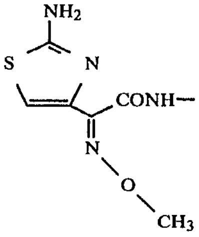 | 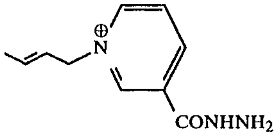 | O | $CO_2^{\ominus}$ | 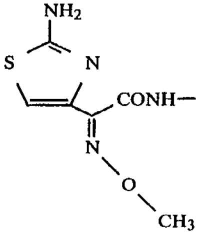 | 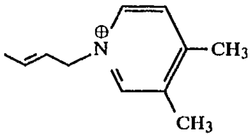 | O | $CO_2^{\ominus}$ |
| " | 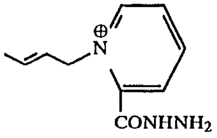 | " | " | " | 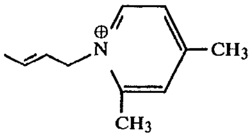 | " | " |
| " | 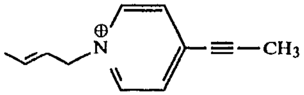 | " | " | " | 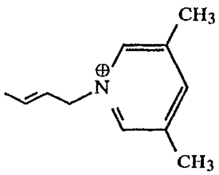 | " | " |

" " " " "
" " " " "
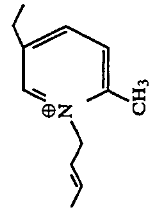 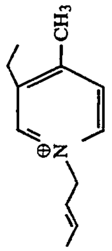 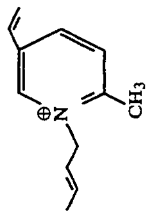 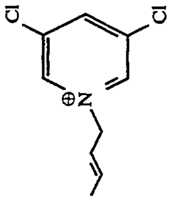 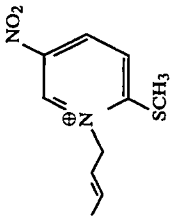
" " " " "
-continued
" " " " "
" " " " "
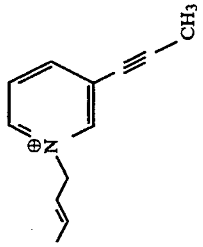 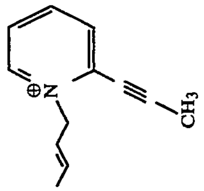 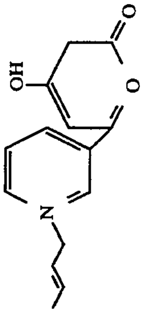 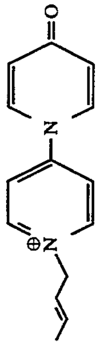 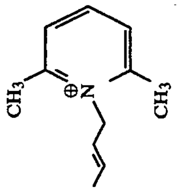
" " " " "

-continued
| | | | | | | | |
|---|---|---|---|---|---|---|---|
| " | 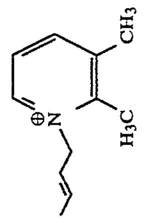 | " | " | " | 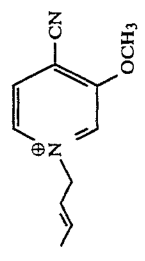 | " | " |
| " | 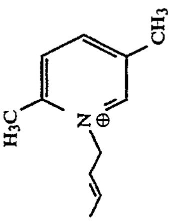 | " | " | " | 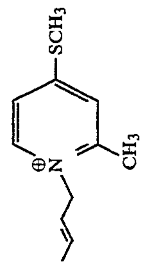 | " | " |

| | | | |
|---|---|---|---|
| 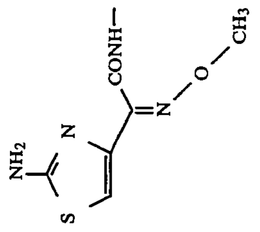 | 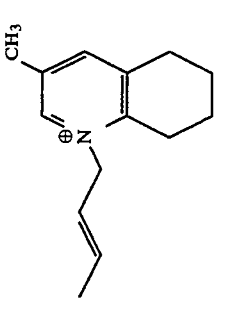 | O | $CO_2^{\ominus}$ |
| " | 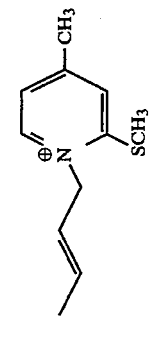 | " | " |
| " | 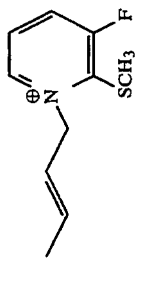 | " | " |
| " | 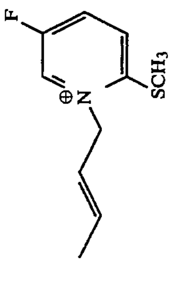 | " | " |
| " | 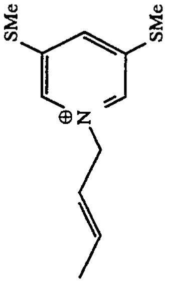 | " | " |
| " | 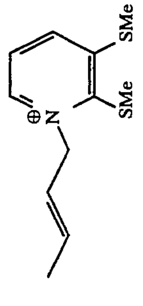 | " | " |
| | | | |
|---|---|---|---|
| 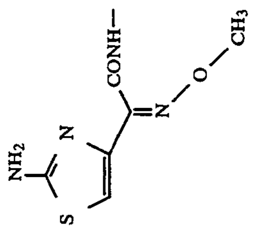 | 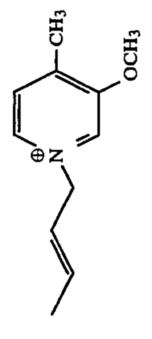 | O | $CO_2^{\ominus}$ |
| " | 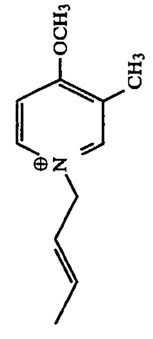 | " | " |
| " | 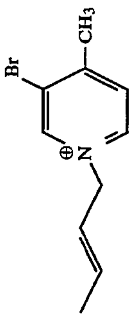 | " | " |
| " | 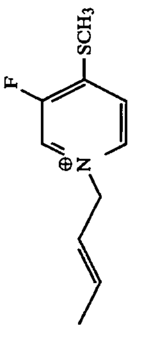 | " | " |
| " | 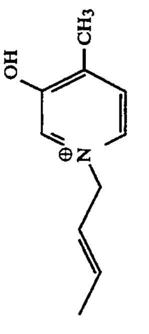 | " | " |
| " | 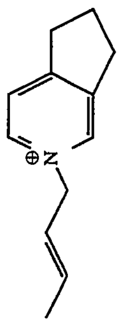 | " | " |

-continued
| | | | |
|---|---|---|---|
| " | 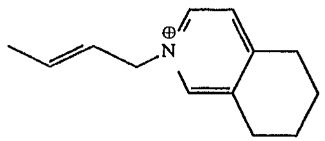 | " | " |
| " | 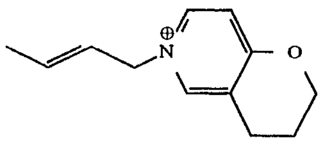 | " | " |
| " | 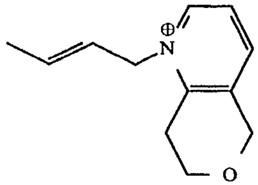 | " | " |
| " | 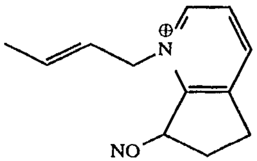 | " | " |
| 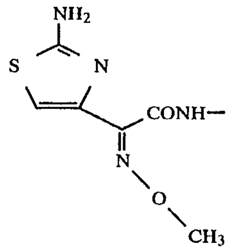 | 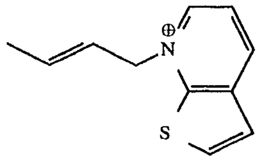 | O | $CO_2^{\ominus}$ |
| | | | |
|---|---|---|---|
| " | 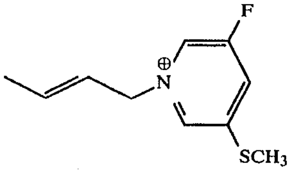 | " | " |
| " | 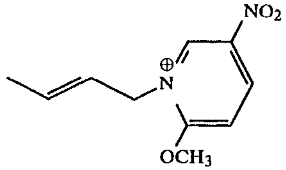 | " | " |
| " | 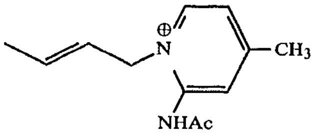 | " | " |
| " | 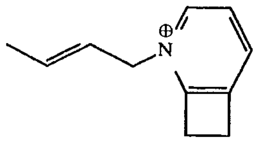 | " | " |
| 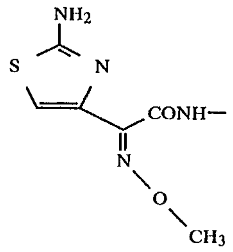 | 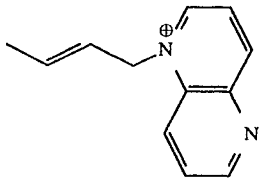 | O | $CO_2^{\ominus}$ |

-continued
| | | | | | | | |
|---|---|---|---|---|---|---|---|
| " | 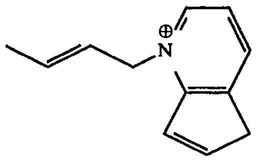 | " | " | " | 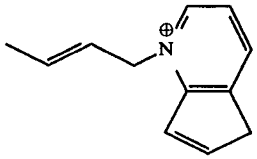 | " | " |
| " | 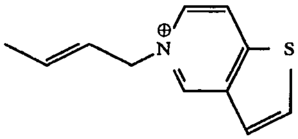 | " | " | " | 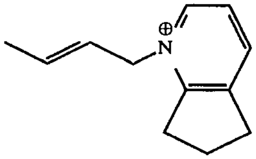 | " | " |
| " | 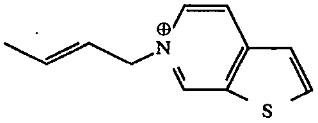 | " | " | " | 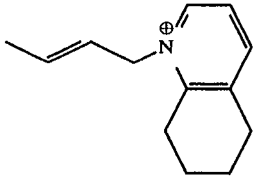 | " | " |
| " | 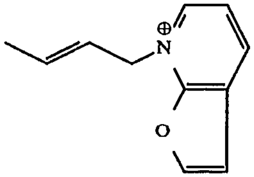 | " | " | " | 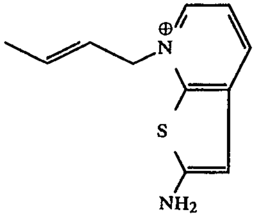 | " | " |
| " | 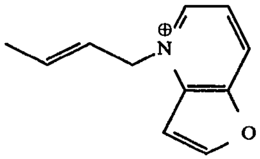 | " | " | " | 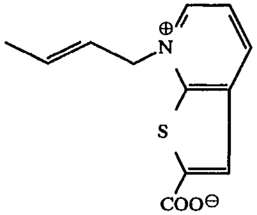 | " | $CO_2H$ |

-continued
| | | | | | | | |
|---|---|---|---|---|---|---|---|
| " | 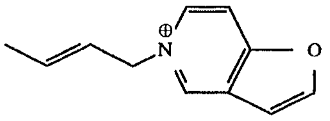 | " | " | " | 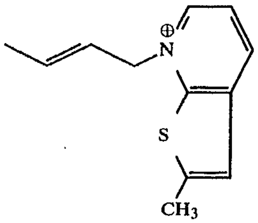 | " | $CO_2^{\ominus}$ |
| " | 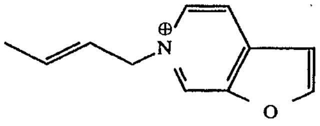 | " | " | " | 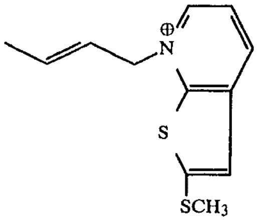 | " | " |
| " | 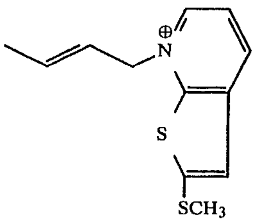 | " | " | " | 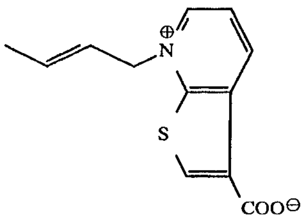 | " | $CO_2H$ |
| " | 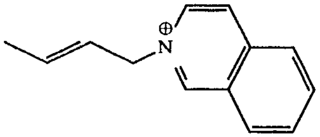 | " | " | " | 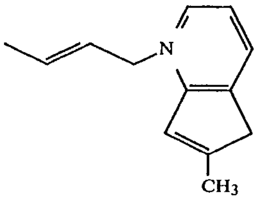 | " | " |

-continued
| | | | | | | | |
|---|---|---|---|---|---|---|---|
| 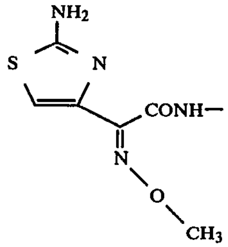 | 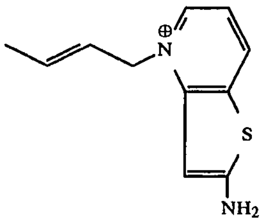 | O | $CO_2^{\ominus}$ | 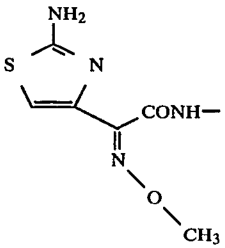 | 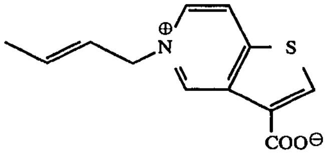 | O | $CO_2H$ |
| " | 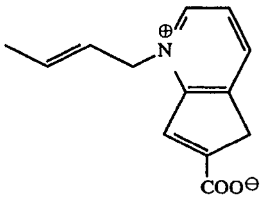 | " | $CO_2H$ | " | 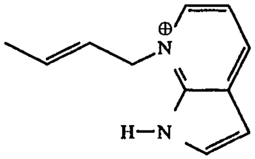 | " | $CO_2^{\ominus}$ |
| " | 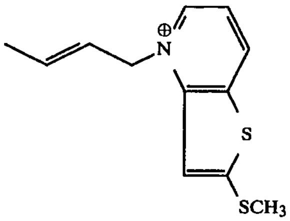 | " | $CO_2^{\ominus}$ | " | 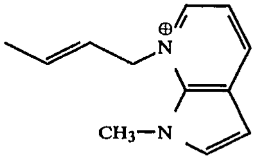 | " | " |
| " | 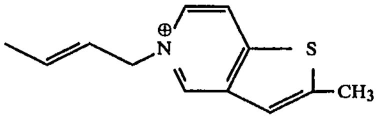 | " | " | " | 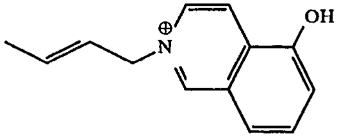 | " | " |
| " | 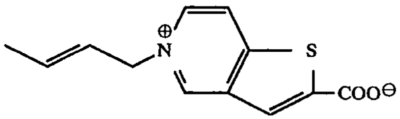 | " | $CO_2H$ | " | 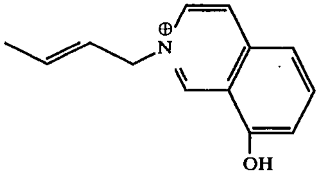 | " | " |

-continued
| | | | | | | | |
|---|---|---|---|---|---|---|---|
| " | 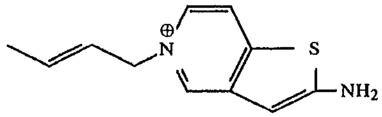 | " | $CO_2^{\ominus}$ | " | 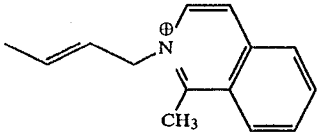 | " | " |
| " | 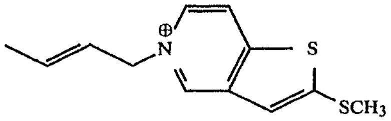 | " | " | " | 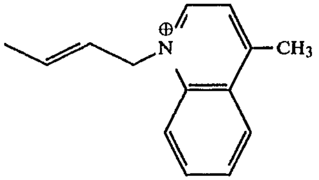 | " | " |
| " | 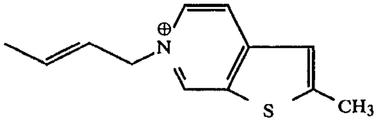 | " | " | " | 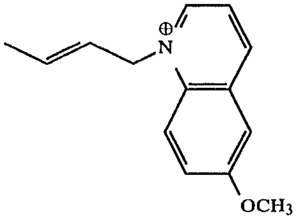 | " | " |
| " | 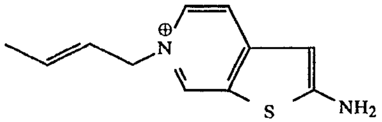 | " | " | " | 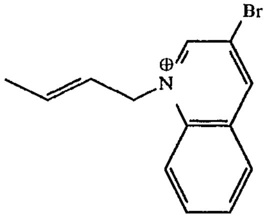 | " | " |

| | | | |
|---|---|---|---|
| ″ | 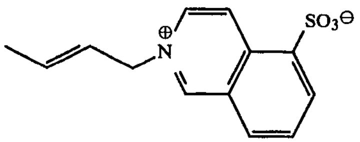 | ″ | $CO_2H$ |
| 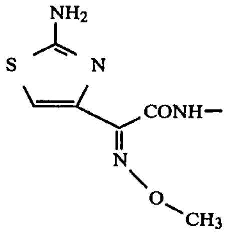 | 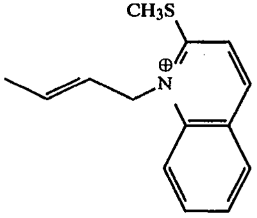 | O | $CO_2^\ominus$ |
| ″ | 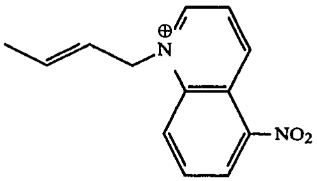 | ″ | ″ |
| ″ | 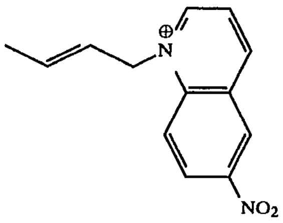 | ″ | ″ |
| ″ | 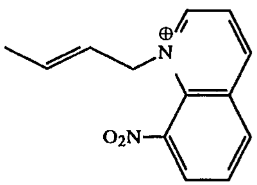 | ″ | ″ |
| | | | |
|---|---|---|---|
| ″ | 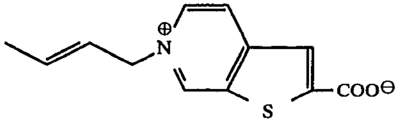 | ″ | $CO_2H$ |
| 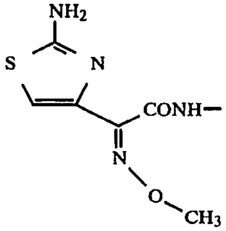 | 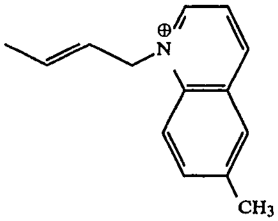 | O | $CO_2^\ominus$ |
| ″ | 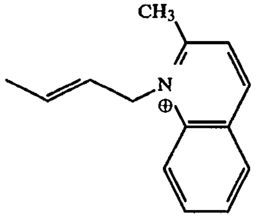 | ″ | ″ |
| ″ | 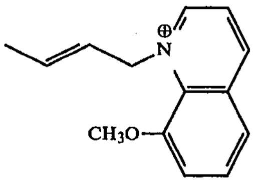 | ″ | ″ |
| ″ | 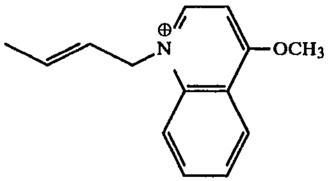 | ″ | ″ |

-continued
| | | | | | | |
|---|---|---|---|---|---|---|
| " | 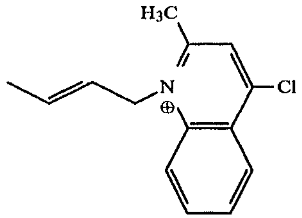 | " | " | " | 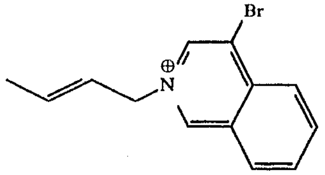 | " | " |
| " | 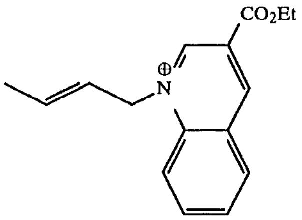 | " | " | " | 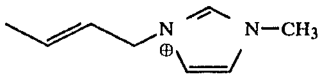 | " | " |
| " | 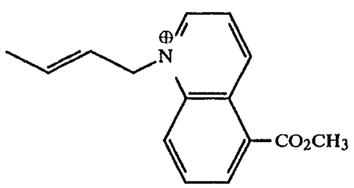 | " | " | " | 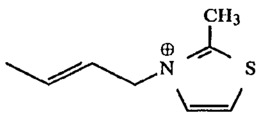 | " | " |
| " | 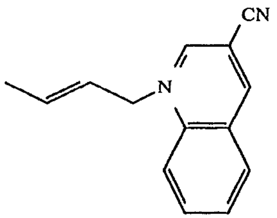 | " | " | " | 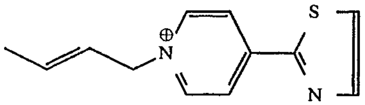 | " | " |
| " | 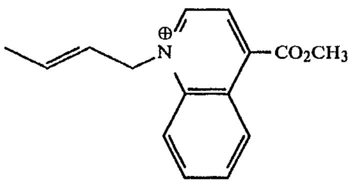 | " | " | " | 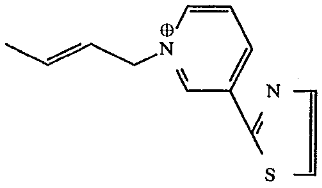 | " | " |

-continued
| | | | | | | | |
|---|---|---|---|---|---|---|---|
| " | 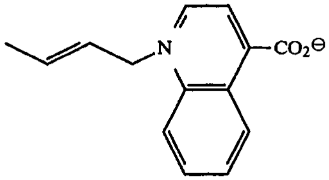 | " | $CO_2H$ | " | 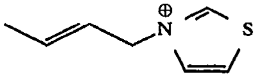 | " | " |
| " | 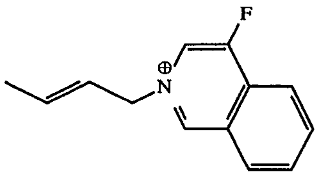 | O | $CO_2^{\ominus}$ | 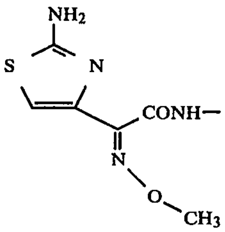 | 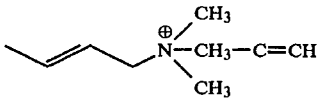 | O | $CO_2^{\ominus}$ |
| " | 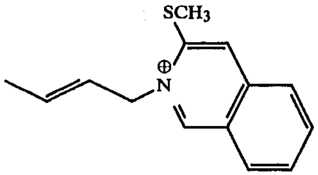 | " | " | " | 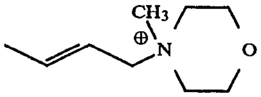 | " | " |
| " | 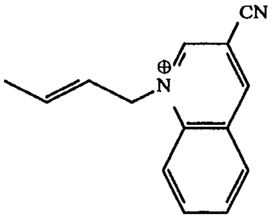 | " | " | " | 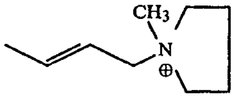 | " | " |
| " | 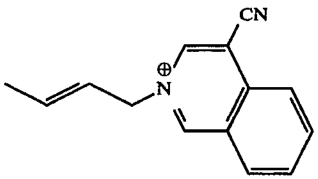 | " | " | " | 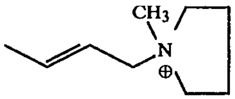 | " | " |

-continued
| | | | | | | | |
|---|---|---|---|---|---|---|---|
| " | 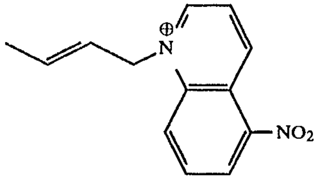 | " | " | " | 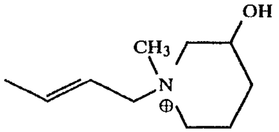 | " | " |
| " | 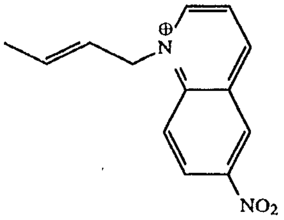 | " | " | " | 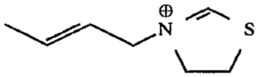 | " | " |
| " | 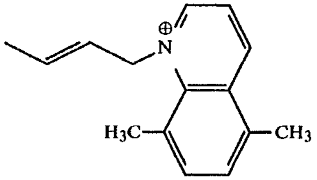 | " | " | " | 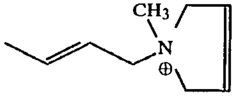 | " | " |
| " | 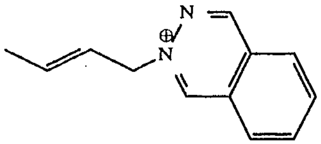 | " | " | " | 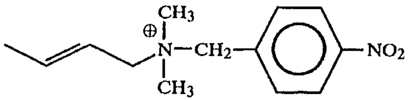 | " | " |
| " | 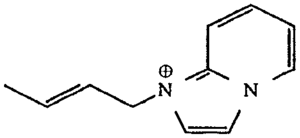 | " | " | " | 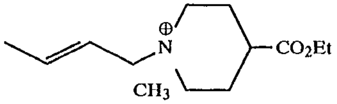 | " | " |

-continued
| | | | |
|---|---|---|---|
| " | 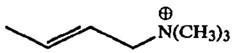 | " | " |
| 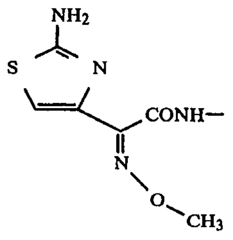 | 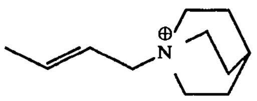 | O | CO2⊖ |
| " | 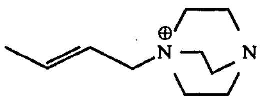 | " | " |
| " | 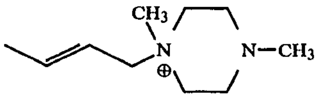 | " | " |
| " | 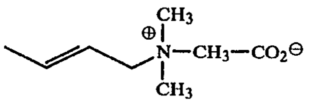 | " | $CO_2H$ |
| " | 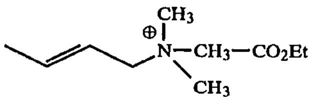 | " | CO2⊖ |
| | | | |
|---|---|---|---|
| " | 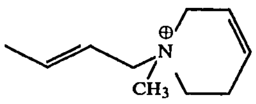 | " | " |
| 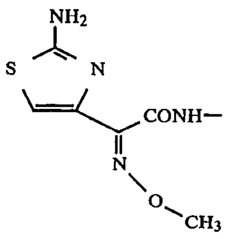 | 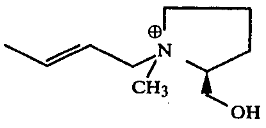 | O | CO2⊖ |
| " | 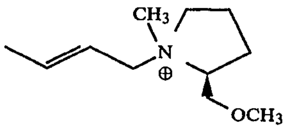 | " | " |
| " | 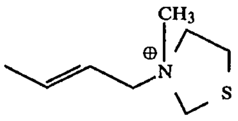 | " | " |
| " | 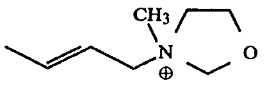 | " | " |
| " | 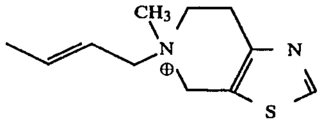 | " | " |

-continued
| | | | | | | | |
|---|---|---|---|---|---|---|---|
| " | 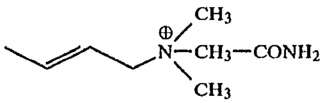 | " | " | " | 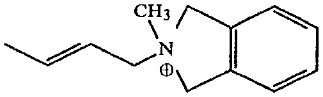 | " | " |
| " | 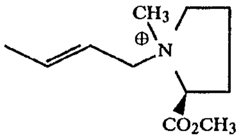 | " | " | " | 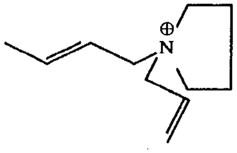 | " | " |
| " | 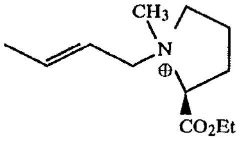 | " | " | " | 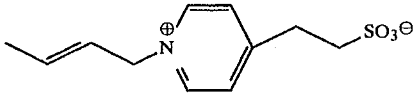 | " | CO2H |
| " | 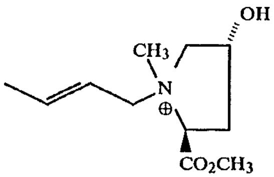 | " | " | | | | |
| " | 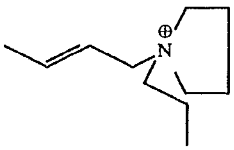 | " | " | | | | |

| | | |
|---|---|---|
| 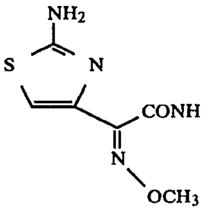 | 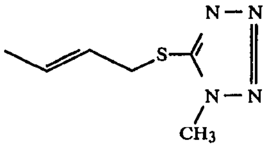 | 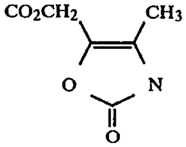 |
| " | 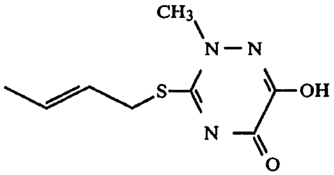 | " |
| " | 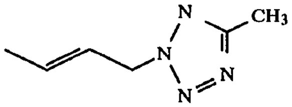 | " |
| " | 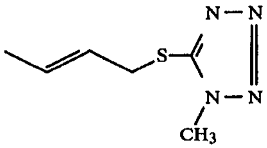 | 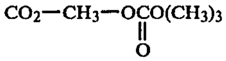 |
| " | 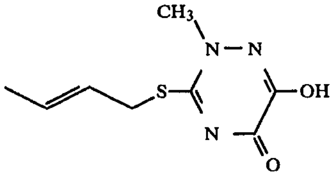 | " |
| " | 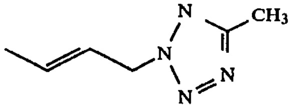 | " |

-continued
| | | | | | | | |
|---|---|---|---|---|---|---|---|
| | 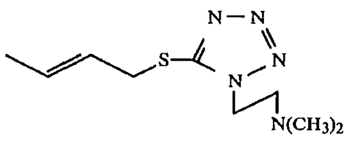 | | | | | | |
| 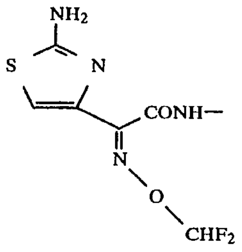 | 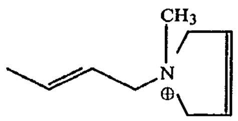 | O | $CO_2^{\ominus}$ | 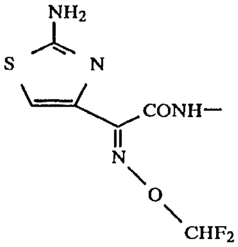 | 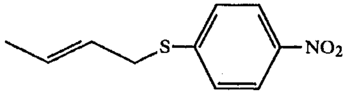 | O | $CO_2H$ |
| " | 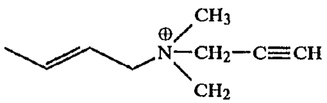 | " | " | " | 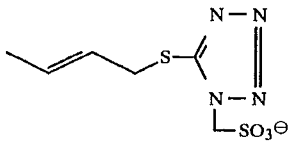 | " | " |
| " | 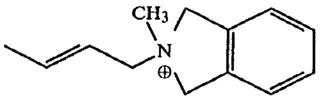 | " | " | " | 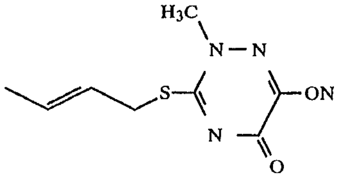 | " | " |
| " | 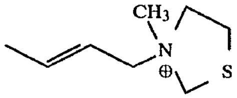 | " | " | " | 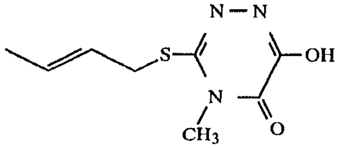 | " | " |

-continued
| | | | | | | | |
|---|---|---|---|---|---|---|---|
| " | 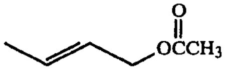 | " | CO2H | " | 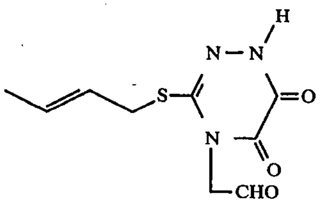 | " | " |
| " | 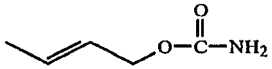 | " | " | " | 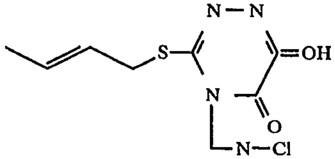 | " | " |
| " | 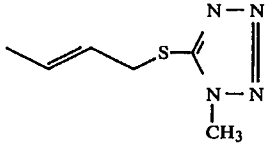 | " | " | " | 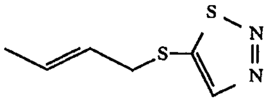 | " | " |
| " | 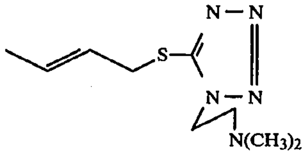 | " | " | " | 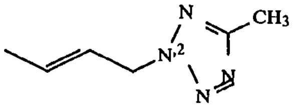 | " | " |
| " | 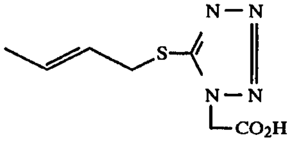 | " | " | " | 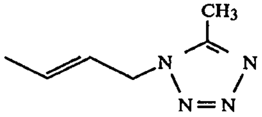 | " | " |
| " | 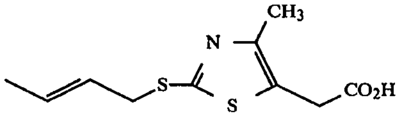 | " | " | " | 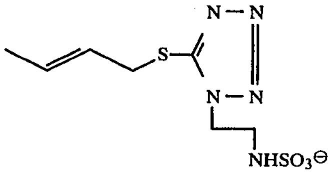 | " | " |

-continued
| | | | | | | | |
|---|---|---|---|---|---|---|---|
| 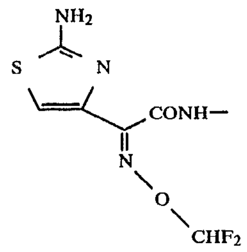 | 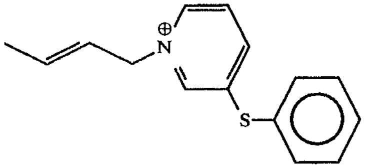 | O | $CO_2^{\ominus}$ | 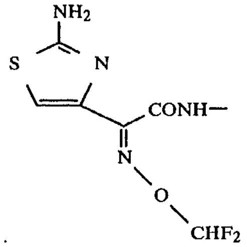 | 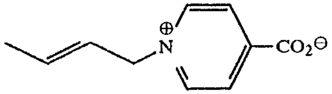 | O | $CO_2H$ |
| " | 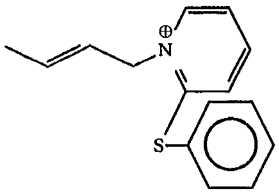 | " | " | " | 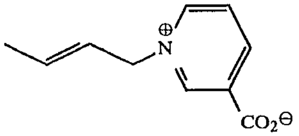 | " | " |
| " | 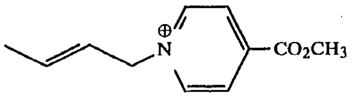 | " | " | " | 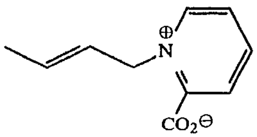 | " | " |
| " | 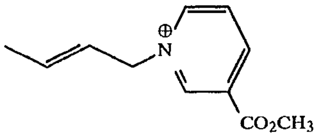 | " | " | " | 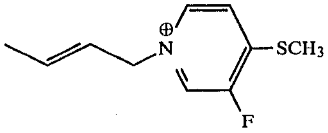 | " | $CO_2^{\ominus}$ |
| " | 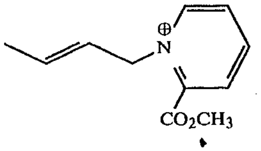 | " | " | " | 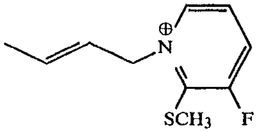 | " | " |

-continued
| | | | | | | | |
|---|---|---|---|---|---|---|---|
| " | 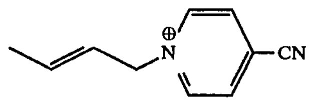 | " | " | " | 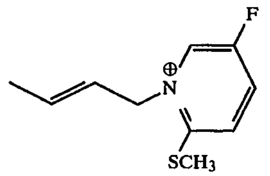 | " | " |
| " | 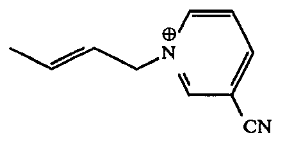 | " | " | " | 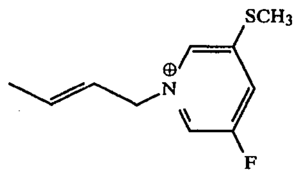 | " | " |
| " | 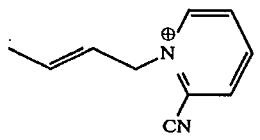 | " | " | " | 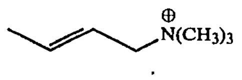 | " | " |
| " | 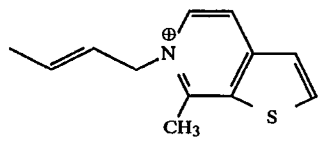 | " | " | " | 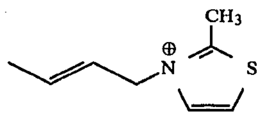 | " | " |
| " | 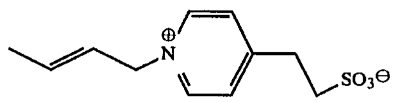 | " | $CO_2H$ | " | 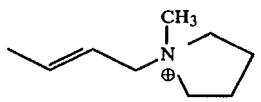 | " | " |

| | | | |
|---|---|---|---|
| 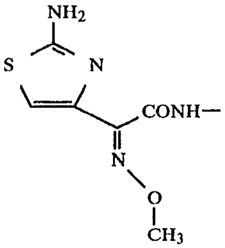 | 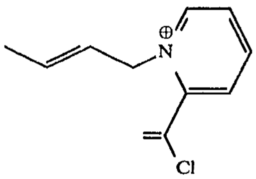 | O | $CO_2^{\ominus}$ |
| " | 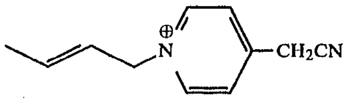 | " | " |
| " | 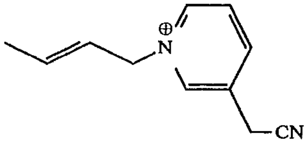 | " | " |
| " | 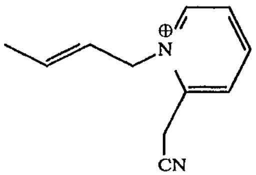 | " | " |
| " | 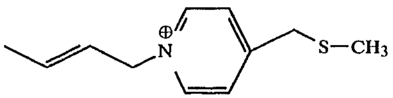 | " | " |
| | | | |
|---|---|---|---|
| 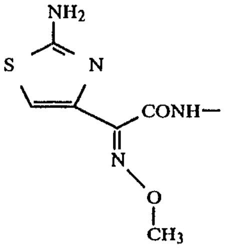 | 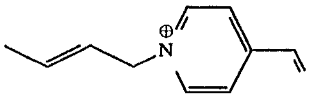 | O | $CO_2^{\ominus}$ |
| " | 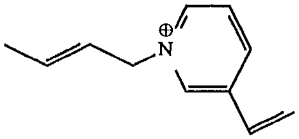 | " | " |
| " | 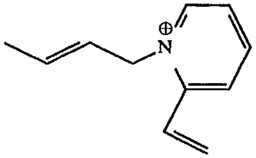 | " | " |
| " | 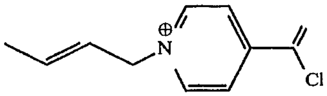 | " | " |
| " | 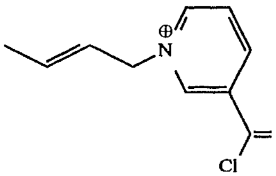 | " | " |

-continued
| | | | | | | | |
|---|---|---|---|---|---|---|---|
| 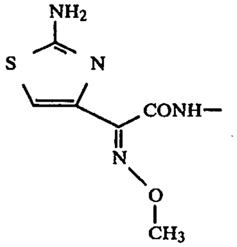 | 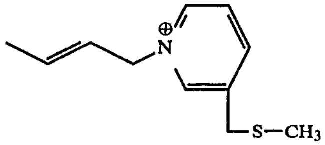 | O | $CO_2^{\ominus}$ | 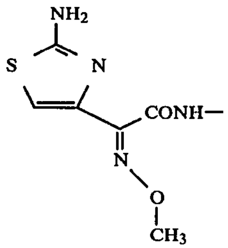 | 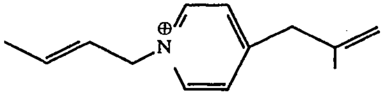 | O | $CO_2^{\ominus}$ |
| " | 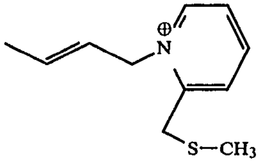 | " | " | " | 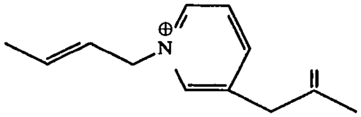 | " | " |
| " | 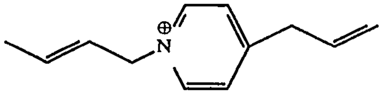 | " | " | " | 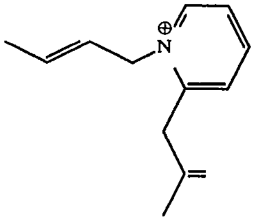 | " | " |
| " | 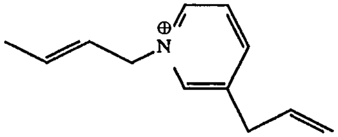 | " | " | " | 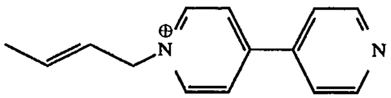 | " | " |
| " | 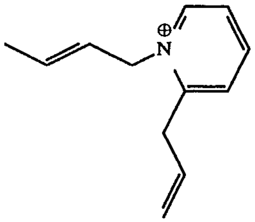 | " | " | " | 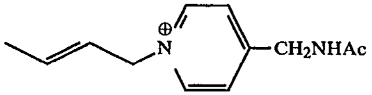 | " | " |

-continued
| | | | |
|---|---|---|---|
| 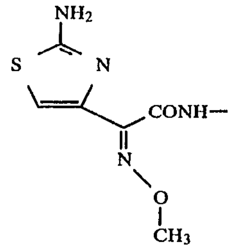 | 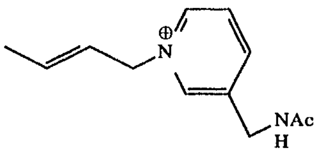 | O | $CO_2^{\ominus}$ |
| ″ | 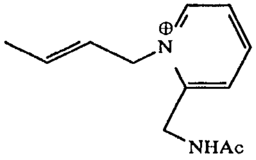 | ″ | ″ |
| ″ | 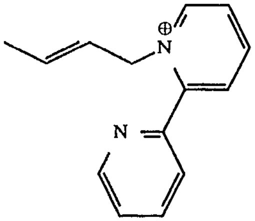 | ″ | ″ |
| ″ | 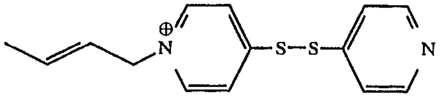 | ″ | ″ |
| ″ | 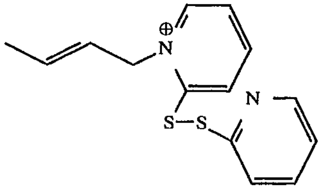 | ″ | ″ |
| | | | |
|---|---|---|---|
| 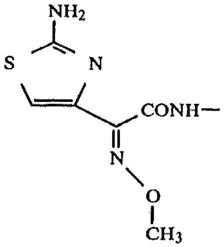 | 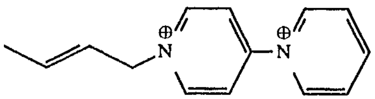 | O | $CO_2^{\ominus}$ |
| ″ | 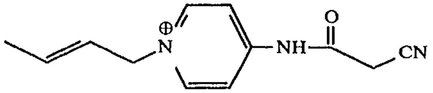 | ″ | ″ |
| ″ | 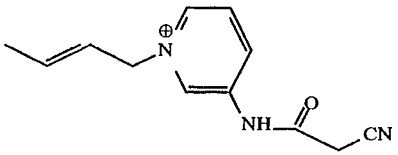 | ″ | ″ |
| ″ | 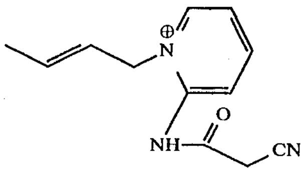 | ″ | ″ |
| ″ | 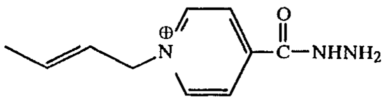 | ″ | ″ |

-continued
| | | | |
|---|---|---|---|
| O | $CO_2^{\ominus}$ | 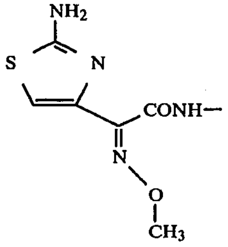 | 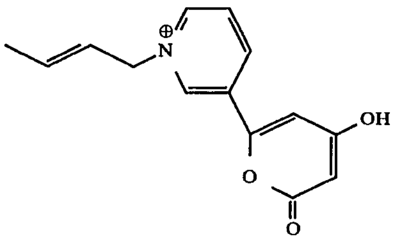 |
| ″ | ″ | ″ | 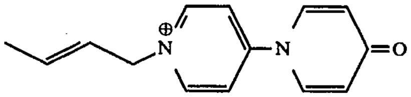 |
| ″ | ″ | ″ | 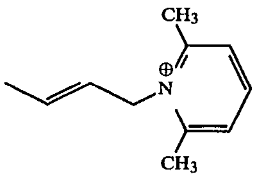 |
| ″ | ″ | ″ | 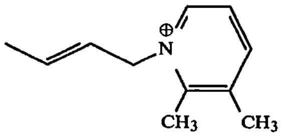 |
| ″ | ″ | ″ | 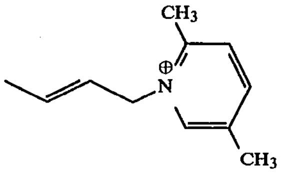 |
| O | $CO_2^{\ominus}$ | 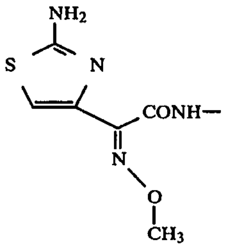 | 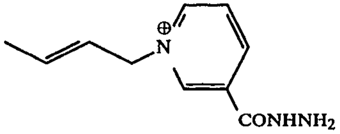 |
| ″ | ″ | ″ | 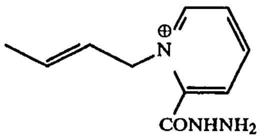 |
| ″ | ″ | ″ | 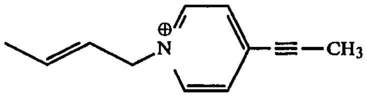 |
| ″ | ″ | ″ | 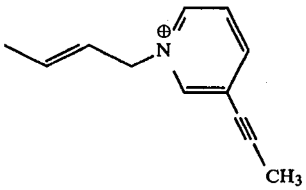 |
| ″ | ″ | ″ | 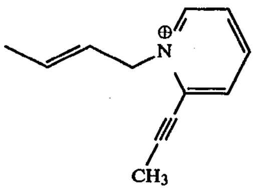

-continued
| | | | | | | | |
|---|---|---|---|---|---|---|---|
| 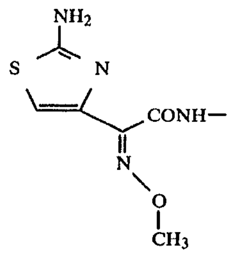 | 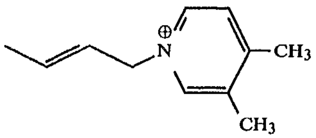 | O | $CO_2^{\ominus}$ | 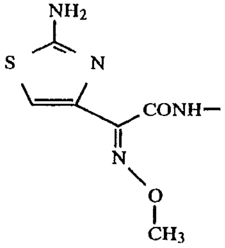 | 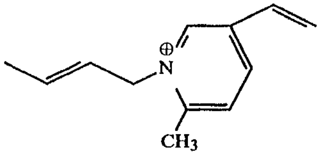 | O | $CO_2^{\ominus}$ |
| " | 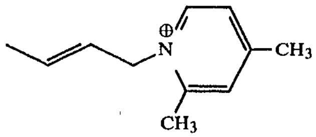 | " | " | " | 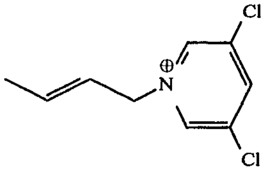 | " | " |
| " | 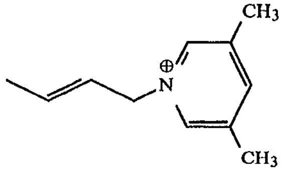 | " | " | " | 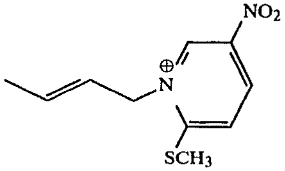 | " | " |
| " | 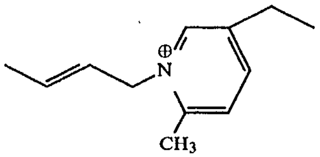 | " | " | " | 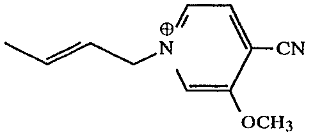 | " | " |
| " | 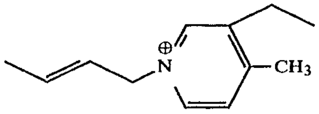 | " | " | " | 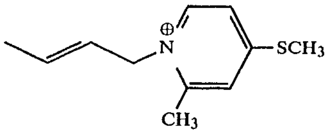 | " | " |

| | | | |
|---|---|---|---|
| 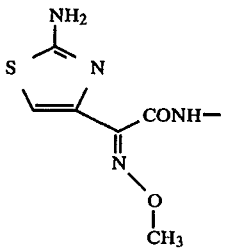 | 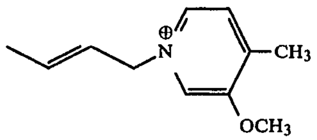 | O | $CO_2^{\ominus}$ |
| " | 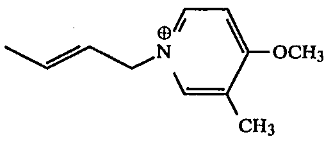 | " | " |
| " | 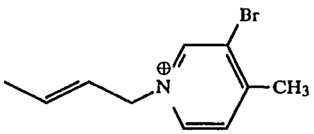 | " | " |
| " | 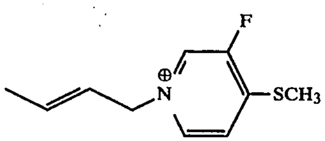 | " | " |
| " | 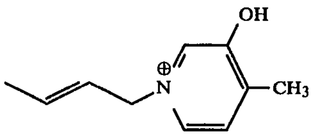 | " | " |
| | | | |
|---|---|---|---|
| 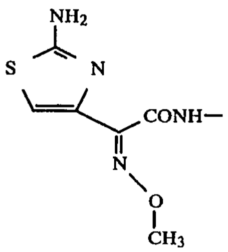 | 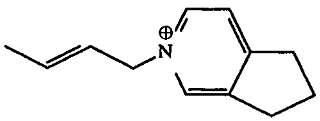 | O | $CO_2^{\ominus}$ |
| " | 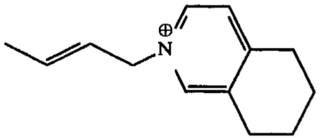 | " | " |
| " | 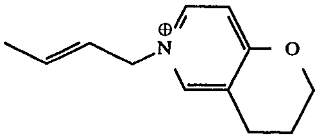 | " | " |
| " | 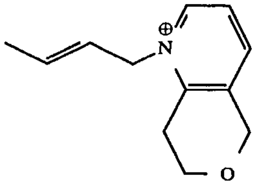 | " | " |
| " | 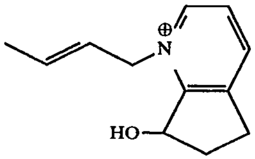 | " | " |

-continued
| | | | |
|---|---|---|---|
| 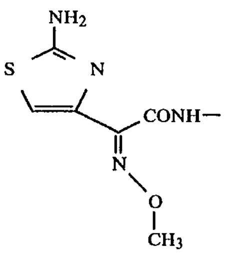 | 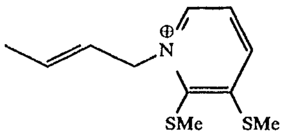 | O | $CO_2^{\ominus}$ |
| " | 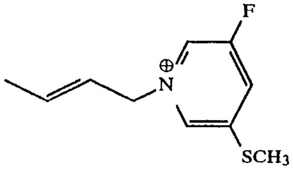 | " | " |
| " | 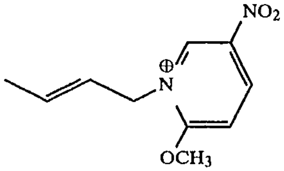 | " | " |
| " | 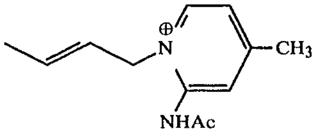 | " | " |
| " | 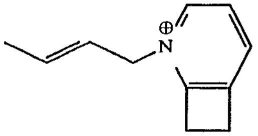 | " | " |
| | | | |
|---|---|---|---|
| 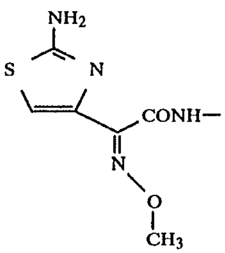 | 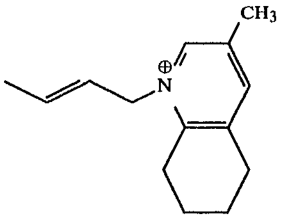 | O | $CO_2^{\ominus}$ |
| " | 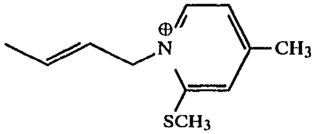 | " | " |
| " | 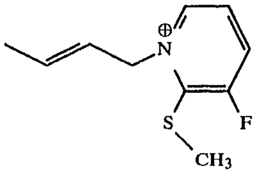 | " | " |
| " | 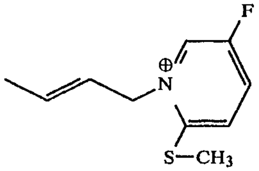 | " | " |
| " | 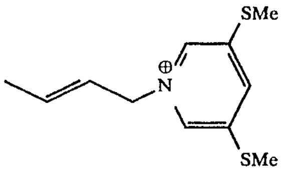 | " | " |

-continued
| | | | | | | | |
|---|---|---|---|---|---|---|---|
| 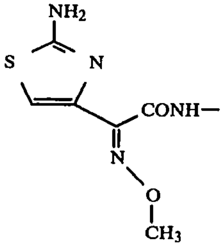 | 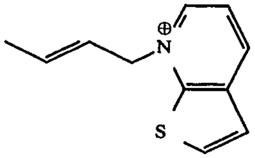 | O | $CO_2^{\ominus}$ | 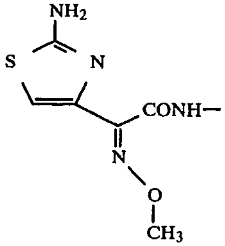 | 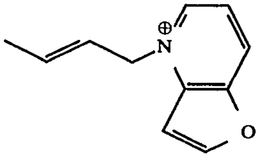 | O | $CO_2^{\ominus}$ |
| " | 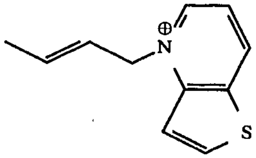 | " | " | " | 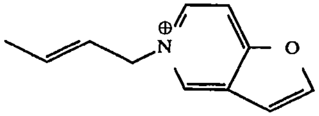 | " | " |
| " | 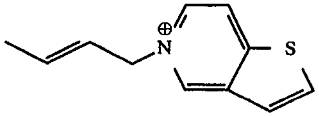 | " | " | " | 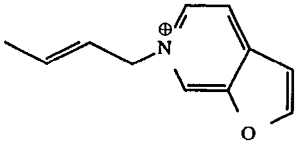 | " | " |
| " | 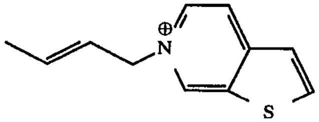 | " | " | " | 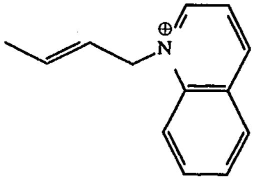 | " | " |
| " | 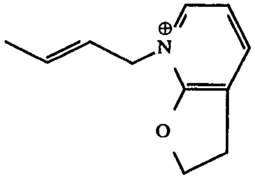 | " | " | " | 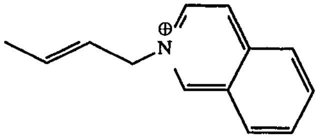 | " | " |

-continued
| | | | |
|---|---|---|---|
| 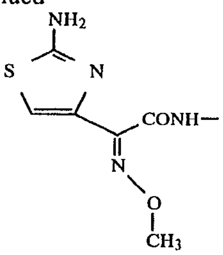 | 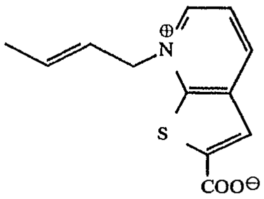 | O | $CO_2H$ |
| " | 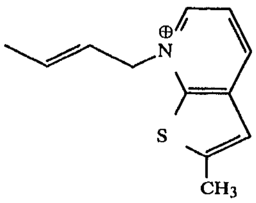 | " | $CO_2\ominus$ |
| " | 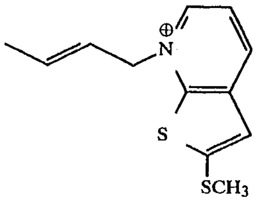 | " | " |
| " | 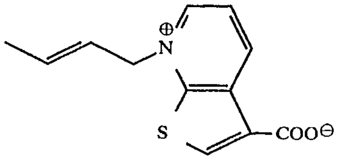 | " | $CO_2H$ |
| " | 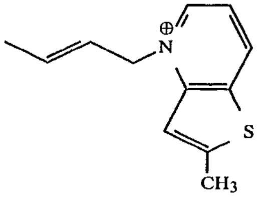 | " | " |
| | | | |
|---|---|---|---|
| 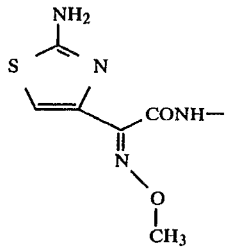 | 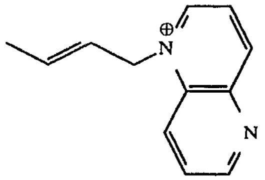 | O | $CO_2\ominus$ |
| " | 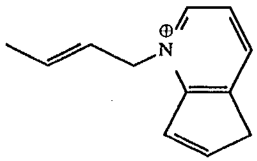 | " | " |
| " | 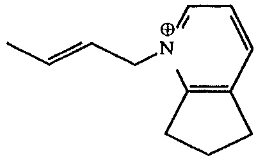 | " | " |
| " | 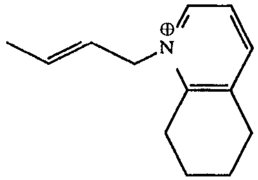 | " | " |
| " | 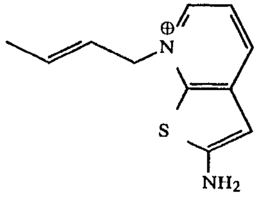 | " | " |

-continued
| | | | | | | | |
|---|---|---|---|---|---|---|---|
| 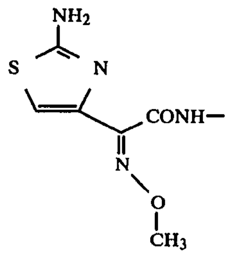 | 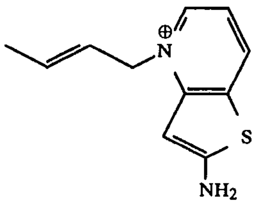 | O | $CO_2^{\ominus}$ | 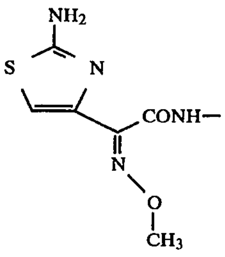 | 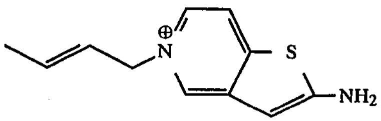 | O | $CO_2^{\ominus}$ |
| " | 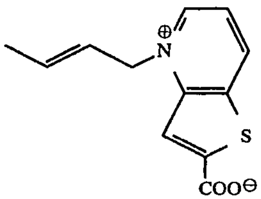 | " | $CO_2H$ | " | 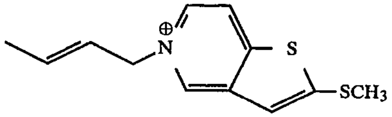 | " | " |
| " | 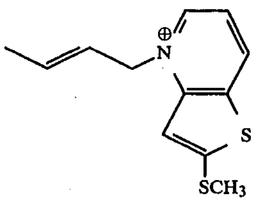 | " | $CO_2^{\ominus}$ | " | 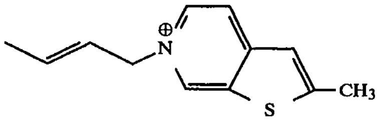 | " | " |
| " | 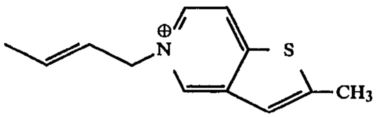 | " | " | " | 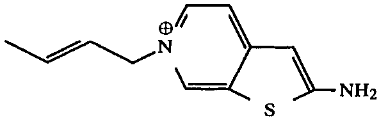 | " | " |
| " | 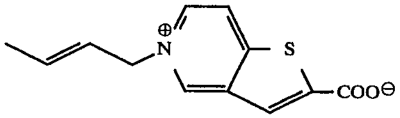 | " | $CO_2H$ | " | 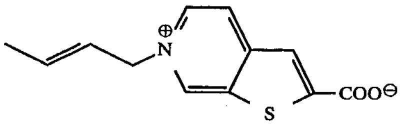 | " | $CO_2H$ |

-continued
| | | | | | | | |
|---|---|---|---|---|---|---|---|
| 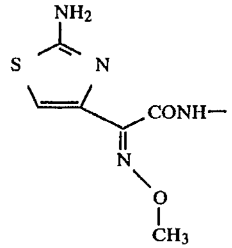 | 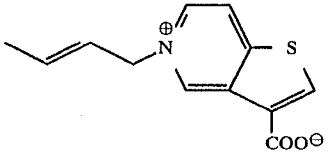 | O | $CO_2H$ | 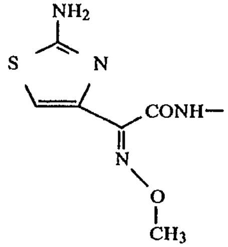 | 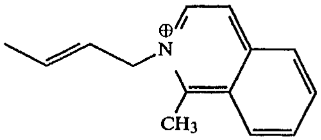 | O | $CO_2^{\ominus}$ |
| " | 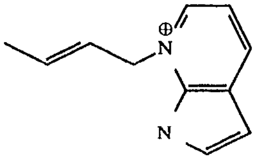 | " | $CO_2^{\ominus}$ | " | 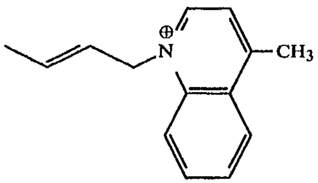 | " | " |
| " | 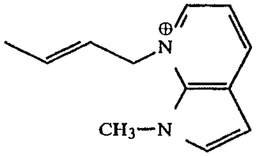 | " | " | " | 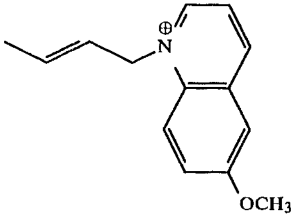 | " | " |
| " | 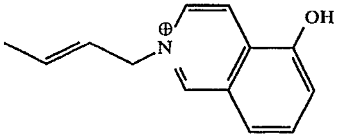 | " | " | " | 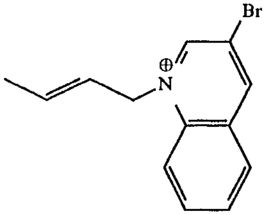 | " | " |
| " | 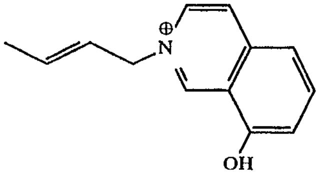 | " | " | " | 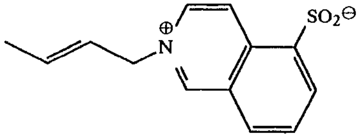 | " | $CO_2H$ |

| | | | |
|---|---|---|---|
| 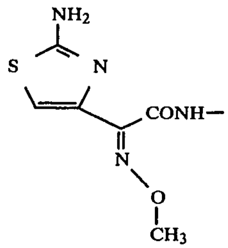 | 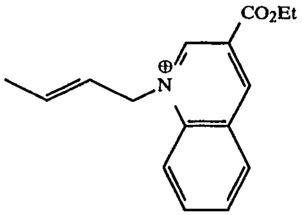 | O | $CO_2^{\ominus}$ |
| " | 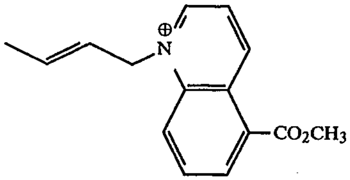 | " | " |
| " | 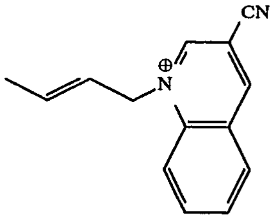 | " | " |
| " | 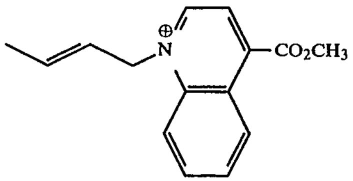 | " | " |
| 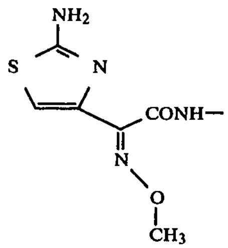 | 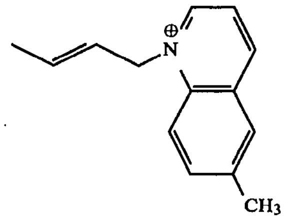 | O | $CO_2^{\ominus}$ |
| " | 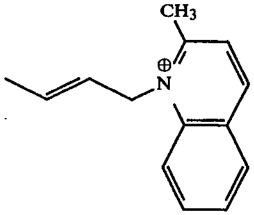 | " | " |
| " | 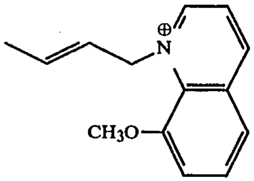 | " | " |
| " | 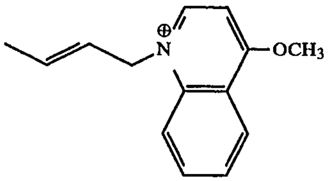 | " | " |

-continued
| | | | | | | | |
|---|---|---|---|---|---|---|---|
| ″ | 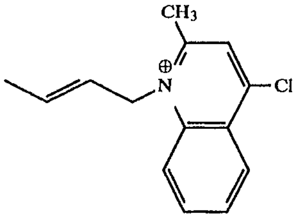 | ″ | ″ | ″ | 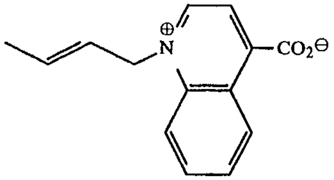 | ″ | $CO_2H$ |
| 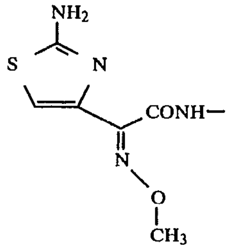 | 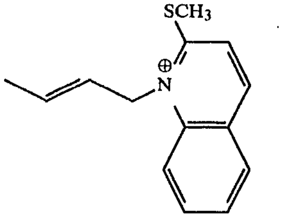 | O | $CO_2^\ominus$ | 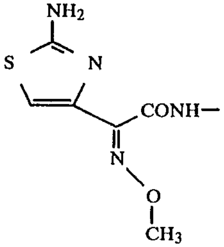 | 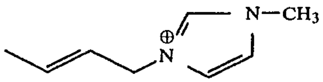 | O | $CO_2^\ominus$ |
| ″ | 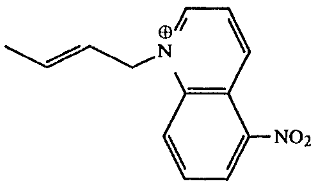 | ″ | ″ | ″ | 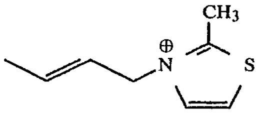 | ″ | ″ |
| ″ | 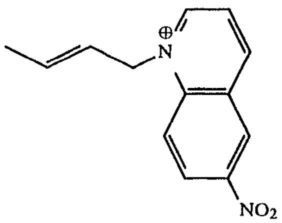 | ″ | ″ | ″ | 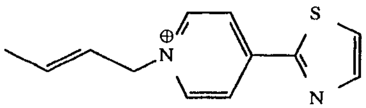 | ″ | ″ |

-continued
| | | | | | | | |
|---|---|---|---|---|---|---|---|
| " | 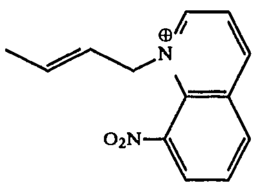 | " | " | " | 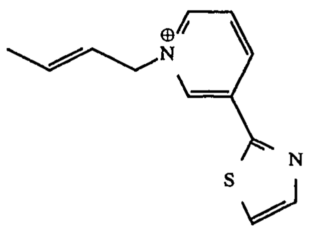 | " | " |
| " | 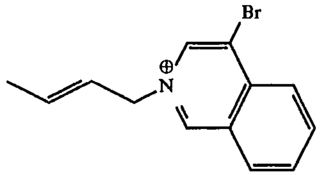 | " | " | " | 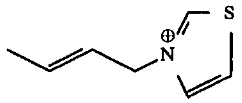 | " | " |
| 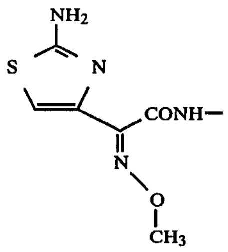 | 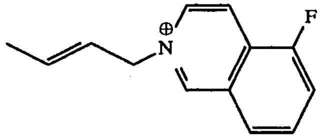 | O | $CO_2^{\ominus}$ | 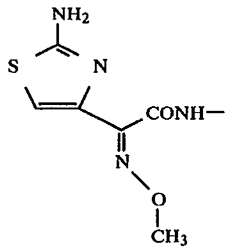 | 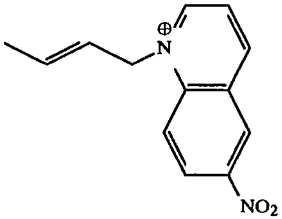 | O | $CO_2^{\ominus}$ |
| " | 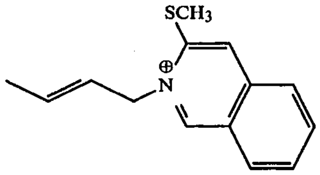 | " | " | " | 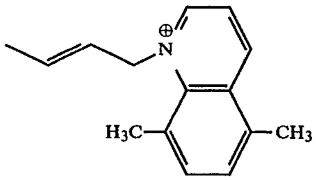 | " | " |
| " | 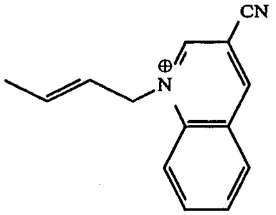 | " | " | " | 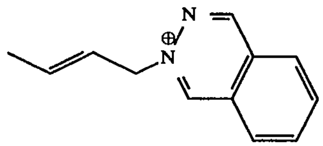 | " | " |

-continued
| | | | |
|---|---|---|---|
| " | 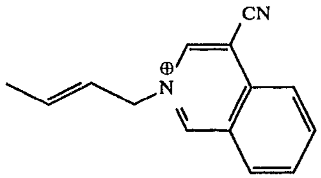 | " | " |
| " | 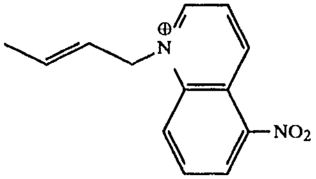 | " | " |
| 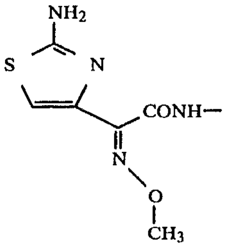 | 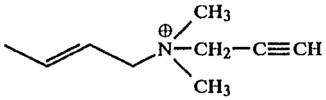 | O | $CO_2^{\ominus}$ |
| " | 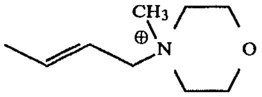 | " | " |
| " | 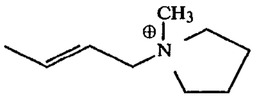 | " | " |
| " | 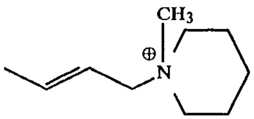 | " | " |
| " | 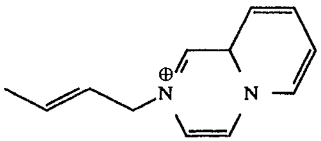 | " | " |
| " | 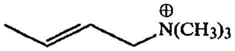 | " | " |
| 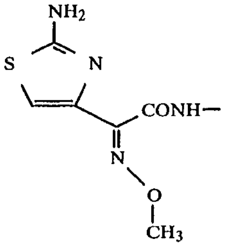 | 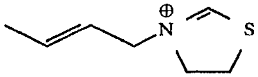 | O | $CO_2^{\ominus}$ |
| " | 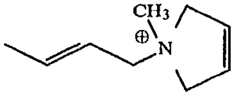 | " | " |
| " | 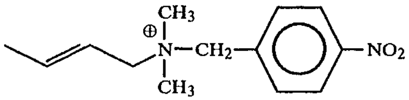 | " | " |
| " | 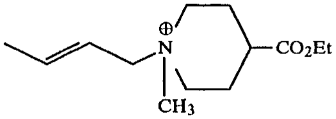 | " | " |

-continued
| | | | | | | | |
|---|---|---|---|---|---|---|---|
| " | 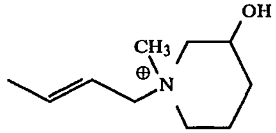 | " | " | " | 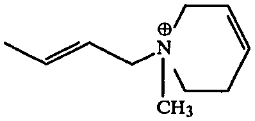 | " | " |
| 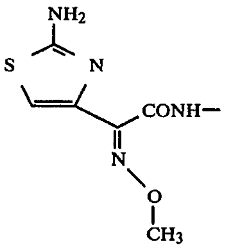 | 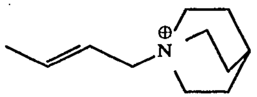 | O | $CO_2^{\ominus}$ | 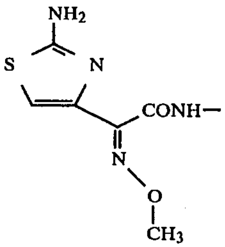 | 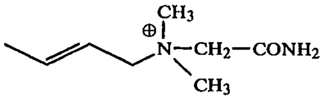 | O | $CO_2^{\ominus}$ |
| " | 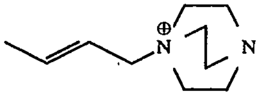 | " | " | " | 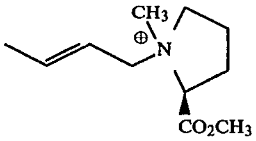 | " | " |
| " | 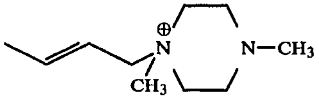 | " | " | " | 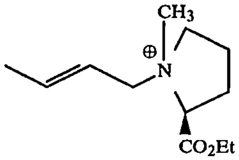 | " | " |
| " | 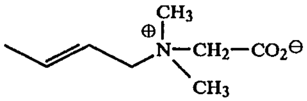 | " | $CO_2H$ | " | 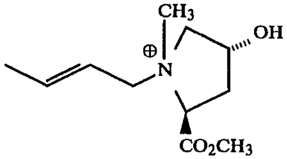 | " | " |

-continued
| | | | |
|---|---|---|---|
| " | 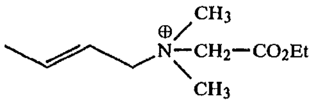 | " | $CO_2^{\ominus}$ |
| 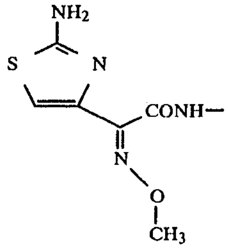 | 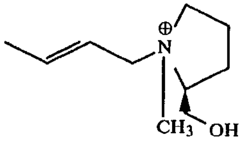 | O | $CO_2^{\ominus}$ |
| " | 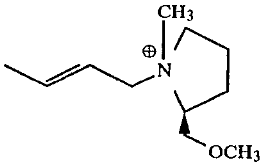 | " | " |
| " | 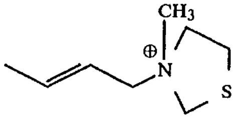 | " | " |
| " | 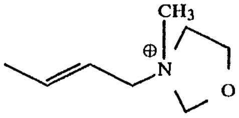 | " | " |
| " | 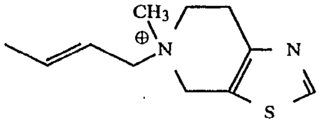 | " | " |
| " | 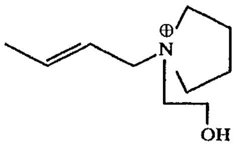 | " | " |
| 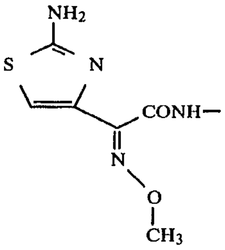 | 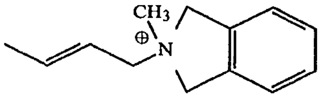 | O | $CO_2^{\ominus}$ |
| " | 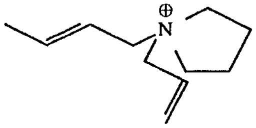 | " | " |
| " | 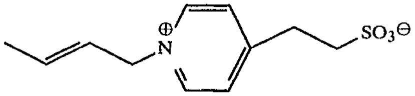 | " | $CO_2H$ |

| | | | |
|---|---|---|---|
| 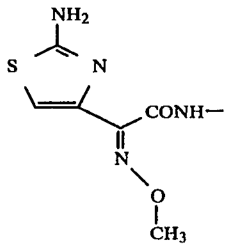 | 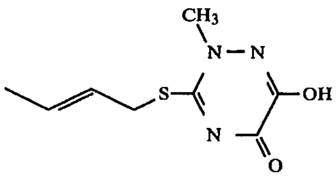 | | 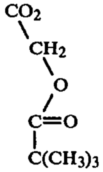 |
| ″ | 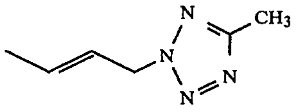 | | ″ |
| | 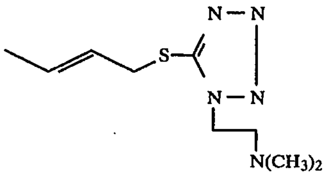 | | |
| 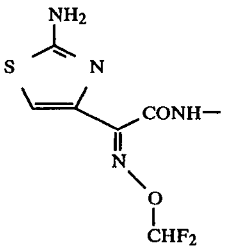 | 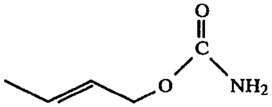 | O | $CO_2H$ |
| 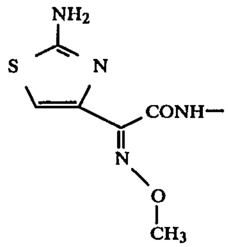 | 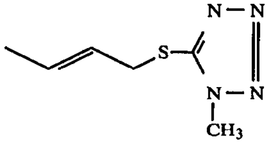 | | 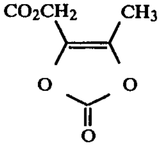 |
| ″ | 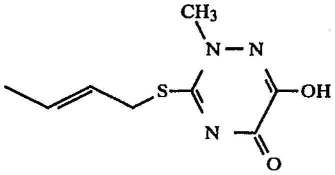 | | ″ |
| ″ | 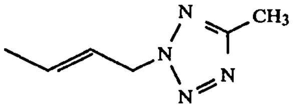 | | ″ |
| ″ | 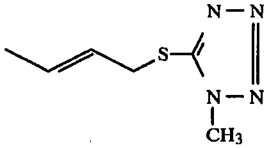 | | 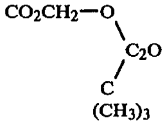 |
| 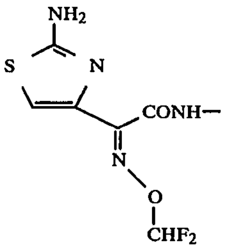 | 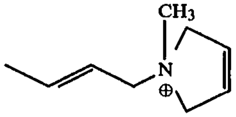 | O | $CO_2^{\ominus}$ |

-continued
| | | | | | | | |
|---|---|---|---|---|---|---|---|
| " | 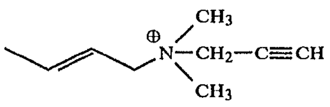 | " | " | " | 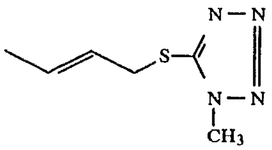 | " | " |
| " | 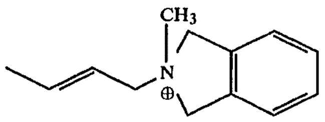 | " | " | " | 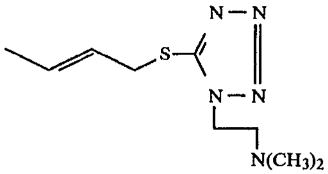 | " | " |
| " | 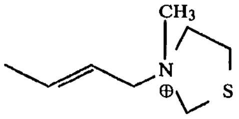 | " | " | " | 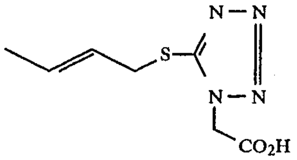 | " | " |
| " | 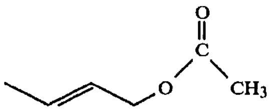 | " | $CO_2H$ | " | 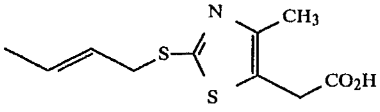 | " | " |
| 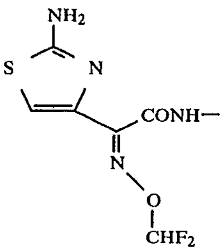 | 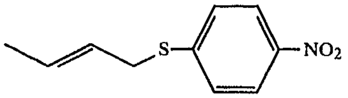 | O | $CO_2H$ | 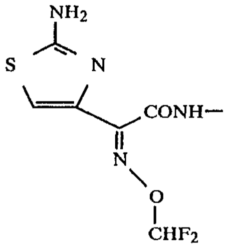 | 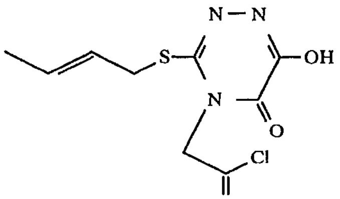 | O | $CO_2H$ |
| " | 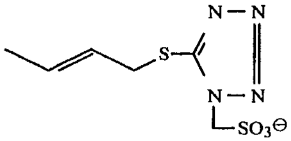 | " | " | " | 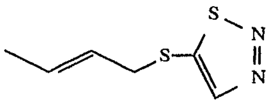 | " | " |

-continued
| | | | | | | | |
|---|---|---|---|---|---|---|---|
| " | 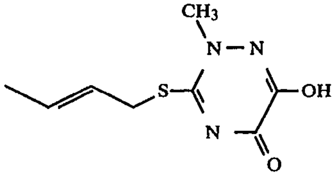 | " | " | " | 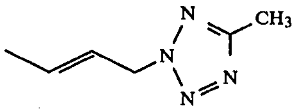 | " | " |
| " | 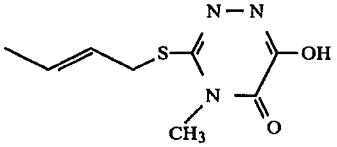 | " | " | " | 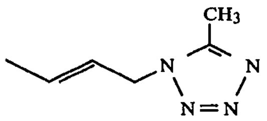 | " | " |
| " | 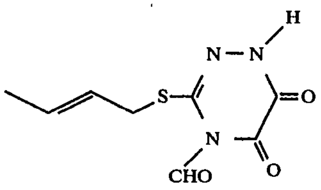 | " | " | " | 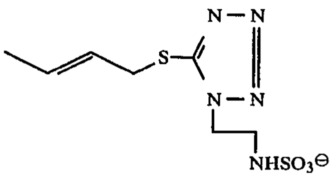 | " | " |
| 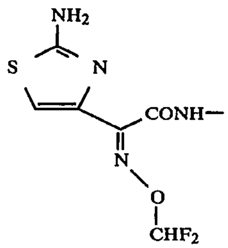 | 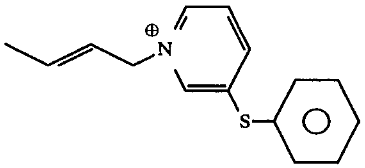 | O | $CO_2^{\ominus}$ | 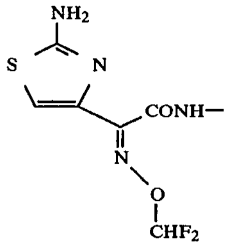 | 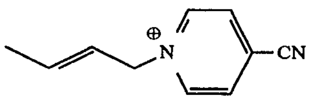 | O | $CO_2^{\ominus}$ |
| " | 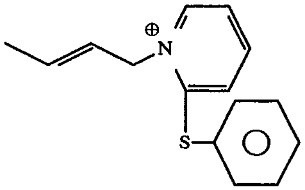 | " | " | " | 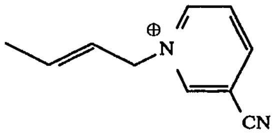 | " | " |

-continued
| | | | | | | | |
|---|---|---|---|---|---|---|---|
| " | 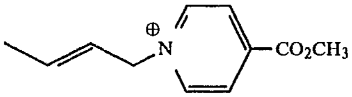 | " | " | " | 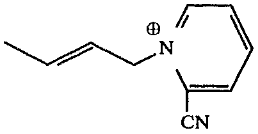 | " | " |
| " | 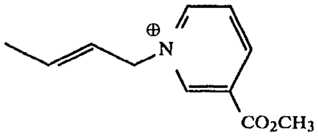 | " | " | " | 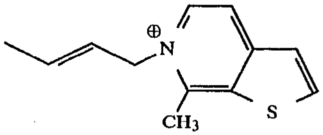 | " | " |
| " | 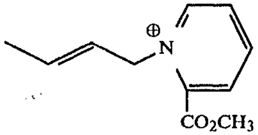 | " | " | " | 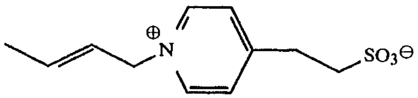 | | $CO_2H$ |
| 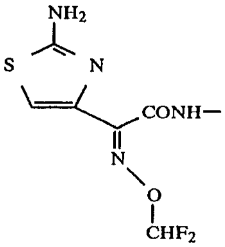 | 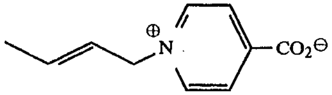 | O | $CO_2H$ | 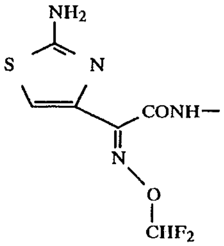 | 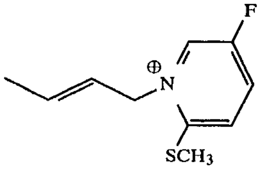 | O | $CO_2^{\ominus}$ |
| " | 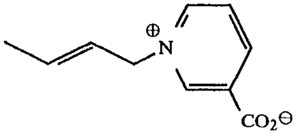 | " | " | " | 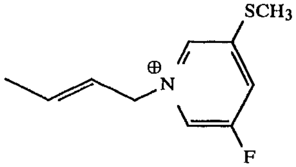 | " | " |
| " | 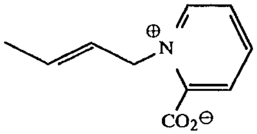 | " | " | " | 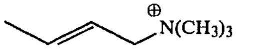 | " | " |

-continued
| | | | | | | | |
|---|---|---|---|---|---|---|---|
| ″ | 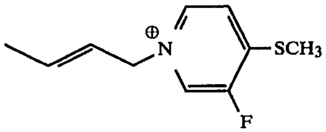 | ″ | $CO_2^\ominus$ | ″ | 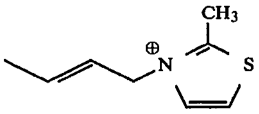 | ″ | ″ |
| ″ | 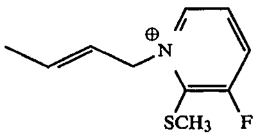 | ″ | ″ | ″ | 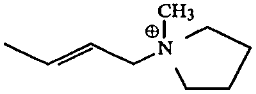 | ″ | ″ |
| 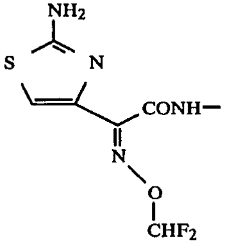 | 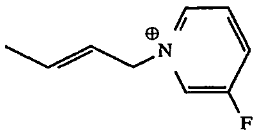 | O | $CO_2^\ominus$ | 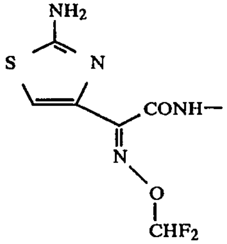 | 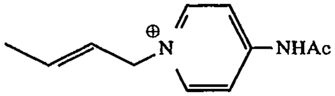 | O | $CO_2^\ominus$ |
| ″ | 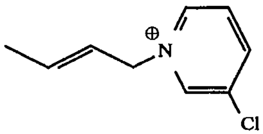 | ″ | ″ | ″ | 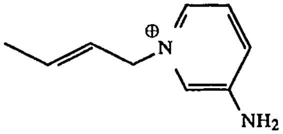 | ″ | ″ |
| ″ | 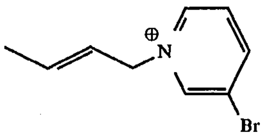 | ″ | ″ | ″ | 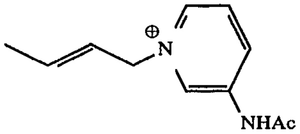 | ″ | ″ |
| ″ | 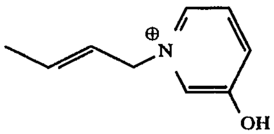 | ″ | ″ | ″ | 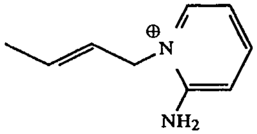 | ″ | ″ |

-continued
| | | | | | | | |
|---|---|---|---|---|---|---|---|
| " | 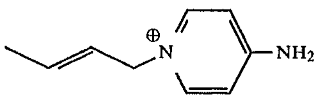 | " | " | " | 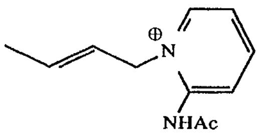 | " | " |
| 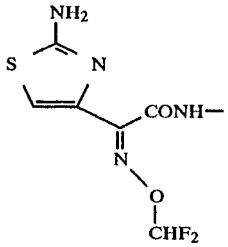 | 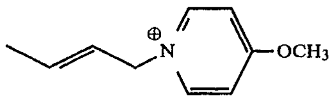 | O | $CO_2^{\ominus}$ | 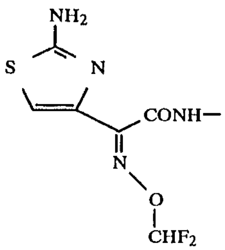 | 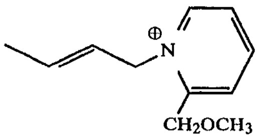 | O | $CO_2^{\ominus}$ |
| " | 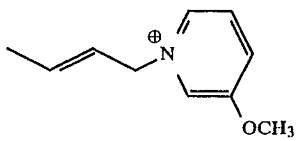 | " | " | " | 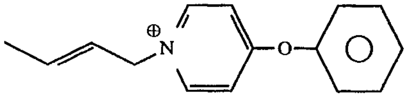 | " | " |
| " | 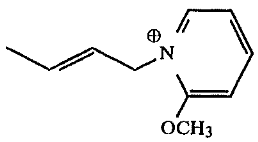 | " | " | " | 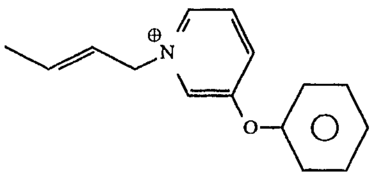 | " | " |
| " | 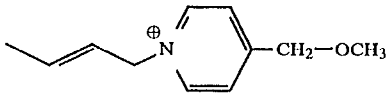 | " | " | " | 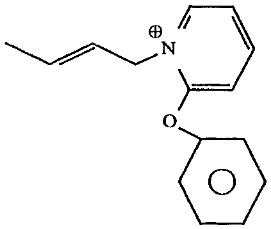 | " | " |

-continued
| | | | | | | | |
|---|---|---|---|---|---|---|---|
| " | 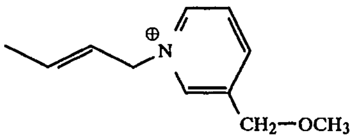 | " | " | " | 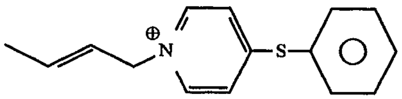 | " | " |
| 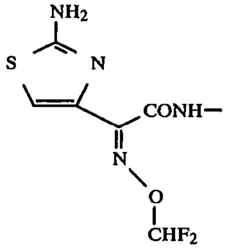 | 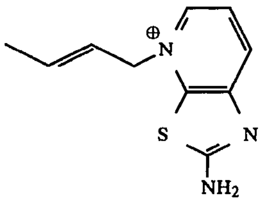 | O | $CO_2^{\ominus}$ | 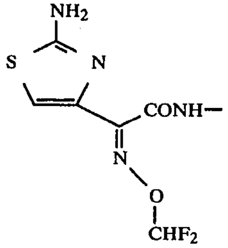 | 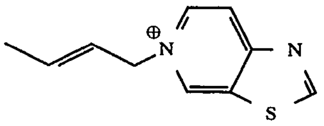 | O | $CO_2^{\ominus}$ |
| " | 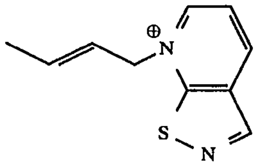 | " | " | " | 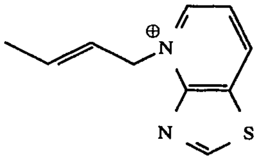 | " | " |
| " | 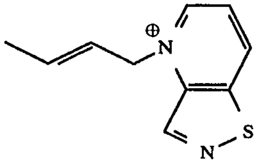 | " | " | " | 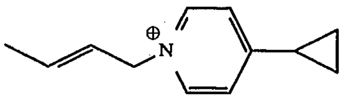 | " | " |
| " | 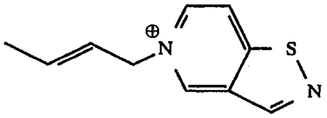 | " | " | " | 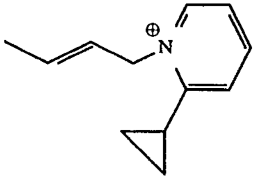 | " | " |

-continued
| | | | | | | | |
|---|---|---|---|---|---|---|---|
| " | 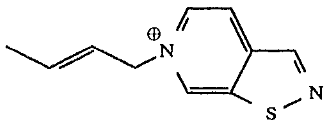 | " | " | " | 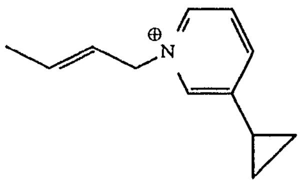 | " | " |
| 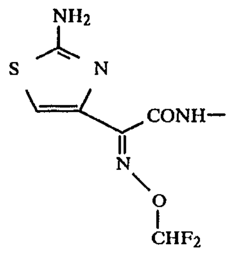 | 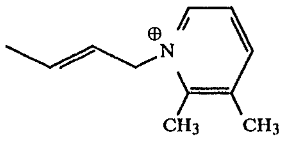 | O | $CO_2^{\ominus}$ | 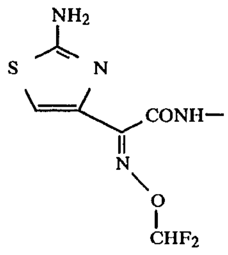 | 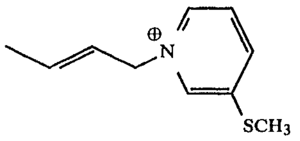 | O | $CO_2^{\ominus}$ |
| " | 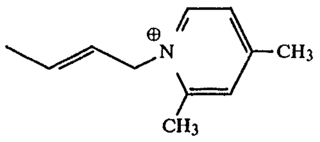 | " | " | " | 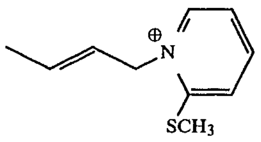 | " | " |
| " | 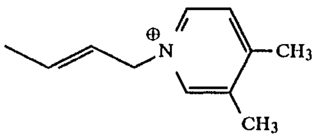 | " | " | " | 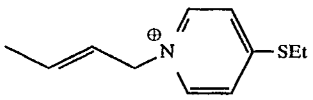 | " | " |
| " | 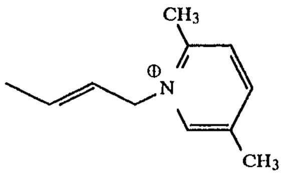 | " | " | " | 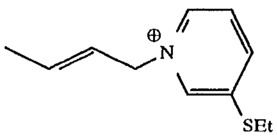 | " | " |
| " | 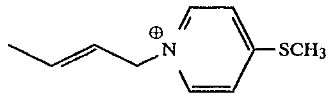 | " | " | " | 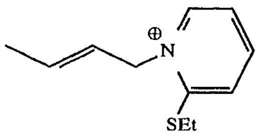 | " | " |

-continued
| | | | | | | | |
|---|---|---|---|---|---|---|---|
| 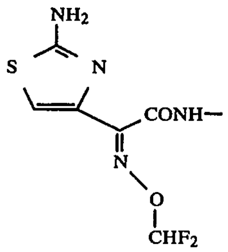 | 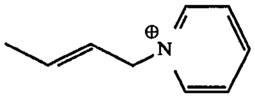 | O | $CO_2^{\ominus}$ | 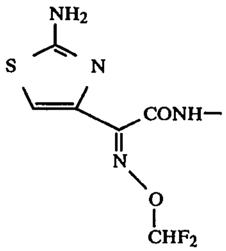 | 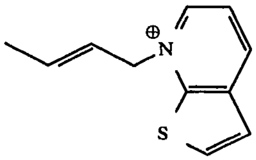 | O | $CO_2^{\ominus}$ |
| " | 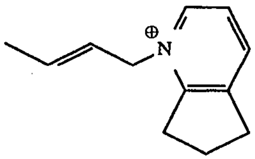 | " | " | " | 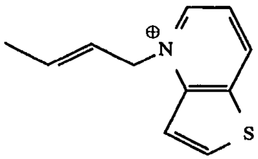 | " | " |
| " | 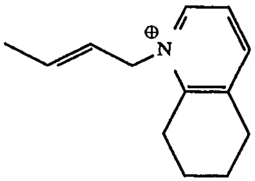 | " | " | " | 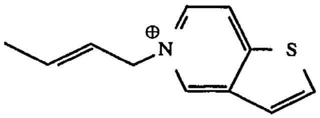 | " | " |
| " | 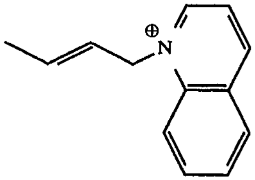 | " | " | " | 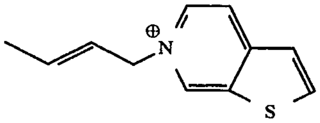 | " | " |
| " | 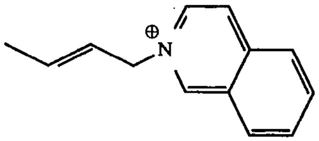 | " | " | " | 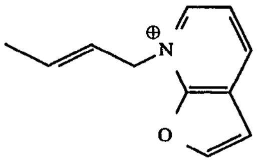 | " | " |

| | | | |
|---|---|---|---|
| 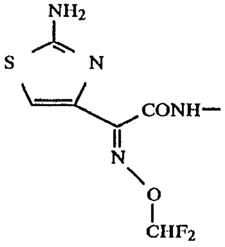 | 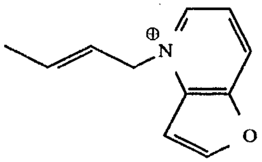 | O | $CO_2^{\ominus}$ |
| " | 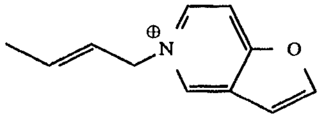 | " | " |
| " | 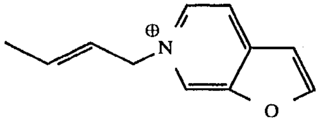 | " | " |
| " | 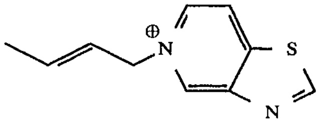 | " | " |
| " | 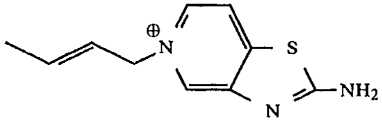 | " | " |
| | | | |
|---|---|---|---|
| 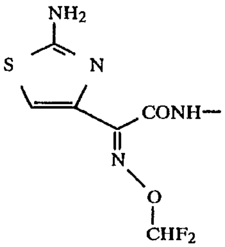 | 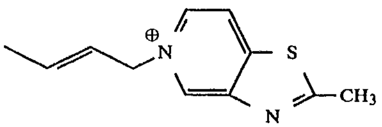 | O | $CO_2^{\ominus}$ |
| " | 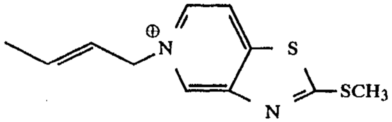 | " | " |
| " | 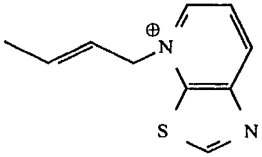 | " | " |
| " | 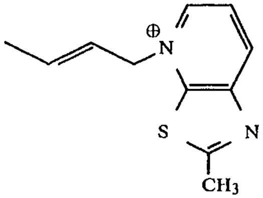 | " | " |
| " | 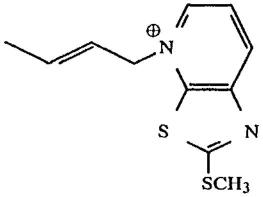 | " | " |

-continued
| | | | |
|---|---|---|---|
| 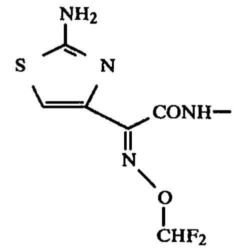 | 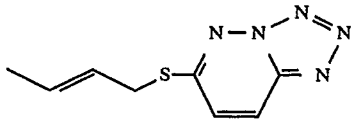 | O | $CO_2$ |
| " | 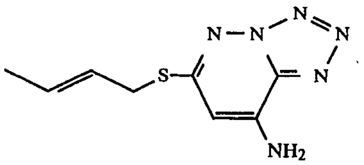 | " | " |
| " | 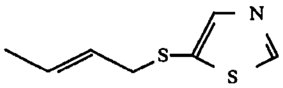 | " | " |
| " | 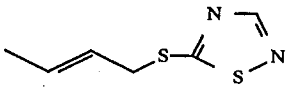 | " | " |
| " | 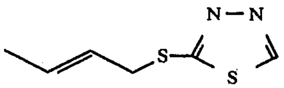 | " | " |
| 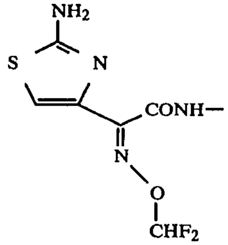 | 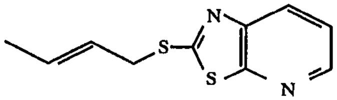 | O | $CO_2$ |
| 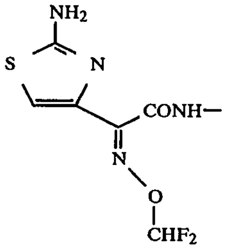 | 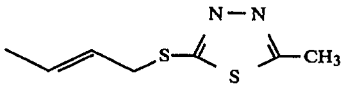 | O | $CO_2$ |
| " | 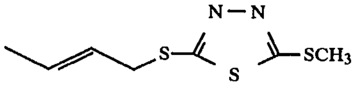 | " | " |
| " | 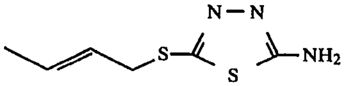 | " | " |
| " | 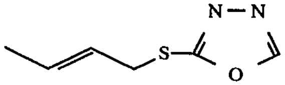 | " | " |
| " | 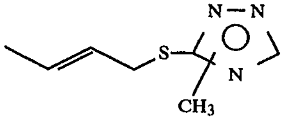 | " | " |

-continued
| | | | |
|---|---|---|---|
| " | 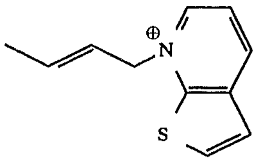 | | |
| " | 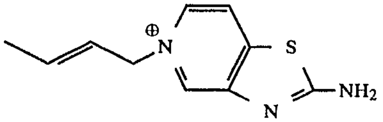 | | |
| 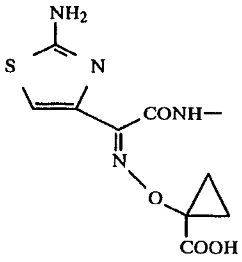 | 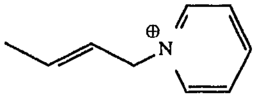 | O | $CO_2^{\ominus}$ |
| " | 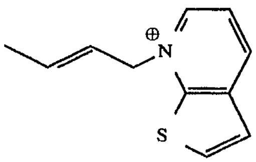 | " | " |
| " | 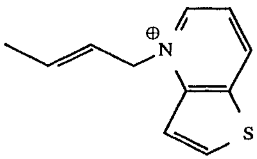 | " | " |
| " | 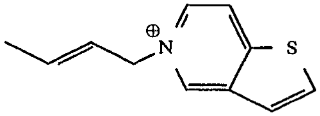 | " | " |
| | | | |
|---|---|---|---|
| 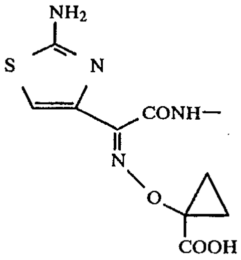 | 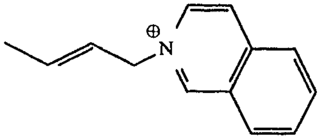 | O | $CO_2^{\ominus}$ |
| " | 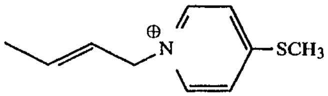 | " | " |
| " | 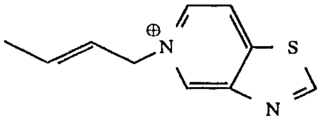 | " | " |
| " | 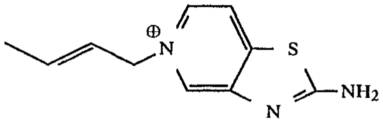 | " | " |

-continued
| | | | | | | | |
|---|---|---|---|---|---|---|---|
| " | 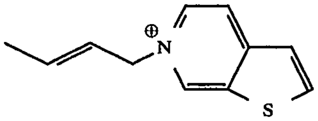 | " | " | " | 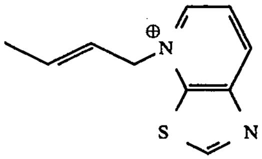 | " | " |
| 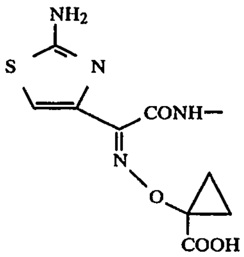 | 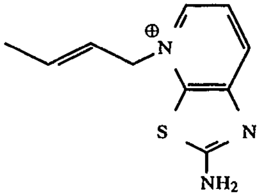 | O | $CO_2^{\ominus}$ | 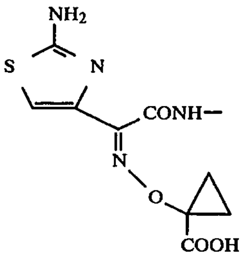 | 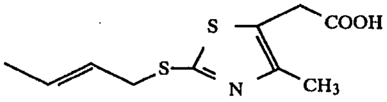 | O | $CO_2H$ |
| " | 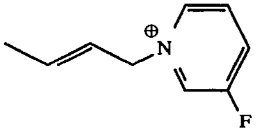 | " | " | " | 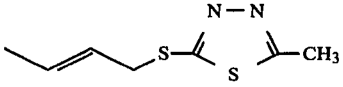 | " | " |
| " | 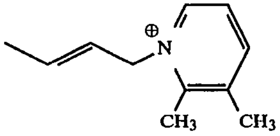 | " | " | " | 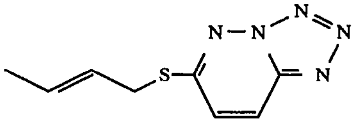 | " | " |
| " | 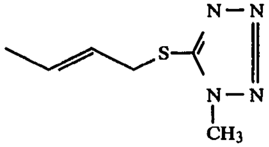 | " | $CO_2H$ | " | 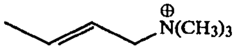 | " | $CO_2^{\ominus}$ |

-continued
| | | | | | | | |
|---|---|---|---|---|---|---|---|
| " | 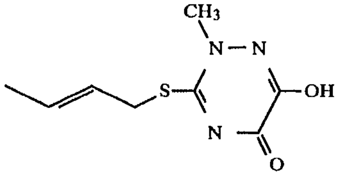 | " | " | " | 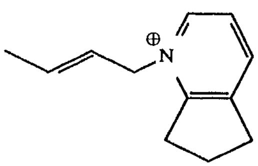 | " | " |
| 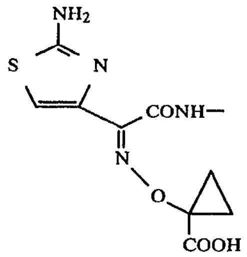 | 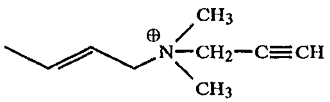 | O | $CO_2^{\ominus}$ | 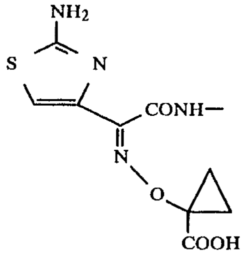 | 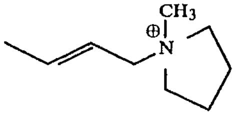 | O | $CO_2^{\ominus}$ |
| " | 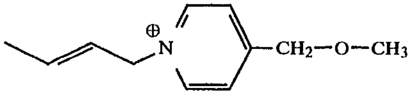 | " | " | " | 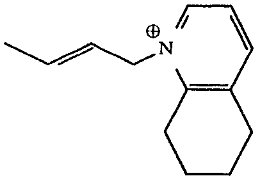 | " | " |
| " | 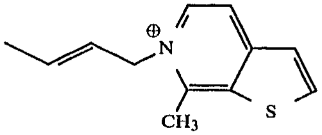 | " | " | " | 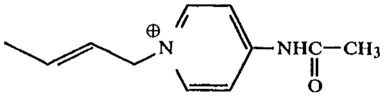 | " | " |
| " | 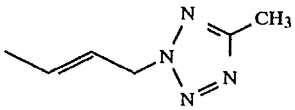 | " | $CO_2H$ | " | 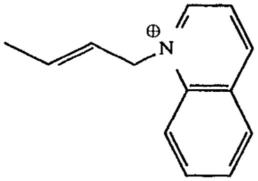 | " | " |

-continued
| | | | | | | | | | |
|---|---|---|---|---|---|---|---|---|---|
| " | 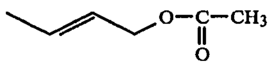 | " | " | " | 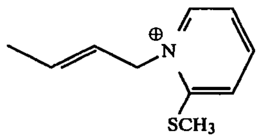 | " | " |
| 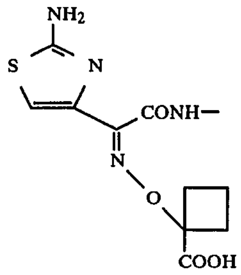 | 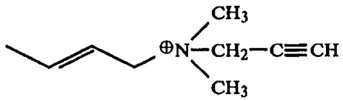 | O | $CO_2^{\ominus}$ | 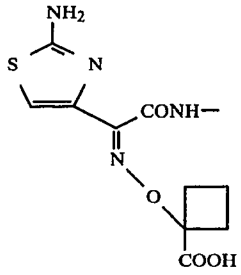 | 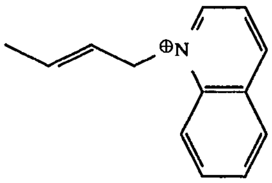 | O | $CO_2^{\ominus}$ |
| " | 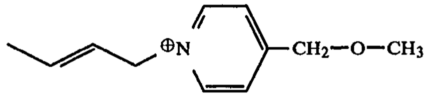 | " | " | " | 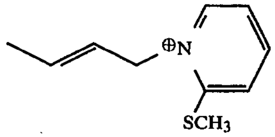 | " | " |
| " | 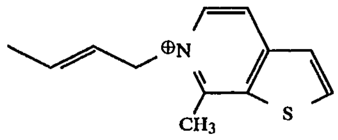 | " | " | " | 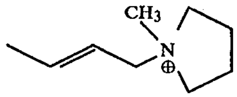 | " | " |
| " | 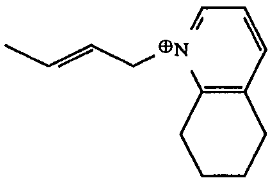 | " | " | " | 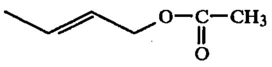 | " | $CO_2H$ |
| " | 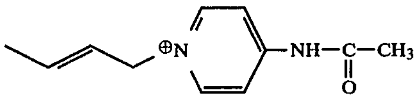 | " | " | " | 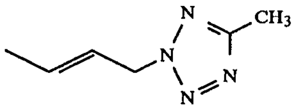 | " | " |

-continued
| | | | | | | | |
|---|---|---|---|---|---|---|---|
| 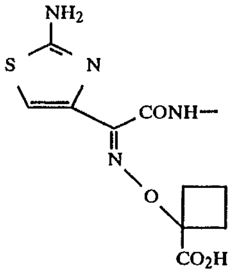 | 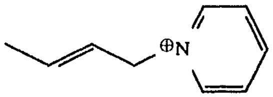 | O | $CO_2^{\ominus}$ | 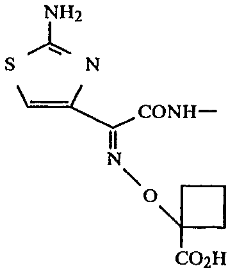 | 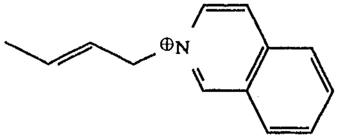 | O | $CO_2^{\ominus}$ |
| " | 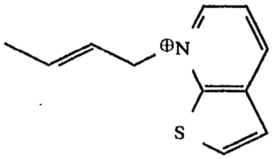 | " | " | " | 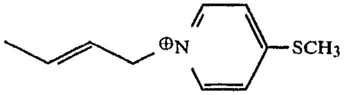 | " | " |
| " | 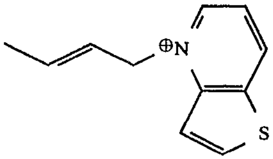 | " | " | " | 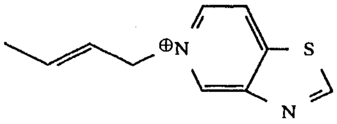 | " | " |
| " | 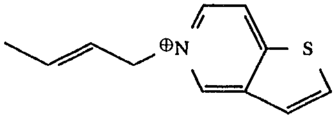 | " | " | " | 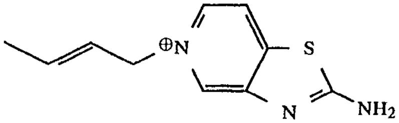 | " | " |
| " | 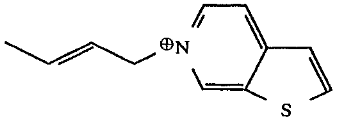 | " | " | " | 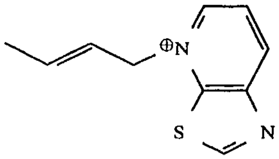 | " | " |

-continued
| | | | | | | | |
|---|---|---|---|---|---|---|---|
| 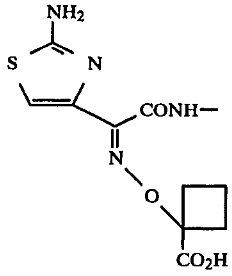 | 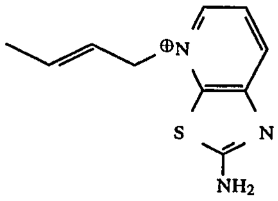 | O | $CO_2^{\ominus}$ | 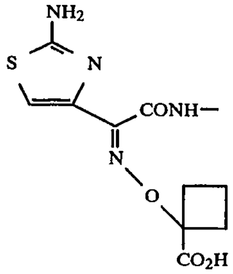 | 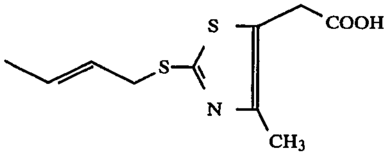 | O | $CO_2H$ |
| " | 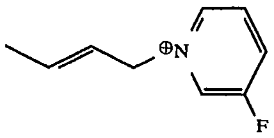 | " | " | " | 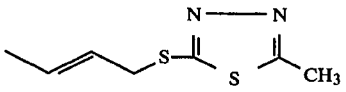 | " | " |
| " | 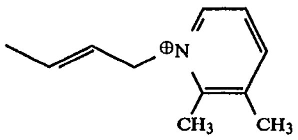 | " | " | " | 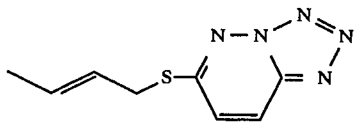 | " | " |
| " | 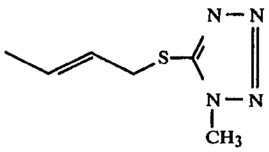 | " | $CO_2H$ | " | 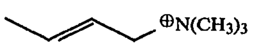 | " | $CO_2^{\ominus}$ |
| " | 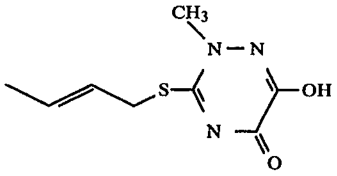 | " | " | " | 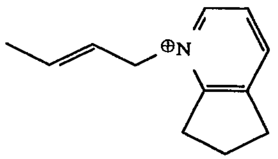 | " | " |

-continued
| | | | | | | | |
|---|---|---|---|---|---|---|---|
| 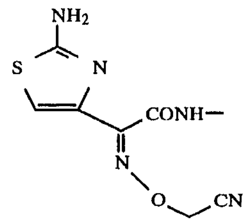 | 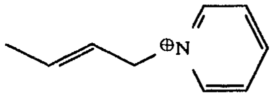 | O | $CO_2^{\ominus}$ | 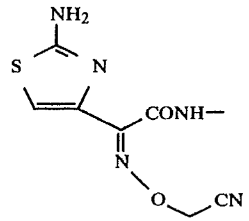 | 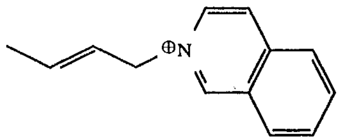 | O | $CO_2^{\ominus}$ |
| " | 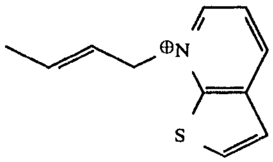 | " | " | " | 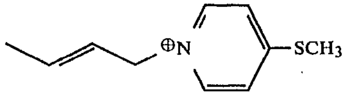 | " | " |
| " | 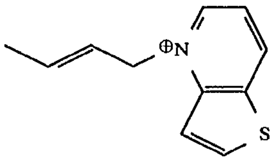 | " | " | " | 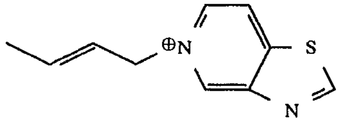 | " | " |
| " | 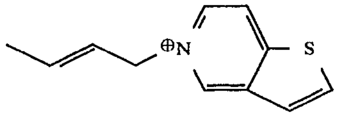 | " | " | " | 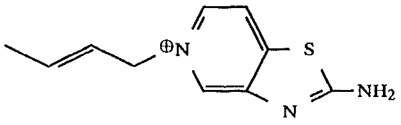 | " | " |
| " | 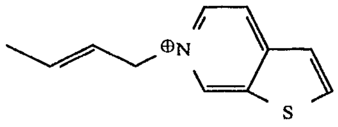 | " | " | " | 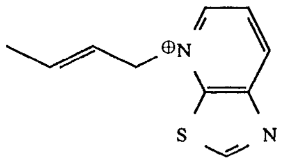 | " | " |

-continued
| | | | | | | | |
|---|---|---|---|---|---|---|---|
| 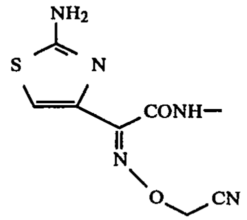 | 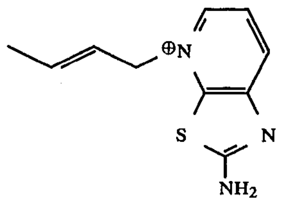 | O | $CO_2^{\ominus}$ | 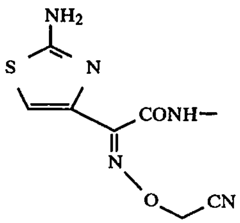 | 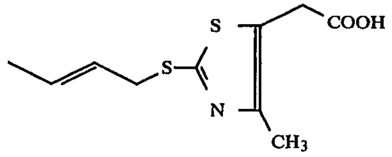 | O | $CO_2H$ |
| " | 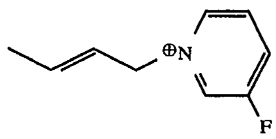 | " | " | " | 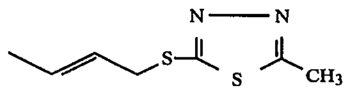 | " | " |
| " | 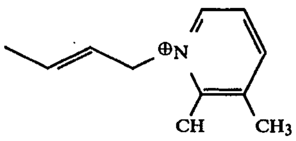 | " | " | " | 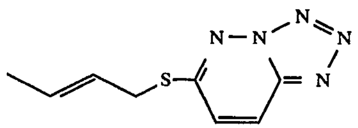 | " | " |
| " | 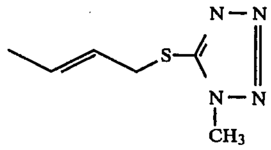 | " | $CO_2H$ | " | 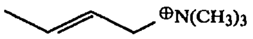 | " | $CO_2^{\ominus}$ |
| " | 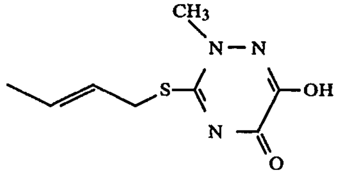 | " | " | " | 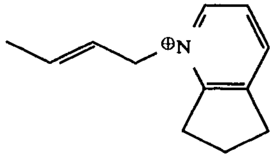 | " | " |

-continued
| | | | | | | | |
|---|---|---|---|---|---|---|---|
| 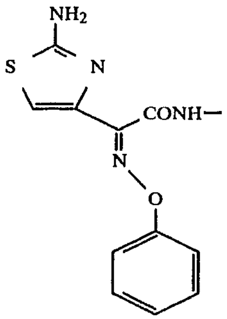 | 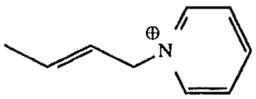 | O | $CO_2^{\ominus}$ | 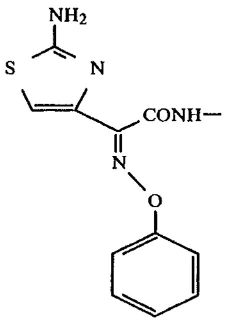 | 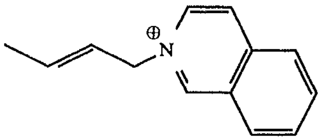 | O | $CO_2^{\ominus}$ |
| ″ | 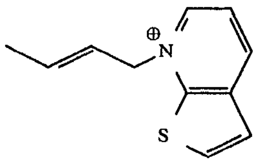 | ″ | ″ | ″ | 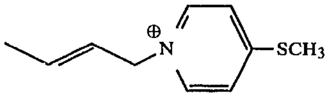 | ″ | ″ |
| ″ | 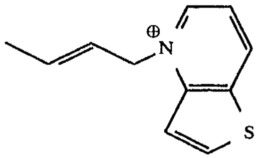 | ″ | ″ | ″ | 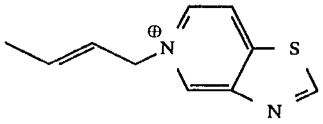 | ″ | ″ |
| ″ | 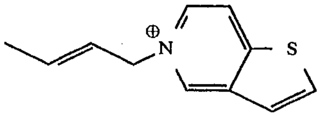 | ″ | ″ | ″ | 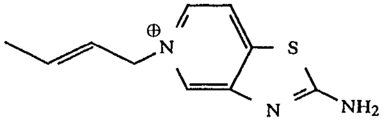 | ″ | ″ |
| ″ | 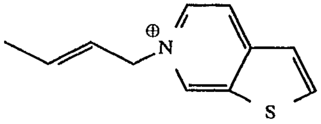 | ″ | ″ | ″ | 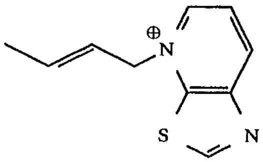 | ″ | ″ |

-continued
| | | | | | | | |
|---|---|---|---|---|---|---|---|
| 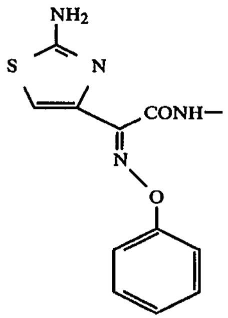 | 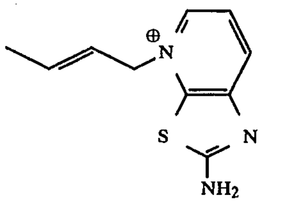 | O | $CO_2^{\ominus}$ | 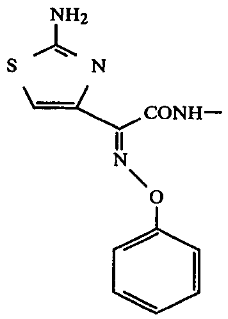 | 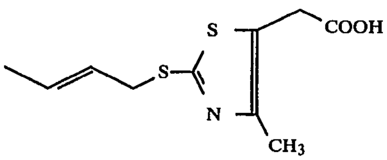 | O | $CO_2H$ |
| " | 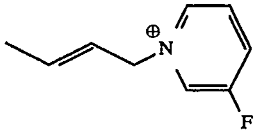 | " | " | " | 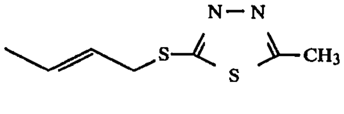 | " | " |
| " | 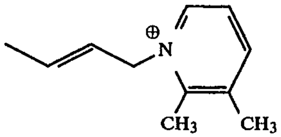 | " | " | " | 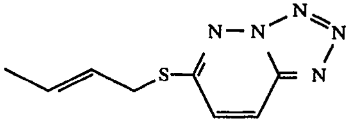 | " | " |
| " | 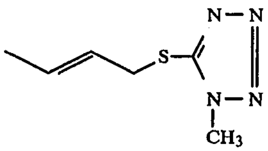 | " | $CO_2H$ | " | 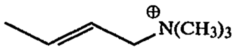 | " | $CO_2^{\ominus}$ |
| " | 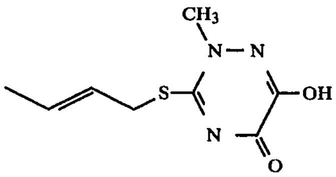 | " | " | " | 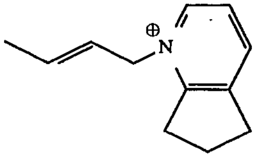 | " | " |

-continued
| | | | |
|---|---|---|---|
| 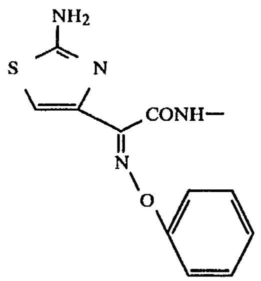 | 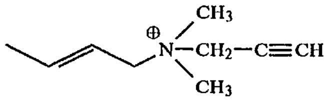 | O | $CO_2^{\ominus}$ |
| " | 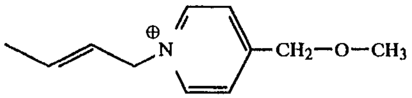 | " | " |
| " | 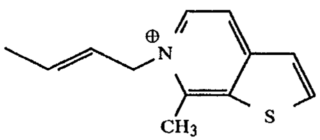 | " | " |
| " | 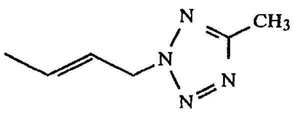 | " | $CO_2H$ |
| " | 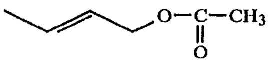 | " | " |
| 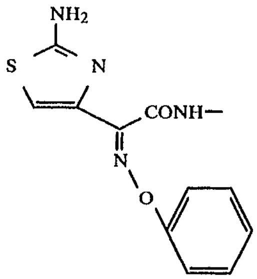 | 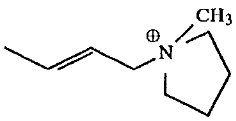 | O | $CO_2^{\ominus}$ |
| " | 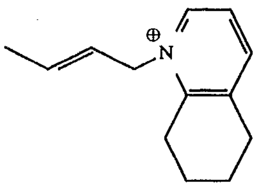 | " | " |
| " | 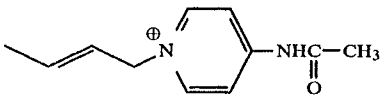 | " | " |
| " | 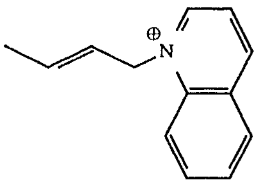 | " | " |
| " | 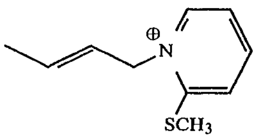 | " | " |

-continued
| | | | |
|---|---|---|---|
| 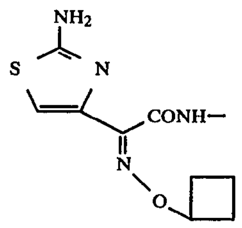 | 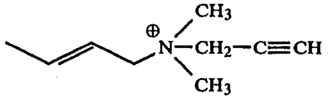 | O | $CO_2^{\ominus}$ |
| " | 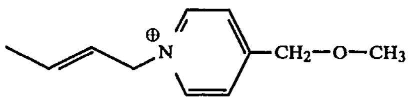 | " | " |
| " | 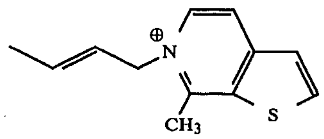 | " | " |
| " | 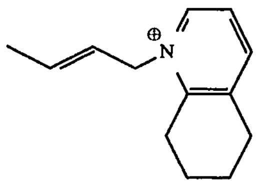 | " | " |
| " | 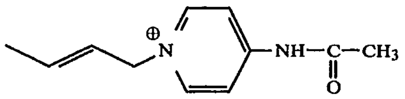 | " | " |
| 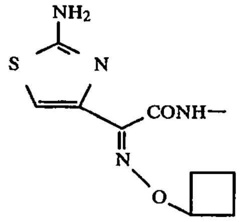 | 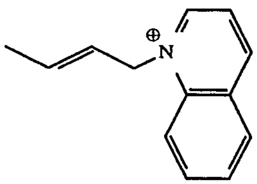 | O | $CO_2^{\ominus}$ |
| " | 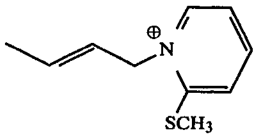 | " | " |
| " | 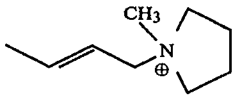 | " | " |
| " | 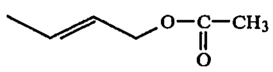 | " | $CO_2H$ |
| " | 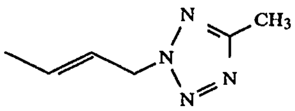 | " | " |

| | | | |
|---|---|---|---|
| 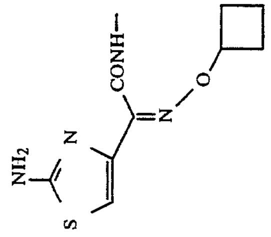 | 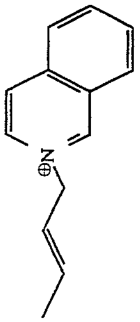 | O | $CO_2^{\ominus}$ |
| " | 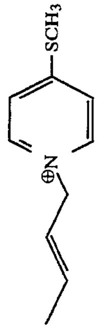 | " | " |
| " | 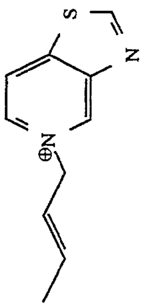 | " | " |
| " | 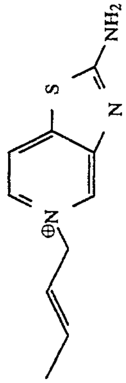 | " | " |
| " | 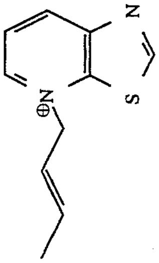 | " | " |
| 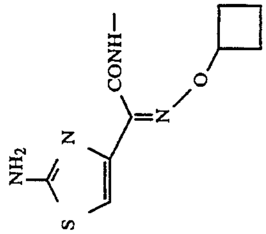 | 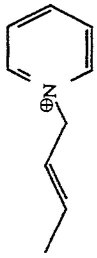 | O | $CO_2^{\ominus}$ |
| " | 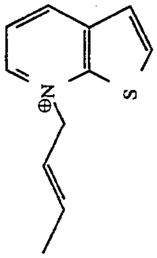 | " | " |
| " | 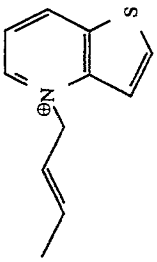 | " | " |
| " | 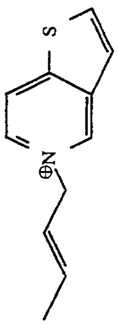 | " | " |
| " | 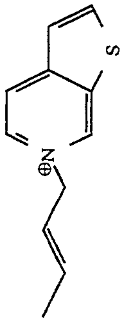 | " | " |

-continued
| | | | |
|---|---|---|---|
| 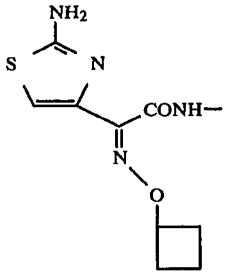 | 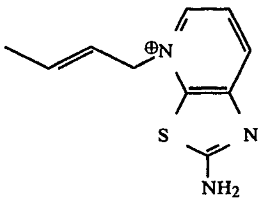 | O | $CO_2^{\ominus}$ |
| " | 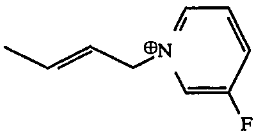 | " | " |
| " | 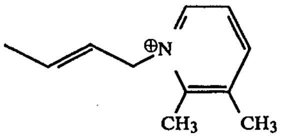 | " | " |
| " | 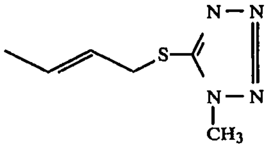 | " | $CO_2H$ |
| " | 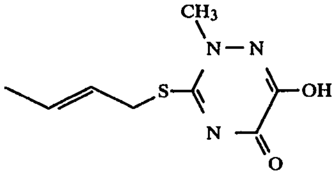 | " | " |
| 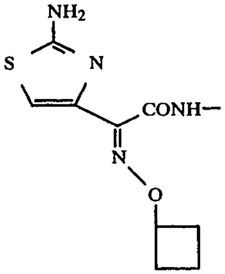 | 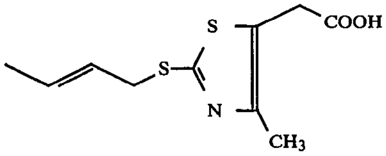 | O | $CO_2H$ |
| " | 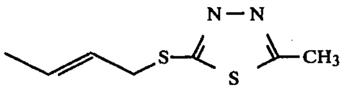 | " | " |
| " | 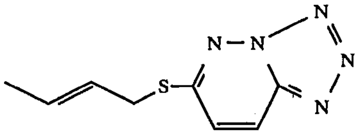 | " | " |
| " | 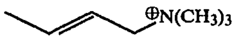 | " | $CO_2^{\ominus}$ |
| " | 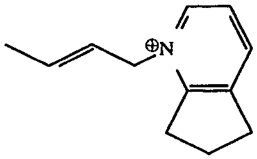 | " | " |

-continued
| | | | | | | | |
|---|---|---|---|---|---|---|---|
| 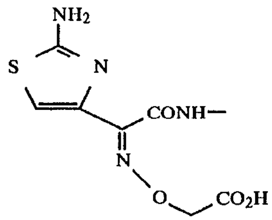 | 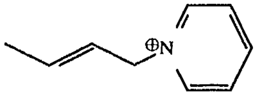 | O | $CO_2^{\ominus}$ | 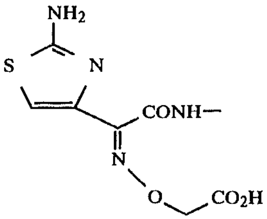 | 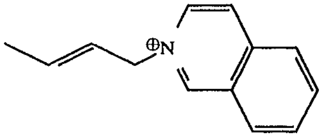 | O | $CO_2^{\ominus}$ |
| " | 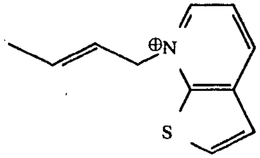 | " | " | " | 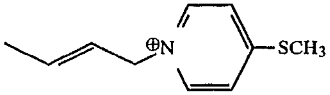 | " | " |
| " | 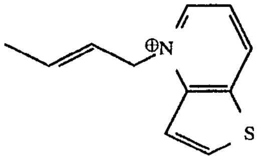 | " | " | " | 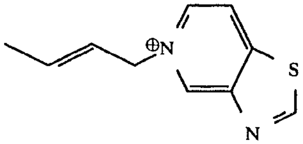 | " | " |
| " | 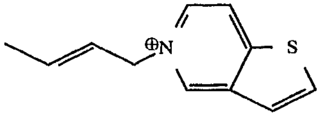 | " | " | " | 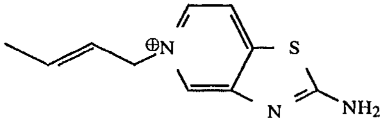 | " | " |
| " | 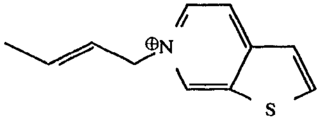 | " | " | " | 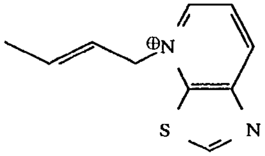 | " | " |

-continued
| | | | | | | | |
|---|---|---|---|---|---|---|---|
| 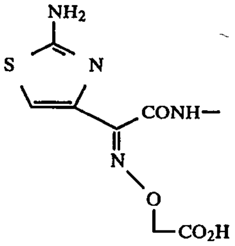 | 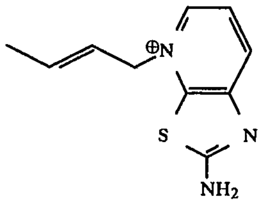 | O | $CO_2^{\ominus}$ | 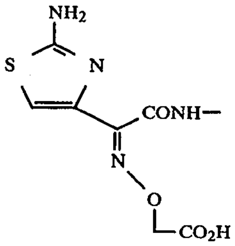 | 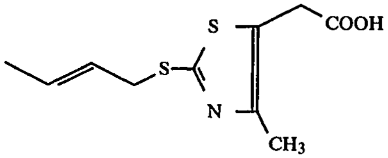 | O | $CO_2H$ |
| " | 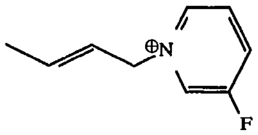 | " | " | " | 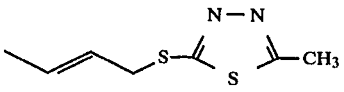 | " | " |
| " | 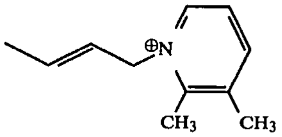 | " | " | " | 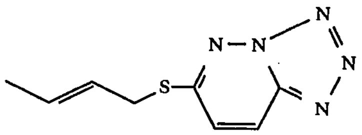 | " | " |
| " | 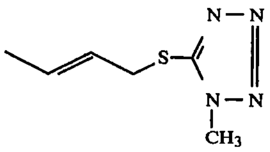 | " | $CO_2H$ | " | 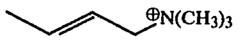 | " | $CO_2^{\ominus}$ |
| " | 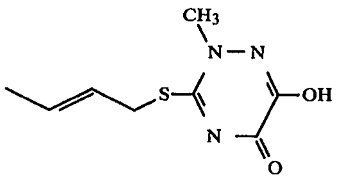 | " | " | " | 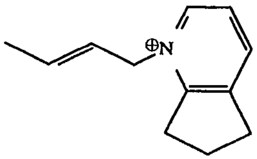 | " | " |

-continued
| | | | | | | | |
|---|---|---|---|---|---|---|---|
| 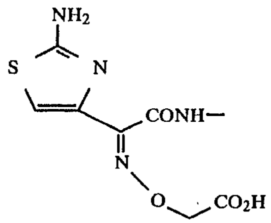 | 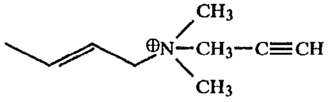 | O | $CO_2^{\ominus}$ | 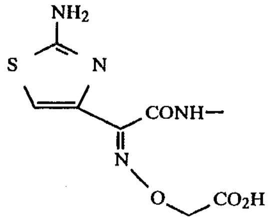 | 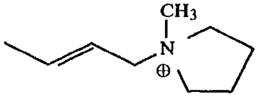 | O | $CO_2^{\ominus}$ |
| " | 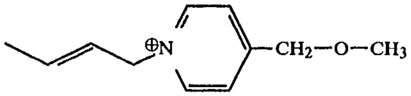 | " | " | " | 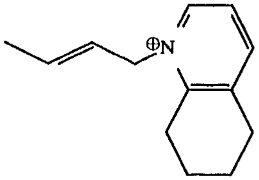 | " | " |
| " | 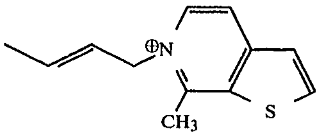 | " | " | " | 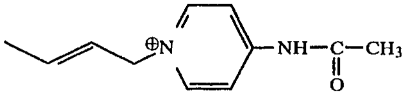 | " | " |
| " | 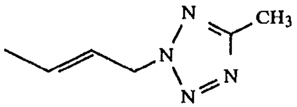 | " | $CO_2H$ | " | 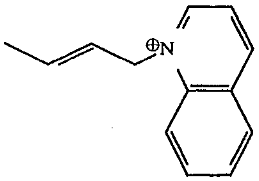 | " | " |
| " | 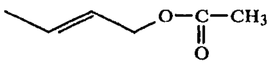 | " | " | " | 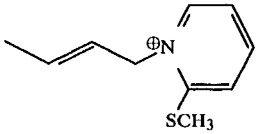 | " | " |

| | | | |
|---|---|---|---|
| 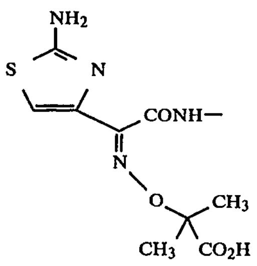 | 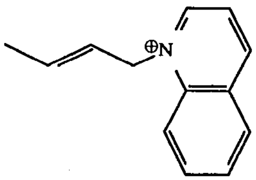 | O | $CO_2^{\ominus}$ |
| " | 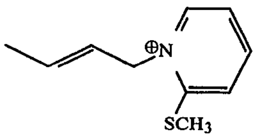 | " | " |
| " | 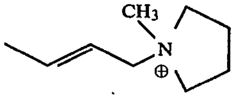 | " | " |
| " | 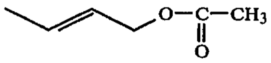 | " | $CO_2H$ |
| " | 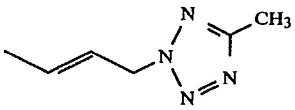 | " | " |
| 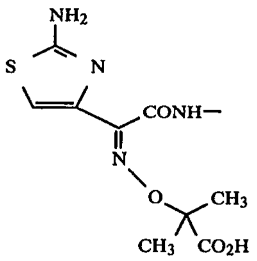 | 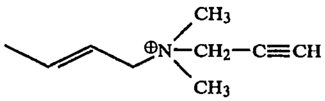 | O | $CO_2^{\ominus}$ |
| " | 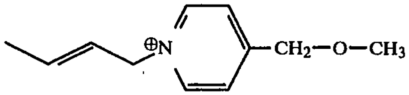 | " | " |
| " | 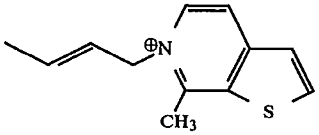 | " | " |
| " | 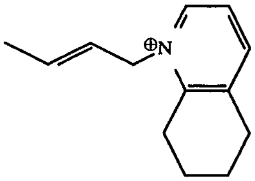 | " | " |
| " | 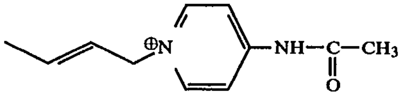 | " | " |

-continued
| | | | | | | | |
|---|---|---|---|---|---|---|---|
| 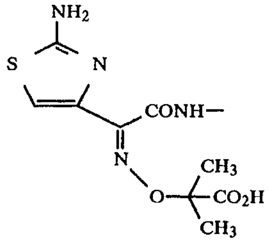 | 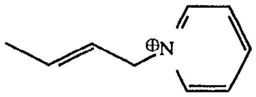 | O | $CO_2^{\ominus}$ | 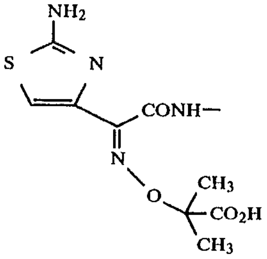 | 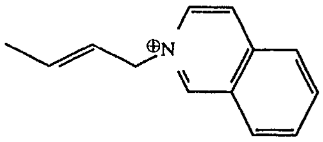 | O | $CO_2^{\ominus}$ |
| " | 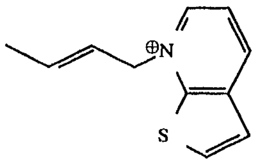 | " | " | " | 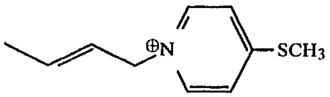 | " | " |
| " | 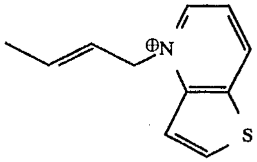 | " | " | " | 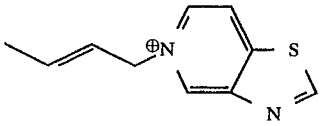 | " | " |
| " | 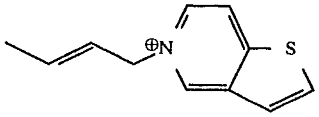 | " | " | " | 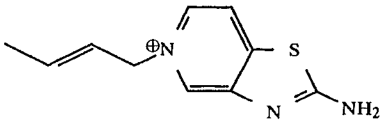 | " | " |
| " | 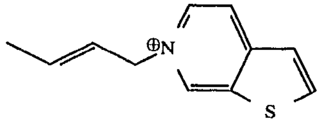 | " | " | " | 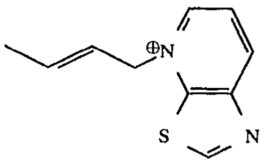 | " | " |

-continued
| | | | | | | | |
|---|---|---|---|---|---|---|---|
| 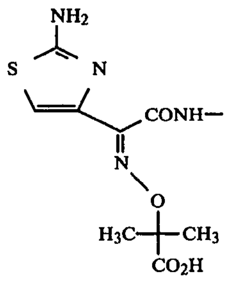 | 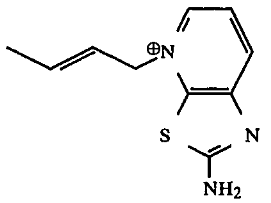 | O | $CO_2^{\ominus}$ | 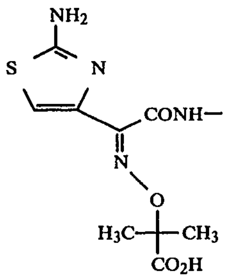 | 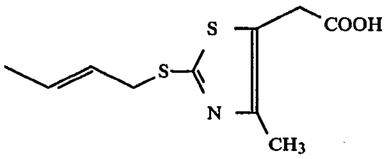 | O | $CO_2H$ |
| " | 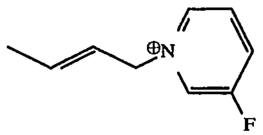 | " | " | " | 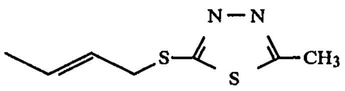 | " | " |
| " | 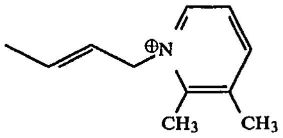 | " | " | " | 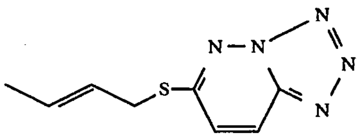 | " | " |
| " | 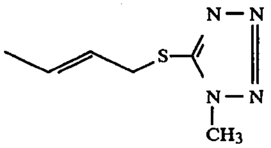 | " | $CO_2H$ | " | 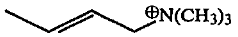 | " | $CO_2^{\ominus}$ |
| " | 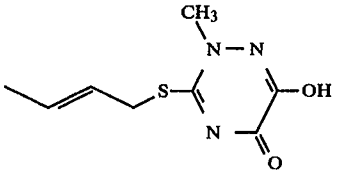 | " | " | " | 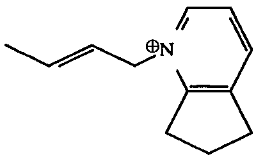 | " | " |

-continued
| | | | |
|---|---|---|---|
| 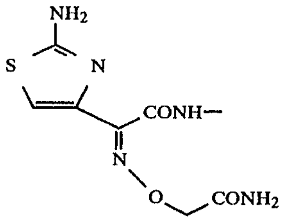 | 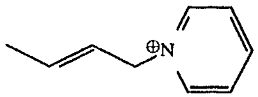 | O | $CO_2^{\ominus}$ |
| " | 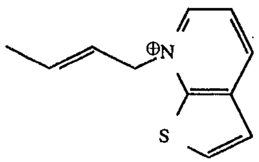 | " | " |
| " | 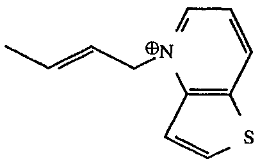 | " | " |
| " | 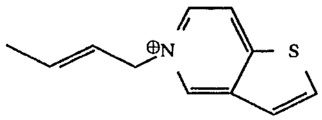 | " | " |
| " | 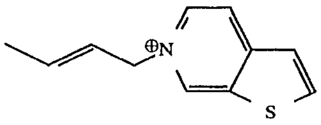 | " | " |
| | | | |
|---|---|---|---|
| 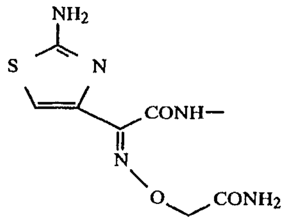 | 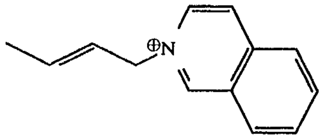 | O | $CO_2^{\ominus}$ |
| " | 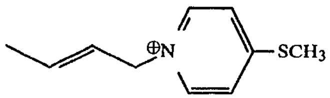 | " | " |
| " | 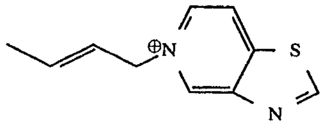 | " | " |
| " | 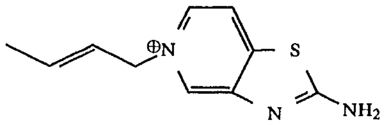 | " | " |
| " | 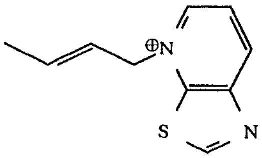 | " | " |

-continued
| | | | | | | | |
|---|---|---|---|---|---|---|---|
| 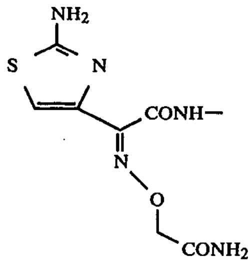 | 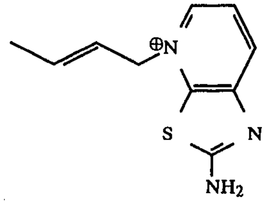 | O | $CO_2^{\ominus}$ | 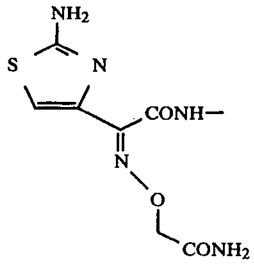 | 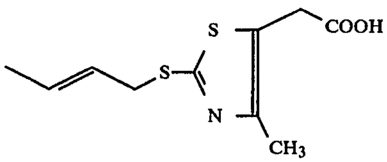 | O | $CO_2H$ |
| " | 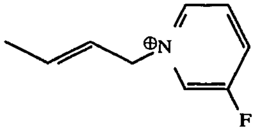 | " | " | " | 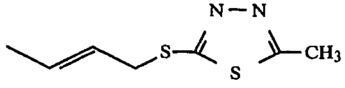 | " | " |
| " | 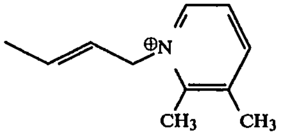 | " | " | " | 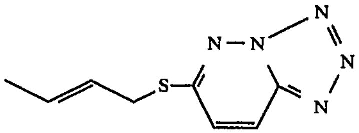 | " | " |
| " | 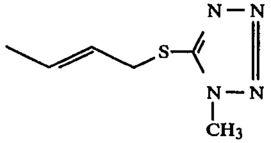 | " | $CO_2H$ | " | 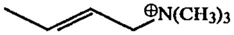 | " | $CO_2^{\ominus}$ |
| " | 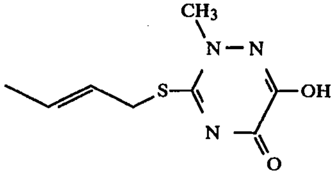 | " | " | " | 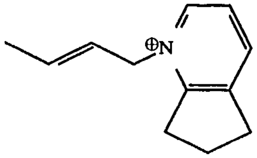 | " | " |

| | | | |
|---|---|---|---|
| 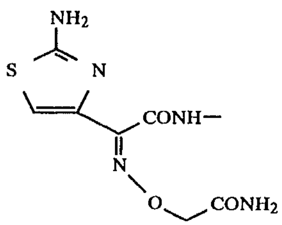 | 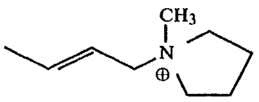 | O | $CO_2^{\ominus}$ |
| " | 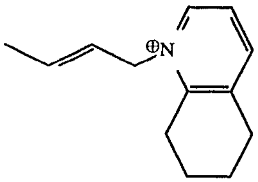 | " | " |
| " | 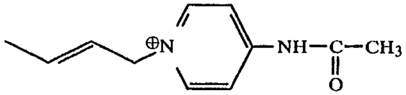 | " | " |
| " | 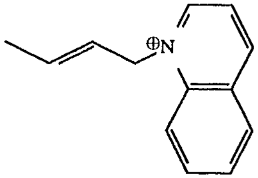 | " | " |
| " | 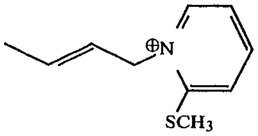 | " | " |
| | | | |
|---|---|---|---|
| 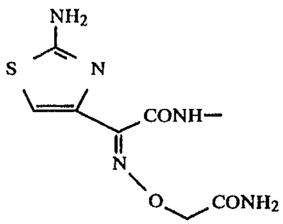 | 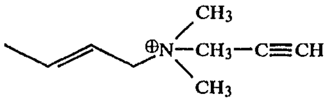 | O | $CO_2^{\ominus}$ |
| " | 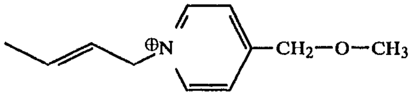 | " | " |
| " | 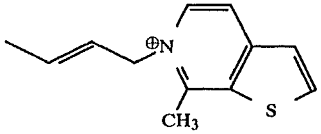 | " | " |
| " | 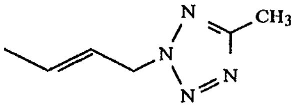 | " | $CO_2H$ |
| " | 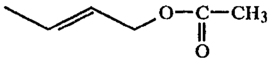 | " | " |

-continued
| | | | | | | | |
|---|---|---|---|---|---|---|---|
| 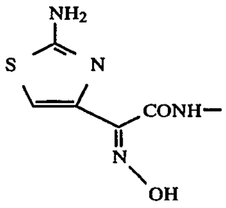 | 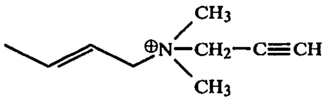 | O | $CO_2^{\ominus}$ | 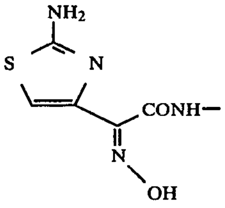 | 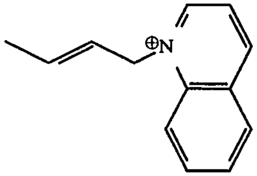 | O | $CO_2^{\ominus}$ |
| " | 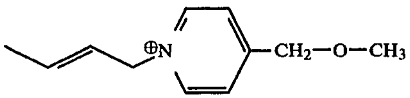 | " | " | " | 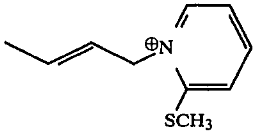 | " | " |
| " | 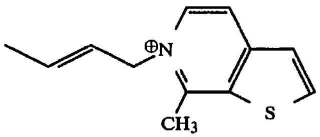 | " | " | " | 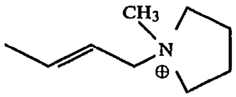 | " | " |
| " | 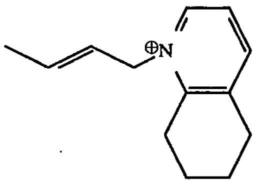 | " | " | " | 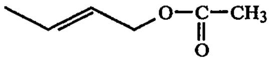 | " | $CO_2H$ |
| " | 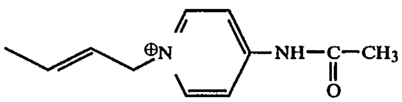 | " | " | " | 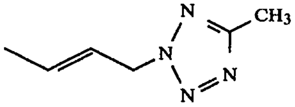 | " | " |
| 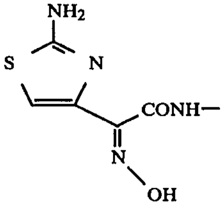 | 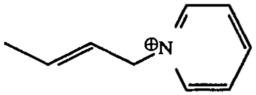 | O | $CO_2^{\ominus}$ | 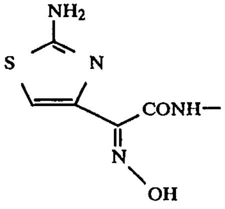 | 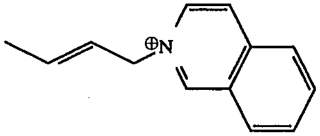 | O | $CO_2^{\ominus}$ |

-continued
| | | | | | | | |
|---|---|---|---|---|---|---|---|
| " | 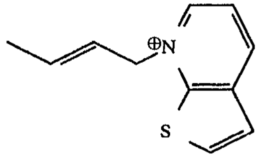 | " | " | " | 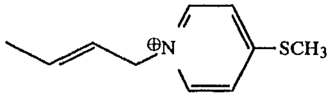 | " | " |
| " | 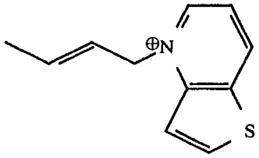 | " | " | " | 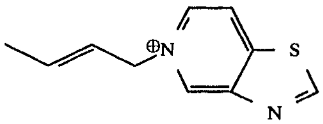 | " | " |
| " | 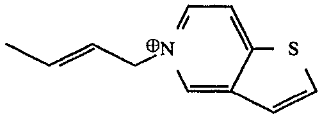 | " | " | " | 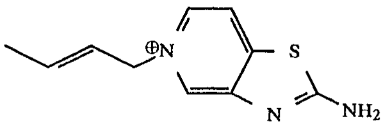 | " | " |
| " | 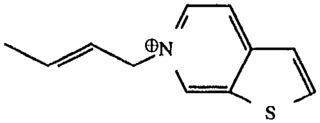 | " | " | " | 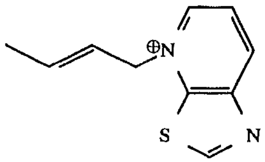 | " | " |
| 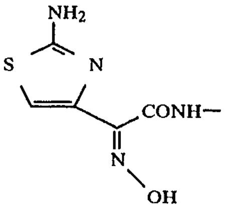 | 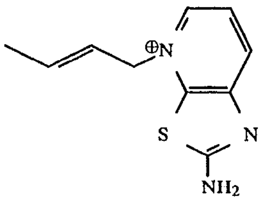 | O | $CO_2^{\ominus}$ | 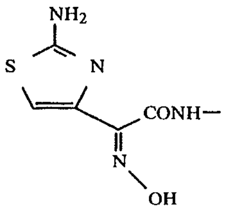 | 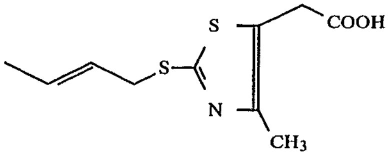 | O | $CO_2H$ |
| " | 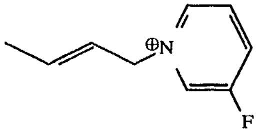 | " | " | " | 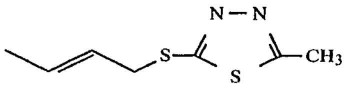 | " | " |

-continued
| | | | | | | | |
|---|---|---|---|---|---|---|---|
| " | 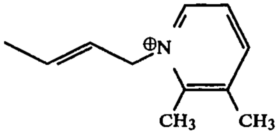 | " | " | " | 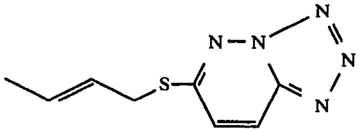 | " | " |
| " | 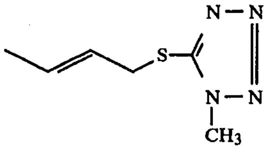 | " | $CO_2H$ | " | 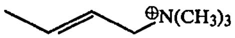 | " | $CO_2^{\ominus}$ |
| " | 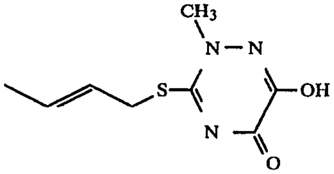 | " | " | " | 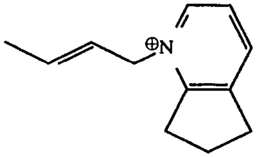 | " | " |
| 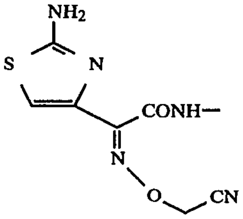 | 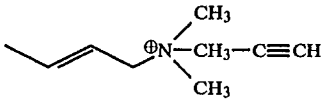 | O | $CO_2^{\ominus}$ | 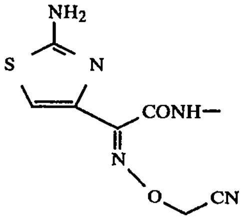 | 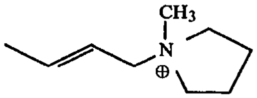 | O | $CO_2^{\ominus}$ |
| " | 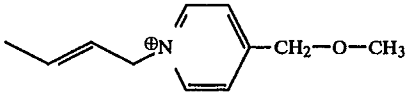 | " | " | " | 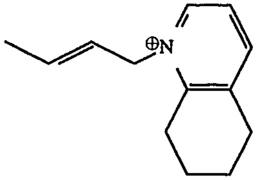 | " | " |
| " | 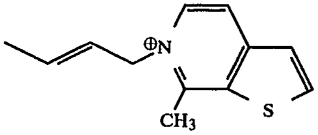 | " | " | " | 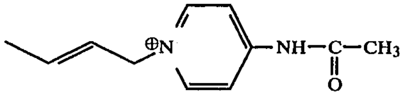 | " | " |

-continued
| | | | | | | | |
|---|---|---|---|---|---|---|---|
| " | 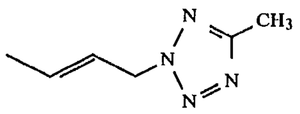 | " | CO$_2$H | " | 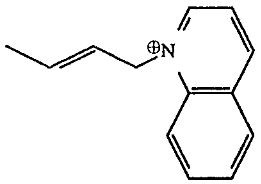 | " | " |
| " | 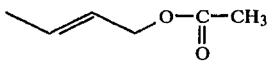 | " | " | " | 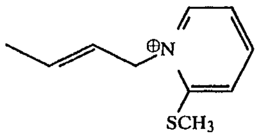 | " | " |

| | | | |
|---|---|---|---|
| 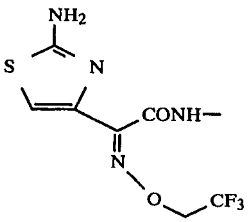 | 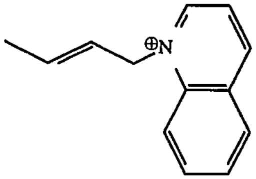 | O | $CO_2^{\ominus}$ |
| " | 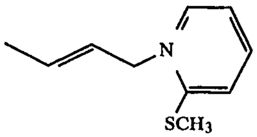 | " | " |
| " | 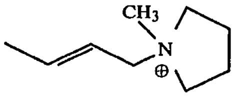 | " | " |
| " | 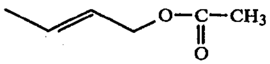 | " | $CO_2H$ |
| " | 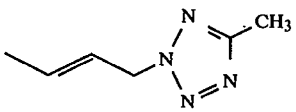 | " | " |
| 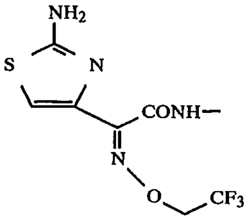 | 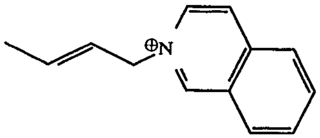 | O | $CO_2^{\ominus}$ |
| | | | |
|---|---|---|---|
| 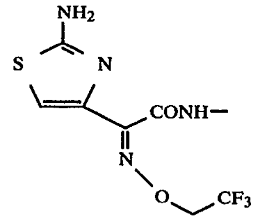 | 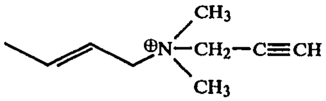 | O | $CO_2^{\ominus}$ |
| " | 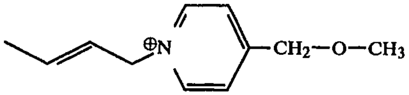 | " | " |
| " | 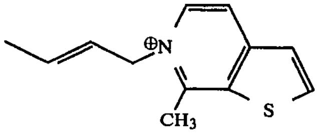 | " | " |
| " | 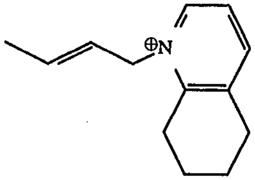 | " | " |
| " | 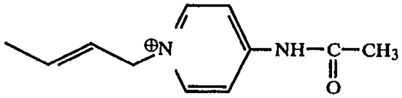 | " | " |
| 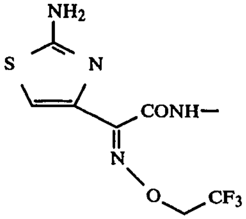 | 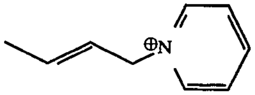 | O | $CO_2^{\ominus}$ |

-continued
| | | | | | | | |
|---|---|---|---|---|---|---|---|
| " | 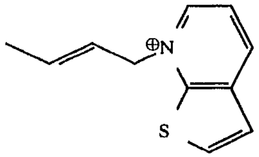 | " | " | " | 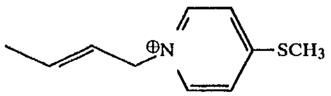 | " | " |
| " | 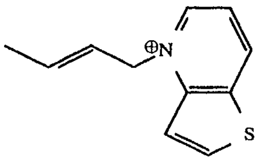 | " | " | " | 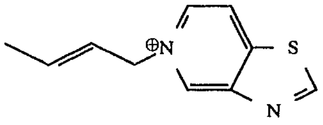 | " | " |
| " | 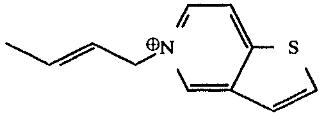 | " | " | " | 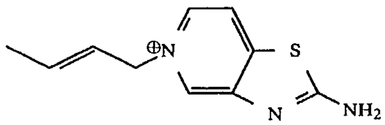 | " | " |
| " | 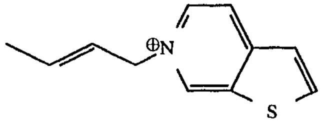 | " | " | " | 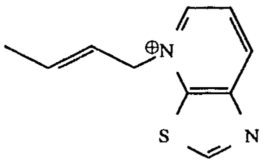 | " | " |
| 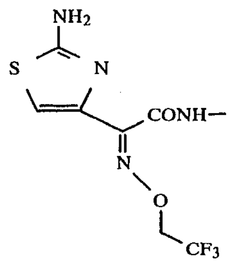 | 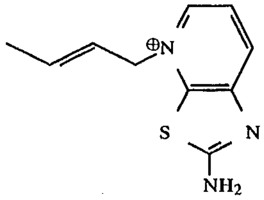 | O | $CO_2^{\ominus}$ | 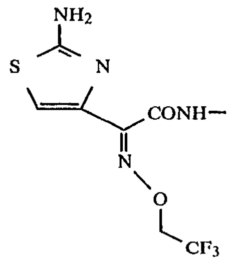 | 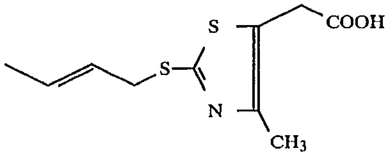 | O | $CO_2H$ |

-continued
| | | | | | | | |
|---|---|---|---|---|---|---|---|
| " | 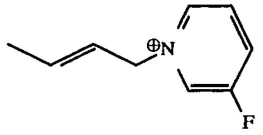 | " | " | " | 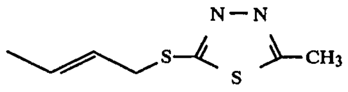 | " | " |
| " | 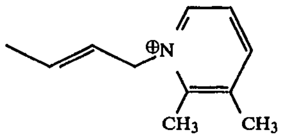 | " | " | " | 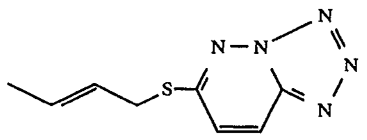 | " | " |
| " | 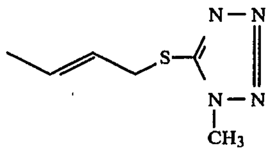 | " | $CO_2H$ | " | 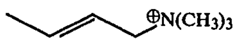 | " | $CO_2^{\ominus}$ |
| " | 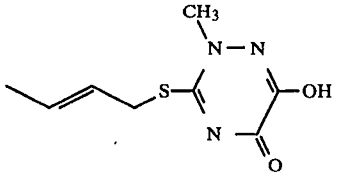 | " | " | " | 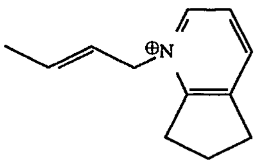 | " | " |
| 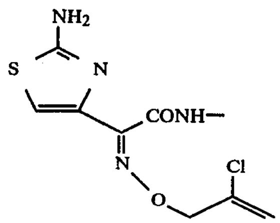 | 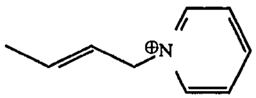 | O | $CO_2^{\ominus}$ | 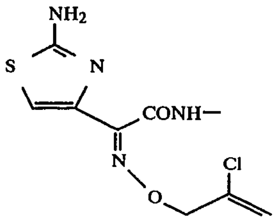 | 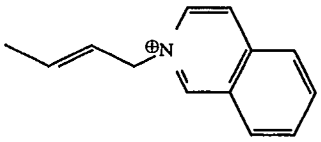 | O | $CO_2^{\ominus}$ |
| " | 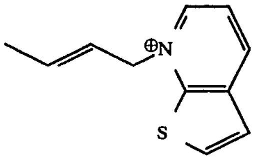 | " | " | " | 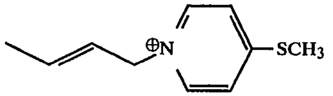 | " | " |

-continued
| | | | | | | | |
|---|---|---|---|---|---|---|---|
| " | 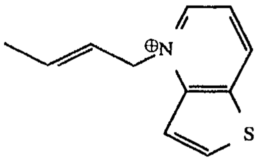 | " | " | " | 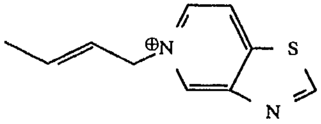 | " | " |
| " | 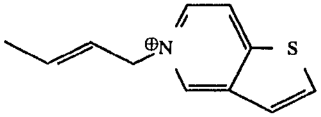 | " | " | " | 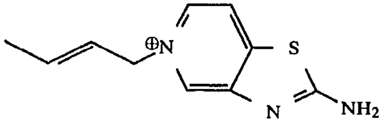 | " | " |
| " | 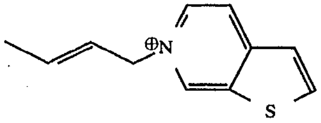 | " | " | " | 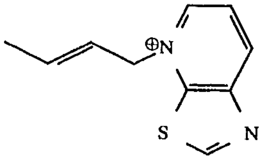 | " | " |
| 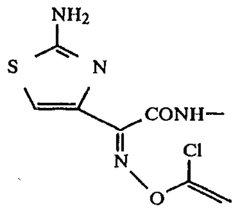 | 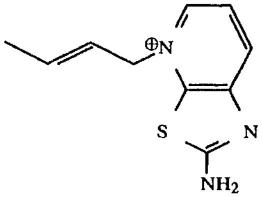 | O | $CO_2^{\ominus}$ | 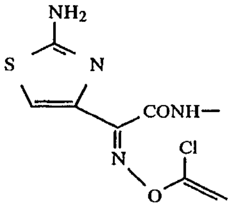 | 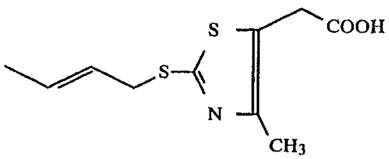 | O | $CO_2H$ |
| " | 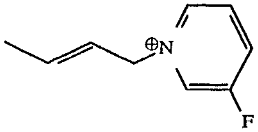 | " | " | " | 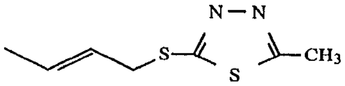 | " | " |
| " | 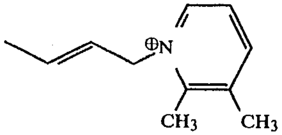 | " | " | " | 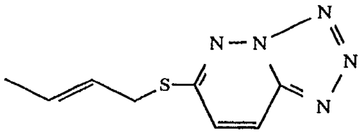 | " | " |

-continued
| | | | | | | | |
|---|---|---|---|---|---|---|---|
| " | 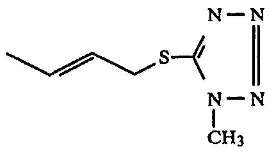 | " | $CO_2H$ | " | 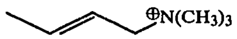 | " | $CO_2^{\ominus}$ |
| " | 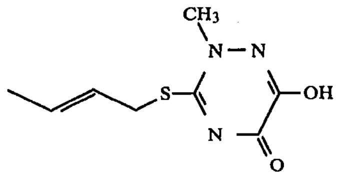 | " | " | " | 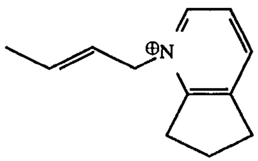 | " | " |

| | | | |
|---|---|---|---|
| 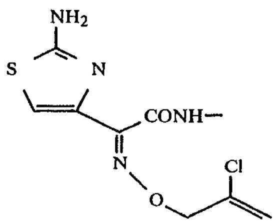 | 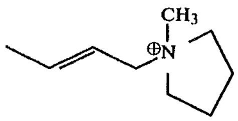 | O | $CO_2^{\ominus}$ |
| " | 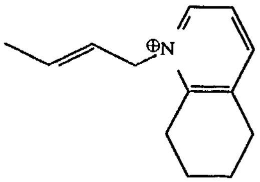 | " | " |
| " | 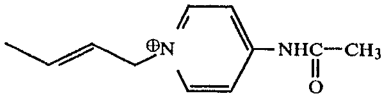 | " | " |
| " | 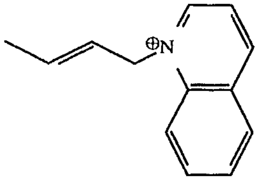 | " | " |
| " | 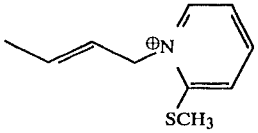 | " | " |
| 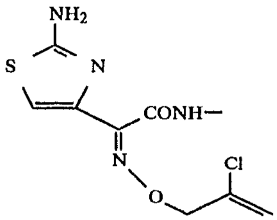 | 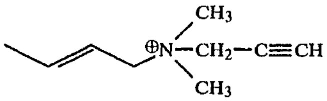 | O | $CO_2^{\ominus}$ |
| " | 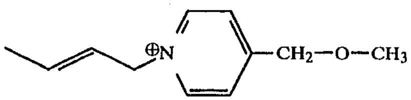 | " | " |
| " | 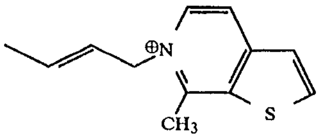 | " | " |
| " | 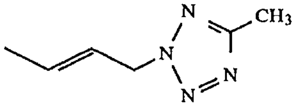 | " | $CO_2H$ |
| " | 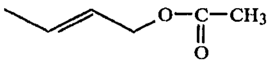 | " | " |

-continued
| | | | | | | | |
|---|---|---|---|---|---|---|---|
| 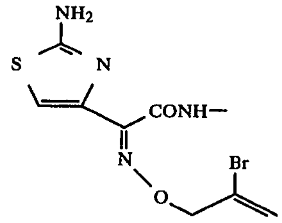 | 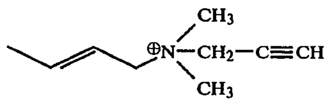 | O | $CO_2^{\ominus}$ | 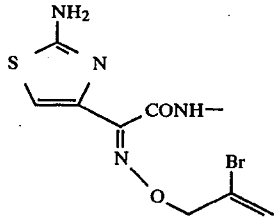 | 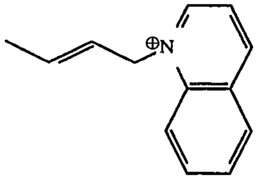 | O | $CO_2^{\ominus}$ |
| " | 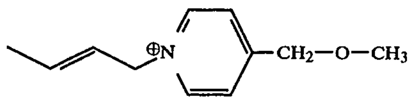 | " | " | " | 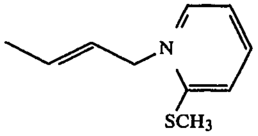 | " | " |
| " | 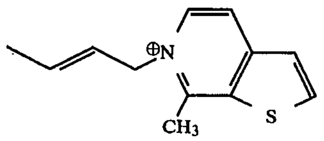 | " | " | " | 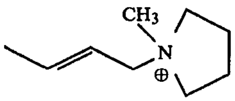 | " | " |
| " | 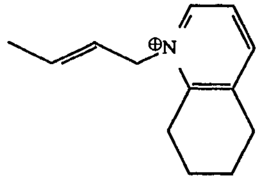 | " | " | " | 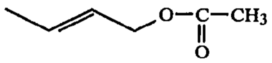 | " | $CO_2H$ |
| " | 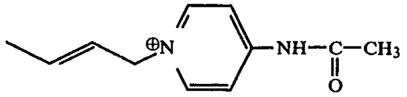 | " | " | " | 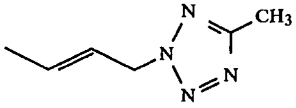 | " | " |
| 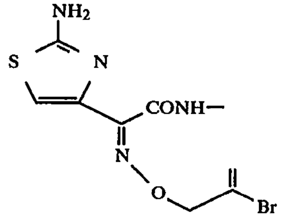 | 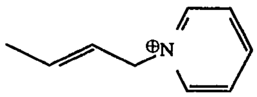 | O | $CO_2^{\ominus}$ | 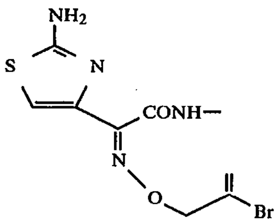 | 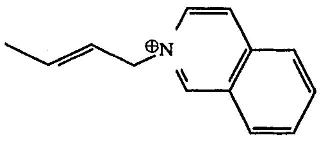 | O | $CO_2^{\ominus}$ |

-continued
| | | | | | | | |
|---|---|---|---|---|---|---|---|
| " | 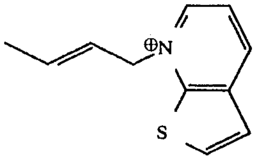 | " | " | " | 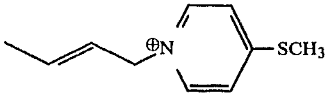 | " | " |
| " | 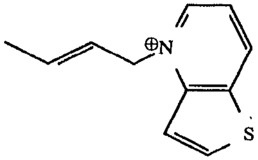 | " | " | " | 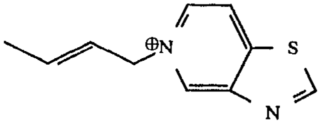 | " | " |
| " | 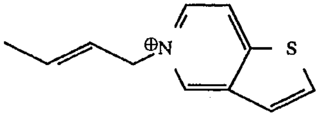 | " | " | " | 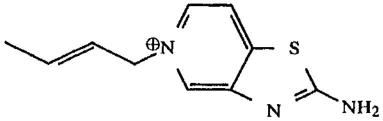 | " | " |
| " | 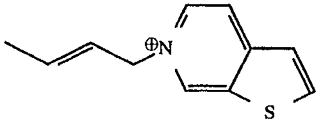 | " | " | " | 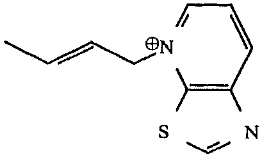 | " | " |
| 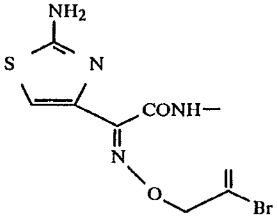 | 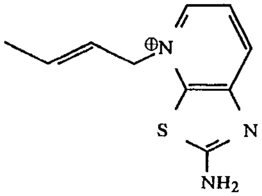 | O | $CO_2^{\ominus}$ | 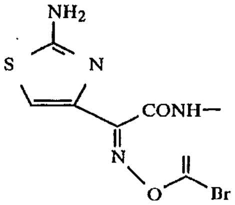 | 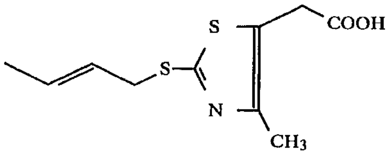 | O | $CO_2H$ |
| " | 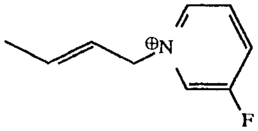 | " | " | " | 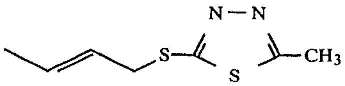 | " | " |

-continued
| | | | | | | | |
|---|---|---|---|---|---|---|---|
| " | 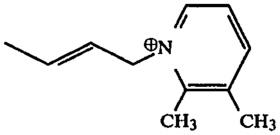 | " | " | " | 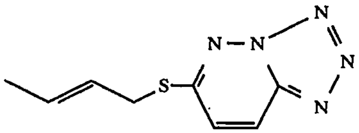 | " | " |
| " | 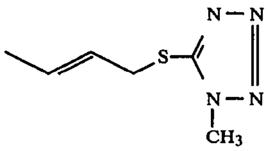 | " | $CO_2H$ | " | 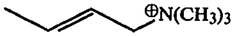 | " | $CO_2^{\ominus}$ |
| " | 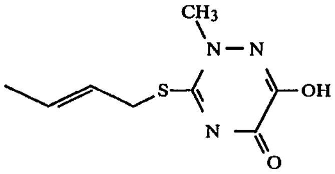 | " | " | " | 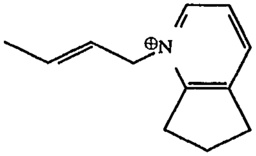 | " | " |

| R | $R_{1A}$ | $n_2$ | $CO_2A$ | R | $R_{1A}$ | $n_2$ | $CO_2A$ |
|---|---|---|---|---|---|---|---|
| 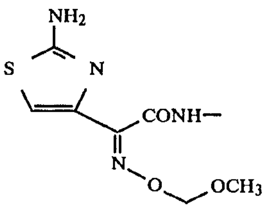 | 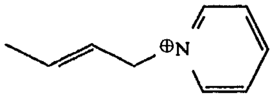 | 0 | $CO_2^{\ominus}$ | 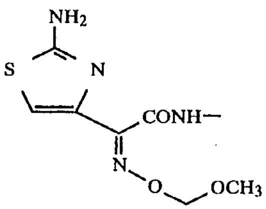 | 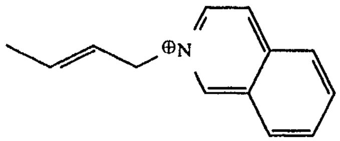 | 0 | $CO_2^{\ominus}$ |
| " | 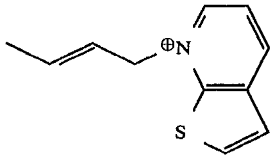 | " | " | " | 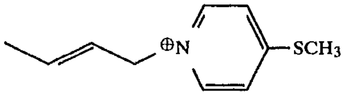 | " | " |
| " | 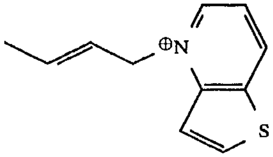 | " | " | " | 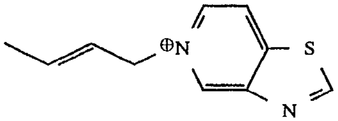 | " | " |
| " | 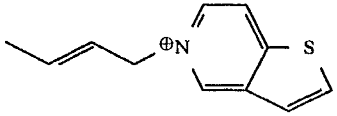 | " | " | " | 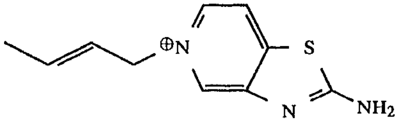 | " | " |
| " | 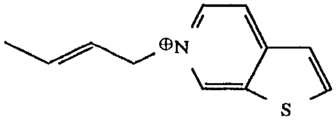 | " | " | " | 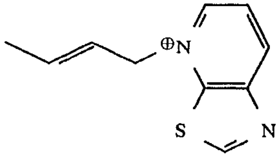 | " | " |

-continued
| R | $R_{1A}$ | $n_2$ | $CO_2A$ | R | $R_{1A}$ | $n_2$ | $CO_2A$ |
|---|---|---|---|---|---|---|---|
| 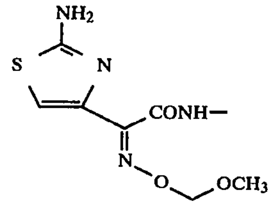 | 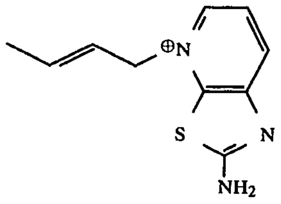 | 0 | $CO_2^{\ominus}$ | 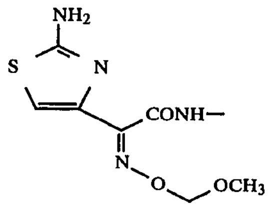 | 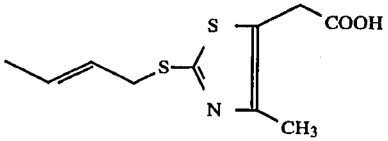 | 0 | $CO_2H$ |
| " | 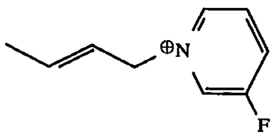 | " | " | " | 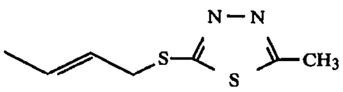 | " | " |
| " | 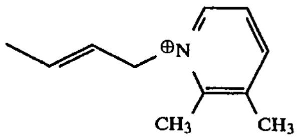 | " | " | " | 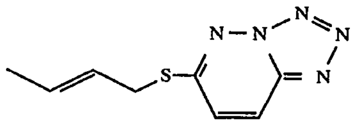 | " | " |
| " | 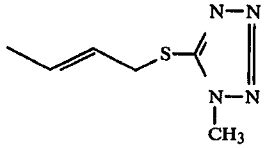 | " | $CO_2H$ | " | 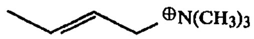 | " | $CO_2^{\ominus}$ |
| " | 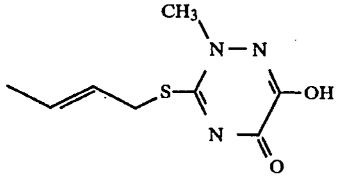 | " | " | " | 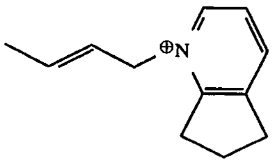 | " | " |

-continued
| R | $R_{1A}$ | $n_2$ | $CO_2A$ | R | $R_{1A}$ | $n_2$ | $CO_2A$ |
|---|---|---|---|---|---|---|---|
| 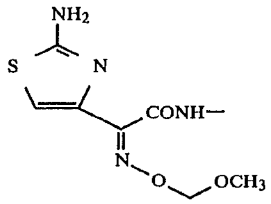 | 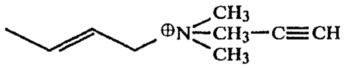 | 0 | $CO_2^{\ominus}$ | 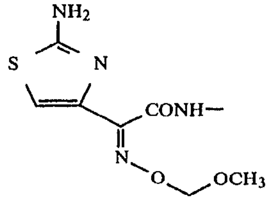 | 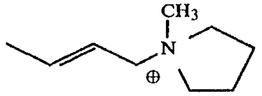 | 0 | $CO_2^{\ominus}$ |
| " | 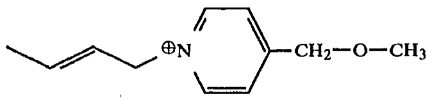 | " | " | " | 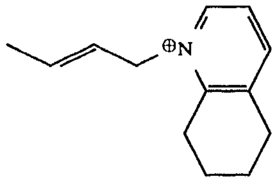 | " | " |
| " | 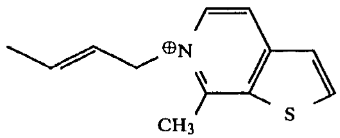 | " | " | " | 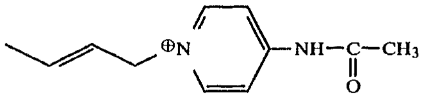 | " | " |
| " | 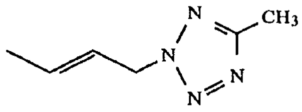 | " | $CO_2H$ | " | 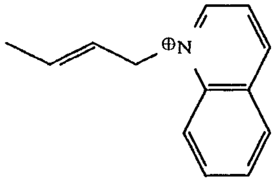 | " | " |
| " | 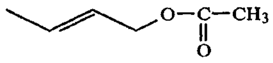 | " | " | " | 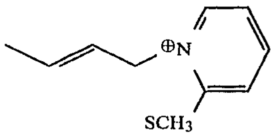 | " | " |

-continued
| R | $R_{1A}$ | $n_2$ | $CO_2A$ | R | $R_{1A}$ | $n_2$ | $CO_2A$ |
|---|---|---|---|---|---|---|---|
| 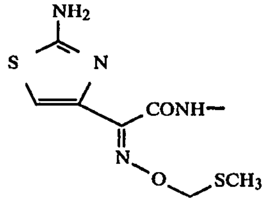 | 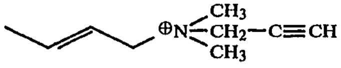 | 0 | $CO_2^{\ominus}$ | 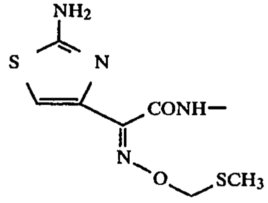 | 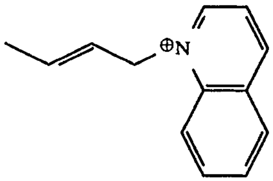 | 0 | $CO_2^{\ominus}$ |
| " | 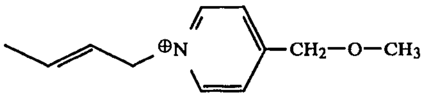 | " | " | " | 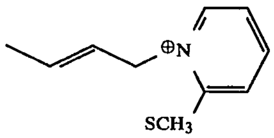 | " | " |
| " | 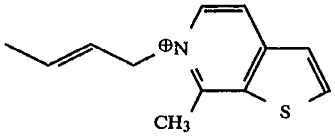 | " | " | " | 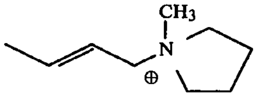 | " | " |
| " | 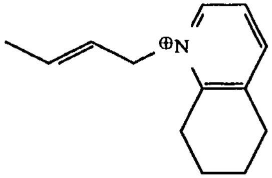 | " | " | " | 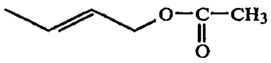 | " | $CO_2H$ |
| " | 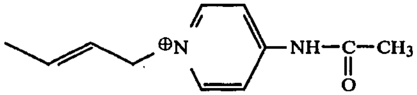 | " | " | " | 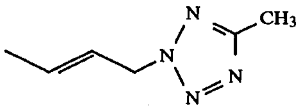 | " | " |
| 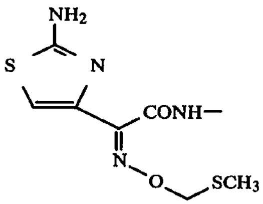 | 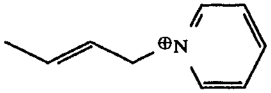 | 0 | $CO_2^{\ominus}$ | 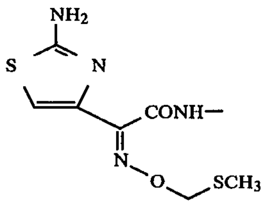 | 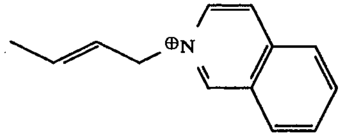 | 0 | $CO_2^{\ominus}$ |

-continued
| R | $R_{1A}$ | $n_2$ | $CO_2A$ | R | $R_{1A}$ | $n_2$ | $CO_2A$ |
|---|---|---|---|---|---|---|---|
| " | 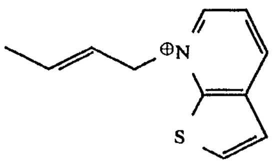 | " | " | " | 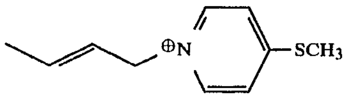 | " | " |
| " | 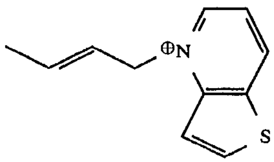 | " | " | " | 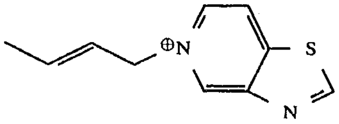 | " | " |
| " | 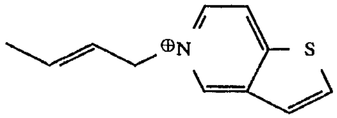 | " | " | " | 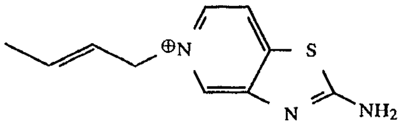 | " | " |
| " | 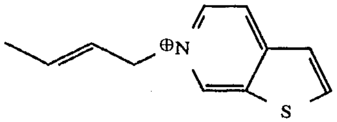 | " | " | " | 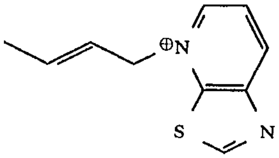 | " | " |
| 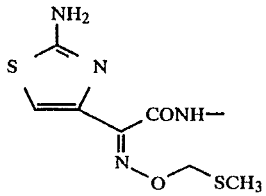 | 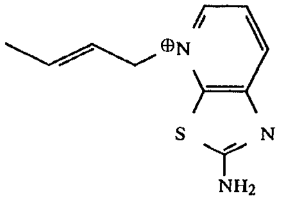 | 0 | $CO_2^{\ominus}$ | 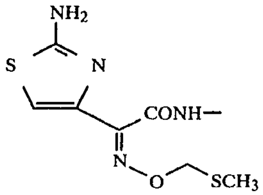 | 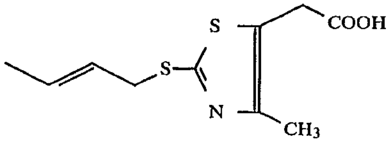 | 0 | $CO_2H$ |

-continued
| R | $R_{1A}$ | $n_2$ | $CO_2A$ | R | $R_{1A}$ | $n_2$ | $CO_2A$ |
|---|---|---|---|---|---|---|---|
| " | 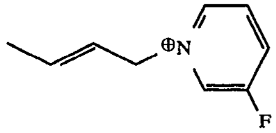 | " | " | " | 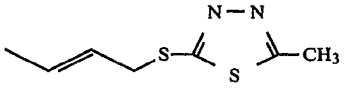 | " | " |
| " | 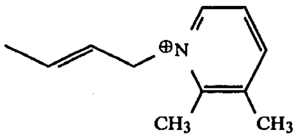 | " | " | " | 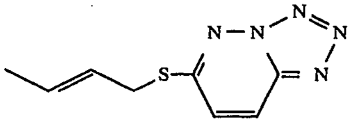 | " | " |
| " | 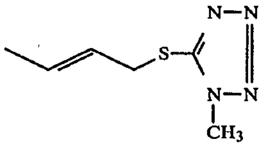 | " | $CO_2H$ | " | 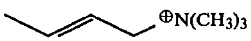 | " | $CO_2^{\ominus}$ |
| " | 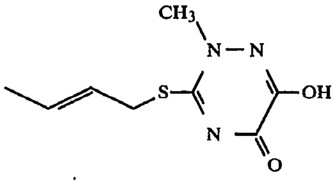 | " | " | " | 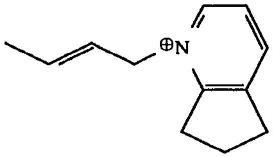 | " | " |
| 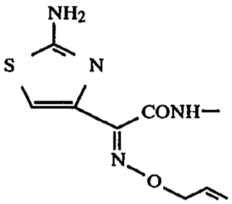 | 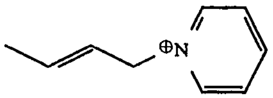 | 0 | $CO_2^{\ominus}$ | 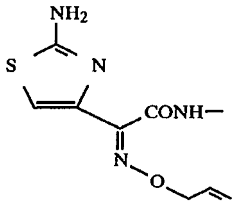 | 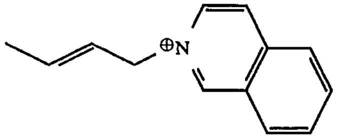 | 0 | $CO_2^{\ominus}$ |
| " | 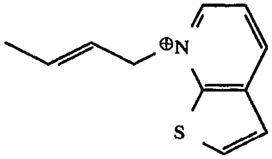 | " | " | " | 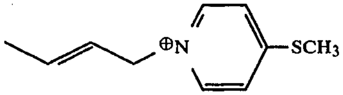 | " | " |

-continued
| R | $R_{1A}$ | $n_2$ | $CO_2A$ | R | $R_{1A}$ | $n_2$ | $CO_2A$ |
|---|---|---|---|---|---|---|---|
| " | 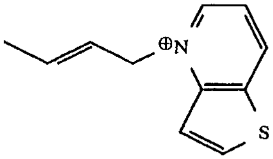 | " | " | " | 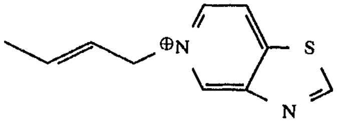 | " | " |
| " | 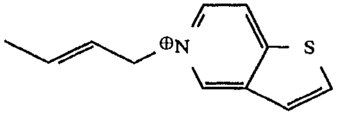 | " | " | " | 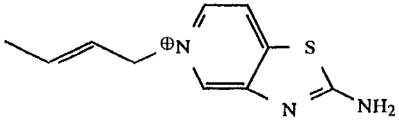 | " | " |
| " | 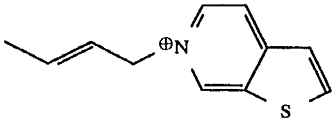 | " | " | " | 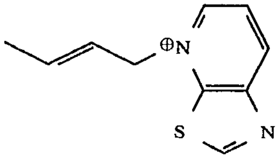 | " | " |
| 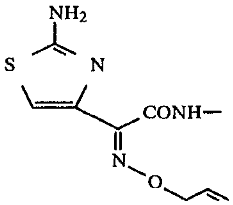 | 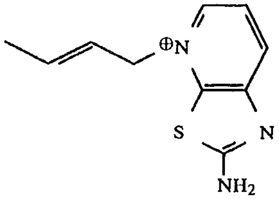 | 0 | $CO_2^{\ominus}$ | 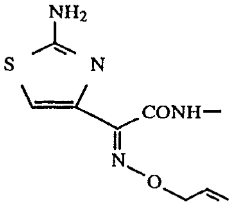 | 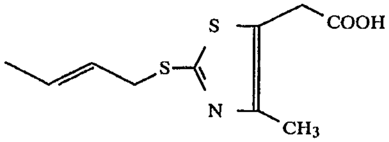 | 0 | $CO_2H$ |
| " | 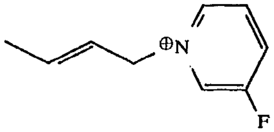 | " | " | " | 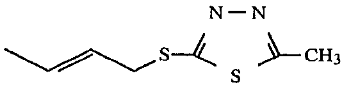 | " | " |
| " | 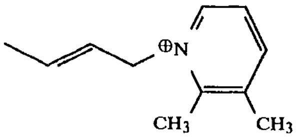 | " | " | " | 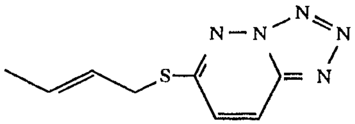 | " | " |

-continued
| R | $R_{1A}$ | $n_2$ | $CO_2A$ | R | $R_{1A}$ | $n_2$ | $CO_2A$ |
|---|---|---|---|---|---|---|---|
| " | 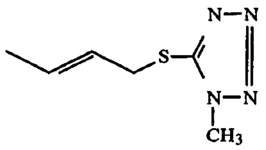 | " | $CO_2H$ | " | 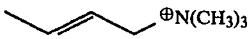 | " | $CO_2^{\ominus}$ |
| " | 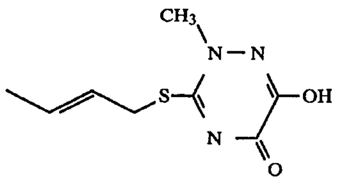 | " | " | " | 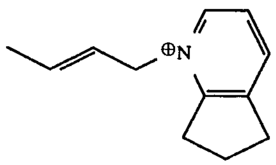 | " | " |
| 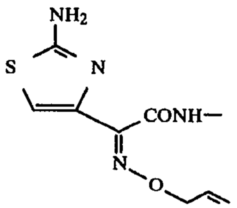 | 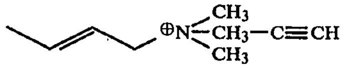 | 0 | $CO_2^{\ominus}$ | 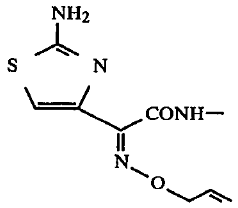 | 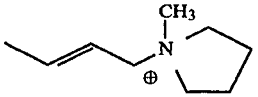 | 0 | $CO_2^{\ominus}$ |
| " | 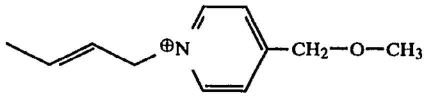 | " | " | " | 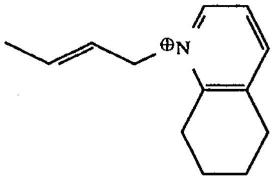 | " | " |
| " | 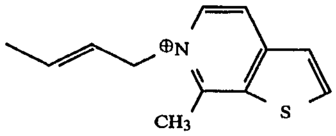 | " | " | " | 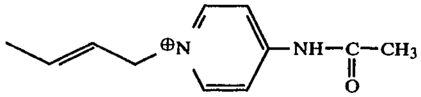 | " | " |

-continued
| R | $R_{1A}$ | $n_2$ | $CO_2A$ | R | $R_{1A}$ | $n_2$ | $CO_2A$ |
| --- | --- | --- | --- | --- | --- | --- | --- |
| " | 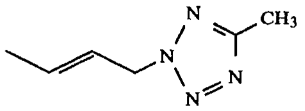 | " | $CO_2H$ | " | 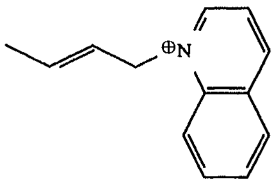 | " | " |
| " | 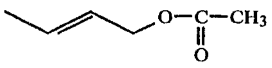 | " | " | " | 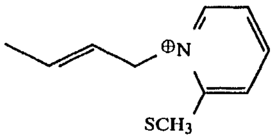 | " | " |
| 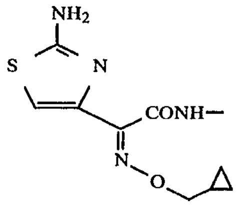 | 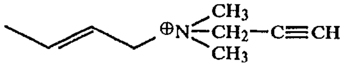 | 0 | $CO_2^{\ominus}$ | 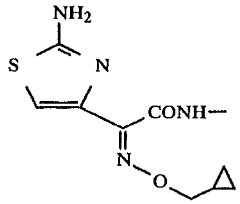 | 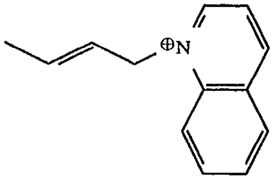 | 0 | $CO_2^{\ominus}$ |
| " | 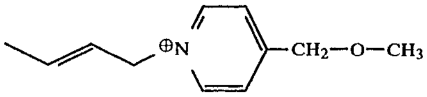 | " | " | " | 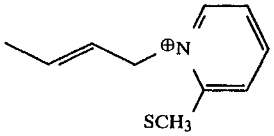 | " | " |
| " | 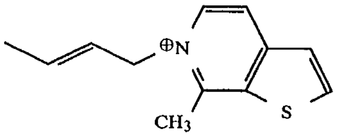 | " | " | " | 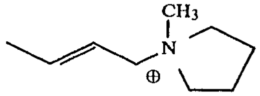 | " | " |

-continued
| R | $R_{1A}$ | $n_2$ | $CO_2A$ | R | $R_{1A}$ | $n_2$ | $CO_2A$ |
| --- | --- | --- | --- | --- | --- | --- | --- |
| " | 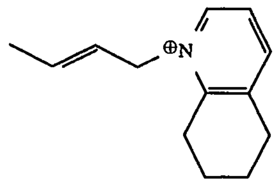 | " | " | " | 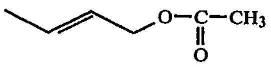 | " | $CO_2H$ |
| " | 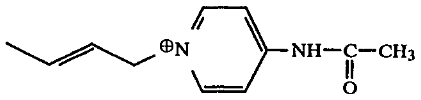 | " | " | " | 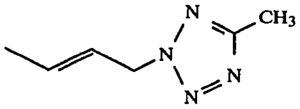 | " | " |
| 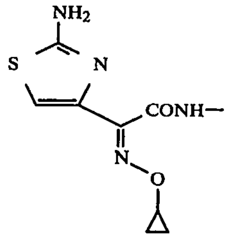 | 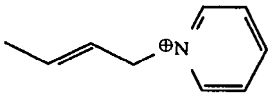 | 0 | $CO_2^{\ominus}$ | 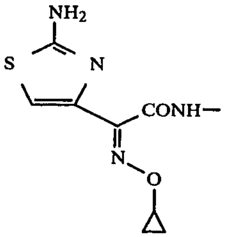 | 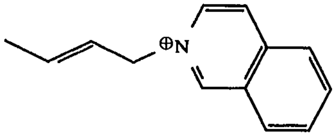 | 0 | $CO_2^{\ominus}$ |
| " | 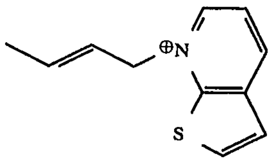 | " | " | " | 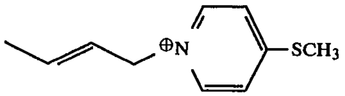 | " | " |
| " | 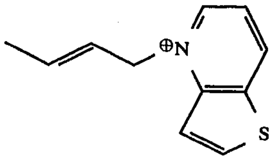 | " | " | " | 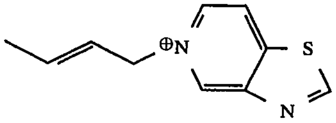 | " | " |

-continued
| R | R1A | n2 | CO2A | R | R1A | n2 | CO2A |
|---|---|---|---|---|---|---|---|
| " | 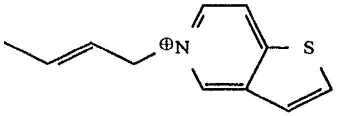 | " | " | " | 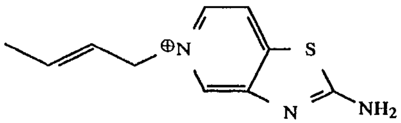 | " | " |
| " | 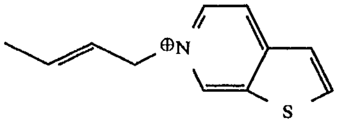 | " | " | " | 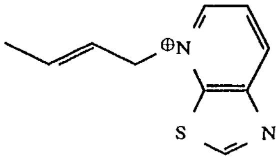 | " | " |
| 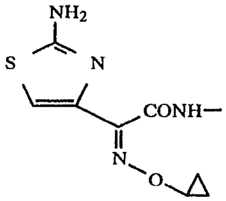 | 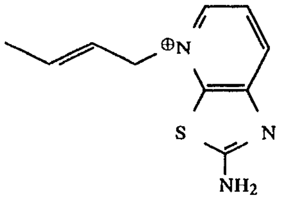 | 0 | $CO_2^{\ominus}$ | 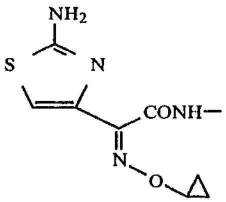 | 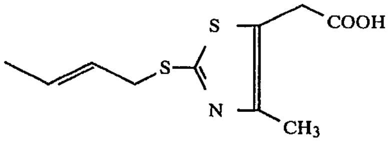 | 0 | $CO_2H$ |
| " | 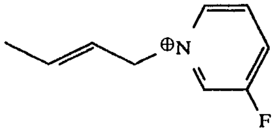 | " | " | " | 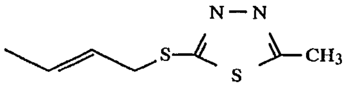 | " | " |
| " | 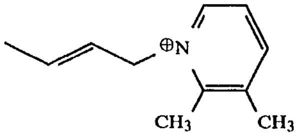 | " | " | " | 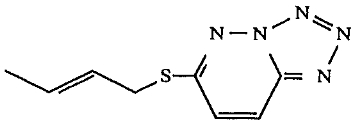 | " | " |
| " | 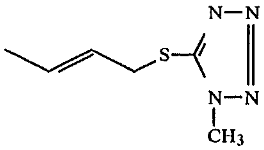 | " | $CO_2H$ | " | 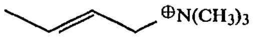 | " | $CO_2^{\ominus}$ |

-continued
| R | $R_{1A}$ | $n_2$ | $CO_2A$ | R | $R_{1A}$ | $n_2$ | $CO_2A$ |
|---|---|---|---|---|---|---|---|
| " | 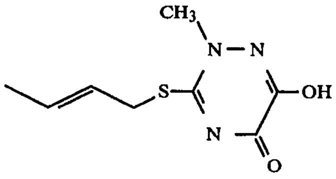 | " | " | " | 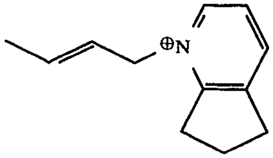 | " | " |
| 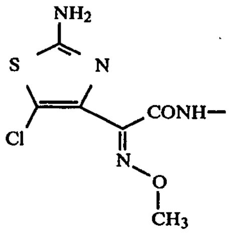 | 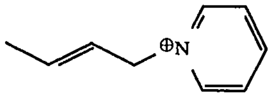 | 0 | $CO_2^{\ominus}$ | 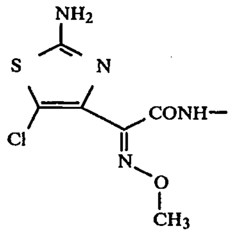 | 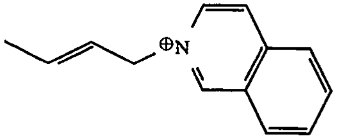 | 0 | $CO_2^{\ominus}$ |
| :: | 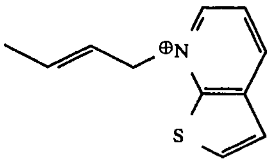 | " | " | " | 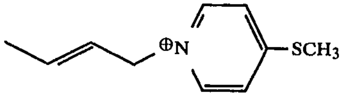 | " | " |
| " | 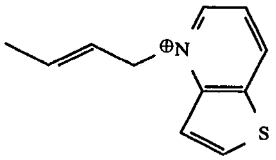 | " | " | " | 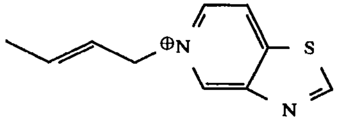 | " | " |
| " | 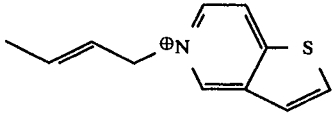 | " | " | " | 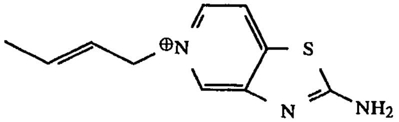 | " | " |

-continued
| R | $R_{1A}$ | $n_2$ | $CO_2A$ | R | $R_{1A}$ | $n_2$ | $CO_2A$ |
|---|---|---|---|---|---|---|---|
| " | 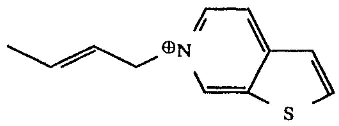 | " | " | " | 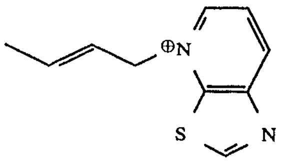 | " | " |
| 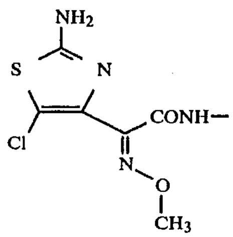 | 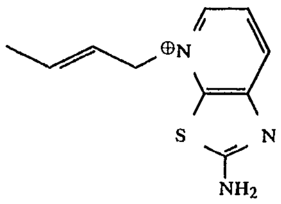 | 0 | $CO_2^{\ominus}$ | 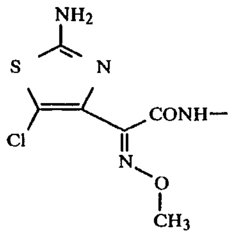 | 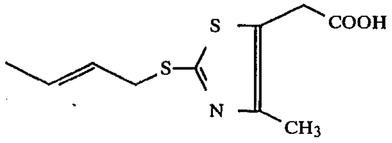 | 0 | $CO_2H$ |
| " | 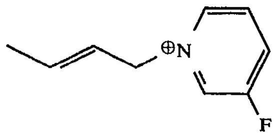 | " | " | " | 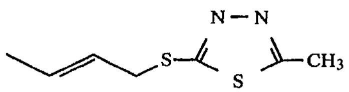 | " | " |
| " | 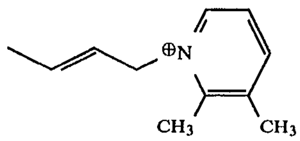 | " | " | " | 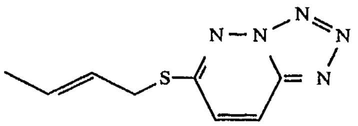 | " | " |
| " | 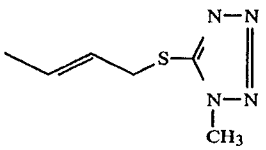 | " | $CO_2H$ | " | 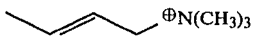 | " | $CO_2^{\ominus}$ |

-continued
| R | $R_{1A}$ | $n_2$ | $CO_2A$ | R | $R_{1A}$ | $n_2$ | $CO_2A$ |
|---|---|---|---|---|---|---|---|
| " | 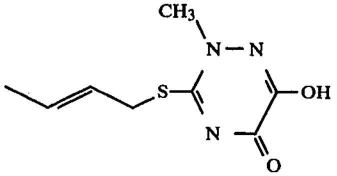 | " | " | " | 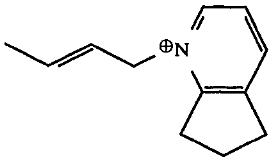 | " | " |
| 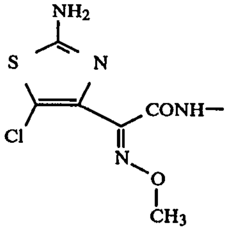 | 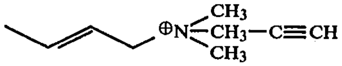 | 0 | $CO_2^{\ominus}$ | 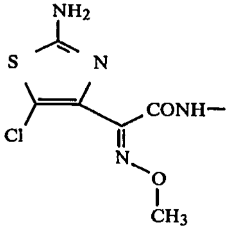 | 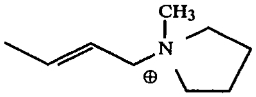 | 0 | $CO_2^{\ominus}$ |
| :: | 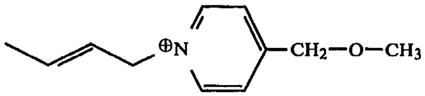 | " | " | " | 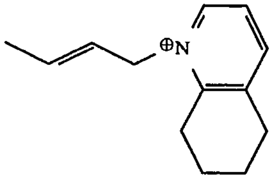 | " | " |
| " | 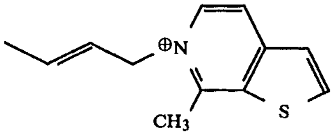 | " | " | " | 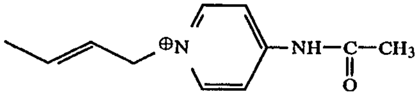 | " | " |
| " | 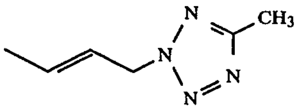 | " | $CO_2H$ | " | 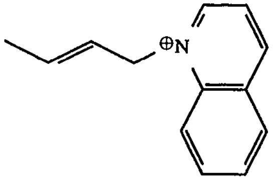 | " | " |

-continued
| R | $R_{1A}$ | $n_2$ | $CO_2A$ | R | $R_{1A}$ | $n_2$ | $CO_2A$ |
|---|---|---|---|---|---|---|---|
| " | 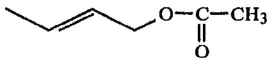 | " | " | " | 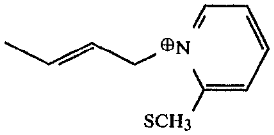 | " | " |
| 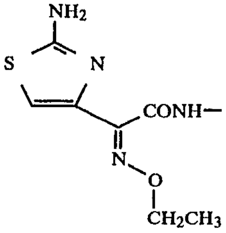 | 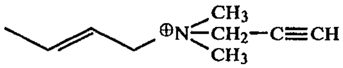 | 0 | $CO_2^{\ominus}$ | 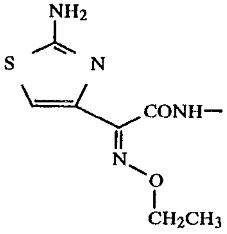 | 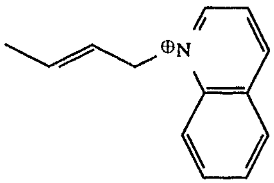 | 0 | $CO_2^{\ominus}$ |
| " | 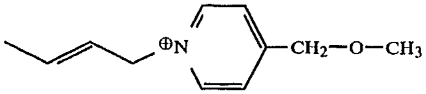 | " | " | " | 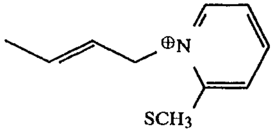 | " | " |
| " | 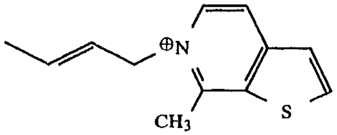 | " | " | " | 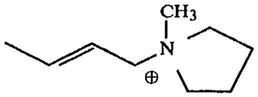 | " | " |
| " | 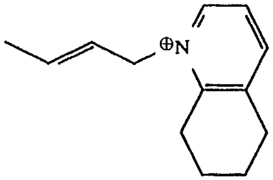 | " | " | " | 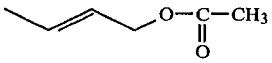 | " | $CO_2H$ |
| " | 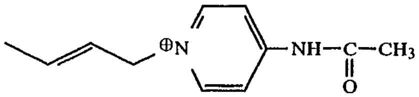 | " | " | " | 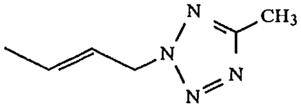 | " | " |

-continued
| R | R1A | n2 | CO2A | R | R1A | n2 | CO2A |
|---|---|---|---|---|---|---|---|
| 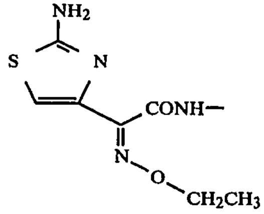 | 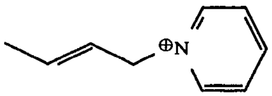 | 0 | $CO_2^{\ominus}$ | 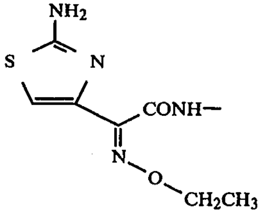 | 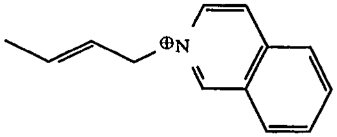 | 0 | $CO_2^{\ominus}$ |
| " | 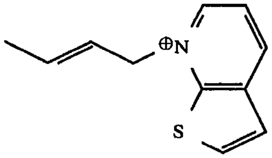 | " | " | " | 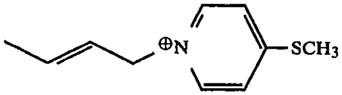 | " | " |
| " | 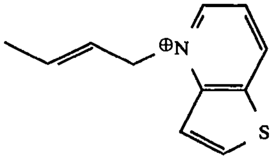 | " | " | " | 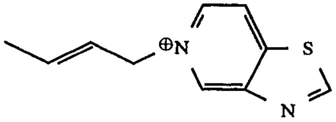 | " | " |
| " | 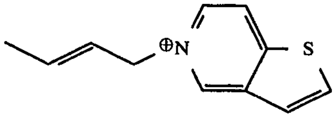 | " | " | " | 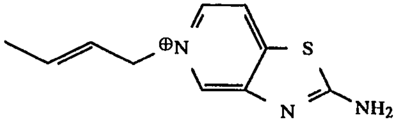 | " | " |
| " | 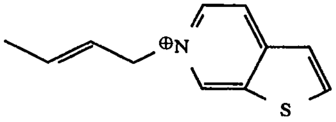 | " | " | " | 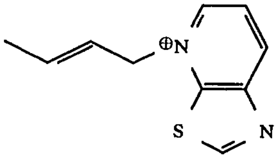 | " | " |

-continued
| R | $R_{1A}$ | $n_2$ | $CO_2A$ | R | $R_{1A}$ | $n_2$ | $CO_2A$ |
|---|---|---|---|---|---|---|---|
| 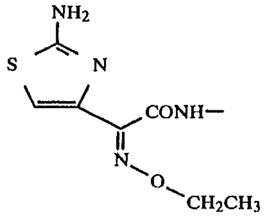 | 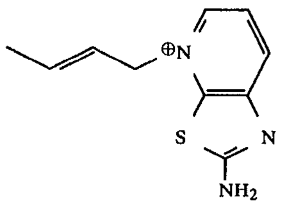 | 0 | $CO_2^{\ominus}$ | 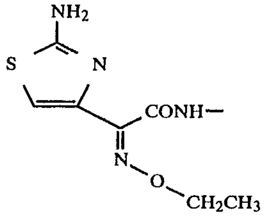 | 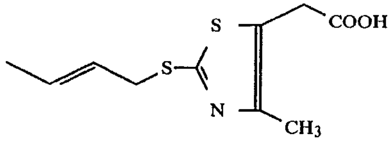 | 0 | $CO_2H$ |
| " | 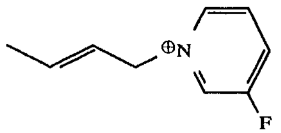 | " | " | " | 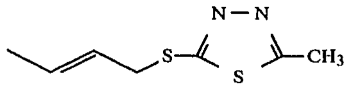 | " | " |
| " | 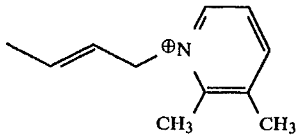 | " | " | " | 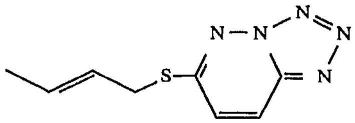 | " | " |
| " | 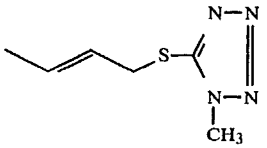 | " | $CO_2H$ | " | 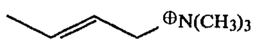 | " | $CO_2^{\ominus}$ |
| " | 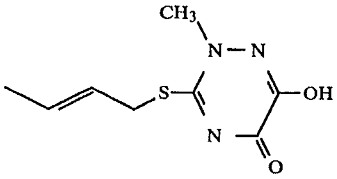 | " | " | " | 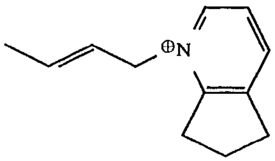 | " | " |
| 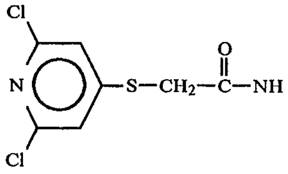 | 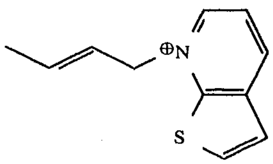 | 0 | $CO_2^{\ominus}$ | 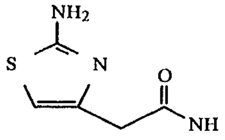 | 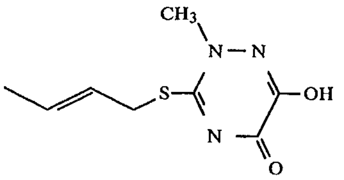 | 0 | $CO_2H$ |

-continued
| R | $R_{1A}$ | $n_2$ | $CO_2A$ | R | $R_{1A}$ | $n_2$ | $CO_2A$ |
|---|---|---|---|---|---|---|---|
| " | 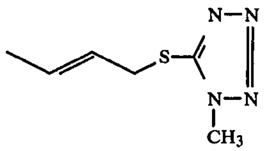 | " | $CO_2H$ | " | 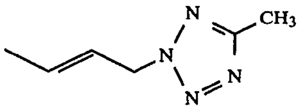 | " | " |
| " | 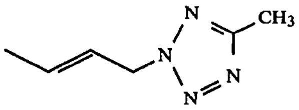 | " | " | 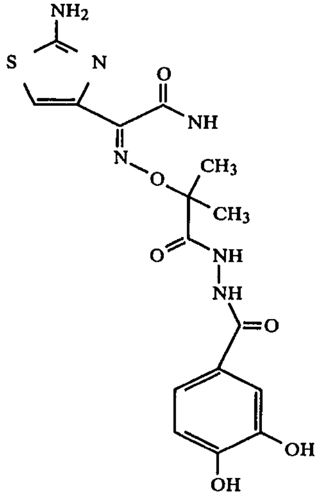 | 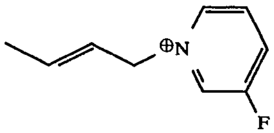 | " | $CO_2^{\ominus}$ |
| $NC-CH_2-S-CH_2-\overset{\overset{\displaystyle O}{\|}}{C}-NH$ | 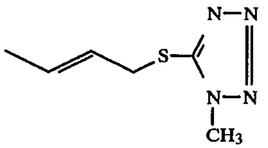 | " | " | " | 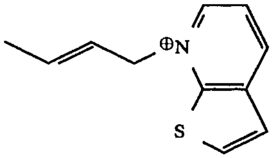 | " | " |
| " | 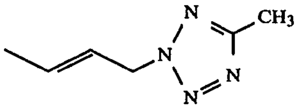 | " | " | " | 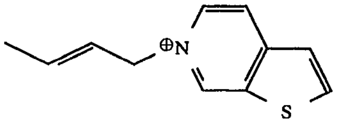 | " | " |

-continued
| R | $R_{1A}$ | $n_2$ | $CO_2A$ | R | $R_{1A}$ | $n_2$ | $CO_2A$ |
|---|---|---|---|---|---|---|---|
| 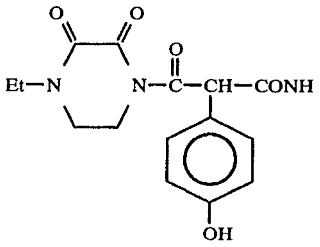 | 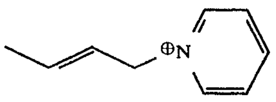 | 0 | $CO_2^{\ominus}$ | 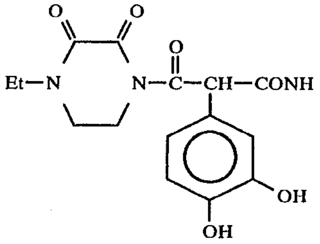 | 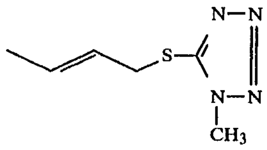 | 0 | $CO_2H$ |
| " | 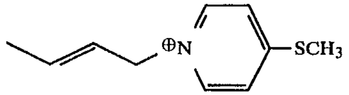 | " | " | " | 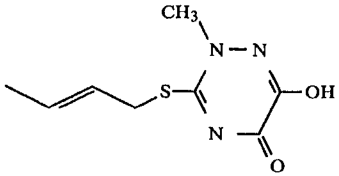 | " | " |
| " | 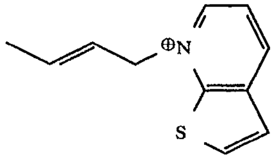 | " | " | " | 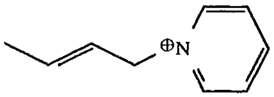 | " | $CO_2^{\ominus}$ |
| " | 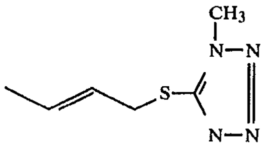 | " | $CO_2H$ | " | 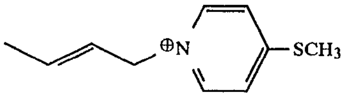 | " | " |
| " | 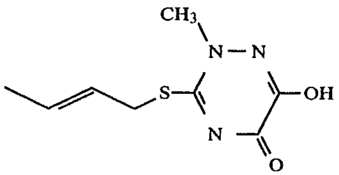 | " | " | " | 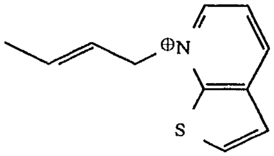 | " | " |

-continued
| R | $R_{1A}$ | $n_2$ | $CO_2A$ | R | $R_{1A}$ | $n_2$ | $CO_2A$ |
|---|---|---|---|---|---|---|---|
| 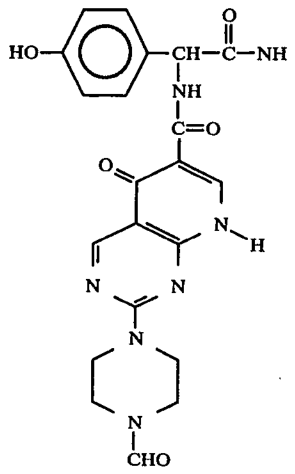 | 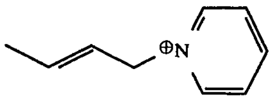 | 0 | $CO_2^{\ominus}$ | 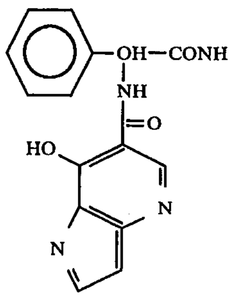 | 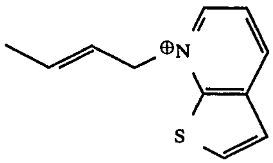 | 0 | $CO_2^{\ominus}$ |
| " | 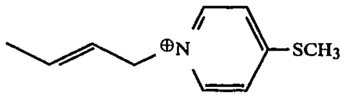 | " | " | " | 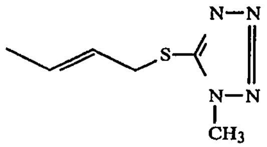 | " | $CO_2H$ |
| " | 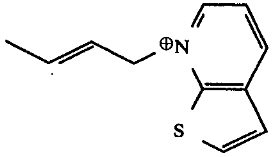 | " | " | 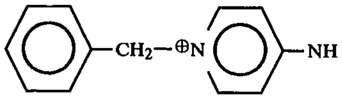 | 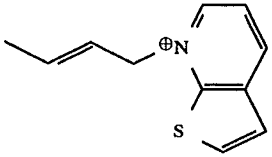 | " | $CO_2^{\ominus}$ |
| " | 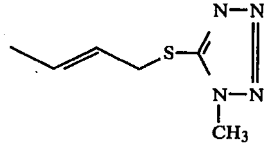 | " | $CO_2H$ | | | | |

-continued
| R | $R_{1A}$ | $n_2$ | $CO_2A$ | R | $R_{1A}$ | $n_2$ | $CO_2A$ |
|---|---|---|---|---|---|---|---|
| " | 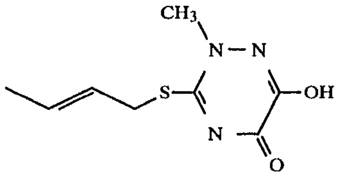 | " | " | " | 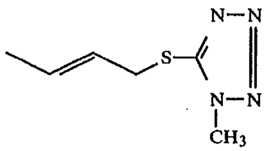 | " | $CO_2H$ |
| 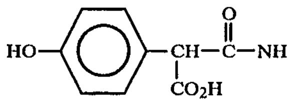 | 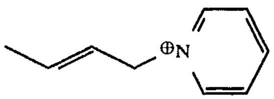 | 0 | $CO_2^{\ominus}$ | 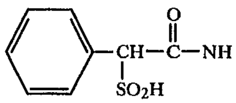 | 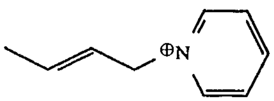 | 0 | $CO_2^{\ominus}$ |
| " | 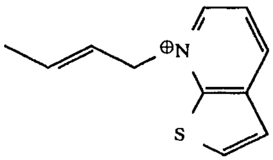 | " | " | " | 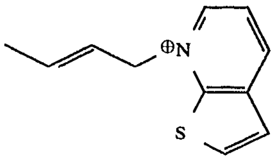 | " | " |
| " | 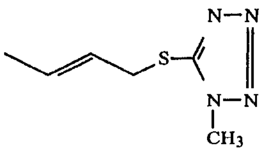 | " | $CO_2H$ | " | 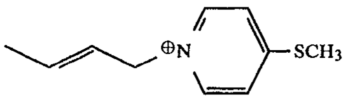 | " | " |
| " | 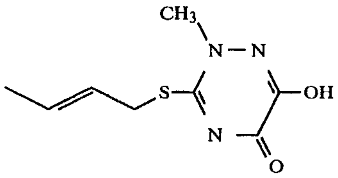 | " | " | " | 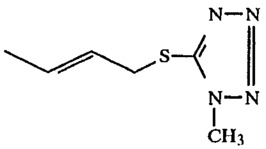 | " | $CO_2H$ |
| " | 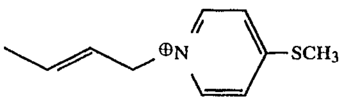 | " | $CO_2^{\ominus}$ | " | 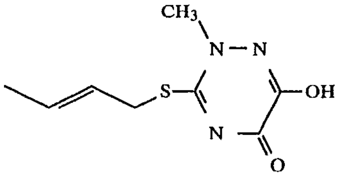 | " | " |

-continued
| R | R1A | n2 | CO2A | R | R1A | n2 | CO2A |
|---|---|---|---|---|---|---|---|
| 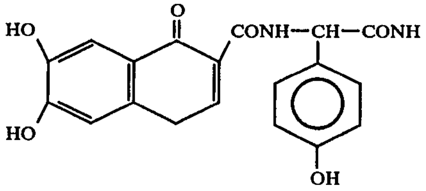 | 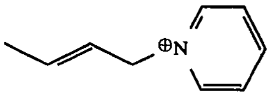 | 0 | $CO_2^{\ominus}$ | 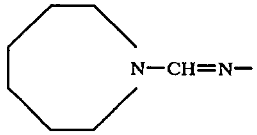 | 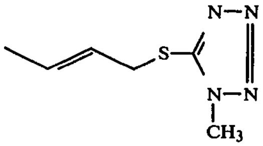 | 0 | $CO_2H$ |
| " | 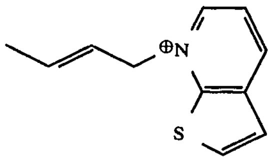 | " | " | " | 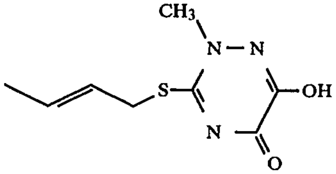 | " | " |
| " | 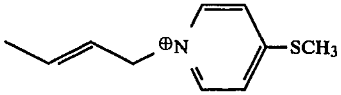 | " | " | " | 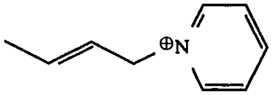 | " | $CO_2^{\ominus}$ |
| " | 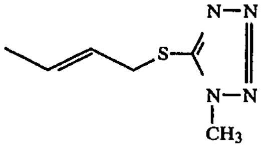 | " | $CO_2H$ | " | 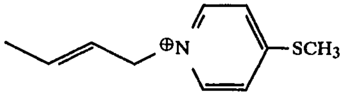 | " | " |
| " | 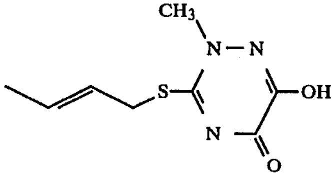 | " | " | " | 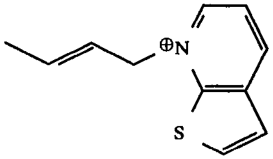 | " | " |

REFERENCE EXAMPLE A: Syn isomer of cis racemic 7-[2-(2-aminothiazol-4-yl)-2-methoxyimino-acetamido]-8-oxo-4-thia-3-methoxymethyl-1-azabicyclo[4,2,0]-oct-2-en-2-carboxylic acid STEP A: Methoxyacetaldehyde 100 ml of dimethyl ketal of methoxyacetaldehyde, 100 ml of water and 3.2 ml of concentrated hydrochloric acid were refluxed and then several fractional distillations were carried out to obtain 8.7 g of methoxyacetaldehyde.

STEP B: 1,1-dimethylethyl 2-chloro-3-methoxymethyloxirane-carboxylate

A mixture of 2.106 g of methoxyacetaldehyde, 3.8 ml of terbutyl dichloroacetate and 25 ml of tetrahydrofuran was cooled to −20° C. and over 15 minutes, 29 ml of potassium tertbutylate in tetrahydrofuran (0.9M) were introduced. The mixture stood for 20 minutes and 25 ml of ether and 25 ml of water were added. The mixture was extracted with ether and the organic phase was washed with water saturated with sodium chloride, then dried and concentrated to dryness under reduced pressure. The residue was chromatographed over silica and eluted with methylene chloride to obtain 1.44 g of 1,1-dimethylethyl 2-chloro-3-methoxymethyloxirane-carboxylate.

STEP C: 1,1-dimethyethyl 7-[2-(2-tritylaminothiazol-4-yl)-2-methoxyimino-acetamido]-8-oxo-2-hydroxy-3-methoxymethyl-4-thia-1-azabicyclo[4,2,0]octane-2-carboxylate 1.38 g of the product of Step B, 2.736 g of syn isomer of cis, racemic 4-mercaptomethyl-3-[2-(2-tritylamino-thiazol-4-yl)-2-methoxyimino-acetamido]-2-oxo-1-azetidine [prepared by the process described in Belgian Patent No. 894,795] and 12 ml of dimethylformamide were mixed together and after 10 minutes of contact, 458 mg of lithium carbonate were added followed by stirring for 2 hours 50 minutes. The reaction mixture was poured into 100 ml of water and 60 ml of ethyl acetate and extraction was done with ethyl acetate. The organic phase was washed with water, dried and concentrated to dryness under reduced pressure. The residue was taken up in ether to obtain 3.058 g of 1,1-dimethylethyl 7-[2-(2-tritylaminothiazol-4-yl)-2-methoxyimino-acetamido]-8-oxo-2-hydroxy-3-methoxymethyl-4-thia-1-azabicyclo[4,2,0]octane-2-carboxylate.

Analysis: $C_{38}H_{41}O_7N_5S_2$: molecular weight=743.91
Calculated: %C 61.35 %H 5.56 %N 9.41 %S 8.62
Found: 61.1 5.7 8.9 8.4

STEP D: 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-en-2-carboxylate 4.44 g of diphosphorus tetraiodide were suspended in 35 ml of pyridine, and after stirring for 5 minutes, 3.058 g of 1,1-dimethylethyl 7-[2-(2-tritylaminothiazol-4-yl)-2-methoxyimino-acetamido]-8-oxo-2-hydroxy-3-methoxymethyl-4-thia-1-azabicyclo[4,2,0]octane-2-carboxylate were added all at once with stirring for 2 hours 40 minutes. The pyridine was distilled off and the residue was taken up in 50 ml of ethyl acetate. After filtering, 50 ml of N hydrochloric acid were added to the filtrate with vigorous stirring and the decanted organic phase was washed with water, dried and concentrated to dryness under reduced pressure. The residue was chromatographed over silica and eluted with a mixture of methylene chloride and ethyl acetate (85-15). The fractions of interest were concentrated to dryness and crystallized from methanol to obtain 703 mg of 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-en-2-carboxylate Analysis: $C_{38}H_{39}O_6N_5S_2$: molecular weight=725.89
Calculated: %C 62.88 %H 5.41 %N 9.65 %S 8.83
Found: 62.7 5.4 9.6 8.8

STEP E: Syn isomer of cis, racemic 7-[2-(2-aminothiazol-4-yl)-2-methoxyimino-acetamido]-8-oxo-4-thia-3-methoxymethyl-1-azabicyclo[4,2,0]oct-2-en-2-carboxylic acid 246 mg of the product of Step D were dissolved in 1 ml of trifluoroacetic acid and the mixture was stirred for 50 minutes at ambient temperature. 12 ml of isopropyl ether were added and the precipiate formed was filtered off to obtain 176 mg of crude trifluoroacetate which was dissolved in ethanol. 2 drops of pyridine were added and crystallization was allowed for 1 hour to obtain 88 mg of syn isomer of cis, racemic 7-[2-(2-aminothiazol-4-yl)-2-methoxyiminoacetamido]-8-oxo-4-thia-3-methoxymethyl-1-azabicyclo[4,2,0]oct-2-en-2-carboxylic acid Analysis: $C_{15}H_{17}O_6N_5S_2$: molecular weight=427.46
Calculated: %C 42.15 %H 4.01 %N 16.38 %S 15.00
Found: 42.2 4.0 16.2 15.0

REFERENCE EXAMPLE B: Syn isomer of cis, racemic 7-[2-(2-aminothiazol-4-yl)-2-methoxyimino-acetamido]-8-oxo-3-[(1-methyl-1H-tetrazol-5-yl)thiomethyl]-4-thia-1-azabicyclo[4,2,0]oct-2-en-2-carboxylic acid STEP A: 2-[(1,1-dimethylethyl)dimethylsilyloxy]-ethanol At 20° C. and under nitrogen: 18 g of tertbutylmethylsilyl, 150 ml of dichloromethane, 17.5 ml of dimethylformamide and 33.6 ml of ethylene glycol were mixed together and after solution has complete, 20.1 ml of triethylamine were added over 5 minutes. Then, 1.8 g of 4-dimethylamino-pyridine were added. After 2 hours 45 minutes of stirring, the solution was poured into 120 ml of water and neutralized with N hydrochloric acid (about 40 ml) to obtain a pH of 3. After decanting, the aqueous phase was extracted with 20 ml of pentane and the combined organic phase was washed with 60 ml of water, which was extracted with 20 ml of pentane. The organic phase was dried and evaporated to dryness under reduced pressure to obtain 13.9 g of 2-[(1,1-dimethylethyl)dimethylsilyloxy]-ethanol with a boiling point of 82°-86° C. at 16 mm/Hg.

STEP B: 2-[(1,1-dimethylethyl)dimethylsilyloxy]-acetaldehyde

Under nitrogen and with stirring, 4.71 ml of oxalyl chloride were dissolved in 120 ml of dichloromethane and the solution was cooled to −70° C. Over 12 minutes while maintaining the temperature at −65° C., a solution of 8 ml of dimethylsulfoxide and 26 ml of dichloromethane was introduced. Then, after 10 minutes of contact at this temperature, a solution of 8.81 g of the product of Step A, 50 ml of dichloromethane and 8.86 ml of pyridine was added over 12 minutes at −65° C. After 15 minutes of contact at this temperature, 35 ml of triethylamine were added over 8 minutes at −65° C. At +13° C., the pH was adjusted to 4 by adding N hydrochloric acid. After decanting, re-extracting with 50 ml of dichloromethane, drying the organic phase and distilling under reduced pressure, the crude product obtained was chromatographed over silica and eluted with dichloromethane to obtain 7.95 g of 2-[(1,1-dimethylethyl)dimethylsilyloxy]-acetaldehyde.

STEP C: 1,1-dimethylethyl 2-chloro-3-(terbutyldimethylsilyloxymethyl)-oxirane-carboxylate Using the procedure of Step B of reference Example A, while taking the precaution of introducing at the same time the solutions of potassium tertbutylate and 7.95 g of aldehyde of Step B at −20° C. into a solution of 1,1-dimethylethyl dichloroacetate, and, after chromatography over silica (eluent: hexane–dichloromethane 6–4), 9.4 g of 1,1-dimethylethyl 2-chloro-3-(tert-butyldimethylsilyloxymethyl)-oxirane-carboxylate.

STEP D: 1,1-dimethylethyl 7-[2-(2-tritylaminothiazol-4-yl)-2-methoxyimino-acetamido]-8-oxo-2-hydroxy-3-[(1,1-dimethylethyl)-dimethylsilyloxymethyl]-4-thia-1-azabicyclo[4,2,0]octane-2-carboxylate Using the procedure of Step C of reference Example A with a reaction time of 16 hours and after chromatography over silica and elution with dichloromethane and ethyl acetate (75–25), 8.31 g of syn isomer of cis 4-mercaptomethyl-3-[2-(2-tritylaminothiazol-4-yl)-2-methoxyimino-acetamido]-2-oxo-1-azetidine, and product of Step C were reacted to obtain 9.09 g of 1,1-dimethylethyl 7-[2-(2-tritylaminothiazol-4-yl)-2-methoxyimino-acetamido]-8-oxo-2-hydroxy-3-[(1,1-dimethylethyl)-dimethylsilyloxymethyl]-4-thia-1-azabicyclo[4,2,0]octane-2-carboxylate.

STEP E: 1,1-dimethylethyl 7[2-(2-tritylaminothiazol-4-yl)-2-methoxyimino-acetamido[-8-oxo-3-[(1,1-dimethylethyl)dimethylsilyloxymethyl]-4-thia-1-azabicyclo[4,2,0]oct-2-ene-2-carboxylate Using the procedure of Step D of reference Example A, the contact was reduced to 55 minutes and the reaction mixture was poured into water, acidified with 2N hydrochloric acid to a pH of 1.6 and was extracted ethyl acetate. 9.09 g of the product of Step D yielded after chromatography 4 g of 1,1-dimethylethyl 7-[2-(2-tritylaminothiazol-4-yl)-2-methoxyimino-acetamido]-8-oxo-3-[(1,1-dimethylethyl)dimethylsiloxymethyl]-4-thia-1-azabicyclo[4,2,0]oct-2-ene-2-carboxylate.

| UV Spectrum - in ethanol | | | |
|---|---|---|---|
| infl.: | 233 nm | $E_1^1$: 364 | |
| infl.: | 265 nm | $E_1^1$: 173 | |
| max.: | 302 nm | $E_1^1$: 229 | ε = 18,900 |

STEP F: 1,1-dimethylethyl 7-[2-(2-tritylaminothiazol-4-yl)-2-methoxyimino-acetamido]-8-oxo-3-hydroxymethyl-4-thia-1-azabicyclo[4,2,0]oct-2-ene-2-carboxylate 2.595 g of the silyl derivative of Step E were suspended in 30 ml of acetone and 4 ml of N hydrochloric acid and the solution cleared little by little after 3 hours of stirring. 7.7 ml of water saturated with sodium bicarbonate were added. The acetone was distilled off under reduced pressure and the residual gum was dissolved in 5.5 ml of ethyl acetate to which 43 ml of ether were added. After 3 hours 15 minutes of stirring, the crystals formed were filtered off, rinsed and dried to obtain 2.232 g of 1,1-dimethylethyl 7-[2(2-tritylaminothiazol-4-yl)-2-methoxyimino-acetamido]-8-oxo-3-hydroxymethyl-4-thia-1-azabicyclo[4,2,0]oct-2-ene-2-carboxylate STEP G: 1,1-dimethylethyl 7-[2-(2-tritylaminothiazol-4-yl)-2-methoxyimino-acetamido]-8-oxo-3-chloromethyl-4-thia-1-azabicyclo[4,2,0]oct-2-ene-2-carboxylate 623 mg of the alcohol of Step F were dissolved in 8 ml of dichloromethane with 834 ml of tosyl chloride, and over 20 minutes, a solution of 534 mg of 4-dimethylamino-pyridine and 5 ml of dichloromethane was added. After stirring for one hour, 2.2 ml of N hydrochloric acid were added with stirring, and after decanting, the organic phase was dried and distilled under reduced pressure. The residue was chromatographed over silica and eluted with dichloromethane–ethyl acetate (9–1) to obtain 245 mg of 1,1-dimethylethyl 7-[2-(2-tritylaminothiazol-4-yl)-2-methoxyimino-acetamido]-8-oxo-3-chloromethyl-4-thia-1-azabicyclo[4,2,0]oct-2-ene-2-carboxylate crystallizing from ether.

| UV Spectrum - EtOH | | | |
|---|---|---|---|
| infl.: | 224 nm | $E_1^1$: 441 | ε = 38,200 |
| infl.: | 264 nm | $E_1^1$: 179 | |
| infl.: | 271 nm | $E_1^1$: 164 | |
| max.: | 306 nm | $E_1^1$: 222 | ε = 19,200 |

STEP H: 1,1-dimethylethyl 7-[2-(2-tritylaminothiazol-4-yl)-2-methoxyimino-acetamido]-8-oxo-3-[(1-methyl-1H-tetrazol-5-yl)-thiomethyl]-4-thia-1-azabicyclo[4,2,0]oct-2-ene-2-carboxylate 301 mg of the product of Step G and 114 mg of the sodium salt of 1-methyl-5-mercapto-1,2,3,4-tetrazole were dissolved in 3 ml of dimethylformamide and after 100 minutes of stirring, the solution was poured into 30 ml of water and was extracted with ethyl acetate. The organic phase was dried and distilled to dryness under reduced pressure. The residue was dissolved in 2 ml of ethyl acetate and ether is added to the limit of solubility. The crystals obtained were filtered off after 45 minutes, rinsed with ether and dried to obtained in two lots 283 mg of 1,1-dimethylethyl 7-[2-(2-tritylaminothiazol-4-yl)-2-methoxyimino-acetamido]-8-oxo-3-[(1-methyl-1H-tetrazol-5-yl)-thiomethyl]-8-oxo-4-thia-1-azabicyclo[4,2,0]oct-2-ene-2-carboxylate STEP I: 7-[2-(2-aminothiazol-4-yl)-2-methoxyiminoacetamido]-8-oxo-3-[(1-methyl-1H-tetrazol-5-yl)-thiomethyl]-4-thia-1-azabicyclo[4,2,0]oct-2-en-2-carboxylic acid Using the procedure of Step E of Example A with the crude product dissolved in sodium bicarbonate water and acidified to pH, then filtered after having distilled off a large part of the water, 371 mg of the product of Step H yielded 61 mg of 7-[2-(2-aminothiazol-4-yl)-2-methoxyimino-acetamido]-8-oxo-3-[(1-methyl-1H-tetrazol-5-yl)-thiomethyl]-4-thia-1-azabicyclo[4,2,0]oct-2-en-2-carboxylic acid.

| UV Spectrum | | | |
|---|---|---|---|
| | 1) in EtOH | | |
| max.: | 302 nm | $E_1^1 = 295$ | $\epsilon = 15{,}100$ |
| | 2) in EtOH/HCl 0.1N | | |
| infl. | 273 nm | $E_1^1$: 304 | |
| max. | 285 nm | $E_1^1$: 318 | $\epsilon = 16{,}300$ |
| infl. | 292 nm | $E_1^1$: 312 | $\epsilon = 16{,}000$ |
| infl. | 309 nm | $E_1^1$: 245 | $\epsilon = 12{,}500$ |

The corresponding optically active products were prepared, particularly the syn isomer of (6S,7S) 1,1-dimethylethyl 7-[2-(2-tritylaminoethiazol-4-yl)-2-methoxyimino-acetamido]-8-oxo-3-hydroxymethyl-4-thia-1-azabicyclo[4,2,0]oct-2-ene-2-carboxylate. Using the procedure of reference Example A and starting with the syn isomer of cis (3S,4S) 4-mercaptomethyl-3-[2-(2-tritylaminothiazol-4-yl)-2-methoxyimino-acetamido]-2-oxo-1-azetidine, described in French application No. 2,538,389. The reaction product possessed the following physicochemico characteristics melting point of 180° C.

| UV Spectrum: | | | |
|---|---|---|---|
| | 1) in ethanol: | | |
| infl.: | 222 nm | $E_1^1 = 444$ | |
| infl.: | 237 nm | $E_1^1 = 352$ | |
| max.: | 302 nm | $E_1^1 = 223$ | $\epsilon = 15{,}900$ |
| | 2) in ethanol + HCl 0.1N | | |
| infl.: | 221 nm | $E_1^1 = 464$ | |
| infl.: | 263 nm | $E_1^1 = 204$ | |
| infl.: | 285 nm | $E_1^1 = 294$ | |
| max.: | 293 nm | $E_1^1 = 340$ | $\epsilon = 22{,}000$ |
| infl.: | 300 nm | $E_1^1 = 299$ | |
| infl.: | 310 nm | $E_1^1 = 230$ | |

REFERENCE EXAMPLE C: (6S,7S) 7-[(2-triphenylmethylaminothiazol-4-yl)-2-(Z)-methoxyimino-acetamido]-2-[(1,1-dimethylethyl)-oxycarbonyl]-8-oxo-4-thia-1-azabicyclo[4,2,0]oct-2-ene-3-yl/-methyl-triphenyl-phosphonium chloride 2.182 g of 1,1-dimethylethyl (6S,7S) 7-[-2-(2-tritylaminothiazol-4-yl)-2-methoxyimino-acetamido]-8-oxo-3-chloromethyl-4-thia-1-azabicyclo[4,2,0]oct-2-en-2-carboxylate, prepared as in Step G of reference Example B and 1.679 g of triphenyl phosphine were dissolved in 24 ml of tetrahydrofuran, and 14.1 g of silica were added. The tetrahydrofuran was distilled off under reduced pressure over 2 hours and the remainder was cooled, stirred for 26 hours at 20° C. then chromatographed over silica (eluent, dichloromethane-methanol, 9/11) to obtain 1.89 g of (6S,7S) 7-[(2-triphenylmethylaminothiazol-4-yl)-2-(Z)-methoxyimino-acetamido]-2-[(1,1-dimethylethyl)-oxycarbonyl]-8-oxo-4-thia-1-azabicyclo[4,2,0]oct-2-ene-3-yl-methyl-triphenyl-phosphonium chloride.

Reference Example D: Trifluoromethane sulfonate of syn isomer of (6S,7S) 7-[3-[7-[[(2-amino-4-thiazolyl)(methoxyimino)-acetamido]-2-carboxy-8-oxo-4-thia-1-azabicyclo[4,2,-0]oct-2-en-3-yl]propen2(E)-yl]thieno[2,3-b]pyridinium

STEP A: 1,1-dimethylethyl (6S,7S) 7-[[2-(2-triphenylmethylamino-thiazol-4-yl]2(Z)methoxyimino acetamido-3-[3-[(1,1-dimethylsilyloxy]propen-1-yl]-8-oxo-4-thia-1-azabicyco[4,2,0]oct-2-en-2-carboxylate 1,89 g of 1,1-dimethylethyl 7-[[2-(2-triphenylmethylamino-thiazol-4-yl]2(Z)methoxyimino-acetamido]-3-methyl triphenyl-phosphonium-8-oxo-4-thia-1-azabicyclo[4,2,0]oct-2-en-2-carboxylate hydrochloride, 30 ml of dichloromethane, 0.68 ml of 2[1,1-dimethylethyl dimethylsilyl oxy]-acetaldehyde and 0.53 ml of triethylamine were mixed together and stirred at +20° C. for 14 hours. The solution was chromatographed over silica and eluted with a mixture of dichloromethane and ethyl acetate (9/1) to obtain 1.305 g of the expected product containing a mixture of isomer E (2/3) and Z (1/3).

| NMR Spectrum ($CDCl_3$): | |
|---|---|
| 0.9–0.92 ppm | SitBu; |
| 1.50–1.53 ppm | $CO_2OtBu$; |
| 2.95–3.11 ppm | $CH_2S$; |
| 4.05 ppm | $OCH_3$; |
| 4.31–4.37 ppm | $CH_2O$; |
| 4.11 ppm | $H_6$; |
| 5.4–5.5 ppm | $H_7$; |
| 5.75–5.87 ppm and | |
| 6.11–6.24 ppm | Z(⅓); |
| 6.17–6.34 ppm and | |
| 6.97–7.16 ppm | E(⅔); |
| 6.50–6.56 ppm | $H_5$ thiazol syn; |
| 7.34 ppm | $\phi_3$. |

STEP B: 1,1-dimethylethyl 7-[[2-(2-triphenylmethylamino-thiazol-4-yl]2(Z)methoxyiminoacetamido]-3-[3-hydroxy-propen-1(E)-yl)-8-oxo-4-thia-1-azabicyclo[4,2,0]oct-2-en-2-carboxylate and 1,1-dimethylethyl 7-[[2-(2-triphenylmethylamino-thiazol-4-yl]2(Z)methoxyimino-acetamido]-3-[3-hydroxy-propen-1(Z)-yl)-8-oxo-4-thia-1-azabicyclo[4,2,0]oct-2-en-2-carboxylate 1.305 g of the product of Step A were dissolved in 15 ml of acetone and 2 ml of a normal aqueous solution of hydrochloric acid were added. The mixture was stirred for 90 minutes. After concentrating to dryness by distilling under reduced pressure, aqueous sodium bicarbonate was added, and extraction was done with dichloromethane. The extracts were concentrated to dryness by distilling under reduced pressure and the residue was chromatographed over silica and eluted with a mixture of dichloromethane and ethyl acetate (1/1) to obtain 536 mg of isomer E and 369 mg of isomer Z of the expected product.

Isomer E:

IR Spectrum. (chloroform). 3607 $cm^{-1}$ OH; 3405 $cm^{-1}$ amide NH; 1684 $cm^{-1}$ C=O; 1515 $cm^{-1}$ amide II; 1772 $cm^{-1}$ beta lactam C=O; 1595, 1544, 1527 $cm^{-1}$: aromatic, thiazol, conjugated system; 1700 $cm^{-1}$ tertbutyl ester; 1370 $cm^{-1}$ $CH_3$; 1154 $cm^{-1}$ C—O—C; 2820 $cm^{-1}$ OMe; 1049 $cm^{-1}$ C=N—OR.

| UV Spectrum: ethanol. | | | |
|---|---|---|---|
| Max. | 231 nm | $E_1^1 = 497$ | $\epsilon = 32{,}200$ |
| Inflexion | 258 nm | $E_1^1 = 290$ | |
| Inflexion | 264 nm | $E_1^1 = 264$ | |
| Inflexion | 270 nm | $E_1^1 = 240$ | |
| Max. | 320 nm | $E_1^1 = 245$ | $\epsilon = 18{,}100$ |

NMR Spectrum, ($CDCl_3$) 1.51 ppm tBu; 3.05 ppm $CH_2S$; 4.02 ppm $OCH_3$; 4.28 ppm $CH_2OH$; 5.48 ppm $H_7$; 6.24–6.41 and 6.97–7.13 ppm ethylene H's, delta E J=15 Hz.; 7.29 ppm $\phi_3$; 6.53 ppm $H_5$ thiazol "syn".

ISOMER Z:

IR Spectrum. (chloroform). 3605 $cm^{-1}$ OH; 3405 $cm^{-1}$ amide NH; 1685 $cm^{-1}$ C=O; 1505 $cm^{-1}$ amide II; 1773 $cm^{-1}$ beta lactam C=O; 1704 $cm^{-1}$ tertbutyl ester; 1368 $cm^{-1}$ Me; 1154 $cm^{-1}$ C—O—C; 1585, 1573, 1527, 1493 $cm^{-1}$, trityl, aromatics, thiazole, conjugated system, 2820 $cm^{-1}$ C=N—OMe; 1050 $cm^{-1}$ C=N—OR.

| UV Spectrum: ethanol. | | | | | |
|---|---|---|---|---|---|
| Inflexion | 230 nm | $E_1^1 = 411$; | Inflexion | 260 nm | $E_1^1 = 220$; |
| Inflexion | 265 nm | $E_1^1 = 198$; | Inflexion | 271 nm | $E_1^1 = 176$; |
| Max. | 308 nm | $E_1^1 = 194$ | $\epsilon = 14{,}300$ | | |

NMR Spectrum, ($CDCl_3$) 1.49 ppm tBu; 3.06 ppm S—$CH_2$; 4.04 ppm OMe; 4.27 ppm $CH_2OH$; 5.48 ppm $H_7$; 5.85–5.98 and 6.21–6.34 ppm ethylene-H's, delta Z J=11 Hz.; 6.56 ppm $H_5$ thiazol "syn"; 7.29 ppm $\phi_3$.

STEP C: Trifluoromethane sulfonate of (6S,7S) 7-[3-[7-[2-(2-triphenyl-methylaminothiazol-4-yl)2(Z) (methoxyimino)-acetamido]-2-[1,1-dimethylethyloxycarbonyl]-8-oxo-4-thia-1-azabicyclo[4,2,0]oct-2-en-3-yl]propen2(E)yl]-thieno[2,2-b]pyridinium 222 mg of isomer E of Step B were dissolved in 4.8 ml of dichloromethane, and 3 ml of solution of 536 mg of thieno-pyridine in 10 ml of methylene chloride were added. The mixture was cooled to −70° C. and then, dropwise 2.7 ml of a solution of trifluoromethane sulfonic anhydride (0.42 ml in 10 ml of methylene chloride) were added. The temperature was taken slowly to +20° C. and the solution was concentrated to dryness by distilling under reduced pressure. Ethyl acetate was added to the residue which was then washed with water containing 0.7 ml of an N aqueous solution of hydrochloric acid, followed by decanting, washing with water and extracting with ethyl acetate. The extracts were concentrated to dryness by distilling under reduced pressure and the residue was chromatographed over silica and eluted with a mixture of dichloromethane and methanol (92/8) to obtain 236 mg of the expected compound (isomer E).

STEP C': Trifluoromethane sulfonate of (6S, 7S) 7-[3-[7-[[(2-triphenylmethylaminothiazol-4-yl)2(Z)(methoxyimino)-acetamido]-2-[[1,1-dimethylethyloxy]-carbonyl]-8-oxo-4-thia-1-azabicyclo[4,2,0]oct-2-en-3-yl]propen2(Z)yl]-thieno[2,3-b]pyridinium 145 ml of isomer Z of Step B were dissolved in 5 ml of dichloromethane, and 120 μl of thieno[2,3-b]pyridine were added. The mixture was cooled to −70° C. and then, dropwise 1.76 ml of a methylene chloride solution of trifluoromethane sulfonic anhydride (0.42 ml in 10 ml of methylene chloride) were added. The temperature was taken slowly to +20° C. and the solution was chromatographed over silica and eluted with a mixture of dichloromethane and methanol (92/8) to obtain 157 mg of the expected compound.

STEP D: Trifluoromethane sulfonate of (6S, 7S, ΔZ) 7-[3-[7-[[(2-(2-amino-4-thiazol-yl)(methoxyimino)-acetamido]-2-carboxy-8-oxo-4-thia-1-azabicyclo[4,2,-0]oct-2-en-3-yl]-propen2(E)-yl]-thieno[2,3-b]pyridinium 221 mg of isomer (E) of Step C and 2.5 ml of a 33% aqueous solution of formic acid were mixed together and heated to 65° C. for 55 minutes and then cooled. The mixture was diluted with water, filtered and washed with ether. The aqueous phase was concentrated to dryness by distilling under reduced pressure and after water was added and drying, 93 mg of the expected product were obtained.

I.R. Spectrum (nujol). 1760 $cm^{-1}$, beta lactame 

1660 $cm^{-1}$; 1550 and 1535 $cm^{-1}$, aromatic+amide II+thiazol+conjugated system. 1030 $cm^{-1}$ $CF_3SO_3$.

| UV Spectrum (ethanol) | | | |
|---|---|---|---|
| Max. | 238 nm | $E_1^1 = 625$; | $\epsilon = 44{,}200$ |
| Max. | 307 nm | $E_1^1 = 251$; | $\epsilon = 17{,}700$ |
| Inflexion | 318 nm | $E_1^1 = 232$; | |
| Inflexion | 338 nm | $E_1^1 = 160$; | |

By formic hydrolysis, isomer Z or syn isomer hydrolyzed totally into isomer E (isomerization).

Preparation of the hydrochloride of (6S, 7S) 7-[[(2-trifluoromethylaminothiazol-4-yl)2(Z)-methoxyimino-acetamido]-2-[1,1-dimethylethyl-oxycarbonyl-8-oxo-4-thia-1-azabicyclo[4,2,0]oct-2-en-3-yl]-methyl-triphenyl phosphonium 2,182 g of 1,1-dimethyl ethyl (6S, 7S) 7-[[2-(2-tritylamino-thiazol-4-yl)2-(Z)methoxyimino-acetamido-3-chloromethyl-8-oxo-4-thia-1-azabicyclo[4,2,0]oct-2-en-2-carboxylate and 1.679 g of triphenyl phosphine were dissolved in 24 ml of tetrahydrofuran and after 14.1 g of silica were added, the tetrahydrofuran was distilled for 2 hours, followed by cooling and stirring for 26 hours at 20° C. After chromatographing over silica and elution with a mixture of dichloromethane and methanol (90/10), 1.89 g of the product sought were obtained.

In the following examples there are described several preferred embodiments to illustrate the invention. However, it should be understood that the invention is not intended to be limited to the specific embodiments.

EXAMPLE 1

Syn isomer of trifluoromethane sulfonate of (6S,7S) 7-[3-[7-[(2-amino-4-thiazolyl)-(methoxyimino)-acetamido]-2-carboxy-8-oxo-4-thia-1-aza-bicyclo[4,2,-0]oct-2-en-3-yl]propen-2(E)-yl]thieno[2,3-b]pyridinium STEP A: 1,1-dimethylethyl (6S,7S) 7-/2-(2-triphenylmethylamino-thiazol-4-yl)-2(Z)-methoxyimino-acetamido]-3-[3-[(1,1-dimethylethyl)-dimethylsilyl-oxy]-propen-1-yl]-8-oxo-4-thia-1-azabicyclo[4,2,0]oct-2-en-2-carboxylate 1.89 g of hydrochloride of 1,1-dimethylethyl 7-[2-(triphenylmethylamino-thiazol-4-yl)-2(Z)methoxyimino-acetamido]-3-[methyltriphenyl-phosphonium]-8-oxo-4-thia-1-azabicyclo[4,2,0]oct-2-en-2-carboxylate, 30 ml of dichloromethane, 0.68 ml of 2-(1,1-dimethylethyl-dimethylsilyl-oxy)-acetaldehyde, and 0.53 ml of triethylamine were mixed together, and stirred at +20° C. for 14 hours. The solution was chromatographed over silica and eluted with a mixture of dichloromethane and ethyl acetate (9/1) to obtain 1.305 g of 1,1-dimethylethyl (6S, 7S) 7-[2-(triphenylmethylamino-thiazol-4-yl)-2(Z)-methoxyimino-acetamido]-3-[3-[(1,1-dimethylethyl)-dimethylsilyl-oxy]-propen-1-yl]-8-oxo-4-thia-1-azabicyclo[4,2,0]oct-2-en-2-carboxylate containing a mixture of isomer E (2/3) and Z (1/3).

| NMR Spectrum ($CDCl_3$): | |
|---|---|
| 0.90–0.92 ppm | SitBu |
| 1.50–1.53 ppm | $CO_2tBu$ |
| 2.95–3.11 ppm | $CH_2S$ |
| 4.05 ppm | $OCH_3$ |
| 4.31–4.37 ppm | $CH_2O$ |
| 4.11 ppm | $H_6$ |
| 5.4–5.5 ppm | $H_7$ |
| 5.75–5.87 ppm and 6.11–6.24 ppm | Z(⅓) |
| 6.17–6.34 ppm and 6.97–7.16 ppm | E(⅔) |
| 6.50–6.56 ppm | $H_5$ thiazole, syn |
| 7.34 ppm | $\phi_3$. |

STEP B: 1,1-dimethylethyl 7-[2-(2-triphenylmethylamino-thiazol-4-yl)-2(Z)-methoxyimino-acetamido]-3-[3-hydroxypropen-1(E)-yl]-8-oxo-4-thia-1-azabicyclo[4,2,0]oct-2-en-2-carboxylate and 1,1-dimethylethyl-7-[2-(2-triphenylmethylamino-thiazol-4-yl)-2(Z)-methoxyimino-acetamido-3-[3-hydroxypropen-1(Z)-yl]-8-oxo-4-thia-1-azabicyclo[4,2,-0]oct-2-en-2-carboxylate 1.305 g of the product of Step A of Example 1 were dissolved in 15 ml of acetone, 2 ml of an aqueous normal solution of hydrochloric acid were added with stirring for 150 minutes, followed by concentration to dryness by distillation under reduced pressure. After adding sodium bicarbonate water, extracting with dichloromethane, and concentrating the extracts to dryness by distilling under reduced pressure, the residue was chromatographed over silica and eluted with a mixture of dichloromethane and ethyl acetate (1/1) to obtain 536 mg of the E isomer of 1,1-dimethylethyl 7-[2(2-triphenylmethylamino-thiazol-4-yl)-2(Z)-methoxyimino-acetamido]-3-[3-hydroxypropen-1(E)-yl]-8-oxo-4-thia-1-aza-bicyclo[4,2,0]oct-2-en-2-carboxylate and 369 mg of the Z isomer of the said product.

| I.R. Spectrum (chloroform): isomer E | | | |
|---|---|---|---|
| 3607 $cm^{-1}$ | | OH | |
| 3405 $cm^{-1}$ | | amide NM | |
| 1684 $cm^{-1}$ | | C=O | |
| 1515 $cm^{-1}$ | | amide II | |
| 1772 $cm^{-1}$ | | lactam C=O | |
| 1595 $cm^{-1}$; 1544 $cm^{-1}$; 1527 $cm^{-1}$: | | aromatic, thiazole, conjugated system. | |
| 1700 $cm^{-1}$ | | tertbutyl ester | |
| 1370 $cm^{-1}$ | | $CH_3$ | |
| 1154 $cm^{-1}$ | | C—O—C | |
| 2820 $cm^{-1}$ | | OMe | |
| 1049 $cm^{-1}$ | | C=N—OR | |
| **U.V. Spectrum (Ethanol)** | | | |
| max. | 231 nm | $E_1^1 = 497$ | $\epsilon = 32{,}200$ |
| infl. | 258 nm | $E_1^1 = 290$ | |
| infl. | 264 nm | $E_1^1 = 264$ | |
| infl. | 270 nm | $E_1^1 = 240$ | |
| max. | 320 nm | $E_1^1 = 245$ | $\epsilon = 18{,}100$ |
| **NMR Spectrum ($CDCl_3$)** | | | |
| 1.51 ppm | | tBu | |
| 3.05 ppm | | $CH_2S$ | |
| 4.02 ppm | | $OCH_3$ | |
| 4.28 ppm | | $CH_2OH$ | |
| 5.48 ppm | | $H_7$ | |
| 6.24–6.41 and 6.97–7.13 ppm, | | H of ethylenes, EJ = 15 Hz | |
| 7.29 ppm | | $\phi 3$ | |
| 6.53 ppm | | $H_5$ thiazole, syn | |
| **I.R. Spectrum (chloroform): isomer Z** | | | |
| 3605 $cm^{-1}$ | | OH | |
| 3405 $cm^{-1}$ | | NH amide | |
| 1685 $cm^{-1}$ | | C=O | |
| 1505 $cm^{-1}$ | | amide II | |
| 1773 $cm^{-1}$ | | $\beta$ lactam C=O | |
| 1704 $cm^{-1}$ | | tertbutyl ester | |
| 1368 $cm^{-1}$ | | Me | |
| 1154 $cm^{-1}$ | | C—O—C | |
| 1585 $cm^{-1}$, 1573 $cm^{-1}$, 1527 $cm^{-1}$, 1493 $cm^{-1}$, | | trityl, aromatics, thiazole, conjugated system | |
| 2820 $cm^{-1}$ | | C=N—OMe | |
| 1050 $cm^{-1}$ | | C=N—OR | |
| **U.V. Spectrum (ethanol)** | | | |
| infl. | 230 nm | $E_1^1 = 411$ | |
| infl. | 260 nm | $E_1^1 = 220$ | |
| infl. | 265 nm | $E_1^1 = 198$ | |
| infl. | 271 nm | $E_1^1 = 176$ | |
| max. | 308 nm | $E_1^1 = 194$ | $\epsilon = 14{,}300$ |
| **NMR Spectrum ($CDCl_3$)** | | | |
| 1.49 ppm | | tBu | |
| 3.06 ppm | | S—$CH_2$ | |
| 4.04 ppm | | OMe | |
| 4.27 ppm | | $CH_2OH$ | |
| 5.48 ppm | | $H_7$ | |
| 5.85 ppm–5.98 ppm and 6.21–6,34 ppm, | | H of ethylenes ΔZ J = 11 Hz | |
| 6.56 ppm | | $H_5$ thiazole "syn" | |
| 7.29 ppm | | $\phi_3$ | |

STEP C: (6S,7S) trifluoromethane sulfonate of 7-[3-[7-[2-(2-triphenylmethylamino-thiazol-4-yl)-2 (Z)-methoxyimino-acetamido-2-1,1-dimethylethyloxy-carbonyl]-8-oxo-4-thia-1-azabicyclo[4,2,0]oct-2-en-3-yl]-propen-2-(E)-yl]thieno[2,3-b]pyridinium 222 mg of the E isomer of Step B were dissolved in 4.8 ml of dichloromethane, and to this was added 3 ml of a solution of 536 mg of thienopyridine and 10 ml of methylene chloride. After cooling to −70° C. 2.7 ml of a solution of 0.43 ml of trifluoromethane sulfonic anhydride in 10 ml of methylene chloride were added dropwise. The temperature was slowly raised to −20° C., followed by concentrating to dryness by distilling under reduced pressure. Ethyl acetate was added to the residue which was then washed with water containing 0.7 ml of a N aqueous solution of hydrochloric acid, decanted, washed with water, extracted with ethyl acetate, and the extracts were concentrated to dryness by distilling under reduced pressure. The residue was chromatographed over silica and eluted with a mixture of dichloromethane and methanol (92/8) to obtain 236 mg of isomer E of (6S,7S) trifluoromethane sulfonate of 7-3-[7-[2-(2-triphenylmethylamino-thiazol-4-yl)2(Z)-methoxyimino-acetamido]-2-[1,1-dimethylethyl-oxy-carbonyl]-8-oxo-4-thia-1-azabicyclo[4,2,0]oct-2-en-3-yl]-propen-2(E)yl]thieno[2,3-b]pyridinium.

STEP C': (6S,7S) trifluoromethane sulfonate of 7-[3-[7-[(2-triphenylmethylamino-thiazol-4-yl)-2(Z)-methoxyimino-acetamido]-2-[1,1-dimethylethyl-oxy-carbonyl]-8-oxo-4-thia-1-azabicyclo[4,2,0]oct-2-en-3-yl]propen-2(Z)-yl]thieno[2,3-b]pyridinium 145 mg of the Z isomer of Step B of Example 1 were dissolved in 5 ml of dichloromethane, and 120 μl of thieno[2,3-b]-pyridine were added followed by cooling to −70° C. 1.76 ml of a solution of 0.42 ml of trifluoromethane sulfonic anhydride in 10 ml of methylene chloride were added dropwise, then the temperature was slowly raised to +20° C. The solution was chromatographed over silica and eluted with a mixture of dichloromethane and methanol (92/8) to obtain 157 mg of (6S,7S) trifluoromethane sulfonate of 7-[3-[2[(2-triphenylmethylamino-thiazol-4-yl)-2(Z)-methoxyimino-acetamido]-2-[1,1-dimethylethyl-oxy-carbonyl]-8-oxo-4-thia-1-azabicyclo[4,2,0]oct-2-en-3-yl]propen-2(Z)-yl]thieno][2,3-b]pyridinium.

STEP D: Syn isomer of (6S,7S) trifluoromethane sulfonate of 7-[3-[7-[(2-amino-4-thiazolyl)-methoxyimino-acetamido]-2-carboxy-8-oxo-4-thia-1-azabicyclo[4,2,0]oct-2-en-3-yl]propen-2(E)-yl]thieno[2,3-b]pyridinium 221 mg of isomer E of Step C and 2.5 ml of a 33% aqueous solution of formic acid were mixed together and heated to 65° C. for 55 minutes, then cooled, diluted with water, filtered and washed with ether. The aqueous phase was concentrated to dryness by distilling under reduced pressure and water was added and after separating and drying, 93 mg of syn isomer of (6S,7S) trifluoromethane sulfonate of 7-[3-[7-[(2-amino-4-thiazolyl)-methoxyimino-acetamido]-2-carboxy-8-oxo-4-thia-1-azabicyclo[4,2,0]oct-2-en-3-yl]propen-2(E)-yl]thieno[2,3-b]pyridinium were obtained.

| | | |
|---|---|---|
| I.R. Spectrum (nujol): | | |
| 1760 $cm^{-1}$ | β lactam C=O | |
| 1660 $cm^{-1}$ | | |
| 1550 and 1535 $cm^{-1}$ aromatic + amide II + thiazole + conjugated system. | | |
| 1030 $cm^{-1}$ | $CF_3SO_3$ | |
| U.V. Spectrum (ethanol): | | |
| max. 238 nm | $E_1^1 = 625$ | ε = 44,200 |
| max. 307 nm | $E_1^1 = 251$ | ε = 17,700 |
| infl. 318 nm | $E_1^1 = 232$ | |
| Infl. 338 nm | $E_1^1 = 166$ | |
| NMR Spectrum (DMSO): | | |
| 3.83 ppm: | $OCH_3$ | |
| 5.55 to 6.44 ppm: | $CH_2^+$ 1H ethylene | |
| 6.81 ppm: | $H_5$ thiazole | |
| 7.23 ppm: | $NH_2$ | |
| 7.84 to 9.24 ppm: | aromatics | |

By hydrolysis with formic acid, the isomer Z hydrolyzed entirely into isomer E (isomerization).

EXAMPLE 2

Syn isomer of (6S,7S) 7-[2-(2-aminothiazol-4-yl)-2(Z)-methoxyimino-acetamido]-3-[3-(1-methyl-1H-1,2,3,4-tetrazol-5-yl)thio-propen-(E)-yl]-8-oxo-4-thia-1-azabicyclo[4,2,0]oct-2-en-2-carboxylic acid STEP A: 1,1-dimethylethyl 7-[2-(2-triphenylmethylamino-thiazol-4-yl)-2(Z)-methoxyimino-acetamido]-3-[3-(1-methyl-1H-1,2,3,4-tetrazol-5-yl)thio-propen-(E)-yl]-8-oxo-4-thia-1-azabicyclo[4,2,0]oct-2-en-2-carboxylate 37 ml of 1,1-dimethylethyl 7-[2-(2-triphenylamino-thiazol-4-yl)-2(Z)-methoxyimino-acetamido]-3-[3-hydroxypropen-1(E)-yl]-8-oxo-4-thia-1-azabicyclo[4,2,-0]oct-2-en-2-carboxylate, 24 mg of tetrabutyl ammonium iodide, 0.8 ml of methylene chloride and 23 μl of 2,6-lutidine were mixed together and cooled to −70° C. Then, dropwise, 0.25 ml of a solution of trichloromethane sulfonic anhydride, titrating 0.42 ml of anhydride per 10 ml of methylene chloride were added, followed by 14 mg of the sodium salt of 1-methyl-5-mercapto-1,2,3,4-tetrazole and then 0.5 ml of dimethylformamide. After stirring at 20° C. and concentrating to dryness, the residue was chromatographed over silica and eluted with a mixture of methylene chloride and ethyl acetate (9/1) to obtain 1,1-dimethylethyl 7-[2-(2-triphen ylmethylamino-thiazol-4-yl)-2(Z)-methoxyimino-acetamido]-3-[3-(1-methyl-1H-1,2,3,4-tetrazol-5-yl)thio-propen-(E)-yl]-8-oxo-4-thia-1-azabicyclo[4,2,0]oct-2-en-2-carboxylate.

STEP B: 7-[2-(2-aminothiazol-4-yl)-2(Z)-methoxyimino-acetamido]-3-[3-(1-methyl-1H-1,2,3,4-tetrazol-5-yl)thio-propen-(E)-yl]-8-oxo-4-thia-1-azabicyclo[4,2,0]oct-2-en-2-carboxylic acid 329 mg of the compound of Step A and 9.6 ml of a 33% aqueous solution of formic acid were mixed together and heated for 25 minutes at +65° C., then cooled, diluted with water, filtered, and concentrated to dryness by distilling under reduced pressure. The residue was triturated in water and the insoluble matter formed was eliminated by filtering, and after concentrating to dryness, 142 mg of 7-[2-(2-aminothiazol-4-yl)-2(Z)-methoxyimino-acetamido]-3-[3-(1-methyl-1H-1,2,3,4-tetrazol-5-yl)thio-propen-(E)-yl]-8-oxo-4-thia-1-azabicyclo[4,2,0]oct-2-en-2-carboxylic acid with a specific rotation of $[\alpha]_D^{20} = -99°$ (c=0.8% DMSO) were obtained.

| | | |
|---|---|---|
| I.R. Spectrum (nujol): | | |
| 3410 $cm^{-1}$; 3300 $cm^{-1}$; 3210 $cm^{-1}$ absorption OH/NH | | |
| 1775 $cm^{-1}$; 1770 $cm^{-1}$ β lactam C=O | | |
| 1665 $cm^{-1}$ other carbonyl; | | |
| 1626 $cm^{-1}$; | | |
| 1556 $cm^{-1}$ aromatic conjugated system $NH_2$ | | |
| U.V. Spectrum (ethanol HCl, 0.1N): | | |
| max. 239 nm | $E_1^1 = 390$ | ε = 21,000 |
| max. 266 nm | $E_1^1 = 414$ | ε = 22,300 |
| Infl. 280 nm | $E_1^1 = 390$ | |
| max. 329 nm | $E_1^1 = 304$ | ε = 16,300 |

-continued

| NMR Spectrum (DMSO) | |
| --- | --- |
| 3.86 and 3.94 ppm | $NCH_3$ and OMe |
| 4.03–4.10 ppm | $=C-CH_2S$ |
| 5.56 to 5.73 ppm | $H_7$ β lactam (cis) |
| 6.07 to 6.39 ppm | 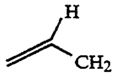 ethylene ΔE |
| 6.88 to 7.05 ppm | 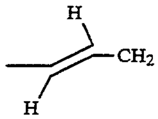 |
| 6.84 ppm | $H_5$ thiazole syn |
| 7.22 ppm | $NH_2$ |
| 9.17–9.27 ppm | NHCO |

EXAMPLE 3

Internal salt of syn isomer of (6S,7S) 7-[3-[7-[2-(2-aminothiazol-4-yl)-2-(methoxyimino)-acetamido]-2-carboxy-8-oxo-4-thia-1-azabiclo[4,2,0]-oct-2-en-3-yl]propen-2-(E)-yl]thieno[2,3-b]pyridinium 281 mg of the product of Step C of Example 1 were dissolved in 3.17 ml of 66% formic acid, and the solution was heated at 65° C. for two hours. It was then diluted with 3.2 ml of water and filtered and the filtrate was concentrated to dryness under reduced pressure. The residue was dissolved in 1.3 ml of a 1M aqueous solution of triethylamine carbonate and 1.3 ml of acetonitrile and chromatographed over silica (eluent:water-acetonitrile 9–1, then 85–15) to obtain 77 mg of internal salt of syn isomer of (6S,7S) 7-[3-[7-[2-(2-aminothiazol-4-yl)-2-(methoxyimino)-acetamido]-2-carboxy-8 -oxo-4-thia-1-azabiclo[4,2,0]-oct-2-en-3-yl]-propen-2-(E)-yl]thieno[2,3-b]pyridinium.

| NMR Spectrum (DMSO): | | |
| --- | --- | --- |
| 3.83 ppm(s): | | $OCH_3$ |
| 5.49 ppm: | | $H_7$ β-lactam, cis |
| 5.88–7.48 ppm: | | H of ethylene |
| 6.80 ppm(s): | | $H_5$ thiazole |
| IR Spectrum (nujol): | | |
| NH/OH | β-lactam C=O: | 1760 $cm^{-1}$ |
| | amide C=O: | 1665 $cm^{-1}$ |
| $NH_2$ def. aromatic, $COO^-$, | | 1635 $cm^{-1}$, 1600 $cm^{-1}$ |
| amide II thiazole: | | 1558 $cm^{-1}$, 1540 $cm^{-1}$ |
| C=N—OR: | | 1035 $cm^{-1}$ |

EXAMPLE 4

Trifluoroacetate of syn isomer of (6S,7S) 7-[2-(2-aminothiazol-4-yl)-2-(methoxyimino)-acetamido]-3-[3-acetoxy-1-(E)-propenyl]-8-oxo-4-thia-1-azabicyclo[4,2,0]oct-2-en-2-carboxylic acid

STEP A: 1,1-dimethylethyl 7-[2-(2-tritylaminothiazol-4-yl)-2-(Z)-methoxyimino-acetamido]-3-[(3-acetoxy)-propen-1(E)-yl]-8-oxo-4-thia-1-azabicyclo[4,2,0]oct-2-en-2-carboxylate 300 mg of the E isomer of Example 1 Step B, 1.5 ml of pyridine and 0.73 ml of acetic anhydride were stirred for 2 hours at ambient temperature. 20 ml of water and 10 ml of N hydrochloric acid were added, followed by extraction with methylene chloride. 395 mg of crude product were obtained which was chromatographed over silica and eluted with a mixture of methylene chloride and ethyl acetate (6–4) to obtain 255 mg of 1,1-dimethylethyl 7-[2-(2-tritylaminothiazol-4-yl)2-(Z)-methoxyimino-acetamido]-3-[(3-acetoxy)-propen-1(E)-yl]-8-oxo-4-thia-1-azabicyclo[4,2,0]oct-2-en-2-carboxylate melting at ≃ 170° C.

STEP B: Trifluoroacetate of syn isomer of (6S,7S) 7-/2-(2-aminothiazol-4-yl)2-(methoxyimino)-acetamido]-3-[3-acetoxy-1(E)-propenyl]-8-oxo-4-thia-1-azabicyclo[4,2,0]oct-2-en-2-carboxylic acid 210 mg of the product of Step A and 1.05 ml of trifluoroacetic acid with 10% of water were stirred for 55 minutes at ambient temperature and 5 ml of ether were added with stirring for a further hour, then, after separating, 133 mg of trifloroacetate of syn isomer of (6S,7S) 7-[2-(2-aminothiazol-4-yl)-2-(methoxyimino)-acetamido]-3-[3-acetoxy-1(E)propenyl]-8-oxo-4-thia-1-azabicyclo[4,2,0]oct-2-en-2-carboxylic acid were obtained.

| NMR Spectrum (DMSO): | |
| --- | --- |
| 6.92 ppm | $H_6$ of the thiazole |
| 9.27–9.37 ppm | H amido |
| 5.63 to 5.68 ppm | $H_7$ |
| 4.02–4.08 ppm | $H_5$ |
| 6.22 to 6.3 and 7.09 to 6.93 ppm | H ethylenes |
| 2.07 ppm | H of acetyl |
| IR Spectrum (nujol): | |
| Absorption region | 1767 $cm^{-1}$, 1740 $cm^{-1}$ |
| OH/NH β-lactam C=O | 1698 $cm^{-1}$, 1667 $cm^{-1}$ |
| | 1640 $cm^{-1}$, |
| Strong absorptions | 1140 $cm^{-1}$, 1250 $cm^{-1}$ |

| UV Spectrum: | | | |
| --- | --- | --- | --- |
| 1) EtOH | | | |
| max. | 236 nm | $E_1^1 = 387$ | $\epsilon = 23,100$ |
| infl. | 260 nm | $E_1^1 = 256$ | |
| max. | 320 nn | $E_1^1 = 260$ | $\epsilon = 15,500$ |
| 2) EtOH + HCl 0.1 N | | | |
| max. | 238 nm | $E_1^1 = 291$ | $\epsilon = 17,300$ |
| max. | 266 nm | $E_1^1 = 331$ | $\epsilon = 19,700$ |
| infl. | 283 nm | $E_1^1 = 289$ | |
| max. | 324 nm | $E_1^1 = 234$ | $\epsilon = 13,900$ |

EXAMPLE 5

Trifluoromethane sulfonate of syn isomer of (6S,7S) 3-[7-[2-[2-aminothiazol-4-yl)-2-methoxyimino-acetamido]-2-carboxy-8-oxo-4-thia-1-azabicyclo[4,2,-0]oct-2-en-3-yl]-2(Z)propenyl trimethylammonium and isomer (E)propenyl

STEP A: Trifluoromethane sulfonate of syn isomer of (6S,7S) 3-[7-[2-(2-tritylamino-thiazol-4-yl)-2-methoxyimino-acetamido]-2-[(1,1-dimethylethoxy)-carbonyl]-8-oxo-4-thia-1-azabicyclo[4,2,0]oct-2-en-3-yl]propen-2(E)yl-trimethylammonium, and the isomer (propen-2(Z)yl)

282 mg of tert.-butyl 7-[2-(2-tritylaminothiazol-4-yl)-2-(methoxyimino)-acetamido]-3-[3-hydroxy-1(E+Z)-propenyl]-8-oxo-4-thia-1-azabicyclo[4,2,0]oct-2-en-2-carboxylate were dissolved in 3 ml of methylene chloride, then cooled to −70° C. and 1.6 ml of a 1.53 mmol of trimethylamine were added. 0.094 ml of trifluoromethane sulfonic anhydride were added dropwise with stirring at −70° C. for 30 minutes. 7 ml of methylene chloride and 5 ml of 0.1N hydrochloric acid were added and the mixture was allowed to warm up again. The organic phase was separated and dried, then chromatographed over silica with elution by a mixture of methylene chloride and methanol (95-5) to obtain 108 mg of isomer Z (30%), 117 mg of isomer E (33%) and 53 mg of a mixture of E and Z.

STEP B: Trifluoromethane sulfonate of syn isomer of 3-[7-[2-(2-aminothiazol-4-yl)-2-methoxyimino-acetamido]-2-carboxy-8-oxo-4-thia-1-azabicyclo[4,2,-0]oct-2-en-3-yl]-2-(Z)propenyl trimethylammonium and the 2(E)propenyl isomer 108 mg of the isomer (Z) of Step A were dissolved in 2 ml of formic acid with 66% of water and stirred for 2 hours at 66° C. after which it was cooled and diluted with 2 ml of water. The reaction mixture was washed with ether, then with methylene chloride, and the aqueous phase was evaporated. The residue was taken up 3 times with 5 ml of acetonitrile and 1 ml of methanol. 5 ml of methylene chloride were added to the residue, and after stirring for 1 hour and separation, 55 mg of trifluoromethane sulfonate of syn isomer of 3-[7-[2-(2-aminothiazol-4-yl)-2-methoxyimino-acetamido]-2-carboxy-8-oxo-4-thia-1-azabicyclo[4,2,0]oct-2-en-3-yl]-2-(Z)propenyl trimethylammonium were obtained.

| NMR Spectrum (DMSO): | |
|---|---|
| 3.06 ppm(s) | $N^{\oplus}(CH_3)_3$ |
| 3.86 ppm(s) | $OCH_3$ |
| ≈4.10 ppm(m) | $CH_2—N^{\oplus}$ |
| 3.02 to 3.27 ppm | $S—CH_2$ |
| 6.72 ppm | $—CH{=}CH—CH_2$ ΔZ |
| 6.81 ppm | $H_5$ thiazole syn |
| 9.3 ppm | NHCO |

| UV Spectrum | | | |
|---|---|---|---|
| 1) EtOH | | | |
| max. | 231 nm | $E_1^1 = 336$ | $\epsilon = 21,200$ |
| max. | 302 nm | $E_1^1 = 202$ | $\epsilon = 12,700$ |
| 2) EtOH + HCl 0.1 N | | | |
| max. | 232 nm | $E_1^1 = 257$ | $\epsilon = 16,200$ |
| max. | 261 nm | $E_1^1 = 250$ | $\epsilon = 15,800$ |
| max. | 284 nm | $E_1^1 = 237$ | $\epsilon = 14,900$ |
| infl. | 310 nm | $E_1^1 = 179$ | |

By starting from the (E) isomer obtained at Step A, and operating as above, 56 mg of the expected 2(E)-propenyl isomer were obtained.

| NMR Spectrum (DMSO) | |
|---|---|
| 3.02 ppm | $N^{\oplus}(Me)_3$ |
| 3.87 ppm(s) | $OMe_3$ |
| 4.11 ppm | $CH_2—N^{\oplus}$ |
| 5.61 to 5.78 ppm | $H_7$ (cis) |
| 6.73 ppm | $H_5$ thiazole syn |
| 5.96 to 6.22 ppm | H ethylene ΔF |
| 7.11-7.28 ppm | |

| UV Spectrum | | | |
|---|---|---|---|
| 1) EtOH | | | |
| max. | 235 nm | $E_1^1 = 381$ | $\epsilon = 24,000$ |
| max. | 325 nm | $E_1^1 = 244$ | $\epsilon = 15,400$ |
| 2) EtOH + HCl 0.1 N | | | |
| infl. | 245 nm | $E_1^1 = 299$ | |
| max. | 263 nm | $E_1^1 = 318$ | $\epsilon = 20,100$ |
| max. | 332 nm | $E_1^1 = 212$ | $\epsilon = 13,400$ |

EXAMPLE 6

Internal salt of syn isomer of (6S,7S) 3-[3-[7-[(2-aminothiazol-4-yl)-2-methoxyimino-acetamido]-2-carboxy-8-oxo-4-thia-1-azabicyclo[4,2,-0]oct-2-en-3-yl]-2(E)propenyloxycarbonyl]-1-methyl-pyridinium STEP A: 1,1-dimethylethyl (6S,7S) 7-[2-(2-trityl-aminothiazol-4-yl)-2-(Z)-(methoxyimino)-acetamido]-3-[(3-(nicotinoyloxy)-1-(E)propenyl]-8-oxo-4-thia-1-azabicyclo[4,2,0]oct-2-en-2-carboxylate 1.5 g of nicotinic acid were heated to reflux in 1.8 ml of thionyl chloride for one and a half hours. After taking up in toluene and evaporating, the residue was triturated with ether, then dried to obtain 2.12 g of nicotinoyl chloride hydrochloride. 258 mg of the E isomer of Step B of Example 1 were dissolved in 1 ml of pyridine, and 93 mg (0.525 mM) of the freshly prepared nicotinoyl chloride hydrochloride were added and stirred for 2 hours under an inert atmosphere. After diluting with 10 ml of methylene chloride, washing with 1N hydrochloric acid and then with a solution of sodium bicarbonate, drying and evaporating, the residue was chromatographed over silica and eluted with a mixture of methylene chloride and acetone (9-1) to obtain 232 mg of 1,1-dimethylethyl (6S,7S) 7-[2-(2-trityl-aminothiazol-4-yl)-2-(Z)-(methoxyimino)-acetamido]-3-[(3-nicotinoyloxy)-1-(E)propenyl]-8-oxo-4-thia-1-azabicyclo[4,2,0]oct-2-en-2-carboxylate.

STEP B: Iodide of E isomer of (6S,7S) 3-[3-[7-[2-(2-tritylaminothiazol -4-yl)-2-(Z)-methoxyimino-acetamido]-2-(1,1-dimethylethoxycarbonyl)-8-oxo-4-thia-1-azabicyclo[4,2,-0]oct-2-en-3-yl]-1-(E)propenyloxycarbonyl-1-methyl-pyridinium 225 mg of the product of Step A were dissolved in 1 ml of dimethylsulfoxide and 0.16 ml of methyl iodide were added. The mixture was stirred for 5 hours and the dimethyl sulfoxide was evaporated under reduced pressure at 40° C. The residue was chromatographed over silica (eluent: methylene chloride-methanol 92-8) to obtain 187 mg of iodide of E isomer of (6S,7S) 3-[3-[7-[2-(2-tritylaminothiazol-4-yl)-2-(Z)-methoxyimino-acetamido]-2-(1,1-dimethylethoxycarbonyl)-8-oxo-4-thia-1-azabicyclo[4,2,0]oct-2-en-3-yl]-1-(E)-propenyloxycarbonyl-1-methyl-pyridinium.

STEP C: Internal salt of syn isomer of (6S,7S) 3-[3-[7-[(2-aminothiazol-4-yl)-2-methoxyimino-acetamido]-2-2-carboxy-8-oxo-4-thia-1-azabicyclo[4,2,0]-oct-2-en-3-yl]-2-(E)propenyloxycarbonyl]-1-methylpyridinium 187 mg of the product of Step B were dissolved in 1 ml of trifluoroacetic acid and left at ambient temperature for 10 minutes. The product was precipitated with 10 ml of isopropyl ether and after separation, the residue was dissolved in 5 ml of hot ethanol. The mixture was concentrated to about 1 ml and redissolved by heating, after which 0.05 ml of pyridine was added. By cooling, stirring for 10 minutes, separating, washing with ethanol and then with ether, 34 mg of internal salt of syn isomer of (6S,7S) 3-[3-[7-[(2-aminothiazol-4-yl)-2-methoxyimino-acetamido]-2-carboxy-8-oxo-4-thia-1-azabicyclo[4,2,0]-oct-2-en-3-yl]-2-(E)-propenyloxycarbonyl]-1-methylpyridinium were obtained.

| NMR Spectrum (DMSO) | |
|---|---|
| 3.78–4.86 ppm(s) | $OCH_3$ |
| 4.05 ppm(m) | $H_6$ |
| 4.37–4.44 ppm | $N^+—CH_3$ |
| 5.05 ppm | $—CH_2O—$ |
| 5.66 ppm | $H_7$ |
| 6.24 ppm(t,d) | $=CH—CH_2$ |
| 7.15 ppm(d) | $—CH=CH—CH_2$ |
| 6.82 ppm | $H_5$ thiazole syn |
| 7.23 ppm | $NH_2$ |
| 8.06 to 9.57 ppm | H pyridine and H mobile |

EXAMPLE 7

Trifluoromethane sulfonate of (6S,7S) 1-[3-[7-[2-(2-aminothiazol-4-yl)-2-(methoxyimino-acetamido]-2-carboxy-8-oxo-4-thia-1-azabicyclo[4,2,-0]oct-2-en-3-yl]-2(Z)-propenyl]-1,4-diazabicyclooctane trifluoroacétate STEP A: Trifluoromethane sulfonate of 1,1-diméthyléthyl(6S,7S) 7-[2-(2-tritylaminothiazol-4-yl)-2-(methoxyimino-acetamido]-3-[3-(1,4diazabicyclooctane)-1-(Z)-propenyl]-8-oxo-4-thia-1-azabicyclo[4,2,0]oct-2-en-carboxylate 300 mg of 1,1-dimethylethyl (6S,7S) 7-[2-(2-tritylaminothiazol-4-yl)-2-(methoxyimino-acetamido]-3-hydroxy-1-(Z)-propenyl]-8-oxo-4-thia-1-azabicyclo[4,2,0]oct-2-en-carboxylate, 6 ml of methylene chloride and 179 mg of 1,4-diazabicyclo-octane were mixed together and then cooled to −70° C. Dropwise 0.114 ml of trifluoromethane sulfonic anhydride were added over 25 minutes at this temperature. After being left for 15 minutes at −15° C. with stirring, 20 ml of water and 6 ml of 0.1N hydrochloric acid were poured in. Extraction was done with methylene chloride and the extracts were dried and concentrated to dryness to obtain 350 mg of crude product which was then chromatographed over silica and eluted with a mixture of methylene chloride and methanol (9–1) to obtain 240 mg of trifluoromethane sulfonate of 1,1-diméthyl ethyl (6S,7S)) 7-[2-(2-tritylaminothiazol-4-yl)-2-methoxyiminoacé tamido]-3-[3-(4-diazabicyclooctane)-1-(Z)-propenyl]8-oxo-4-thia-1-azabicyclo[4,2,0]oct-2-en-carboxylate.

STEP B: Trifluoromethane sulfonate of (6S,7S) 1-[3-[7-[[2-(2-aminothiazol-4-yl)-2-methoxyimino-acetamido]-2-carboxy-8-oxo-4-thia-1-azabicyclo[4,2,-0]oct-2-en-3-yl]-2-(Z)propenyl]-1,4-diazabicyclooctane trifluoroacetate 190 mg of the product of Step A and 1 ml of trifluoroacetic acid with 10% of water were stirred for 60 minutes and precipitation was caused by adding 6 ml of ether, and after filtering and drying, 146 mg of trifluoromethane sulfonate of (6S,7S) 1-[3-[7-[[2-(2-aminthiazol-4-yl)2-methoxyimino-acetamido]-2-carboxy-8-oxo-4-thia-1-azabicyclo[4,2,0]oct-2-en-3-yl]-2-(Z)propenyl]-1,4-diazabicyclooctane trifluoroacetate melting at 190° C. were obtained.

| NMR Spectrum (DMSO) | |
|---|---|
| 6.88 ppm | $H_5$ of thiazole |
| 9.3–9.4 ppm | H of amido |
| 5.58 to 5.73 ppm | $H_6$ |
| 6.73–6.87 ppm | H ethylenes ΔZ |

-continued

| | | | |
|---|---|---|---|
| 5.86 to 6.11 ppm | | | |

| UV Spectrum | | | |
|---|---|---|---|
| 1) EtOH | | | |
| max. 231 nm | $E_1^1 = 236$ | | $\epsilon = 18{,}800$ |
| max. 303 nm | $E_1^1 = 150$ | | $\epsilon = 12{,}000$ |
| 2) EtOH + 0.1 N HCl | | | |
| max. 233 nm | $E_1^1 = 176$ | | $\epsilon = 14{,}000$ |
| max. 261 nm | $E_1^1 = 177$ | | $\epsilon = 14{,}000$ |
| infl. 283 nm | $E_1^1 = 164$ | | |
| infl. 291 nm | $E_1^1 = 157$ | | |
| infl. 311 nm | $E_1^1 = 119$ | | |

EXAMPLE 8

Internal salt of syn isomer of (6S,7S) 4-[3-[7-[2-(2-aminothiazol-4-yl)-2-methoxyimino-acetamido]-2-carboxy-8-oxo-4-thia-1-azabicyclo[4,2,-0]oct-2-en-3-yl]-2-(E)-propenyl]-2-methylthiazolo[5,4-b]pyridinium STEP A: Trifluoromethane sulfonate of syn isomer of (6S,7S) 4-[[7-[2-tritylaminothiazol-4-yl)-2-(Z)-methoxyimino-acetamido]-2-[1,1-dimethylethoxycarbonyl]-8-oxo-4-thia-1-azabicyclo-[4,2,0]oct-2-en-3-yl]-2-(E)propenyl]-2-methyl-thiazolo[5,4-b]pyridinium 350 mg of the Z isomer of Step B of Example 1 in 10 ml of methylene chloride and 356 mg of methyl-thiazolo-pyridine were cooled to −70° C. and 2.34 ml of a solution made up of 0.5 ml of trifluoromethane sulfonic anhydride in 10 ml of methylene chloride were introduced. The mixture was stirred for 5 minutes at −70° C. under nitrogen and then the temperature was allowed to return to 20° C. After diluting with methylene chloride, washing with water, drying and evaporating to dryness under reduced pressure, the residue obtained was chromatographed over silica (eluant: methylene chloride-acetone, 9–1 then methylene chloride-methanol 92–8) to abtain 347 mg of trifluoromethane sulfonate of syn isomer of (6S,7S) 4-[[7-[2-(2-tritylaminothiazol-4-yl)-2-(Z)-methoxyimino-acetamido]-2-[1,1-dimethylethoxycarbonyl]-8-oxo-4-thia-1-azabicyclo-[4,2,0] oct-2-en-3-yl]2-(E)-propenyl]-2-methylthiazolo[5,4-b]pyridinium STEP B: Internal salt of syn isomer of (6S,7S) 4-[3-[7-[2-(2-aminothiazol-4-yl)-2-methoxyimino-acetamido]-2-carboxy-8-oxo-4-thia-1-azabicyclo[4,2,-0]oct-2-en-3-yl]-2-(E)-propenyl]-2-methylthiazolo[5,4-b]pyridinium Using the procedure of Example 3,330 mg of the product of Step A were reacted and elution was done with distilled water containing 5% of acetonitrile, then 10% and finally 20%. The acetonitrile was evaporated off and the residue was taken up with 1 ml of acetone, isolated and rinsed with a minimum ofacetone by centrifuging to obtain 98 mg of internal salt of syn isomer of (6S,7S) 4-[3-[7-[2-(2-aminothiazol-4-yl)-2-methoximino-acetamido]-2-carboxy-8-oxo-4-thia-1-azabicyclo[4,2,0]oct-2-en-3-yl]-2-(E) propenyl]-2-methyl-thiazolo[5,4, -b]pyridinium.

| NMR Spectrum (DMSO) | |
|---|---|
| 3.84 ppm | $OCH_3$ |
| 6.80 ppm | $H_5$ of the thiazole |
| 5.58 ppm | $H_6$ β-lactam, cis |

-continued

| 5.93 and 7.41 ppm | H ethylenes, ΔE | | |
|---|---|---|---|
| UV Spectrum | | | |
| 1) EtOH | | | |
| max. | 225 nm | $E_1^1$ = 598 | ε = 34,200 |
| infl. | 260 nm | $E_1^1$ = 332 | |
| infl. | 295 nm | $E_1^1$ = 306 | |
| max. | 304 nm | $E_1^1$ = 333 | ε = 19,000 |
| infl. | 320 nm | $E_1^1$ = 256 | |
| 2) EtOH + HCl 0.1 N | | | |
| max. | 220 nm | $E_1^1$ = 526 | ε = 30,100 |
| max. | 265 nm | $E_1^1$ = 413 | ε = 23,600 |
| infl. | 280 nm | $E_1^1$ = 381 | |
| infl. | 289 nm | $E_1^1$ = 357 | |
| infl. | 299 nm | $E_1^1$ = 316 | |
| max. | 331 nm | $E_1^1$ = 200 | ε = 11,400 |

EXAMPLE 9

Internal salt of syn isomer of (6S,7S) 1-[3-[7-[2-(2-aminothiazol-4-yl)-2-methoxyimino-acetamido]-2-carboxy-8-oxo-4-thia-1-azabicyclo[4,2,-0]oct-2-en-3-yl]-2-(E)-propenyl]5,6,7,8-tetrahydroquinolinium STEP A: Trifluoromethane sulfonate of syn isomer of (6S,7S) 1-[3-[7-[2-(2-tritylaminothiazol-4-yl)-2-methoxyimino-acetamido]-2-(1,1-dimethyl ethyloxycarbonyl)-8-oxo-4-thia-1-azabicyclo[4,2,0]oct-2-en-3-yl]-2-(E)-propenyl]-5,6,7,8-tetrahydroquinolinium Using the procedure of Step A of Example 8, 162 μl of 2,3-cyclohexenopyridine were reacted to obtain 73 mg of trifluoromethane sulfonate of syn isomer of (6S,7S) 1-[3-[7-[2-(2-tritylaminothiazol-4-yl)-2-methoxy-acetamido]-2-(1,1-dimethyl ethyloxycarbonyl)-8-oxo-4-thia-1-azabicyclo[4,2,0]oct-2-en-3-yl]-2-(E)-propenyl]5,6,7,8-tetrahydroquinolinium.

STEP B: Internal salt of syn isomer of (6S,7S) 1-[3-[7-[2-(2-aminothiazol-4-yl)-2-methoxyimino-acetamido]-2-carboxy-8-oxo-4-thia-1-azabicyclo[4,2,-0]oct-2-en-3-yl]-2-(E)-propenyl]-5,6,7,8-tetrahydroquinolium 136 mg of the product of Step A were dissolved in 1.5 ml of 66% formic acid and the operation was continued as in Example 3 to obtain 25 mg of internal salt of syn isomer of (6S,7S) 1-[3-[7-[2-(2-aminothiazol-4-yl)-2-methoxyimino-acetamido]-2-carboxy-8-oxo-4-thia-1-azabicyclo[4,2,0]oct-2-en-3-yl]-2-(E)-propenyl]-5,6,7,8-tetrahydroquinolinium.

| NMR Spectrum (DMSO) | | | |
|---|---|---|---|
| 3.84 ppm | $OCH_3$ | | |
| 5.46 ppm | $H_7$ β-lactam (cis) | | |
| 6.8 ppm | $H_5$ of the thiazole syn | | |
| 7.09 ppm | H ethylene ΔE | | |
| max. | 232 nm | $E_1^1$ = 411 | ε = 22,800 |
| infl. | 264 nm | $E_1^1$ = 290 | |
| infl. | 274 nm | $E_1^1$ = 269 | |
| infl. | 282 nm | $E_1^1$ = 239 | |
| max. | 317 nm | $E_1^1$ = 277 | ε = 15,400 |

EXAMPLE 10

Internal salt of syn isomer of (6S,7S) 7-[3-[7-[2-(2-aminothiazol-4-yl)-2-difluoromethoxyimino-acetamido]-2-carboxy-8-oxo-4-thia-1-azabicyclo[4,2,0]oct-2-en-3-yl]-2-(E)propenyl]thieno[2,3-b]pyridinium Using the procedure of Example 5, 2.527 g of 1,1-dimethylethyl 7-[2-(2-tritylaminothiazol-4-yl)-2-(Z)-difluoromethoxyimino-acetamide]-3-(3-hydroxy-(E+Z)-propen-1-yl)-8-oxo-4-thia-1-azabicyclo[4,2,-0]oct-2-en-3-yl-2-carboxylate and 1.89 ml of thieno-[2,3-b]pyridine were reacted and after hydrolysis with formic acid, 813 mg of internal salt of syn isomer of (6S,7S) 7-[3-[7-[2-(2-aminothiazol-4-yl)-2-difluoromethoxyimino-acetamido]-2-carboxy-8-oxo-4-thia-1-azabicyclo[4,2,0]oct-2-en-3-yl)-2-(E)propenyl]thieno[2,3-b]pyridinium with a specific rotation of $[\alpha]_D=132.5°\pm2°$ (c=1% in (1—1) mixture of $H_2O$—$CH_3CN$) were obtained.

| NMR Spectrum (DMSO) | | | |
|---|---|---|---|
| 2.89 to 3.06 ppm | S—$CH_2$ | | |
| 5.51 ppm | $H_7$ β-lactam (cis) | | |
| 7.06 ppm | H of the thiazole, syn | | |
| 7.48 ppm | H ethylenes, ΔE | | |
| UV Spectrum (ethanol) - HCl 0.1 N | | | |
| max. | 240 nm | $E_1^1$ = 614 | ε = 36,400 |
| infl. | 260 nm | $E_1^1$ = 316 | |
| infl. | 280 nm | $E_1^1$ = 296 | |
| infl. | 300 nm | $E_1^1$ = 258 | |
| max. | 329 nm | $E_1^1$ = 238 | ε = 14,100 |

EXAMPLE 11

Internal salt of syn isomer of (6S,7S) 4-[3-[7-[2-(2-aminothiazol-4-yl)-2-difluoromethoxyimino-acetamido[-2-carboxy-8-oxo-4-thia-1-azabicyclo[4,2,0]oct-2-en-3-yl[-2-(E)-propenyl]thieno[3,2-b]pyridinium Using the procedure of Example 5, 300 mg of 1,1-dimethylethyl 7-[2-(2-tritylaminothiazol-4-yl)-2-(Z)-difluoromethoxyimino-acetamido]-3-[3-hydroxy-(E)-propen-1-yl]-8-oxo-4-thia-1-azabicyclo[4,2,0]oct-2-en-3-yl-2-carboxylate and 210 mg of thieno[3,2-b]pyridine were reacted and after treatment with formic acid and then with trifluoroacetic acid, 117 mg of product were obtained which was taken up with 0.5 ml of acetonitrile and 0.5 ml of triethylamine carbonate. The mixture was chromatographed over silica and eluted with a mixture of acetonitrile with 5% of water, then with 10% and finally with 15% of water to obtain 43 mg of internal salt of syn isomer of (6S,7S) 4-[3-[7-[2-(2-aminothiazol-4-yl-2-difluoromethoxyimino-acetamido]-2-carboxy-8-oxo-4-thia-1-azabicyclo[4,2,0[oct-2-en-3-yl]-2-(E)-propenyl thieno[3,2-b]pyridinium.

| UV Spectrum EtOH - HCl 0.1 N | | | |
|---|---|---|---|
| max. | 239 nm | $E_1^1$ = 569 | ε = 33,700 |
| infl. | 260 nm | $E_1^1$ = 274 | |
| max. | 290 nm | $E_1^1$ = 260 | ε = 15,400 |
| max. | 327 nm | $E_1^1$ = 254 | ε = 15,100 |

EXAMPLE 12

Trifluoromethane sulfonate of syn isomer of (6S,7S) 7-[3-[7-[2-(2-aminothiazol-4-yl)-2-propenyloxyimino-acetamido]-2-carboxy-8-oxo-4-thia-1-azabicyclo[4,2,-0]oct-2-en-3-yl]-2-(E)-propenyl]thieno[2,3-b]pyridinium Using the procedure of Example 5, 160 mg of 1,1-dimethylethyl 7-[2-(2-tritylaminothiazol-4-yl)-2-(Z)-propenyloxyimino-acetamido]-3-(3-hydroxy-(E)-propenyl-8-oxo-4-thia-1-azabicyclo[4,2,0]oct-2-en-3-yl-2-carboxylate mg/5 $cm^3$ and 2.2 ml of a solution of thienopyridine (266 mg/5 $cm^3$ of $CH_2Cl_2$) were reacted and after hydrolysis with formic acid, 53 mg of trifluoromethane sulfonate of syn isomer of (6S,7S) 7-[3-[7-[2-(2-aminothiazol-4-yl)-2-propenyloxyimino-acetamido]-2-carboxy-8-oxo-4-thia-1-azabicyclo[4,2,-0]oct-2-en-3-yl]-2-(E)-propenyl thieno[2,3-b]pyridinium were obtained.

| NMR Spectrum (DMSO) | | | |
|---|---|---|---|
| 6.80 ppm | $H_5$ of the thiazole | | |
| 6.33 ppm<br>7.18 ppm | H ethylene, trans | | |
| 5.95 ppm | $-CH=CH_2$ | | |
| 7.88 ppm | $H_3$ | bicyclic aromatic | |
| 8.27 ppm | $H_2$ | | |
| 8.14 ppm | $H_6$ | | |
| 9.08 ppm | $H_5$ | | |
| 9.22 ppm | $H_7$ | | |
| **UV Spectrum** | | | |
| **1) EtOH** | | | |
| max. | 239 nm | $E_1^1 = 686$ | $\epsilon = 50{,}600$ |
| infl. | 260 nm | $E_1^1 = 263$ | |
| max. | 306 nm | $E_1^1 = 264$ | $\epsilon = 19{,}500$ |
| infl. | 322 nm | $E_1^1 = 244$ | |
| **2) EtOH + HCl 0.1 N** | | | |
| max. | 240 nm | $E_1^1 = 612$ | $\epsilon = 45{,}200$ |
| max. | 270 nm | $E_1^1 = 363$ | $\epsilon = 25{,}500$ |
| infl. | 280 nm | $E_1^1 = 333$ | |
| infl. | 291 nm | $E_1^1 = 288$ | |
| infl. | 301 nm | $E_1^1 = 237$ | |
| max. | 330 nm | $E_1^1 = 218$ | $\epsilon = 16{,}000$ |

EXAMPLE 13

Syn isomer of (6S,7S) 7-[(2-(2-aminothiazol-4-yl)-2-methoxyimino-acetamido]-3[3-[(5-methyl-1,3,4-thiadiazol-2-yl)thio]-1-(E)propenyl]-8-oxo-4-thia-1-azabicyclo[4,2,0]oct-2-en-2-carboxylic acid STEP A: Syn isomer of (6S,7S) 1,1-dimethylethyl 7-[(2-triphenylmethylaminothiazol-4-yl)-2-methoxyimino-acetamido]-3-[3-[(5-methyl-1,3,4-thiadiazol-2-yl)thio]-1-(E)-propenyl]-8-oxo-4-thia-1-azabicyclo[4,2,-0]oct-2-en-carboxylate A mixture of 184.5 mg of the E isomer of Step B of Example 1 in 4 ml of anhydrous methylene chloride, 120 mg of tetrabutylammonium iodide and 116 µl of 2,6-lutidine was cooled to −70° C. and 620 µl of a solution (0.609M/l) of trifluoromethane sulfonic anhydride in methylene chloride was added dropwise. After 10 minutes at −70° C., the temperature was allowed to return to 20° C. and the solvent was evaporated off under reduced pressure. Then there were added successively while stirring, 66.1 mg of 2-mercapto 5-méthyl-1,3,4-thiadiazole, 2.5 ml of dimethylformamide and 104 mg of anhydrous potassium carbonate. The mixture was stirred for half-an-hour at 20°-25° C. and then poured into 10 ml of N hydrochloric acid and was extracted with ethyl acetate. The extracts were washed with a 5% aqueous solution of sodium bicarbonate, then with water, dried and evaporated to dryness under reduced pressure. The residue was chromatographed over silica and eluted with a mixture of ethyl acetate and methylene chloride (15-85) to obtain 147 mg of syn isomer of (6S,7S) 1,1-dimethylethyl 7-[(2-triphenylmethylaminothiazol-4-yl)-2-methoxyimino-acetamido]-3-[3-[(5-methyl-1,3,4-thiadiazol-2-yl)-thio]-1-(E)-propenyl]-8-oxo-4-thia-1-azabicyclo[4,2,0]oct-2-en-carboxylate.

STEP B: Syn isomer of (6S,7S) 7-[(2-(2-aminothiazol-4-yl)-2-methoxyimino-acetamido]-3-[3-[(5-methyl-1,3,4-thiadiazol-2-yl)thio]-1-(E)-propenyl]-8-oxo-4-thia-1-azabicyclo[4,2,0]oct-2-en-2-carboxylic acid At ambient temperature, 118 mg of the product of Step A and 2.3 ml of trifluoroacetic acid were stirred for 20 minutes. 25 ml of anhydrous ether were added dropwise and the mixture was centrifuged. The residue was taken up in 5 ml of ether and then the centrifuging was repeated, with the residue again taken up with 5 ml of ether, followed by drying under reduced pressure. The product was taken up in 1.5 ml of ethanol and 100 µl of a 1M/l solution of pyridine in ethanol, then centrifuged twice more, with the residue being taken up in 1 ml of ether each time. After drying, 52 mg of syn isomer of (6S,7S) 7-[(2-(2-aminothiazol-4-yl)-2-methoxyimino-acetamido]-3-[3-[(5-methyl-1,3,4-thiadiazol-2-yl)thio]-1-(E)-propenyl]-8-oxo-4-thia-1-azabicyclo[4,2,0]oct-2-en-2-carboxylic acid were obtained.

| NMR Spectrum (DMSO) | | | |
|---|---|---|---|
| 6.81 ppm | | $H_5$ of the thiazole | |
| 5.64 ppm | | $H_7$ | |
| 4.01 ppm | | $H_6$ | |
| 6.96 and 6.19 ppm | | H ethylenes | |
| 7.23 ppm | | H of amino | |
| 3.85 ppm | | H of the methoxy | |
| 2.68 ppm | | H of the methyl of the thiadizaole | |
| **UV Spectrum EtOH − HCl 0.1 N** | | | |
| infl. | 243 nm | $E_1^1 = 430$ | |
| max. | 267 nm | $E_1^1 = 580$ | $\epsilon = 29{,}300$ |
| max. | 329 nm | $E_1^1 = 340$ | $\epsilon = 18{,}800$ |
| IR Spectrum (nujol) | | | |
| **General absorption NH/OH** | | | |
| -lactam C=O | | $1759\ cm^{-1}$ | |
| others C=O | | $1660\ cm^{-1}$ | |
| region C=C; C=N | | $1630\ cm^{-1}$ | |
| amide II | | $1540\ cm^{-1}$ | |

EXAMPLE 14

(6S,7S) 7-[2-(2-aminothiazol-4-yl)-2-(Z)-methoxyimino-acetamido]-3-[3-(1H-tetrazol-1-yl)-1-(E)-propenyl]-8-oxo-4-thia-1-azabicyclo-[4,2,0]oct-2-en-2-carboxylic acid and (6S,7S) 7-[2-(2-aminothiazol-4-yl)-2-(Z)-(methoxyimino-acetamido]-3-[3-(2H-tetrazol-2-yl)-1-(E)-propenyl]-8-oxo-4-thia-1-azabicyclo[4,2,0]oct-2-en-2-carboxylic acid STEP A: 1,1-dimethylethyl 7-[2-(2-tritylaminothiazol-4-yl)-2-(Z)methoxyimino-acetamido]-3-[3-(1H-tetrazol-1-yl)-1-(E)-propenyl]-8-oxo-4-thia-1-azabicyclo[4,2,0]oct-2-en-2-carboxylate and 1,1-dimethylethyl 7-[2-(2-tritylaminothiazol-4-yl)-2-(Z)-methoxyimino-acetamido]-3-[3-(2H-tetrazol-2-yl)-1-(E)-propenyl]-8-oxo-4-thia-1-azabicyclo[4,2,0]oct-2-en-2-carboxylate 230 mg of the isomer of Step B of Example 1, 149 mg of tetrabutylammonium, and 0.143 ml of 2,6-lutidine were dissolved in 5 ml of dichloroethane. The solution was cooled to −70° C., and 1.7 ml of a solution of trifluoromethyl sulfonic anhydride (0.42 ml in q.s. for 10 ml of $CH_2Cl_2$) were added dropwise. The temperature was allowed to return to 20° C. and the solvent was evaporated off. 44 mg of 1H-tetrazole, 131 mg of potassium carbonate and 3 ml of dimethylformamide were added and after 30 minutes of stirring, the solution was poured into water containing 1.5 ml of 2N hydrochloric acid, and was extracted with ethyl acetate. The organic phase was washed with water containing 0.2N thiosulfate in excess, then dried and concentrated to dryness. The residue was chromatographed over silica and eluted with a mixture of methylene chloride and ethyl acetate, first (75/25), then (50—50) 90 mg of the "position 2" isomer and 99 mg of the "position 1" isomer were isolated.

STEP B: (6S, 7S) 7-[2-(2-aminothiazol-4-yl)-2-(Z)-methoxyimino-acetamido]-3-[3-(1H-tetrazol-1-yl)-1-(E)-propenyl]-8-oxo-4-thia-1-azabicyclo[4,2,0]oct-2-en-2-carboxylic acid The 99 mg of the "position 1" isomer were dissolved in 1.2 ml of 66% formic acid and the solution was heated to 65° C. for 2 hours then cooled, diluted with 1.5 ml of water, filtered and the filtrate was rinsed with water and then with ether to obtain 49 mg of (6S,7S) 7-[2-(2-aminothiazol-4-yl)-2-(Z)-methoxyimino-acetamido]-3-[3-(1H-tetrazol-1-yl)-1-(E)-propenyl]-8-oxo-4-thia-1-azabicyclo[4,2,0]oct-2-en-2-carboxylic acid.

| NMR Spectrum (DMSO) | | | |
|---|---|---|---|
| 3.87 ppm | | H $OCH_3$ | |
| 6.11 to 6.41 and 6.84 to 7.0 ppm | | H ethylenes ΔE | |
| 6.84 ppm | | $H_5$ of the thiazole, syn | |
| 5.61 to 5.76 ppm | | $H_7$ β-lactam cis | |
| UV Spectrum EtOH + HCl 0.1 N | | | |
| max. | 238 nm | $E_1^1 = 377$ | ε = 18,500 |
| max. | 263 nm | $E_1^1 = 419$ | ε = 20,600 |
| infl. | 280 nm | $E_1^1 = 356$ | |
| max. | 325 nm | $E_1^1 = 299$ | ε = 14,700 |

STEP C: (6S,7S) 7-[2-(2-aminothiazol-4-yl)-2-(Z)-methoxyimino-acetamido]-3-[3-(2H-tetrazol-2-yl)-1-(E)-propenyl]-8-oxo-4-thia-1-azabicyclo[4,2,0]-oct-2-en-2-carboxylic acid Using the procedure of Step B, 90 mg of the "position 2" isomer were reacted to obtain 31 mg of the expected product.

| NMR Spectrum (DMSO) | | | |
|---|---|---|---|
| 3.88 ppm | | H of $OCH_3$ | |
| 6.11 to 6.44 and 6.9–7.07 ppm | | H ehtylenes ΔE | |
| 6.87 ppm | | $H_5$ of the thiazole, syn | |
| 5.7 ppm | | $H_7$ β lactam, cis. | |
| UV Spectrum EtOH | | | |
| max | 234 nm | $E_1^1 = 470$ | ε = 23,400 |
| infl. | 260 nm | $E_1^1 = 302$ | |
| max. | 320 nm | $E_1^1 = 303$ | ε = 15,100 |

EXAMPLE 15

Syn isomer of (6S,7S) 7-[2-(2-aminothiazol-4-yl)-2-methoxyimino-acetamido]-3-[3-(2-methyl-1H-imidazol-1-yl)-1-(E)-propenyl]-8-oxo-4-thia-1-azabicyclo[4,2,0]oct-2-en-2-carboxylic acid STEP A: Syn isomer of (6S,7S) 1,1-dimethylethyl 7-[2-(2-tritylaminothiazol-4-yl)-2-methoxyimino-acetamido]-3-[3-(2-methylimidazol-1-yl)-1-(E)-propenyl]-8-oxo-4-thia-1-azabicyclo[4,2,0]oct-2-en-2-carboxylate Using the procedure of Step A of Example 13, 62 mg of 2-methylimidazole were reacted to obtain 82 mg of syn isomer of (6S,7S) 1,1-dimethylethyl 7-[2-(2-tritylaminothiazol-4-yl)-2-methoxyimino-acetamido]-3-[3-(2-methylimidazol-1-yl)-1-(E)-propenyl]-8-oxo-4-thia-1-azabicyclo[4,2,0]oct-2-en-2-carboxylate.

STEP B: Syn isomer of (6S,7S) 7-[2-(2-aminothiazol-4-yl)-2-methoxyimino-acetamido]-3-[3-(2-methyl-1H-imidazol-1-yl)-1-(E)-propenyl]-8-oxo-4-thia-1-azabicyclo[4,2,0]oct-2-en-2-carboxylic acid 80.5 mg of the product of Step A and 1 ml of 66% formic acid were heated for 3 hours at 60°–65° C. and then was evaporated to dryness under reduced pressure. The residue was taken up twice consecutively with 5 ml of water, then evaporated to dryness. The residue was taken up in 7 ml of ether, stirred for half-an-hour, then separated to obtain 41.5 mg of syn isomer of (6S,7S) 7-[2-(2-aminothiazol-4-yl)-2-methoxyimino-acetamido]-3-[3-(2-methyl-1H-imidazol-1-yl)1-(E)-propenyl]-8-oxo-4-thia-1-azabicyclo[4,2,0]oct-2-en-2-carboxylic acid

| NMR Spectrum (DMSO) | | |
|---|---|---|
| 3.85 ppm (s) | | $OCH_3$ |
| 6.55–6.61 ppm (d – j = 16) | | H ethylenes ΔE |
| 5.58 to 5.64 ppm (m) | | $H_7$ β lactam, cis |
| 7.13 ppm | | $H_5$ of the thiazole |
| UV Spectrum EtOH + HCl 0.1 N | | |
| infl. | 217 nm | |
| max. | 238 nm | ε = 17,300 |
| max. | 264 nm | ε = 19,100 |
| infl. | 281 nm | |
| max. | 327 nm | ε = 13,100 |

EXAMPLE 16

Syn isomer of (6S,7S) 7[2-(2-aminothizaol-4-yl)-2-methoxyimino-acetamido]-3-[(5-methylthio-1,3,4-thiadiazol-2-yl)thio)-1-(E)-propenyl]-8-oxo-4-thia-1-azabicyclo[4,2,0]oct-2-en-2-carboxylic acid Using the procedure of Example 13, 2-mercapto-5-methylthio-1,3,4-thiadiazole was reacted and eluting the chromatography with a mixture of methylene chloride and ethyl acetate (95-5), then (9-1) and after unblocking the functions and purification, 69 mg of syn isomer of (6S,7S) 7-[2-(2-aminothiazol-4-yl)-2-methoxyimino-acetamido]-3-[(5-methylthio-1,3,4-thiadiazol-2-yl)thio)-1-(E)-propenyl]-8-oxo-4-thia-1-azabicyclo[4,2,0]oct-2-en-2-carboxylic acid were obtained.

| | | | |
|---|---|---|---|
| NMR Spectrum (DMSO) | | | |
| 6.81 ppm | | $H_5$ of the thiazole, syn | |
| 5.85 ppm | | $OCH_3$ | |
| 5.64 ppm | | $H_7$ β-lactam, cis | |
| 6.18 and 6.98 ppm | | H of ethylenes, trans | |
| 2.74 ppm | | S—$CH_3$ | |
| UV Spectrum | | | |
| 1) EtOH + (1 ml DMSO) | | | |
| max. | 298 nm | $E_1^1 = 378$ | $\epsilon = 22{,}100$ |
| infl. | 320 nm | $E_1^1 = 350$ | $\epsilon = 20{,}500$ |
| 2) EtOH – HCl 0.1 N | | | |
| max. | 280 nm | $E_1^1 = 469$ | $\epsilon = 27{,}500$ |
| max. | 330 nm | $E_1^1 = 310$ | $\epsilon = 18{,}200$ |

EXAMPLE 17

Syn isomer (6S,7S) 7-[2-(2-aminothiazol-4-yl)-2-methoxyimino-acetamido]-3-[3-(5-amino-1,3,4-thiadiazol-2-yl)thio)-[1-(E)-propenyl]-8-oxo-4-thia-1-azabicyclo[4,2,0]oct-2-en-2-carboxylic acid Using the procedure of Example 13, 184.5 mg of the E isomer of Step B of Example 1, and 66.6 mg of 2-amino-5-mercapto-1,3,4-thiadiazole in dimethylformamide were reacted. The chromatography over silica was eluted with a mixture of methylene chloride and ethyl acetate (1-1) and the blocked functions were freed by trifluoroacetic acid to obtain 60.5 mg of syn isomer of (6S,7S) 7-[2-(2-aminothiazol-4-yl)-2-methoxyimino-acetamido]-3-[3-(5-amino-1,3,4-thiadiazol-2-yl)thio)-[1-(E)-propenyl]-8-oxo-4-thia-1-azabicyclo[4,2,0]oct-2-en-2-carboxylic acid.

| | | | |
|---|---|---|---|
| NMR Spectrum (DMSO) | | | |
| 6.82 ppm | | $H_5$ of the thiazole | |
| 3.86 ppm | | $OCH_3$ | |
| 5.64 ppm | | $H_7$ | |
| 6.90 ppm (d = J = 1.5) | | H ethylenes E | |
| 6.15 ppm (d + J = 7.5 and 15) | | | |
| UV Spectrum | | | |
| 1) EtOH | | | |
| max. | 287 nm | $E_1^1 = 411$ | $\epsilon = 22{,}800$ |
| infl. | 282 nm | $E_1^1 = 309$ | |
| max. | 322 nm | $E_1^1 = 312$ | $\epsilon = 17{,}300$ |
| 2) EtOH – HCl 0.1 N | | | |
| max. | 271 nm | $E_1^1 = 472$ | $\epsilon = 26{,}200$ |
| max. | 330 nm | $E_1^1 = 285$ | $\epsilon = 15{,}800$ |

EXAMPLE 18

Syn isomer of (6S,7S) 7-[2-(2-aminothiazol-4-yl)-2-methoxyimino-acetamido]-3-[3-[(9H-purin-6-yl)thio]-1-(E)-propenyl]-8-oxo-4-thia-1-azabicyclo[4,2,0]oct-2-en-2-carboxylic acid Using the procedure of Example 13, 76 mg of 6-mercaptopurine were reacted and the product was chromatographed on silica, Elution firs with a mixture of methylene chloride and ethyl acetate (75-25), then with ethyl acetate alone and finally with a mixture of methylene chloride and methanol (95-5) after unblocking and the purification yielded 76 mg of syn isomer of (6S,7S) 7-[2-(2-aminothiazol-4-yl)-2-methoxyimino-acetamido]-3-[3-[(9H-purin-6-yl)thio-1-(E)-propenyl]-8-oxo-4-thia-1-azabicyclo[4,2,0]oct-2-en-2-carboxylic acid

| | | | |
|---|---|---|---|
| NMR Spectrum (DMSO) | | | |
| 6.82 ppm (s) | | $H_5$ of the thiazole | |
| 5.64 ppm | | $H_7$ β-lactam, cis | |
| 6.26 ppm | | H ethylenes ΔE | |
| 7.06 ppm | | | |
| UV Spectrum | | | |
| 1) EtOH + 2 $cm^3$ DMSO | | | |
| max. | 240 nm | $E_1^1 = 401$ | $\epsilon = 23{,}000$ |
| max. | 292 nm | $E_1^1 = 423$ | $\epsilon = 24{,}300$ |
| max. | 320 nm | $E_1^1 = 311$ | $\epsilon = 17{,}800$ |
| infl. | 257.410 nm | | |
| 2) EtOH – HCl 0.1 N | | | |
| infl. | 240 nm | $E_1^1 = 319$ | |
| infl. | 264 run | $E_1^1 = 375$ | |
| max. | 287 nm | $E_1^1 = 475$ | $\epsilon = 27{,}200$ |
| max. | 323 nm | $E_1^1 = 286$ | $\epsilon = 16{,}400$ |

EXAMPLE 19

Syn isomer of (6S,7S) 7-[2-(2-aminothiazol-4-yl)-2-methoxyimino-acetamido]-3-[3-(1,3,4-thiadiazol-2-yl)thio]-1-(E)-propenyl]-8-oxo-4-thia-1-azabicyclo[4,2,0]oct-2-en-2-carboxylic acid Using the procedure of Example 13, 59.1 mg of 5-mercapto-1,3,4-thiadiazole were reacted to obtain 47.1 mg of the expected product.

| | | | |
|---|---|---|---|
| NMR Spectrum (DMSO) | | | |
| 6.85 ppm (s) | | $H_5$ of the thiazole | |
| 3.87 ppm(s) | | $OCH_3$ | |
| 3.65 ppm | | β-lactam, cis | |
| 6.01 ppm (d – J = 15.5) | | H, ethylenes, E | |
| 7.06 ppm (d – J = 15.5 and 7) | | | |
| UV Spectrum | | | |
| EtOH – HCl 0.1 N | | | |
| infl. | 241 nm | $E_1^1 = 335$ | |
| max. | 269 nm | $E_1^1 = 425$ | $\epsilon = 22{,}900$ |
| max. | 329 nm | $E_1^1 = 278$ | $\epsilon = 15{,}000$ |

EXAMPLE 20

Syn isomer of (6S,7S) 7-[2-(2-aminothiazol-4-yl)-2-methoxyimino-acetamido]3-[3-[(1,2,3-triazol-5-yl)thio]-1-(E)-propenyl]-8-oxo-4-thia-1-azabicyclo[4,2,0]oct-2-en-2-carboxylic acid Using the procedure of Example 13, sodium thiolate was reacted without addition of potassium carbonate and the chromatography was done by elution with a mixture of methylene chloride and ethyl acetate (75-25). The deblocking of the functions was done with formic acid: 2 ml of 66% for 149 mg of blocked product. Stirring was maintained for 3 hours at 60°-65° C. and the formic acid was expelled at 30° C. under reduced pressure. The residue was taken up twice in water and evaporating off each time. The residue was triturated with ether, then separated to obtain 89 mg of product which was dissolved in 6 ml of tetrahydrofuran and 1 ml of methanol. This solution was introduced dropwise into 100 ml of ether under vigorous stirring and then after separation, 69.5 mg of syn isomer of (6S,7S)-7-[2-(2-aminothiazol-4-yl)-2-methoxyimino-acetamido]-3-[3-[(1,2,3-triazol-5-yl)-thio]-1-(E)-propenyl]-8-oxo-4-thia-1-azabicyclo[4,2,0]oct-2-en-2-carboxylic acid were obtained.

| NMR Spectrum (DMSO) | | | |
|---|---|---|---|
| 6.81 ppm (s) | | $H_5$ of the thiazole, syn | |
| 3.85 ppm (s) | | $OCH_3$ | |
| 5.63 ppm | | $H_7$ β-lactam, cis | |
| 6.76 ppm | | H ethylene ΔE | |
| 6.08 ppm | | | |
| UV Spectrum EtOH − HCl 0.1 N | | | |
| max. | 240 nm | $E_1^1$ = 396 | ε = 20,700 |
| max. | 266 nm | $E_1^1$ = 416 | ε = 21,700 |
| infl. | 282 nm | $E_1^1$ = 387 | |
| max. | 328 nm | $E_1^1$ = 320 | ε = 16,700 |

EXAMPLE 21

Syn isomer of (6S, 7S) 7-[2-(2-aminothiazol-4-yl)-2-methoxyimino-acetamido]-3-[3-[(4-methyl-5-trifluoromethyl-4H-1,2,4-triazol-3-yl)-thio-1-(E)-propenyl]-8-oxo-4-thia-1-azabicyclo[4,2,-0]oct-2-en-2-carboxylic acid Using the procedure of Example 13, 90 mg of 4-methyl-5-trifluoromethyl-4H-1,2,4-triazol-3-thione were reacted and chromatography was done by eluting with a mixture of methylene chloride and ethyl acetate (75-25). After treatment with 66% formic acid, 78 mg of syn isomer of (6S, 7S) 7-[2-(2-aminothiazol-4-yl)-2-methoxyimino-acetamido]-3-[3-[(4-methyl-5-trifluoromethyl-4H-1,2,4-triazol-3-yl)-thio-1-(E)-propenyl]-8-oxo-4-thia-1-azabicyclo[4,2,0]oct-2-en-2-carboxylic acid were obtained.

| NMR Spectrum (DMSO) | | | |
|---|---|---|---|
| 3.67 and 3.35 ppm | | N—$CH_3$ and O—$CH_3$ | |
| 5.64 ppm | | $H_7$ β-lactam, cis | |
| 6.2 and 6.89 ppm | | H ethylenes, ΔE | |
| 6.81 ppm | | H5l of the triazole | |
| UV Spectrum EtOH − HCl 0.1 N | | | |
| infl. | 240 nm | $E_1^1$ = 328 | |
| max. | 260 nm | $E_1^1$ = 345 | ε = 20,900 |
| infl. | 280 nm | $E_1^1$ = 303 | |
| max. | 326 nm | $E_1^1$ = 215 | ε = 13,000 |

EXAMPLE 22

Syn isomer of (6S,7S) 7-[2-(2-aminothiazol-4-yl)-2-methoxyimino-acetamido]-3-[3-(thiazolo[5,4-b]pyridin-2-yl)-thio-1-(E)-propenyl]-8-oxo-4-thia-1-azabicyclo[4,2,0]oct-2-en-2-carboxylic acid Using the procedure of Example 13, 205 mg of 2-mercaptothiazolo[5,4-b]pyridine were reacted and chromatographed and eluted with a mixture of methylene chloride and acetone (9-1). The functions were unblocked by formic acid on 150 mg of the product obtained and 67 mg of crude product were obtained. 45 mg of the latter were chromatographed over silica and eluted with ethyl acetate, then with a mixture of acetone, ethyl acetate and water (5-4-1) to obtain 17 mg of syn isomer of (6S, 7S) 7-[2-(2-aminothiazol-4-yl)-2-methoxyimino-acetamido]-3-[3-(thiazolo[5,4-b]pyridin-2-yl)-thio-1-(E)-propenyl]-8-oxo-4-thia-1-azabicyclo[4,2,0]oct-2-en-2-carboxylic acid.

| NMR Spectrum (DMSO) | |
|---|---|
| 6.79 ppm | $H_5$ of the triazole |
| 3.84 ppm | $OCH_3$ |
| 5.54 ppm | $H_7$ β-lactam |
| 5.98 and 7.27 ppm | H ethylenes |
| IR Spectrum (nujol) | |
| General absorption region OH/NH | |
| C=O β-lactam | 1754 $cm^{-1}$ |
| shoulder | 1660 $cm^{-1}$ |
| maximum | 1650 $cm^{-}$ |
| region —C=C C=N | large absorption |
| aromtic | 1580 $cm^{-1}$, 1620 $cm^{-1}$ |
| NH def. amide II | 1535 $cm^{-1}$ |
| region —CH=CH— | 975 $cm^{-1}$ |

EXAMPLE 23

Syn isomer of (6S, 7S) 7-[2-(2-aminothiazol-4-yl)-2-methoxyimino-acetamido]-3-[3-(1H-1,2,4-triazol-3-yl)thio-1-(E)-propenyl]-8-oxo-4-thia-1-azabicyclo[4,2,0]oct-2-en-2-carboxylic acid Using the procedure of Example 21, 50 mg of 1H-1,2,4-triazol-3-thione were reacted to obtain 62 mg of the expected product.

| NMR Spectrum (DMSO) | | | |
|---|---|---|---|
| 5.56 to 5.71 ppm | | $H_7$ β-lactam | |
| 6.04 to 6.4 ppm and 6.84-7.02 ppm | | H ethylenes ΔE | |
| 6.84 ppm | | $H_5$ of the triazole, syn. | |
| UV Spectrum EtOH | | | |
| max. | 234 nm | $E_1^1$ = 481 | ε = 25,100 |
| max. | 320 nm | $E_1^1$ = 323 | ε = 16,900 |

EXAMPLE 24

Internal salt of syn isomer of (6S, 7S) 2-[3-[7-[2-(2-aminothiazol-4-yl)-2-methoxyimino-acetamido]-2-carboxy-8-oxo-4-thia-1-azabicyclo[4,2,-0]oct-2-en-3-yl]-2-(E)-propenyl]isoquinolinium Using the procedure of Example 21, 148 mg of the E isomer of Step B of Example 1 were reacted and after adding the trifluoromethane sulfonic anhydride and distilling off the solvent, 5 ml of acetonitrile and 52 μl of isoquinoline were added. After 75 minutes, the aceonitrile was driven off and the residue was dissolved in ethyl acetate, washed with water containing an excess of 0.2N sodium thiosulfate, washed with water, dried and concentrated to dryness. The residue was chromatographed over silica and eluted with a mixture of methylene chloride and methanol (92-8) to obtain 83 mg of the blocked intermediate product. After treatment with 66% formic acid, filtering and evaporating the solvent, the residue obtained was taken up in 1 ml of acetonitrile and 1 ml of a 1M solution of triethylamine, then chromatographed over silica and eluted first with a water-acetonitrile mixture (9-1) and then with a (85-15) mixture to obtain 16.76 mg of internal salt of syn isomer of (6S,7S) 2-[3-[7-[2-(2-aminothiazol-4-yl)-2-methoxyimino-acetamido]-2-carboxy-8-oxo-4-thia-1-azabicyclo[4,2,0]oct-2-en-3-yl]-2-(E)-propenyl-]isoquinolinium.

| NMR Spectrum (DMSO) | |
|---|---|
| 3.83 ppm | $OCH_3$ |
| 5.45 ppm | $H_7$ and $CH_2—N^+$ |
| 6.79 ppm | $H_5$ of the triazole |
| 5.91–7.42 ppm | H ethylenes, ΔE |
| UV Spectrum EtOH | |

-continued

| | | | |
|---|---|---|---|
| max. | 224 nm | $E_1^1 = 951$ | $\epsilon = 52{,}400$ |
| infl. | 232 nm | $E_1^1 = 840$ | |
| infl. | 262 nm | $E_1^1 = 296$ | |
| infl. | 277 nm | $E_1^1 = 252$ | |
| max. | 289 nm | $E_1^1 = 226$ | $\epsilon = 12{,}400$ |
| max. | 323 nm | $E_1^1 = 280$ | $\epsilon = 15{,}400$ |

EXAMPLES 25 to 39

Using the procedure of the foregoing examples the products of the Tables hereafter were obtained.

| R | $R_1$ | $n_2$ | $CO_2A$ | |
|---|---|---|---|---|
| 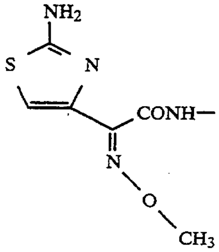 | 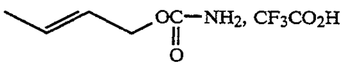 | 0 | $CO_2H$ | Example 25 |
| " | 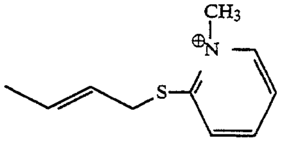 | " | $CO_2^{\ominus}$ | Example 26 |
| " | 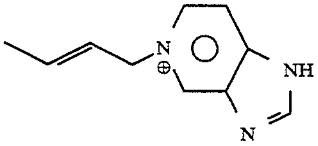 | " | $CO_2^{\ominus}$ | Example 27 |
| " | 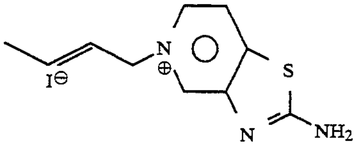 | " | $CO_2H$ | Example 28 |
| " | 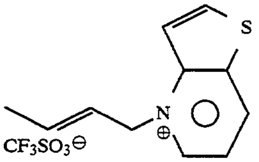 | " | $CO_2H$ | Example 29 |
| " | 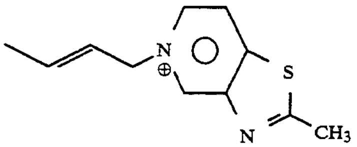 | " | $CO_2^{\ominus}$ | Example 30 |
| 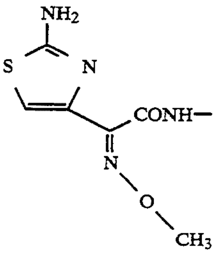 | 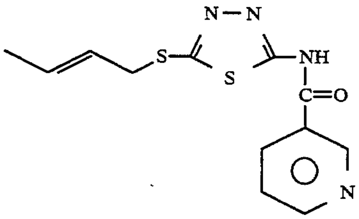 | 0 | $CO_2H$ | Example 31 |

-continued
| R | $R_1$ | $n_2$ | $CO_2A$ | |
|---|---|---|---|---|
| ″ | 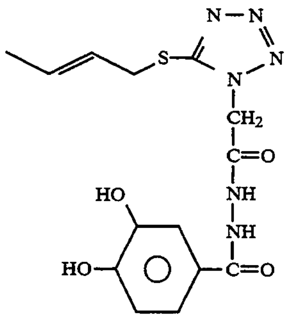 | ″ | $CO_2H$ | Example 32 |
| ″ | 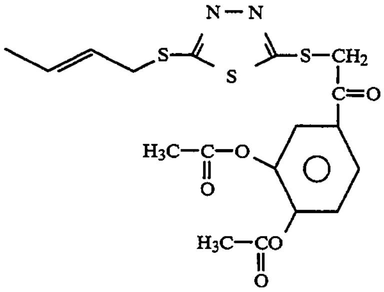 | ″ | $CO_2H$ | Example 33 |
| ″ | 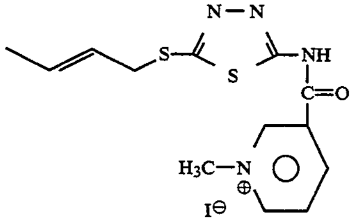 | ″ | $CO_2H$ | Example 34 |
| 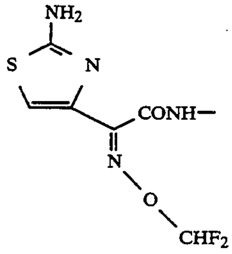 | 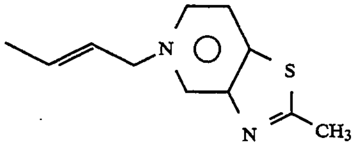 | ″ | $CO_2^-$ | Example 35 |
| 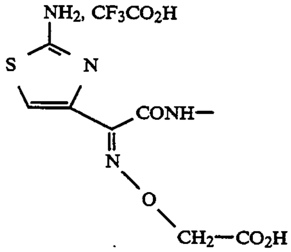 | 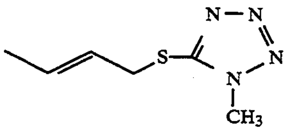 | ″ | $CO_2H$ | Example 36 |
| 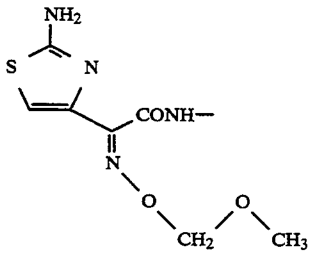 | 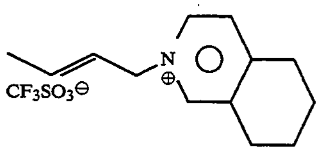 | 0 | $CO_2H$ | Example 37 |

-continued

| R | $R_1$ | $n_2$ | $CO_2A$ | |
|---|---|---|---|---|
| " | 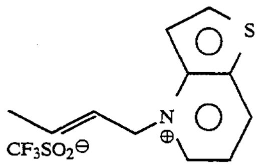 | " | $CO_2H$ | Example 38 |
| 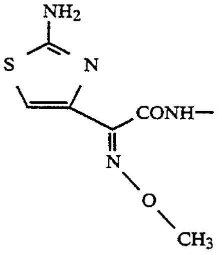 | 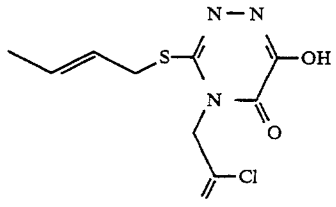 | " | $CO_2H$ | Example 39 |

EXAMPLE 40

Trifluoroacetate of (6S,7S,ΔZ) 5-[3-[7-[(2-amino-4-thiazolyl)-(methoxyimino)-acetamido]-2-carboxy-8-oxo-4-thia-1-azabicyclo[4,2,-0]oct-2-en-3-yl]-2(E)propenyl]-2-(trifluoromethyl)-thiazolo[4,5-c]pyridinium 321 mg of 1,1-dimethylethyl 7-[(2tritylamino-thiazol-4-yl) (methoxyimino)-acetamido]-8-oxo-3-iodopropenyl-4-thia-1-azabicyclo[4,2,0]oct-2-en-2-carboxylate and 85 mg of trifluoromethyl-thiazolo-pyridine were stirred for 90 minutes by centrifuging in 1 ml of dry dimethylsulfoxide. After distilling off as much as possible of the solvent and concentrating to dryness under pressure reduced to less than 1 mm Hg for 3 hours, the residue was chromatographed over silica and eluted with methylene chloride, then with mixtures of methylene chloride and acetone (90–10) and methylene chloride and methanol (92–8) to obtain 410 mg of the blocked iodide of the expected product.

2 ml of trifluoroacetic acid with 10% of anisole were added to the product with stirring for 20 minutes. After cooling slightly, 25 ml of isopropyl ether were added slowly with stirring for 20 minutes to obtain 137 mg of the expected product by centrifuging.

EXAMPLE 41

(6S,7S,ΔZ) 7-[(2-amino-4-(thiazolyl) (methoxyimino)-acetamido]-3-[3-[1,4-dihydro-3-formylamino-4-oxo-1-pyridyl]1(E)propenyl-8-oxo-4-thia-1-azabicyclo[4,2,0]oct-2-ene-2-carboxylic acid The procedure of Example 40 was repeated with 85 mg of oxazolapyridine to obtain 311 mg of trifluoroacetate of the expected product. 200 mg of the latter were chromatographed over silica in HPLC in a mixture of acetonitrile and water (1-1) and eluted successively with mixtures of water with 5,10 and then 15% of acetonitrile to obtain after lyophilization 48 mg of the expected product.

| NMR Spectrum, DMSO, 250 MHz, in ppm | | |
|---|---|---|
| 6.81 | $H_5$ | of thiazol |
| 3.85 | H | of $OCH_3$ |
| 5.63 | $H_7$ | of the cephem |

-continued

| NMR Spectrum, DMSO, 250 MHz, in ppm | |
|---|---|
| 4.07 | $H_6$ |
| 6.90 6.08 | H ethylenes |
| 6.25–7.28 | $H_5$ and $H_6$ of pyridine |
| 8.71–8.30 | $H_2$ of the pyridine and H of the formyl. |

EXAMPLE 42

Iodide of (6S,7S,ΔZ) 5-[3-[7-[(2-amino-4-thiazolyl)(difluoromethoxyimino)-acetamido]-2-carboxy-8-oxo-4-thia-1-azabicyclo[4,2,-0]oct-2-en-3-yl]-2(E)propenyl]-thieno[3,2-c]pyridinium, trifluoroacetate Using the procedure of Example 40, 200 mg of 1-1-methylethyl-7-[(2-tritylamino-thiazol-4-yl) (difluoromethoxyimino)-acetamido]-8-oxo-4-thia-3-iodopropenyl-1-azabicyclo[4,2,0]oct-2-en-2-carboxylate, 38 mg of thieno[3,2-c]pyridine were reacted to obtain 44 mg of the expected product.

| UV Spectrum, in EtOH: | | | |
|---|---|---|---|
| Max. | 238 nm | $E_1^1 = 620$; | $\epsilon = 51,700$ |
| Inflexion | 260 nm | $E_1^1 = 232$; | |
| Max. | 319 nm | $E_1^1 = 235$; | $\epsilon = 19,600$ |
| UV Spectrum, in EtOH/HCl 0.1 N: | | | |
| Max. | 239 nm | $E_1^1 = 566$ | $\epsilon = 47,200$ |
| Inflexion | 260 nm | $E_1^1 = 286$ | |
| Inflexion | 275 nm | $E_1^1 = 249$ | |
| Inflexion | 284 nm | $E_1^1 = 226$ | |
| Max. | 327 nm | $E_1^1 = 190$ | $\epsilon = 15,900$ |

EXAMPLE 43

Iodide of (6S,7S ΔZ) 5-[3-[7-[(2-amino-thiazol-4-yl)(difluoromethoxyimino)-acetamido]-2-carboxy-8-oxo-4-thia-1-azabicyclo[4,2,-0]oct-2-en-3-yl]-2(E)propenyl]-4-methyl-thieno[3,2-c]pyridinium, (trifluoroacetate)

Using the procedure of Example 42, 50 mg of methyl thieno[3,2-c]pyridine, were reacted to obtain 59 mg of the expected product.

| UV Spectrum, in EtOH: | | | |
|---|---|---|---|
| Inflexion | 212 nm | $E_1^1 = 438$ | $\epsilon = 37,200$ |
| Max. | 238 nm | $E_1^1 = 666$ | $\epsilon = 56,600$ |
| Inflexion | 260 nm | $E_1^1 = 233$ | |
| Max. | 317 nm | $E_1^1 = 236$ | $\epsilon = 20,000$ |
| UV Spectrum, in EtOH/HCl 0.1 N: | | | |
| Max. | 234 nm | $E_1^1 = 619$ | $\epsilon = 52,600$ |
| Inflexion | 259 nm | $E_1^1 = 290$ | |
| Inflexion | 266 nm | $E_1^1 = 277$ | |
| Inflexion | 280 nm | $E_1^1 = 236$ | |
| Inflexion | 295 nm | $E_1^1 = 193$ | |
| Max. | 323 nm | $E_1^1 = 143$ | $\epsilon = 16,400$ |
| Inflexion | 323 nm | $E_1^1 = 181$ | |

EXAMPLE 44

Iodide of (6S,7S, ΔZ) 5-[3-[7-[(2-amino-thiazol-4-yl)(fluoromethoxyimino)-acetamido]-2-carboxy-8-oxo-4-thia-1-azabicyclo[4,2,-0]oct-2-en-3-yl]-2(E)propenyl]-thiazolo[4,5-c]pyridinium (trifluoroacetate)

Using the procedure of Example 40, 200 mg of 1,1-dimethylethyl-7-[2-tritylamino-thiazol-4-yl]-fluoromethoxyimino-acetamido]-8-oxo-4-thia-3-iodopropenyl-1-azabicyclo[4,2,0]oct-2-en-2-carboxylate and 35 mg of thiazolo[4,5-c]pyridine were reacted to obtain 82 mg of the expected product.

| UV Spectrum, in EtOH/HCl 0.1 N: | | | |
|---|---|---|---|
| Max. | 224 nm | $E_1^1 = 647$ | $\epsilon = 52,900$ |
| Max. | 264 nm | $E_1^1 = 336$ | $\epsilon = 27,500$ |
| Max. | 331 nm | $E_1^1 = 190$ | $\epsilon = 15,500$ |
| NMR Spectrum, DMSO, 250 MHz, in ppm: | | | |
| 6.98 | | $H_5$ of thiazol | |
| 7.14 | | $\underline{CH}=CH-CH_2$ | |
| 5.45 to 5.90 | | $CH_2F$ and $CH_2N^+$. | |

EXAMPLE 45

Iodide of (6S,7S,ΔZ) 5-[3-[7-[2-amino-thiazol-4-yl)(fluoromethoxyimino)-acetamido]-2-carboxy-8-oxo-4-thia-1-azabicyclo[4,2,-0]oct-2-en-3-yl]-2(E)propenyl]-4-methyl-thieno[3,2-c]pyridinium, (trifluoroacetate)

Using the procedure of Example 44, 38 mg of methyl-thieno[3,2-c]pyridine were reacted to obtain 42 mg of the expected product.

| UV Spectrum, in EtOH | | | |
|---|---|---|---|
| Max. | 212 nm | $E_1^1 = 440$ | $\epsilon = 36,500$ |
| Max. | 238 nm | $E_1^1 = 642$ | $\epsilon = 53,300$ |
| Inflexion | 260 nm | $E_1^1 = 231$ | |
| Max. | 317 nm | $E_1^1 = 217$ | $\epsilon = 18,000$ |
| UV Spectrum, in EtOH/HCl 0.1 N: | | | |
| Max. | 239 nm | $E_1^1 = 604$ | $\epsilon = 50,200$ |
| Inflexion | 257 nm | $E_1^1 = 322$ | |
| Inflexion | 280 nm | $E_1^1 = 249$ | |
| Max. | 324 nm | $E_1^1 = 181$ | $\epsilon = 15,000$ |

EXAMPLE 46

Iodide of (6S,7S, ΔZ) 5-[3-[7-[(2-amino-thiazol-4-yl)(fluoromethoxyimino)-acetamido]2-carboxy-8-oxo-4-thia-1-azabicyclo 4,2,0]oct-2-en-3-yl[-2(E)propenyl]thieno[3,2-c]pyridinium Using the procedure of Example 44, 52 mg of thieno[3,2-c]pyridine were reacted to obtain 77 mg of the blocked iodide of the product. The 77 mg and 0.924 ml of formic acid with 66% of water were stirred at 70° C. for 150 minutes. After cooling, the precipitate was separated and the filtrate was evaporated to dryness. The residue was taken up in 0.5 ml of ethanol and 1 ml of water and taken to dryness. The residue was taken up again in 5 ml of ethyl acetate and the solid product was triturated, separated and dried to obtain 47 mg of the expected product.

| UV Spectrum, in EtOH | | | |
|---|---|---|---|
| Max. | 238 nm | $E_1^1 = 440$ | $\epsilon = 36,500$ |
| Inflexion | 260 nm | $E_1^1 = 251$ | |
| Max. | 320 nm | $E_1^1 = 220$ | $\epsilon = 15,500$ |
| UV Spectrum, in EtOH/HCl 0.1 N: | | | |
| Max. | 240 nm | $E_1^1 = 634$ | $\epsilon = 44,600$ |
| Inflexion | 260 nm | $E_1^1 = 304$ | |
| Max. | 325 nm | $E_1^1 = 192$ | $\epsilon = 13,500$ |

EXAMPLE 47

Internal salt of (6S,7S,ΔZ) 5-[3-[7-[(2-amino-thiazol-4-yl)-(methoxyimino)-acetamido]2-carboxy-8-oxo-4-thia-1-azabicyclo[4,2,-0]oct-2-en-3-yl]-2(E)propenyl]-thiazolo[4,5-c]pyridinium Using the procedure of Example 40, thiazolo[4,5-c]pyridine was reacted to obtain 151 mg of the trifluoroacetate of the expected product which was dissolved in a (1-1) acetonitrile-water mixture and then chromatographed by HPLC over silica and eluted successively with mixtures of water with 5,10 and 20% of acetonitrile to obtain 46.5 mg of the expected product.

| UV Spectrum, in EtOH | | | |
|---|---|---|---|
| Max. | 225 nm | $E_1^1 = 870$ | $\epsilon = 48,500$ |
| Inflexion | 260 nm | $E_1^1 = 381$ | |
| Max. | 320 nm | $E_1^1 = 305$ | $\epsilon = 17,000$ |
| UV Spectrum, in EtOH/HCl 0.1 N: | | | |
| Max. | 225 nm | $E_1^1 = 782$ | $\epsilon = 43,600$ |
| Max. | 268 nm | $E_1^1 = 468$ | $\epsilon = 26,100$ |
| Max. | 330 nm | $E_1^1 = 249$ | $\epsilon = 13,900$ |

EXAMPLE 48

Internal salt of (6S, 7S, ΔZ) 5-[3-[7-[(2-amino-thiazol-4-yl)(methoxy-imino)-acetamido]-2-carboxy-8-oxo-4-thia-1-azabicyclo[4,2,-0]oct-2-en-3-yl]-2(E)propenyl]2-methyl 1H-imidazolo[4,5,-c]pyridinium Using the procedure of Example 47, 2-methyl-1H-imidazolo[4,5-c]pyridine was reacted to obtain 50 mg of the expected product.

| UV Spectrum, in EtOH/HCl 0.1 N: | | | |
|---|---|---|---|
| Max. | 213 nm | $E_1^1 = 856$ | $\epsilon = 47,400$ |
| Inflexion | 242 nm | $E_1^1 = 350$ | |

-continued

| UV Spectrum, in EtOH/HCl 0.1 N: | | | |
|---|---|---|---|
| Max. | 267 nm | $E_1^1 = 454$ | $\epsilon = 25,200$ |
| Max. | 330 nm | $E_1^1 = 250$ | $\epsilon = 13,900$ |

EXAMPLE 49

Internal salt of (6S, 7S, ΔZ) 5-[3-[7-[(2-amino-thiazol-4-yl)(methoxyimino)-acetamido]-2-carboxy-8-oxo-4-thia-2-carboxy-8-oxo-4-thia-1-azabicyclo[4,2,0]oct-2-en-3-yl]-2(E)-propenyl]-2-phenyl-oxazolo[4,5-c]pyridinium Using the procedure of Example 47, 2-phenyl-oxazolo[4,5-c]pyridine was reacted to obtain 90 mg of the expected product.

| UV Spectrum, in EtOH: | | | |
|---|---|---|---|
| Max. | 239 nm | $E_1^1 = 582$ | $\epsilon = 36,000$ |
| Inflexion | 270 nm | $E_1^1 = 464$ | |
| Inflexion | 287 nm | $E_1^1 = 524$ | |
| Max. | 293 nm | $E_1^1 = 555$ | $\epsilon = 34,300$ |
| Inflexion | 304 nm | $E_1^1 = 467$ | |
| Inflexion | 311 nm | $E_1^1 = 305$ | |
| UV Spectrum, in EtOH/HCl 0.1 N: | | | |
| Max. | 241 nm | $E_1^1 = 508$ | $\epsilon = 31,400$ |
| Inflexion | 278 nm | $E_1^1 = 616$ | |
| Max. | 284 nm | $E_1^1 = 617$ | $\epsilon = 38,100$ |
| Inflexion | 291 nm | $E_1^1 = 609$ | |
| Inflexion | 305 nm | $E_1^1 = 403$ | |
| Max. | 330 nm | $E_1^1 = 241$ | $\epsilon = 14,900$ |

EXAMPLE 50

Internal salt of the syn isomer of (6S,7S) 5-[3-[7-[(2-amino-thiazol-4-yl)-2-(methoxyimino)-acetamido]-2-carboxy-8-oxo-4-thia-1-azabicyclo[4,2,0]-oct-2-en-3-yl]-2(E)propenyl]2-ethyl thiazolo ]4,5-c]pyridinium Using the procedure of Example 47, 2-ethyl-thiazolo[4,5-c]pyridine was reacted to obtain 16 mg of the expected product.

| NMR Spectrum, DMSO, 250 MHz, in ppm: | | |
|---|---|---|
| 6.79 | $H_5$ | of the thiazol |
| 5.47 | $H_7$ | of the cephem |
| 3.96 | $H_6$ | of the cephem |
| 7.33 | ethylene H of the propenyl | |
| 5.91 | ethylene H of the propenyl | |
| 9.88 | $H_2$ of the pyridinium | |
| 8.86 | $H_5$ and $H_6$ of the pyridinium | |
| 3.33 | H of the $CH_2$ of the ethyl | |
| 1.43 | H of the $CH_3$ of the ethyl | |

EXAMPLE 51

Internal salt of (6S, 7S) synisomer of 5-[3-[7-[(2-aminothiazol-4-yl)(difluoromethoxyimino)-acetamido]-2-carboxy-8-oxo-4-thia-1-azabicyclo[4,2,-0]oct-2-en-3-yl]-2(E)propenyl]-thiazolo[4,5-c]pyridinium Using the procedure of Example 47, 1,1-dimethylethyl 7-[(2-tritylamino-thiazol-4-yl)(difluoromethoxyimino)-acetamido]-8-oxo-3-iodopropenyl-4-thia-1-azabicyclo[4,2,0]oct-2-ene-2-carboxylate was reacted to obtain 183 mg of the expected product.

| UV Spectrum, in EtOH: | | | |
|---|---|---|---|
| Max. | 225 nm | $E_1^1 = 855$ | $\epsilon = 50,800$ |
| Inflexion | 253 nm | $E_1^1 = 355$ | |
| Max. | 320 nm | $E_1^1 = 300$ | $\epsilon = 17,800$ |
| UV Spectrum,in EtOH/HCl 0.1 N: | | | |
| Max. | 226 nm | $E_1^1 = 760$ | $\epsilon = 45,100$ |
| Max. | 262 nm | $E_1^1 = 400$ | $\epsilon = 23,700$ |
| Max. | 330 nm | $E_1^1 = 242$ | $\epsilon = 14,400$ |

EXAMPLE 52

Trifluoroacetate of (6S, 7S, ΔZ) 2-amino-5-[3-[7-[(2-amino-thiazol-4-yl)(difluoromethoxyimino)-acetamido]-2-carboxy-8-oxo-4-thia-1-azabicyclo[4,2,0]oct-2-en-3-yl]-2(E)propenyl]-thiazolo[4,5-c]pyridinium Using the procedure of Example 51, 2-amino-thiazolo [4,5-c] pyridine was reacted to obtain after stirring for 15 minutes 62 mg of trifluoroacetate of the unblocked product in 0.3 ml of ethanol and 13 μl of pyridine, then centrifuging 31 mg of the expected product.

| UV Spectrum, in EtOH: | | | |
|---|---|---|---|
| Inflexion | 233 nm | $E_1^1 = 494$ | |
| Max. | 249 nm | $E_1^1 = 782$ | $\epsilon = 57,600$ |
| Inflexion | 291 nm | $E_1^1 = 195$ | |
| Max. | 323 nm | $E_1^1 = 285$ | $\epsilon = 21,000$ |
| UV Spectrum, in EtOH/HCl 0.1 N | | | |
| Max. | 248 nm | $E_1^1 = 812$ | $\epsilon = 59,800$ |
| Max. | 273 nm | $E_1^1 = 324$ | |
| Max. | 329 nm | $E_1^1 = 240$ | $\epsilon = 17,700$ |

EXAMPLE 53

Trifluoromethane sulfonate of 7-[3-[7-(2-amino-4-thiazolyl)(fluoromethoxyimino)-acetamido]-2-carboxy-8-oxo-4-thia-1-azabicyclo[4,2,-0]oct-2-en-3-yl]-2(E)propenyl]thieno[2,3-b]pyridinium(trifluoroacetate)

Under an inert atmosphere, 150 mg of 1,1-dimethylethyl (6S, 7S, ΔZ) 3-hydroxy(E)propenyl-7-[3-[7-[(2-tritylamino-4-thiazolyl]-[(2fluoromethyloxyimino]-acetamido]-8-oxo-4-thia-1-azabicyclo[4,2,0]oct-2-en-3-yl]-2-carboxylate, 5 ml of methylene chloride and 107 mg of thieno[2,3-b]pyridine were mixed together, and at −70° C. over about 5 minutes, 1.34 ml of a 5% by volume solution of trifluoromethane sulfonic anhydride in methylene chloride were introduced with stirring at −70° C. for 15 minutes. The temperature was raised to 0° C. over 15 minutes, and the solution was concentrated to dryness under reduced pressure at 5° C. The residue was chromatographed on silica under nitrogen pressure and eluted with a mixture of methylene chloride and methanol (90/10) to obtain 141 mg of the expected product.

Under an inert atmosphere, the 141 mg of the said product and 1.7 ml of a 66% aqueous solution of formic acid were mixed together and stirred at 66° C. for 150 minutes and then cooled. The precipitate formed was eliminated by filtering and washed with water. 20 ml of ethanol were added to the filtrate which was then concentrated to dryness by distilling under reduced pressure. 1 ml of water and 1 ml of ethanol were added to the residue which was again concentrated to dryness. 5 ml of ethyl acetate were added to the residue which was then triturated and the precipitate formed was separated, washed and dried to obtain 80 mg of incompletely unblocked product. Under an inert atmosphere, the 80 mg of the said product and 320 μl of trifluoroacetic acid with 10% of water were mixed together and stirred at 20° C. for 20 minutes. 5 ml of ether were added slowly, and after stirring, the precipitate formed was separated, washed and dried to obtain 68 mg of the product.

| | | | |
|---|---|---|---|
| UV Spectrum, (ethanol) | | | |
| Max. | 238 nm | $E_1^1 = 497$ | $\epsilon = 41{,}700$ |
| Inflexion | 260 nm | $E_1^1 = 190$ | |
| Inflexion | 300 nm | $E_1^1 = 191$ | |
| Max. | 308 nm | $E_1^1 = 203$ | $\epsilon = 17{,}000$ |
| Max. | 323 nm | $E_1^1 = 195$ | $\epsilon = 16{,}400$ |
| UV Spectrum, (ethanol + HCl 0.1 N): | | | |
| Max. | 240 nm | $E_1^1 = 439$ | $\epsilon = 36{,}800$ |
| Inflexion | 262 nm | $E_1^1 = 240$ | |
| Inflexion | 260 nm | $E_1^1 = 227$ | |
| Inflexion | 301 nm | $E_1^1 = 176$ | |
| Max. | 331 nm | $E_1^1 = 170$ | $\epsilon = 14{,}300$ |

EXAMPLE 54

Internal salt of (6S,7S, ΔZ) 1-[3-[7-[(2-amino-thiazol-4-yl)(methoxyimino)-acetamido]-2-carboxy-8-oxo-4-thia-1-azabicyclo[4,2,-0]oct-2-en-3-yl]-2(E)propenyl]-2(5-nitro-1H-imidazol-1-yl)-ethyl]-pyrrolidinium Using the procedure of Step C of reference Example D,1-[5-nitro-1H-imidazol-1-yl)ethyl]-pyrrolidine was heated to obtain 77 mg of trifluoromethylsulfonate of the blocked product. After treatment with trifluoroacetic acid with 10% of anisole, and precipitation by isopropyl ether as in Example 47, the product obtained was chromatographed by HPLC with a water-acetonitrile mixture (85-15) to obtain 19 mg of the expected product after lyophylization.

| UV Spectrum (DMSO) 250 MHz, in ppm. | | | |
|---|---|---|---|
| | 6.81 | $H_5$ | of the thiazol |
| | 5.52 | $H_7$ | of the cephem |
| about | 3.96 | $H_6$ | of the cephem |
| | 7.48 (m) | | Delta E |
| | 5.73 (d, J = 16 Hz) | | Delta E |
| about | 2.12 | $H_3$ and $H_4$ pyrrolidine | |
| | 3.10 to 4.87 | $H_2$ and $H_5$ pyrrolidine, H of ethyl. | |
| | 8.16 and 8.69 | $H_2$ and $H_3$ imidazol. | |

EXAMPLE 55

Internal salt of (6S,7S) 7-[3-[7-[(5-amino-1,2,4-thiadiazol-3-yl)(methoxyimino)-acetamido]-2-carboxy-8-oxo-4-thia-1-azabicyclo[4,2,-0]oct-2-en-3-yl]-2(E)-propenyl]-thieno[2,3-b]pyridinium Using the procedure of Example 53, 1,1-dimethylethyl 7-[2-(5-tritylamino-1,2,4-thiadiazol-3-yl)-2-methoxyimino)-acetamido]-2-[3-hydroxypropen(Z)-1-yl]-8-oxo-4-thia-1-azabicyclo[4,2,0]oct-2-en-2-carboxylate (prepared like the product of Step B of reference Example D) to obtain the trifluoromethylsulfonate of the blocked product. The unblocking was done as in Example 47 and chromatographed in HPLC over lichrosorb with a mixture of water and acetonitrile (85-15) to obtain 52 mg of the expected product after lyophylization.

| UV Spectrum, (ethanol + HCl 0.1 N): | | | |
|---|---|---|---|
| Max. | 239 nm | $E_1^1 = 780$ | $\epsilon = 43{,}500$ |
| Inflexion | 270 nm | $E_1^1 = 302$ | $\epsilon = 16{,}800$ |
| Inflexion | 294 and 304 nm, | | |
| Max. | 330 nm | $E_1^1 = 249$ | $\epsilon = 13{,}900$ |

EXAMPLE 56

(6S,7S syn ΔE) 7-[(2-aminothiazol-4-yl)(methoxyimino-acetamido]-8-oxo-3-[3-[-8-oxo-3-[3-[(1,3,4-thiadiazol-2-yl)-thio]-1-(E)-propenyl]-4-thia-1-azabicyclo[4,2,0]oct-2-en 2-carboxylate of 2,2-dimethyl-1-oxo-propoxyl]-methyl

STEP A: Iodomethyl pivalate 1.55 g of potassium iodide were dissolved in 8 ml of acetone and 1.40 g of chloromethyl pivalate were added. The mixture was stirred for 45 minutes at +70° C. and then for one hour at ambient temperature and filtered to obtain solution A.

STEP B: Potassium salt of 7-[(2-aminothiazol-4-yl)(methoxyimino)-acetamido]-8-oxo-3-[3-[(3-[(3-[(1,3,4-thiadiazol-2-yl)-thio-2(E)-propenyl]-4-thia-1-azabicyclo[4,2,0]oct-2-en-2-carboxylic acid 0.129 g of anhydrous potassium carbonate was stirred for one hour at ambient temperature in 5 ml of dimethylformamide and 0.500 g of the acid prepared like the product of the example described below, starting with 2-mercapto 1,3,4-thiadiazol were added and stirred for 5 minutes to obtain solution B.

STEP C: 2,2-dimethyl-1-oxo-propoxy]-methyl (6S,7S syn ΔE) 7-[(2-aminothiazol-4-yl)-(methoxyimino)-acetamido]-8-oxo-3-[3-[(1,3,4-thiadiazol-2-yl)thio]-2(E)-propenyl]-4-thia-1-azabicyclo[4,2,0]oct-2-en-2-carboxylate Solution A was introduced rapidly into solution B and stirred for 30 minutes under an inert atmosphere. The reaction mixture was poured into 70 g of water and ice and 50 ml of ethyl acetate were added. After decanting, the mixture was re-extracted and the combined organic phases were washed with a 0.2 N solution of sodium thiosulfate, a solution of sodiu M bicarbonate and an aqueous solution of sodium chloride, followed by drying and evaporating to dryness. The residue was triturted in isopropyl ether, filtered, washed with a little petroleum ether (b.p. 60°-80° C.) and then with isopropyl ether. The dried product was chromatographed over silica and eluted with ethyl acetate to obtained 275 mg of the expected product.

| | | | |
|---|---|---|---|
| UV Spectrum, in EtOH: | | | |
| Max. | 238 nm | $E_1^1 = 372$ | $\epsilon = 24{,}300$ |
| Inflexion | 250 nm | $E_1^1 = 299$ | |
| Max. | 333 nm | $E_1^1 = 234$ | $\epsilon = 15{,}300$ |
| UV Spectrum, in HCl 0.1 N: | | | |
| Inflexion | 245 nm | $E_1^1 = 317$ | |
| Max. | 265 nm | $E_1^1 = 349$ | $\epsilon = 22{,}800$ |
| Max. | 335 nm | $E_1^1 = 226$ | $\epsilon = 14{,}800$ |

Preparation of syn isomer of (6S, 7S) 7-[2-(2-amino-thiazol-4-yl)2-(Z)methoxyimino-acetamido]-3-[[3-1-methyl-1H-1,2,3,4-tetrazol-5-yl)-thio]-propen(E)yl]-8-oxo-4-thia-1-azabicyclo[4,2,0]oct-2-en-2-carboxylic acid STEP A: 1,1-dimethyl ethyl[7-[2-(2-triphenylmethylamino-thiazol-4-yl]-2(Z)-methoxyimino-acetamido]-3-[[3-(1-methyl-1H-1,2,3,4-tetrazol-5-yl)-thio]-propen(E)yl]-8-oxo-4-thia-1-azabicyclo[4,2,0]oct-2-en-2-carboxylate 37 mg of 1,1-dimethylethyl7-[2-(2-triphenylmethylamino-thiazol-4-yl]-2(Z)methoxyimino-acetamido]-3-[[(3-hydroxy)-propen-1(E)-yl]-8-oxo-4-thia-1-azabicyclo[4,2,0]oct-2-en-2-carboxylate, 24 mg of tetrabuty ammonium iodide, 0.8 ml of methylene chloride and 23 μl of 2,6-lutidine were mixed together and cooled to −70° C. 0.25 ml of a solution of trifluoro methane sulfonic anhydride titrating 0.42 ml of anhydride for 10 ml of methylene chloride, were added dropwise and then 14 mg of sodium salt of 1-methyl-5-mercapto-1,2,3,4-tetrazol and then 0.5 ml of dimethylformamide were added. The mixture was stirred at 20° C. and after concentrating to dryness, the residue was chromatographed over silica and eluted with a mixture of methylene chloride and ethyl acetate (9/1) to obtain the expected product.

STEP B: 7-[(2-amino-thiazol-4-yl)-2(Z)methoxyimino-acetamido]-3-[[3-[1-methyl-1H-[(1,2,3,4-tetrazol-5-yl)-thio]-propen-(E)-yl]-8-oxo-4-thia-1-azabicyclo[4,2,-0]oct-2-en-2-carboxylic acid 329 mg of the compound of Step A and 9.6 ml of a 33% aqueous solution of formic acid were mixed together and heated for 75 minutes at +65° C. and then cooled, diluted with water. The mixture was filtered, and the filtrate was concentrated to dryness by distilling under reduced pressure. The residue was triturated in water and the insoluble matter formed was eliminated by filtering. The filtrate was concentrated to dryness to obtain 142 mg of the expected compound.

Preparation of 1,1-dimethylethyl7-[(2-tritylamino-thiazol-4-yl)-(Z)(methoxyimino)-acetamido]-3-[3-iodopropen-1-(E)-yl]-8-oxo-4-thia-1-azabicyclo[4,2,0]oct-2-en-2-carboxylate 1.476 g of 1,1-dimethylethyl7-[-(2-tritylamino-thiazol-4-yl)-(Z)(methoxyimino)-acetamido]-3-[3-hydroxy-propen-1-(E)-yl]-8-oxo-4-thia-1-azabicyclo[4,2,0]oct-2-en-2-carboxylate, 900 mg of tetrabutylammonium iodide in 25 ml of methylene chloride and 0.932 ml of lutidine were cooled to −70° C. and at −65° C. to −70° C. and over 5 minutes, 8.52 ml of 0.5 ml of trifluoromethylsulfonic acid anhydride extended to 10 ml with methylene chloride were added with stirring for 5 minutes. At ambient temperature, 25 ml of a 0.2N aqueous solution of sodium thiosulfate were added with stirring for 5 minutes. Then, after decanting, extraction was done with methylene chloride. The organic phases were dried and concentrated to dryness. The residue was chromatographed over silica and eluted with a mixture of methylene chloride and ethyl acetate (80–20). The product was taken up in isopropyl ether and 1.215 g of the expected product were obtained.

In the same way, the 2-(fluoromethoxyimino) or 2-(difluoromethoxyimino) derivatives were obtained with the corresponding alcohols.

EXAMPLE 57

Injectable preparations were prepared comprising 500 mg of the internal salt of (6S, 7S) 7-[3-[7-[2-[(2-amino-4-thiazolyl)-2-(Z)-difluoromethoxyimino-acetamido]-2-carboxy-8-oxo-4-thia-1-azabicyclo[4,2,-0]oct-2-en-3-yl-2-(E)propenyl]-thieno[2,3-b]pyridinium, or 500 mg of internal salt of (6S,7S, ΔZ) 5-[3-[7-[(2-amino-thiazol-4-yl)-(methoxyimino)-acetamido]2-carboxy-8-oxo-4-thia-1-azabicyclo[4,2,0]oct-2-en-3-yl]-2(E)propenyl]-thiazolo[4,5-c]pyridinium, or 500 mg of internal salt of (6S,7S) syn isomer of 5-[3-[7-[(2-amino-thiazol-4-yl)(difloromethoxyimino)-acetamido]-2-carboxy-8-oxo-4-thia-1-azabicyclo[4,2,0]oct-2-en-3-yl]-2(E)propenyl]-thiazolo[4,5-c]pyridinium or 500 mg of trifluoromethane sulfonate of 7-[3-[-7-(2-amino-4-thiazolyl)(fluoromethoxyimino)-acetamido]-2-carboxy-8-oxo-4-thia-1-azabicyclo[4,2,0]oct-2-en-3-yl]-2(E)-propenyl]thieno[2,3-b]pyridinium (trifluoroacetate) and sterile aqueous excipient q.s. for 5 ml.

PHARMACOLOGICAL STUDY OF THE PRODUCTS OF THE INVENTION

Activity in vitro, method of dilutions in liquid medium

A series of tubes were prepared, in each of which the same quantity of a sterile nutritive medium was distributed, together with an increasing quantity of the product under study; then each tube was inoculated with a bacterial strain. After incubation for twenty-four or forty-eight hours in an oven at 37° C., the inhibition to growth was evaluated by transillumination which enabled the minium inhibiting concentration (M.I.C.) express in μg/ml to be determined. The following results were obtained.

| STRAINS | Prod. Ex. 3 | | Prod. Ex. 10 | | Prod. Ex. 30 | | Prod. Ex. 19 | |
|---|---|---|---|---|---|---|---|---|
| | 24 H | 48 H | 24 H | 48 H | 24 H | 48 H | 24 H | 48 H |
| *Staphylococcus aureus* SG 511 | 0,08 | 0,15 | 0,08 | 0,15 | 0,3 | 0,3 | 0,6 | 0,6 |
| *Staphylococcus aureus* 285 | 0,15 | 0,3 | 0108 | 0,15 | 0,3 | 0,3 | 0,6 | 0,6 |
| *Staphylococcus aureus* 54146 | 0,15 | 0.15 | 0,15 | 0,3 | 0,3 | 0,6 | 0,6 | 1,2 |
| *Streptococcus pyogenes* A 561 | ≦0,01 | ≦0,01 | ≦0,01 | ≦0,01 | ≦0,01 | ≦0,01 | ≦0,01 | ≦0,01 |
| *Streptococcus pyogenes* 77 A | ≦0,01 | ≦0,01 | ≦0,01 | ≦0,01 | ≦0,01 | ≦0,01 | ≦0,01 | ≦0,01 |
| *Escherichia Coli* 1894 | ≦0,01 | ≦0,01 | ≦0,01 | ≦0,01 | ≦0,01 | ≦0,01 | ≦0,01 | ≦0,01 |
| *Escherichia Coli* 078 | ≦0,01 | ≦0,01 | ≦0,01 | ≦0,01 | ≦0,01 | ≦0,01 | 0,04 | 0,04 |
| *Escherichia Coli* TEM | ≦0,01 | ≦0,04 | ≦0,04 | 0,08 | 0,02 | 0,02 | 0,15 | 0,15 |
| *Escherichia Coli* 1507 E | ≦0,01 | ≦0,01 | ≦0,01 | ≦0,01 | ≦0,01 | ≦0,01 | ≦0,01 | ≦0,01 |
| *Escherichia Coli* DC0 | ≦0,01 | ≦0,02 | ≦0,02 | 0,04 | 0,04 | 0,04 | 0,15 | 0,15 |
| *Escherichia Coli* DC2 | ≦0,01 | ≦0,01 | ≦0,01 | ≦0,01 | ≦0,01 | ≦0,01 | ≦0,01 | ≦0,01 |
| *Salmonella typhimurium* MZ 11 | ≦0,01 | 0,01 | 0,04 | 0,04 | 0,02 | 0,02 | 0,15 | 0,15 |
| *Klebsielia pneumoniae* 52145 | 0,04 | 0,04 | 0,04 | 0,04 | 0,02 | 0,02 | 0,3 | 0,3 |
| *Klebsiella aerogenes* 1522 E | 0,08 | 0,08 | 0,15 | 0,15 | 0,04 | 0,04 | 0,3 | 0,3 |

-continued

| | | | | | | | | |
|---|---|---|---|---|---|---|---|---|
| *Enterobacter cloacae* 1321 E | ≦0,01 | ≦0,01 | 0,02 | 0,02 | ≦0,01 | ≦0,01 | 0,04 | 0,08 |
| *Proteus mirabilis* A 235 | 0,02 | 0,02 | 0,04 | 0,04 | 0,02 | 0,04 | 0,08 | 0,08 |
| *Proteus vulgaris* A 232 | 0,08 | 0,3 | 0,08 | 0,08 | 0,02 | 0,04 | 0,04 | 0,04 |

| STRAINS | Product Example 40 | Product Example 41 | Product Example 42 | Product Example 43 | Product Example 44 | Product Example 45 | Product Example 46 | Product Example 47 |
|---|---|---|---|---|---|---|---|---|
| *STAPHYLOCOCCUS AUREUS* SG511 | 1.200 | 2.500 | 0.150 | 0.080 | 0.300 | 0.150 | 0.150 | 0.150 |
| *STAPHYLOCOCCUS AUREUS* SG511 S | 5.000 | 2.500 | 0.150 | 0.150 | 0.600 | 0.300 | 0.150 | 0.150 |
| *STAPHYLOCOCCUS AUREUS* 285 | 1.200 | 2.500 | 0.150 | 0.150 | 0.300 | 0.150 | 0.150 | 0.150 |
| *STAPHYLOCOCCUS AUREUS* 54146 | 5.000 | 2.500 | 0.300 | 0.150 | 0.600 | 0.300 | 0.150 | 0.300 |
| *STREPTOCOCCUS PYOGENES* A 561 | 0.020 | <=0.010 | <=0.010 | <=0.010 | 0.020 | <=0.010 | <=0.010 | <=0.010 |
| *STREPTOCOCCUS PYOGENES* 77 A | 0.020 | <=0.010 | <=0.010 | <=0.010 | <=0.010 | <=0.010 | <=0.010 | <=0.010 |
| *STREPTOCOCCUS FAECIUM* M 78 L | >20.000 | >20.000 | >20.000 | >20.000 | >20.000 | >20.000 | >20.000 | 20.000 |
| *ESCHERICHIA COLI* UC 1894 | 0.040 | 0.150 | <=0.010 | <=0.010 | <=0.010 | <=0.010 | <=0.010 | <=0.010 |
| *ESCHERICHIA COLI* 0 78 | 0.150 | 1.200 | <=0.010 | 0.020 | <=0.010 | <=0.010 | <=0.010 | <=0.010 |
| *ESCHERICHIA COLI* TEM | 0.600 | 2.500 | 0.020 | 0.080 | 0.020 | 0.040 | 0.020 | <=0.010 |
| *ESCHERICHIA COLI* 1507 E | 0.080 | 0.150 | <=0.010 | <=0.010 | <=0.010 | <=0.010 | <=0.010 | <=0.010 |
| *ESCHERICHIA COLI* DC 0 | 0.600 | 2.500 | 0.040 | 0.080 | 0.020 | 0.040 | 0.020 | <=0.010 |
| *ESCHERICHIA COLI* DC 2 | 0.080 | 1.200 | <=0.010 | <=0.010 | <=0.010 | <=0.010 | <=0.010 | <=0.010 |
| *SALMONELLA TYPHIMURIUM* MZ 11 | 0.150 | 1.200 | <=0.010 | 0.040 | 0.020 | 0.020 | <=0.010 | <=0.010 |
| *KLEBSIELLA PNEUMONIAE* 52145 | 0.600 | 5.000 | 0.040 | 0.150 | 0.040 | 0.040 | 0.040 | <=0.010 |
| *KLEBSIELLA AEROGENES* 1082 E | 20.000 | >20.000 | 0.150 | 1.200 | 5.000 | 2.500 | 0.300 | 2.500 |
| *KLEBSIELLA AEROGENES* 1522 E | 0.600 | 2.500 | 0.300 | 0.600 | 0.150 | 0.150 | 0.080 | 0.040 |
| *ENTEROBACTER CLOACAE* P 99 | >20.000 | >20.000 | 2.500 | 2.500 | 5.000 | 5.000 | 2.500 | 5.000 |
| *ENTEROBACTER CLOACAE* 1321 E | 0.300 | 1.200 | 0.020 | 0.080 | 0.040 | 0.040 | 0.020 | <=0.010 |
| SERRATIA RG 2532 | 2.500 | 20.000 | 0.300 | 0.300 | 0.150 | 0.300 | 0.150 | 0.080 |
| *PROTEUS MIRABILIS* A 235 | 0.300 | 0.600 | 0.020 | 0.040 | 0.040 | 0.080 | 0.020 | 0.020 |
| *PROTEUS VULGARIS* A 232 | 2.500 | 2.500 | 0.040 | 0.040 | 0.020 | 0.080 | 0.020 | 0.020 |
| PROVIDENCIA DU 48 | 2.500 | 5.000 | 0.600 | 0.300 | 0.600 | 0.150 | 0.300 | 0.300 |

| STRAINS | Product Example 48 | Product Example 49 | Product Example 50 | Product Example 51 | Product Example 52 | Product Example 53 | Product Example 54 | Product Example 55 |
|---|---|---|---|---|---|---|---|---|
| *STAPHYLOCOCCUS AUREUS* SG511 | 0.600 | 0.150 | 0.300 | 0.300 | 0.300 | 0.150 | 0.300 | 0.150 |
| *STAPHYLOCOCCUS AUREUS* SG511 S | 0.600 | 0.150 | 0.300 | 0.300 | 0.300 | 0.150 | 0.300 | 0.300 |
| *STAPHYLOCOCCUS AUREUS* 285 | 0.300 | 0.150 | 0.150 | 0.150 | 0.150 | 0.080 | 0.300 | 0.150 |
| *STAPHYLOCOCCUS AUREUS* 54146 | 1.200 | 0.150 | 0.300 | 0.600 | 0.300 | 0.150 | 0.600 | 0.300 |
| *STREPTOCOCCUS PYOGENES* A 561 | <=0.010 | <=0.010 | 0.020 | <=0.010 | <=0.010 | <=0.010 | <=0.010 | <=0.010 |
| *STREPTOCOCCUS PYOGENES* 77 A | <=0.010 | <=0.010 | <=0.010 | <=0.010 | <=0.010 | <=0.010 | <=0.010 | <=0.010 |
| *STREPTOCOCCUS FAECIUM* M 78 L | >20.000 | >20.000 | >20.000 | 10.000 | >20.000 | 10.000 | >20.000 | 10.000 |
| *ESCHERICHIA COLI* UC 1894 | 0.080 | <=0.010 | <=0.010 | <=0.010 | <=0.010 | <=0.010 | <=0.010 | <=0.010 |
| *ESCHERICHIA COLI* 0 78 | 0.080 | 0.150 | <=0.010 | <=0.010 | 0.020 | <=0.010 | 0.080 | 0.080 |
| *ESCHERICHIA COLI* TEM | 0.300 | 0.600 | 0.020 | 0.040 | 0.040 | 0.020 | 0.300 | 0.080 |
| *ESCHERICHIA COLI* 1507 E | 0.040 | <=0.010 | <=0.010 | <=0.010 | <=0.010 | <=0.010 | <=0.010 | 0.020 |
| *ESCHERICHIA COLI* DC 0 | 0.300 | 0.600 | 0.040 | 0.040 | 0.040 | 0.020 | 0.300 | 0.040 |
| *ESCHERICHIA COLI* DC 2 | 0.040 | <=0.010 | <=0.010 | <=0.010 | <=0.010 | <=0.010 | 0.020 | 0.040 |
| *SALMONELLA TYPHIMURIUM* MZ 11 | 0.150 | 0.150 | <=0.010 | 0.020 | 0.020 | <=0.010 | 0.080 | 0.080 |
| *KLEBSIELLA PNEUMONIAE* 52145 | 0.300 | 0.300 | 0.040 | 0.040 | 0.150 | 0.040 | 0.600 | 0.080 |
| *KLEBSIELLA AEROGENES* 1082 E | 20.000 | 10.000 | 0.600 | 1.200 | 0.600 | 1.200 | 10.000 | >20.000 |
| *KLEBSIELLA AEROGENES* 1522 E | 1.200 | 1.200 | 0.080 | 0.150 | 0.150 | 0.150 | 0.600 | 0.150 |
| *ENTEROBACTER CLOACAE* P 99 | >20.000 | 5.000 | 5.000 | 2.500 | 2.500 | 2.500 | 5.000 | 20.000 |
| *ENTEROBACTER CLOACAE* 1321 E | 0.600 | 0.150 | 0.040 | 0.040 | 0.080 | 0.020 | 0.150 | 0.080 |
| SERRATIA RG 2532 | 2.500 | 2.500 | 0.300 | 0.300 | 0.300 | 0.040 | 1.200 | 0.300 |
| *PROTEUS MIRABILIS* A 235 | 0.300 | 0.300 | 0.040 | 0.040 | 0.040 | 0.020 | 0.300 | 0.080 |
| *PROTEUS VULGARIS* A 232 | 0.300 | 0.300 | 0.150 | 0.040 | 0.040 | 0.040 | 2.500 | 0.600 |
| PROVIDENCIA DU 48 | 1.200 | 5.000 | 0.600 | 1.200 | 1.200 | 1.200 | 5.000 | 0.300 |

Various modifications of the compounds and methods of the invention may be made without departing from the spirit or scope thereof and it is to be understood that the invention is intended to be limited only as defined in the appended claims.

What we claim is:

1. A compound selected from the group consisting of a compound of the formula

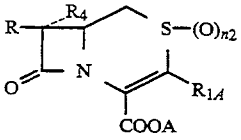

I wherein R is selected from the group consisting of

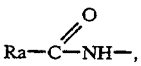, 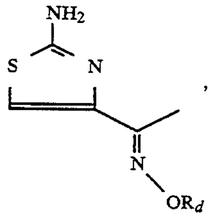,

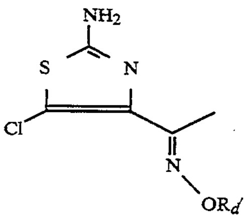 and 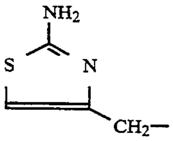

$R_a$ is selected from the group consisting of ArO—$CH_2$—, ArS—$CH_2$— and $R_e$—NH—, Ar and $R_e$ are individually selected

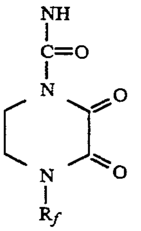

from the group consisting of phenyl and phenyl substituted with at least one member of the group consisting of halogen, alkyl and alkoxy and alkylthio of 1 to 4 carbon atoms, alkylsulfinyl and alkylsulfonyl of 1 to 4 carbon atoms, —$NH_2$, nitro, —OH, aminoalkyl of 1 to 4 carbon atoms, —CN and —$CF_3$, $R_f$ is alkyl of 1 to 4 carbon atoms, $R_d$ is selected from the group consisting of a) hydrogen, b) alkyl of 1 to 6 carbon atoms, c) alkenyl and alkynyl of 2 to 6 carbon atoms, d) cycloalkyl of 3 to 8 carbon atoms unsubstituted or substituted with a member of the group consisting of halogen, acyl of 1 to 7 carbon atoms, —CN, carbamoyl, amino, —OH, —SH, alkylthio and alkoxy of 1 to 4 carbon atoms, oxo, carboxyl and salified or esterified carboxyl, $R_{1A}$ is selected from the group consisting of

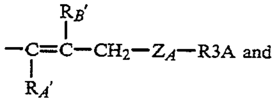 and 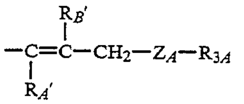

$R_A$ and $R_B$ are individually selected from the group consisting of hydrogen and alkyl of 1 to 4 carbon atoms, $Z_A$ is selected from the group consisting of a simple bond, —O—, —S— and oxidized sulfur, $R_{3A}$ is quaternary ammonium optionally substituted with at least one member of the group consisting of a) alkyl of 1 to 4 carbon atoms unsubstituted or substituted with at least one member of the group consisting of carbocyclic aryl and carbocyclic aryloxy where the carbocyclic aryl is phenyl, diphenyl or naphthyl, alkyl, alkoxy, carbonyl, halogen, —OH, protected, —OH, carboxy, salified or esterified carboxy, —$NH_2$, acetamido monoalkylamino and dialkylamino, b) alkenyl and alkynyl of 2 to 4 carbon atoms, c) carbocyclic aryl, d) halogen, e) —$NH_2$, f) —$NO_2$, g) alkoxy and alkylthio of 1 to 4 carbon atoms, h) —OH or —SH, i) free salified or esterified carboxy, j) carbamoyl and k) cyclopentyl or cyclohexyl, $R_4$ is selected from the group consisting of hydrogen and methoxy, a is selected from the group consisting of hydrogen, alkali, metal, alkaline earth metal, magnesium, —$NH_2$, an organic amine selected form the group consisting of methylamine, propylamine, trimethylamine, diethylamine, triethylamine, N, N-dimethylthanolamine, tris(hydroxymethyl)amino methane, ethanolamine, pyridine, picoline, dicyclohexylamine, morpholine, benzylamine, procaine, lysine, arginine, histidine, and N-methylglucamine and esterified carboxy or —COOA is —$COO^-$, $n_2$ is an integer from 0 to 2 or a non-toxic, pharmaceutically acceptable acid addition salt.

2. A compound of claim 1 having the formula

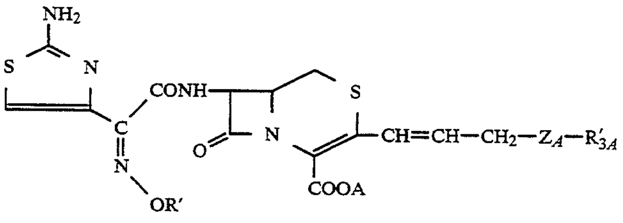

$I_A$ syn isomer wherein R' is selected from the group consisting of hydrogen, alkyl of 1 to 6 carbon atoms, alkenyl and alkynyl of 2 to 6 carbon atoms and cycloalkyl of 3 to 6 carbon atoms, all unsubstituted or substituted as in claim 1, phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyurimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl, benzoxazole, $R_{3A}$ is selected from the group consisting of, pyridinium, quinolinium, isoquinolinium, cyclopentylpyridinium, and trimethylammonium and $Z_A$ has the definition of claim 1.

3. A compound of claim 2 wherein R' is selected from the group consisting of hydrogen, allyl, allyl substituted with chlorine of bromine, cyclobutyl and cyclopropyl unsubstituted or substituted with carboxy, phenyl, difluoromethyl, trifluoromethyl and methyl and isopropyl unsubstituted or substituted with carboxy, carbamoyl, nitrile, $CH_3S$— or $CH_3O$—.

4. A compound of claim 2 wherein $Z_A$ is a simple bond and $R'_{3A}$ is an unsubstituted or substituted pyridinium.

5. A compound of claim 1 selected from the group consisting of the internal salt of (6S, 7S) 7-[3-[7-[[(2-a mino-4-thiazolyl)-2-[Z-(difluoromethoxyimino-acetamido]-2-carboxy-8-oxo-4-thia-1-azabicyclo[4,2,-0]oct-2-en-3-yl)-2-(E)-propenyl]thieno-[2,3-b]-pyridinium; the internal salt of the (6S, 7S) 5-[3-[7-[[(2-amino-4-thiazolyl)-(methoxyiminoacetamidoe]-2-carboxy-8-oxo-4-thia-1-azabicyclo-[4,2,0]-oct-2-en-3-yl]-2(E)-propenyl]-2-methyl-thiazolo[4,5-c]-pyridinium; the internal salt of (6S, 7S) 7-[3-[7-[[(2-amino-4-thiazolyl)-2-(Z)-(methoxyiminoacetamido]-2-carboxy-8-oxo-4-thia-1-azabicyclo-[4,2,0]-oct-2-en-3-yl]-propen-2-(E)-yl]thieno[2,3-b]pyridinium; the internal salt of the Z isomer of (6S, 7S) 5-[3-[7-[[(2-amino-4-thiazolyl (difluoromethoxy)iminoacetamido]2-carboxy 8-oxo 4-thia 1-azabicyclo[4,2,0]-oct-2-en-3-yl]-2-(E)-propenyl]-2-méthyl-thiazolo[4,5-c] pyridinium, 6S,7S,ΔZ 5-[3-[7-[(2-amino thiazol 4-yl)-(methoxyimino) acetamido] 2-carboxy-8-oxo-4-thia-1-azabyciclo[4,2,0]oct-2-en-3-yl]-2(E)propenyl]-thiazolo[4,5c]pyridinium and 6S,7S syn isomer of 5-[3-[7-[(2-aminothiazol-4-yl) (difluoromethoxyimino) acetamido]2-carboxy-8-oxo-4-thia-1-azabicyclo[4,2,0]oct-2-en-3-yl]-2 (E)propenyl]-thiazolo[4,5,c]pyridinium and 6S,7S syn isomer of 7-[3-[7-(2-aminothiazol-4-yl)(fluoromethoxuyimino) acetamido]2-carboxy-8-oxo-4-thia-1-azabicyclo[4,2,-0]oct-2-en-3-yl]2-(E)propenyl]thieno[2,3-b]pyridinium.

6. An antibacterial composition comprising an antibacterially effective amount of a compound of claim 1 and an inert pharmaceutical carrier.

7. A composition of claim 6 wherein R' is selected from the group consisting of hydrogen, allyl optionally substituted with chlorine or bromine, cyclobutyl and cyclopropyl optionally substituted with carboxy, phenyl, difluoromethyl, trifluoromethyl and methyl and isopropyl optionally substituted with carboxy, carbamoyl, nitrile $CH_3S$— or $CH_3O$—.

8. A composition of claim 6 wherein $Z_A$ is a simple bond and $R'_{3A}$ is an unsubstituted or substituted pyridinium.

9. A composition of claim 6 wherein the compound is selected from the group consisting of the internal salt of (6S,7S) 7-[3-[7-[[2-amino-4-thiazolyl)-2-[Z-(difluoromethoxyiminoacétamido]-2-carboxy-8-oxo-4-thia-1-azabicyclo[4,2,0]oct-2-en-3-yl 2-(E)-propenyl]-thieno[2,3-b]pyridinium; the internal salt of the syn isomer of (6S,7S) 5-[3-[7-[[(2-amino-4-thiazolyl) (methoxyiminoacetamido]-2-carboxy-8-oxo-4-thia-1-azabicyclo-[4,2,0]-oct-2-en-3-yl]-2(E)-propenyl]-2-methyl thiazolo-[4,5-c]-pyridinium; the internal salt of (6S,7S) 7-[3-[7-[[(2-amino-4-thiazolyl)-2-(Z)-(methoxyiminoacetamido]-2-carboxy-8-oxo-4-thia-1-azabicyclo[4,2,0]oct-2-en-3-yl]propen-2-(E)-yl]-thieno-[2,3-b]pyridinium; the internal salt of the Z isomer of (6S,7S) 5-[3-[7-[[(2-amino-4-thiazolyl (difluoromethoxy)iminoacetamido]2-carboxy 8-oxo 4-thia 1-azabicyclo[4,2,0]-oct-2-en-3-yl]-2-(E)-propenyl]-2-méthyl-thiazolo[4,5-c]pyridinium, 6S,7S,ΔZ 5-[3-[7-[(2-amino thiazol 4-yl)-(methoxyimino) acetamido]2-carboxy-8-oxo-4-thia-1-azabicyclo[4,2,0]oct-2-en-3-yl]-2(E)-propenyl]thiazolo[4,5-c]pyridinium, 6S,7S syn isomer of 5-[3-[7-[(2-aminothiazol-4-yl) (difluoromethoxyimino) acetamido]2-carboxy-8-oxo-4-thia-1-azabicyclo[4,2,0]oct-2-en-3-yl]-2(E)propenyl]-thiazolo[4,5,c-]pyridinium and 6S,7S syn isomer of 7-[3-[7-(2-aminothiazol-4-yl)(fluoromethoxyimino)acetamido]2-carboxy-8-oxo-4-thia-1-azabicyclo[4,2,0]oct-2-en-3-yl]2-(E)propenyl]thieno[2,3-b]pyridinium.

10. A method of treating or preventing bacterial infections in warm-blooded animals comprising administering to warm-blooded animals an antibacterioidally effective amount of a compound of claim 1.

11. A method of claim 10 wherein R' is selected from the group consisting of hydrogen, allyl unsubstituted or substituted with chlorine or bromine, cyclobutyl and cyclopropyl unsubstituted or substituted with carboxy, phenyl, difluoromethyl, trifluoromethyl and methyl and isopropyl unsubstituted or substituted with carboxy, carbamoyl, nitrile, $CH_3S$— or $CH_3O$—.

12. A method of claim 10 wherein $Z_A$ is a simple bond and $R'_{3A}$ is an unsubstituted or substituted pyridinium.

13. A method of claim 10 wherein the compound is selected from the group consisting of the internal salt (6S,7S) of 7-[3-[7-[[2-amino-4-thiazolyl)-2-[Z-(difluoromethoxyimino-acetamido]-2-carboxy-8-oxo-4-thia-1-azabicyclo[4,2,0]oct-2-en-3-yl-2-(E)-propenyl]-thieno[2,3-b]pyridinium; the internal salt of the syn isomer of (6S,7S) 5-[3-[7-[[(2-amino-4-thiazolyl)-(methoxyiminoacetamido]-2-carboxy-8-oxo-4-thia-1-azabicyclo[4,2,0]oct-2-en-3-yl]-2-(E)-propenyl]-2-methyl-thiazolo[4,5-c]pyridinium; the internal salt of (6S,7S) 7-[3-[7-[[(2-amino-4-thiazolyl)-2-(Z)-(methoxyiminoacetamido]-2-carboxy-8-oxo-4-thia-1-azabicyclo[4,2,0]oct-2-en-3-yl]-propen-2-(E)-yl]-thieno-[2,3-b]pyridinium; the internal salt of the Z isomer of (6S,7S) 5-[3-[7-[[(2-amino-4-thiazolyl) (difluoromethoxy) iminoacetamido]2-carboxy 8-oxo 4-thia 1-azabicyclo-[4,2,0]-oct-2-en-3-yl]-2-(E)-propenyl]-2-methyl-thiazolo[4,5-c]pyridinium, 6S,7S,ΔZ 5-[3-[7-[(2-amino thiazol 4-yl)-(methoxyimino) acetamido]2-carboxy-8-oxo-4-thia-1-azabicyclo[4,2,0]oct-2-en-3-yl]-2(E)-propenyl]thiazolo[4,5-c]pyridinium, 6S,7S syn isomer of 5-[3-[7-[(2-aminothiazol-4-yl) (difluoromethoxyimino) acetamido]2-carboxy-8-oxo-4-thia-1-azabicyclo[4,2,0]oct-2-en-3-yl]-2(E)propenyl]-thiazolo[4,5,c-]pyridinium and 6S,7S syn isomer of 7-[3-[7-(2-aminothiazol-4-yl)(fluoromethoxyimino)acetamido]2-carboxy-8-oxo-4-thia-1-azabicyclo[4,2,0]oct-2-en-3-yl]2-(E)propenyl]thieno[2,3-b]pyridinium.

14. A composition of claim 6 wherein the active compound has the formula

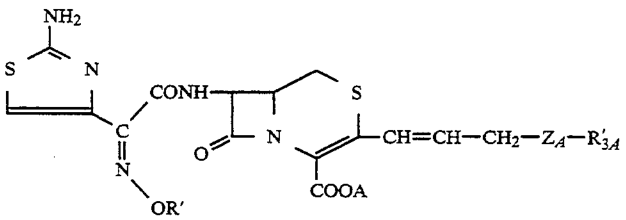

$I_A$ syn isomer, wherein R' is selected from the group consisting of hydrogen, alkyl of 1 to 6 carbon atoms, alkenyl and alkynyl of 2 to 6 carbon atoms all unsubstituted or substituted as in claim 1, phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl pyimidinyl, pyrimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl, benzoxazole, $R_{3A}$ is selected from the group consisting of pyridinium, quinolinium, isoquinolinium cyclopentylpyridinium, and trimethylammonium and $Z_A$ has the definition of claim 1.

15. A method of claim 10 wherein the active compound has the formula

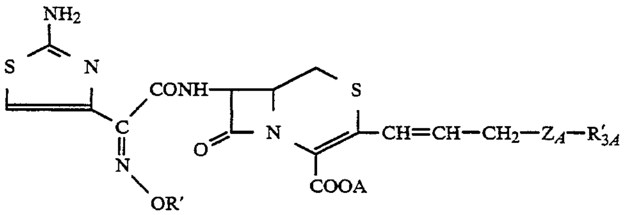

$I_A$ syn isomer, wherein R' is selected from the group consisting of hydrogen, alkyl of 1 to 6 carbon atoms, alkenyl and alkynyl of 2 to 6 carbon atoms and cycloalkyl of 3 to 6 carbon atoms and cycloalkyl of 3 to 6 carbon atoms, all unsubstituted or substituted as in claim 2, phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl, benzoxazole, $R_{3A}$ is selected from the group consisting of pyridinium, quinolinium, isoquinolium, cyclopentyl pyridinium, trimethylammonium and $Z_A$ has the definition of claim 1.

* * * * *